US012741125B2

(12) United States Patent
Gad et al.

(10) Patent No.: US 12,741,125 B2
(45) Date of Patent: Sep. 22, 2026

(54) DEVICES AND METHODS FOR INSERTION AND/OR PRESSURIZATION OF A BALLOON CATHETER FOR BALLOON DILATION OF THE EUSTACHIAN TUBE AND OTHER ANATOMICAL PASSAGEWAYS ACCESSIBLE THROUGH THE NOSTRIL OF A HUMAN

(71) Applicant: Venteus ApS, Copenhagen (DK)

(72) Inventors: Jens Gad, Copenhagen (DK); Martin Nue Møller, Copenhagen (DK)

(73) Assignee: Venteus ApS, Copenhagen (DK)

(*) Notice: Subject to any disclaimer, the term of this patent is extended or adjusted under 35 U.S.C. 154(b) by 0 days.

(21) Appl. No.: 18/874,498

(22) PCT Filed: Jul. 10, 2023

(86) PCT No.: PCT/DK2023/050184
§ 371 (c)(1),
(2) Date: Dec. 12, 2024

(87) PCT Pub. No.: WO2024/008263
PCT Pub. Date: Jan. 11, 2024

(65) Prior Publication Data
US 2025/0161641 A1 May 22, 2025

(30) Foreign Application Priority Data
Jul. 8, 2022 (DK) ............................. PA202200658

(51) Int. Cl.
*A61M 29/02* (2006.01)
*A61B 1/233* (2006.01)
(Continued)

(52) U.S. Cl.
CPC ............. *A61M 29/02* (2013.01); *A61B 1/233* (2013.01); *A61B 1/32* (2013.01); *A61B 17/24* (2013.01);
(Continued)

(58) Field of Classification Search
CPC .......... A61M 29/02; A61M 2210/0675; A61M 2210/0681; A61M 25/0136;
(Continued)

(56) References Cited

U.S. PATENT DOCUMENTS

| | | | | |
|---|---|---|---|---|
| 11,510,564 B2* | 11/2022 | Bendory | .......... | A61B 17/22032 |
| 2010/0211007 A1* | 8/2010 | Lesch, Jr. | ....... | A61M 25/10185 600/101 |

(Continued)

FOREIGN PATENT DOCUMENTS

| | | |
|---|---|---|
| EP | 3368139 | 9/2018 |
| EP | 3395231 | 10/2018 |

(Continued)

OTHER PUBLICATIONS

International Preliminary Report dated May 27, 2024 from IA No. PCT/DK2023/050184.
International Search Report dated Oct. 27, 2023 from from IA No. PCT/DK2023/050184.

*Primary Examiner* — Anh T Dang
(74) *Attorney, Agent, or Firm* — Crockett & Crockett, PC; K. David Crockett, Esq.

(57) ABSTRACT

Methods and apparatuses for insertion and/or pressurization of a balloon catheter for balloon dilation of anatomical passageways in the head of a person such as the Eustachian tube and Sinus passageways. The insertion devices comprise a balloon catheter guiding tube for receiving and guiding the balloon catheter, and a device body rigidly attached to a proximal end of the balloon catheter guiding tube. The pressurization devices comprise a syringe body with a syringe barrel, a proximal thruster guide section, external hand or finger engagement geometries, a plunger with a distal plunger head and a plunger rod, and a thruster having a proximal end with a finger or hand engagement portion.

23 Claims, 81 Drawing Sheets

(51) Int. Cl.

| | |
|---|---|
| ***A61B 1/32*** | (2006.01) |
| ***A61B 17/24*** | (2006.01) |
| ***A61F 11/20*** | (2022.01) |
| *A61B 17/00* | (2006.01) |

(52) U.S. Cl.

CPC ..... *A61F 11/20* (2022.01); *A61B 2017/00557* (2013.01); *A61M 2210/0675* (2013.01); *A61M 2210/0681* (2013.01)

(58) Field of Classification Search

CPC .......... A61M 25/0138; A61M 25/0141; A61M 25/0147; A61M 25/10185; A61M 25/10186; A61M 25/0662; A61M 25/10182; A61M 2025/015; A61M 2025/0681; A61B 1/233; A61B 1/32; A61B 1/0014; A61B 17/24; A61B 2017/00557; A61F 11/20

See application file for complete search history.

(56) References Cited

U.S. PATENT DOCUMENTS

| | | | |
|---|---|---|---|
| 2011/0071393 | A1 | 3/2011 | Liu et al. |
| 2016/0287065 | A1 | 10/2016 | Ha et al. |
| 2017/0259043 | A1 | 9/2017 | Chan et al. |
| 2018/0085174 | A1 | 3/2018 | Radtke et al. |
| 2018/0110407 | A1 | 4/2018 | Makower et al. |
| 2018/0125515 | A1* | 5/2018 | Jenkins ............. A61M 25/0068 |
| 2021/0085929 | A1 | 3/2021 | Ngo-Chu et al. |

FOREIGN PATENT DOCUMENTS

| | | |
|---|---|---|
| EP | 3395392 | 10/2018 |
| JP | 2022514701 | 2/2022 |

* cited by examiner 26
25
24
25
22
27
23
18
21
17
20
20
20

19
21
21

A
190
189
194
193
188
191
192

188
190
197
195
196
193
202
189
198
201
200
199
191
192

190
197
196
195
193
189
198
202
201
191
200
199
192
188

205
204
200
206
210
210
202
208
20
204
200
206
210
210
202
208
20
204
200
206
210
210
202
208

20
204
206
207
200
214
219
215
220
212
211
202
230
208

206
210
210
213
202
217
217
217
219
211
232
230
231
208
20
214
212
207
20
207
214
211
232
230
231
208
211
217
202
217
219
217

400
402
406
408
412
413
414
415
417
418

705
706
707
20
709
708
75

704
706
700
707
702
709
708
750

705
704
706
700
707
702
709
708
750

705
704
706
700
707
702
709
708
750

705
704
20
706
700
707
702
709
708
750

900
905
931
922
Detailed view A
906
920
918
909
916
912
915
917
907
914
908
924
925
913

927
921
926
906

922
906
920
921
902
Detailed view A 1220
1204
1248
1202
1259
1243
1249
1250
1242
1245
1204
1204
1248
1202
1243
1249
1250
1259
1242
1245
1204
1220
1248
1255
1202
1243
1249
1254
1259
1250
1252
1242
1245
1251

Optionally rotating or bending at least part of the guiding tube to point the distal tip of the guiding tube towards the passageway to be dilated.

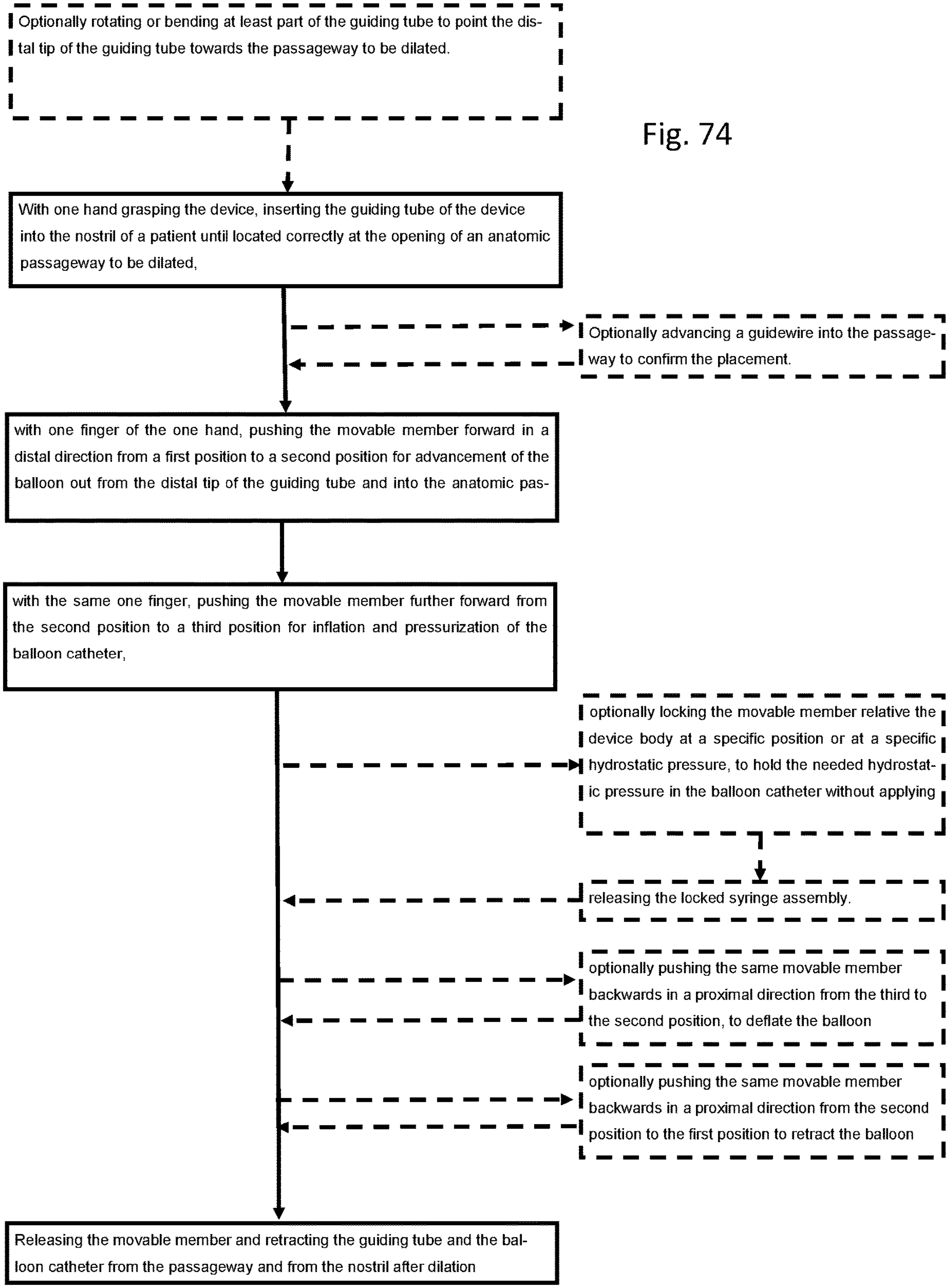

Fig. 74
With one hand grasping the device, inserting the guiding tube of the device into the nostril of a patient until located correctly at the opening of an anatomic passageway to be dilated,
Optionally advancing a guidewire into the passageway to confirm the placement.
with one finger of the one hand, pushing the movable member forward in a distal direction from a first position to a second position for advancement of the balloon out from the distal tip of the guiding tube and into the anatomic pas-
with the same one finger, pushing the movable member further forward from the second position to a third position for inflation and pressurization of the balloon catheter,
optionally locking the movable member relative the device body at a specific position or at a specific hydrostatic pressure, to hold the needed hydrostatic pressure in the balloon catheter without applying
releasing the locked syringe assembly.
optionally pushing the same movable member backwards in a proximal direction from the third to the second position, to deflate the balloon
optionally pushing the same movable member backwards in a proximal direction from the second position to the first position to retract the balloon
Releasing the movable member and retracting the guiding tube and the balloon catheter from the passageway and from the nostril after dilation

Fig. 76B

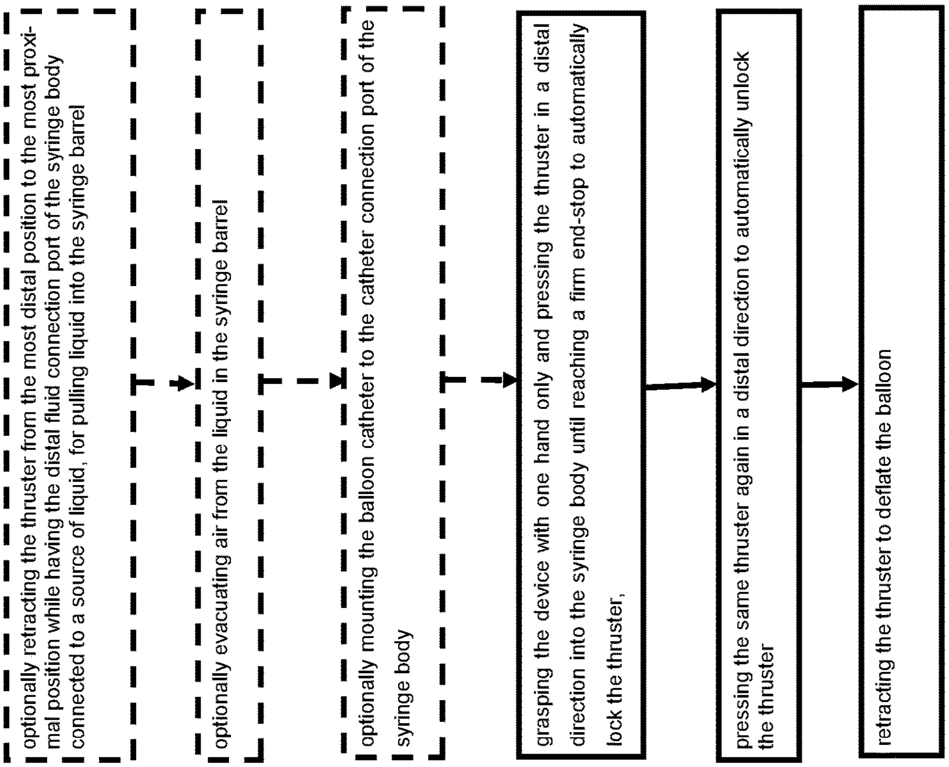

Fig. 76A

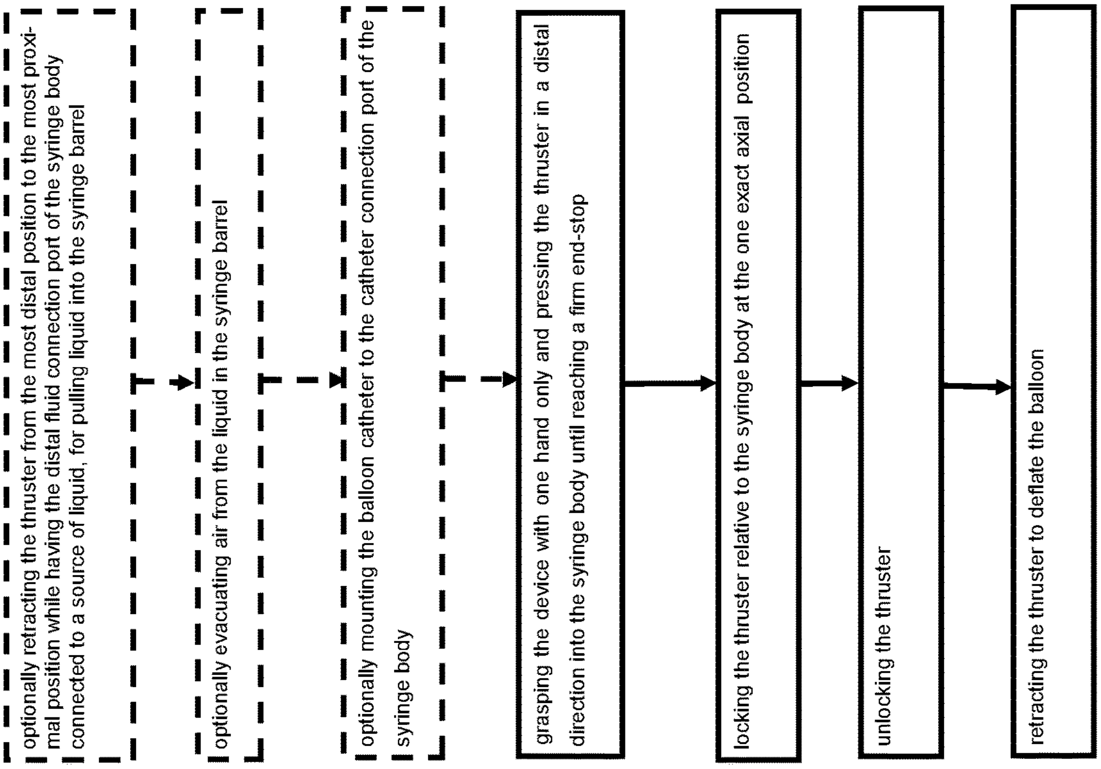

optionally retracting the thruster from the most distal position to the most proximal position while having the distal fluid connection port of the syringe body connected to a source of liquid, for pulling liquid into the syringe barrel
optionally evacuating air from the liquid in the syringe barrel
optionally mounting the balloon catheter to the catheter connection port of the syringe body
grasping the device with one hand only and pressing the thruster in a distal direction into the syringe body until reaching a firm end-stop
locking the thruster relative to the syringe body at the one exact axial position
unlocking the thruster
retracting the thruster to deflate the balloon
optionally retracting the thruster from the most distal position to the most proximal position while having the distal fluid connection port of the syringe body connected to a source of liquid, for pulling liquid into the syringe barrel
optionally evacuating air from the liquid in the syringe barrel
optionally mounting the balloon catheter to the catheter connection port of the syringe body
grasping the device with one hand only and pressing the thruster in a distal direction into the syringe body until reaching a firm end-stop to automatically lock the thruster,
pressing the same thruster again in a distal direction to automatically unlock the thruster
retracting the thruster to deflate the balloon

DEVICES AND METHODS FOR INSERTION AND/OR PRESSURIZATION OF A BALLOON CATHETER FOR BALLOON DILATION OF THE EUSTACHIAN TUBE AND OTHER ANATOMICAL PASSAGEWAYS ACCESSIBLE THROUGH THE NOSTRIL OF A HUMAN

FIELD

The disclosure relates to the field of medical devices. More specifically the disclosure relates to methods and apparatuses for insertion and/or pressurization of a balloon catheter for balloon dilation of anatomical passageways in the head of a person such as the Eustachian tube and Sinus passageways.

BACKGROUND

Balloon dilation of the Eustachian tube is a treatment for Eustachian Tube Dysfunction (ETD). This disease is characterized by the inability of the Eustachian tube to ventilate the middle ear. Consequently, patients report multiple symptoms such as a plugged feeling in the ears, ears feeling like they are filled with water, tinnitus, or ringing in the ear, muffled hearing or partial hearing loss, ticking or popping sounds, pain, and tenderness around the ear, a tickling or tingling sensation and trouble with balance. Additionally, ETD can lead to other more severe middle ear diseases. The potential patient population is huge with prevalence of ETD being reported as high as 4.6% among the background population, which makes this a widespread disease by definition. Barometric related problems such as when flying or diving exists in as many as 10% of cases. The socioeconomic burden of this disease should not be underestimated. Studies have reported that medical care visits associated with ETD exceed 4 million per annum in the US alone.

Balloon dilation of the Eustachian tube is a relatively new procedure, which has gained rapid ground worldwide in the treatment of Eustachian Tube Dysfunction (ETD). The procedure has evolved from being strictly reserved for the adult population in general anesthesia, to now being performed in the clinical office, and trials with children are ongoing. In essence, the procedure is that a small balloon is inserted in the lumen of the Eustachian tube via the nostril. The balloon is subsequently dilated for a few minutes, whereby a small scarification is created which in the end improves the opening of the tube.

Multiple companies offer equipment suited for this procedure. They are all characterized by including the following three elements: a flexible balloon catheter, an insertion instrument, and a pressurization device. A flexible or static endoscope is needed for visualization to ensure safe and correct movement and positioning of the equipment inside the nose.

The flexible balloon catheter is for one-time use only and has a distal inflatable balloon portion, a middle catheter portion, and a proximal connector portion. The distal balloon portion can have a diameter of approximately 1 mm and increases in diameter to e.g. 5 mm over a 20 mm length, when inflated. At the proximal connector portion, the flexible balloon catheters typically have a Luer-lock connection for connection with a separate pressurization device for inflation. The balloon is inflated using water at 8-12 bar, and the water flows from the proximal end to the distal end through a flexible middle section with an internal lumen. The distance from the nostril opening to the eustachian tube opening is on average 90-120 mm for adults.

The balloon insertion instrument is a handheld device that includes a stiff hollow tubular guiding tube for insertion of the flexible balloon catheter into the opening of the eustachian tube or other openings via the nostril. To accommodate for variations in anatomy, the guiding tube must have an adjustable bend at the distal end. In multiuse instruments, there are often 3 interchangeable tip-angles to choose between. In some single-use instruments, the tip can be bent to the desirable angle by deforming the tip with a special tool. It is normal procedure to adjust the angle at least one time for a patient to adapt to the specific anatomy, hence the instruments must be inserted and reinserted several times until the correct angle is found. As the nasal opening is narrow in a horizontal direction and more spacious in a vertical direction, it is normal procedure to have the bent tip pointing vertically upwards or downwards during insertion through the narrow nasal opening until the distal part has reached the required depth. Once the tip of the guiding tube is inserted at the correct depth in the nose, there is space to rotate the tip 45-90 degrees without discomfort to locate the eustachian tube opening. Prior to insertion of the insertion instrument, the flexible balloon catheter is loaded into the insertion instrument and guiding tube in such way, that the balloon catheter can slide inside the lumen of the insertion instrument guiding tube and in such way that the inflatable balloon portion of the balloon catheter can be advanced out and extend out from the distal tip of the guiding tube of the insertion instrument. Available insertion instruments can include features to ease one-handed advancement of the flexible balloon catheter, out of the insertion instrument tip, and into the Eustachian tube. Available insertion instruments can furthermore include features to limit the movement of the balloon to avoid damaging the inner ear. When the insertion instrument is positioned correctly having the distal tip of the guiding tube located at the opening of e.g. the Eustachian tube, the physician may normally attempt several times to advance the balloon into the Eustachian tube without success. For the same reason, finger engagement means on available insertion devices allow the physician to advance and retract the balloon catheter in and out of the distal tip of the guiding tube of the insertion device. Changing between pushing and pulling with fingers on the insertion device leads to unwanted movements of the portion of the device inserted deep into the nose, leading to discomfort for the patient. Some available insertion instruments are made from stainless steel for multiple use and some devices like the Acclarant Aera™ are for single use only and is an integrated and prepared device holding the flexible balloon catheter inside a plastic insertion instrument.

The pressurization devices serve the purpose of inflating the balloon, holding the pressure of e.g., 8-12 bar for approximately 2 minutes, and then subsequently releasing the pressure and deflating the balloon before extraction. The available pressurization devices are typically comprising a syringe-like body with a pressure gauge and a threaded plunger rod for controlled and geared pressure actuation. A Luer-lock connection at the tip of the pressurization device allows for pressure-tight connection to the flexible balloon catheter, either directly or more typically via an extra flexible connecting tube. These pressurization devices are always disposable and must be unpacked, prepared, filled with water, and have air evacuated, prior to connection with the balloon catheter. Most devices used for this application are general purpose devices designed for a broader range of dilation balloons of other and much bigger sizes, thus having a larger water volume capacity of >20 ml. and hence a large plunger seal sectional areal leading to a need for very high plunger actuation forces which again demands a threaded geared actuation solution and generally very robust and expensive components. Due to the threaded plunger, most of the commercially available devices must be operated by two hands and thus requires a dedicated clinician. Often, the general-purpose pressurization devices can hold far larger volumes than needed for the eustachian tube balloon dilation, and the pressurization devices are filled with sterile water from a separate container such as a plastic bag, holding again far more water than necessary. Less than 1 ml is needed for the Eustachian tube balloon dilation, but the general-purpose pressurization devices can typically hold 20 ml or more and the smallest possible sterile water containers seen in the clinics and private practices are typically larger than 100 ml. Consequently, each procedure leads to unnecessary waste of sterile water, unnecessary waste of sterile water plastic packaging, and unnecessary waste of plastics in oversized separate pressurization devices. One-hand operated pressurization devices are emerging on the market and are found in the patent literature, but all still need preparation, prefilling, and air evacuation and all are still separate devices connectable to separate balloon catheter insertion devices. A pressure gauge or other pressure indicator types are integrated into most pressurization devices, and the clinician monitors this gauge during balloon inflation and pressurization to ensure that a constant pressure of e.g. 8-12 bar is held constant for e.g. 2 minutes. Some pressurization devices have means to restrict pressure from exceeding a predetermined value of e.g. 10 bar. However, these solutions require constant engagement from the hand of an operator.

Endoscopic optics are used to locate the position of the anatomic passageway such as the Eustachian tube and serves to monitor the movement and placement of the distal tip of the insertion instrument guiding tube throughout the procedure. During the procedure, two instruments are introduced simultaneously through one nostril; the insertion instrument holding the balloon catheter and a visualization instrument such as endoscopic optics to ensure visually guided balloon insertion and inflation. Both instruments are cylindrical and approximately 3-5 mm in diameter. As the nasal opening is very narrow in the horizontal direction and wider in the vertical direction, it is best practice to keep the instruments vertically over and under each other.

The endoscopes used may either be “static” having a stiff tubular section that goes into the nose or may be flexible with a flexible section and a movable tip. The procedure today is primarily performed using digital versions of the endoscopes that are connected to separate expensive digital monitors that provide a more convenient view for the physician. Currently, available devices do not support the use of analogue flexible endoscopes with an eyepiece that are most commonly used in smaller ENT practices.

A procedure using a costly digital static endoscope connected to a monitor requires minimum of two persons during a procedure in local needle injected anesthesia or general anesthesia due to high patient discomfort. The physician will handle the static endoscope with one hand and the insertion instrument with the other hand while looking at the monitor. A clinician will inflate and pressurize the balloon using either one or two hands for pressurization depending on the device. Movement of two stiff instruments inside the nose is very uncomfortable for the patient and in many cases, general anesthesia or needle injected local anesthesia into the tissue inside the nose is needed, for the procedure to be tolerable for the patient and to avoid sudden movements from the patient during critical moments of the procedure. Fear of general anesthesia and needle phobia may keep many candidates for the procedure from having the procedure.

A procedure using a costly digital flexible endoscope connected to a monitor requires a minimum of two but typically three persons. The physician will handle the insertion instrument while looking at the monitor. A flexible endoscope is always a two-handed instrument needing one hand on the proximal end to operate the knob that controls the bendable distal tip and a second hand that supports the distal flexible part of the endoscope outside the nostril of the patient. Hence, one clinician will operate the flexible endoscope using two hands and yet another clinician would be needed to operate a two-hand operated pressurization device. The physician may be able to use one hand to operate the insertion device and the other hand to operate a one hand operated pressurization device. The flexible endoscope is more comfortable for the patient as it yields to the inner anatomy and puts less pressure on the soft tissue. Highly skilled surgeons have performed the procedure with flexible endoscopes using only anesthetic gel or spray, but due to instrument movements inside the nose not all can tolerate it.

Having fewer movements and using flexible endoscopes would lead to less patient discomfort and would increase the willingness to have the procedure performed.

The analogue flexible endoscope with an eye-piece that does not require an expensive monitor is the main diagnostic tool for the Ear, Nose, and Throat (ENT) practitioner and is available in every private practice. However, the analogue flexible endoscope can unfortunately not be used for the procedure in combination with any available balloon dilation equipment. The reason is, that the physician needs to be the one that has the visual image and is therefore forced to be the operator of the analogue flexible endoscope having one hand on the proximal end to support the handle and eye-piece against the eye and having the other hand supporting the flexible part of the endoscope just outside the nostril. Hence, the physician does not have a free hand to operate the insertion instrument. It is not feasible that the insertion instrument is operated by a clinician under instructions from the physician or vice versa as one cannot blindly operate any instruments inside the nose.

For balloon dilation of the Sinus opening, all the above aspects are the same. The Sinus openings however may be more difficult to locate, and the Sinus balloon insertion devices may have a very thin and flexible guidewire that is maneuvered into a given Sinus cavity prior to balloon insertion. Guidewire advancement features may be a part of the Sinus balloon insertion devices along with separate balloon advancement features.

There is a need for devices and procedure that supports the use of flexible analogue endoscopes to significantly improve the availability of the balloon dilation procedure for Eustachian tube and Sinus passageways.

To further increase the availability of the procedures, it would be beneficial to be able to perform them at lower cost, in private practices, and with less patient discomfort not requiring general anesthesia nor needle injected local anesthesia.

US20140074140 discloses several pressurization devices with different grip options, different pressure indicator options, and different locking mechanism options for locking and releasing a plunger body. The embodiments that allow for one hand operated pressurization all include a direct non-geared linear force transfer from the squeeze of a hand and with a finite number of lockable plunger body positions on a linear path relative to a syringe barrel such as seen in a linear ratchet lock. When a separate pressurization device is connectable to a range of balloon catheter sizes and with the possibility of adding an unknown number of extension tubes in-between, the needed water volume pumped from the pressurization device will be unknown, and a pressure monitor and several plunger locking positions will be necessary.

US20160106960 discloses several one hand operated pressurization devices with means for preventing the hydraulic pressure from exceeding a certain predetermined value. One embodiment shows a conventional pressure relief valve assembly in fluid connection with the distal end of the syringe assembly through a y- or t-connection. Other embodiments show different arrangements that in different ways provide audible and or tactile feedback to the operator when an axial force on the plunger exceeds a certain predetermined value. All embodiments require the operator to keep applying a certain grip force onto the plunger during the dilation procedure, which may be exhausting and may result in hydraulic pressure fluctuations in case the operator loosens the grip.

U.S. Pat. No. 9,700,705 discloses a one hand operated pressurization device with means for preventing the hydraulic pressure from exceeding a certain predetermined value, by having a valve function that blocks the fluid connection between the syringe barrel and the Luer-Lock outlet, when the internal hydraulic pressure exceeds a certain value. The operator is required to apply a certain force onto the plunger throughout the procedure, which may be exhausting and may result in hydraulic pressure fluctuations in case the operator loosens the grip.

In all embodiments shown in the above prior art patent application, the pressurization device is a completely separated device connectable to a separate balloon catheter. Hence, at least one assistant is steel needed. Integration of the balloon insertion functionality and the pressurization functionality into a single one-hand operated instrument would be needed to allow for the physician to perform the procedure without assistants.

EP3368139B1 discloses an integrated device including a balloon catheter, an insertion instrument, and a pressurization unit wherein the pressurization part is a squeezable bladder directly connected to the balloon catheter. In EP3368139 B1 it is argued that this design enables an easy ergonomic one-handed advancement of the balloon as well as an easy and ergonomic one-handed dilation of the balloon. However, even though each operation alone can be operated with one hand, it is two very different hand grip positions for advancement of the balloon and for dilation of the balloon, and a change of grip with only one hand on the insertion instrument at this point of the procedure is not practically feasible. Once the balloon is inserted into the eustachian tube, the instrument must be held extremely steady. Thus, it is not possible to change grip without using both hands. Hence, the other hand is not free to operate an endoscope and the procedure cannot be performed without at least one assistant. Furthermore, squeezing a bladder with the hand of an operator can never generate a hydraulic pressure coming close to the needed pressure interval of 8-12 bar seen for e.g., Eustachian tube and Sinus balloon dilations.

US20180110407 discloses a configuration of an instrument where the balloon catheter insertion device includes a fluid delivery mechanism, such that no separate pressurization device is necessary. The fluid delivery mechanism in this configuration consists of a fluid reservoir containing compressed gas, the fluid reservoir being connected the balloon catheter proximal filling port via a valve, such that opening of such valve would release pressurized gas from the reservoir and would inflate and pressurize the balloon. In this device configuration, the consequence of balloon rupture would be catastrophic as large amounts of stored potential energy would be released inside the inner ear. Furthermore, the device is likely to require use of two hands as balloon advancement is done by moving one movable part of the device and where opening of any valve is likely to require movement of another movable part of the device. Operating such a device with only one hand may be possible but would in any case require the operator to change position of part of the hand or part of the fingers to first operate the movable part of the device that causes advancement of the balloon and secondly operate the movable part of the device that causes the valve to open. Any change of the grip on the device will cause a slight movement of the entire device and when the device is far into the nose of a patient, it is very likely to cause increased patient discomfort.

US20180110407 further discloses another configuration of an instrument where a balloon catheter is connected to a one-hand operated pressurization device. In the disclosed configuration, the balloon is expanded by pulling a trigger that is connected to a plunger that is further connected to a fluid reservoir inside the instrument. This disclosed configuration has no means for advancement of the balloon relative to the instrument body nor advancement of the balloon out from the tip of a guiding tube. The disclosed configuration relies on a separately operated guiding tube and the procedure would require one hand to hold the guiding tube and another hand to operate the disclosed instrument configuration consisting of a balloon catheter and a pressurization device. For advancement of the balloon, the operator must move the entire instrument forward relative to the guiding tube having one hand on each instrument.

US20180110407 discloses a plural of insertion instrument embodiments having the capability of attachment of the distal end of the insertion instrument to a portion of the distal end of a static or flexible endoscope. In these examples, the endoscope and the insertion instrument are bundled at the distal end inside the nose of a patient and are guided simultaneously. The physician would first insert the insertion instrument and the static endoscope having the bent tip of the insertion instrument pointing upwards for better access and least possible discomfort for the patient. Once in position, the physician would rotate the complete bundled assembly to have the tip of the insertion instrument oriented sideways against the opening of the eustachian tube or one of the Sinus openings. This rotation of the bundled instruments will lead to high discomfort for the patient because the two circular instruments in this rotated configuration become wider inside the narrow nasal cavity. Furthermore, any means for attaching the two instruments such as external tubes or clips will in any case increase the overall cross-sectional area of the inserted instrumentation and is likely to introduce edges. Furthermore, a rigid fixture and connection of the distal ends of the two instruments will make it more difficult to insert through the narrow and uneven nasal passageway without causing more pain than two individual instruments that can move independently, each finding the best possible passage and best possible position for lest possible pain. In fact, any means for attaching the distal end of an insertion instrument to the distal end of a visualization instrument will lead to increased discomfort for the patient. A rigid connection of the distal end of the scope to the distal end of an insertion instrument, will allow a free hand for a one-hand operated pressurization device, but will eliminate or severely reduce the movability of the endoscope relative to the insertion instrument and limit the ability to adjust the optimal field of view, as the optimal field of view is likely to change during the procedure. In some ways, it is clever to attach the endoscope to the insertion instrument but in many ways, it would be better if the endoscope was only supported slightly outside the nostril of the patient to allow free movement of the tip of the endoscope and to allow adjustments of the field of view throughout the procedure.

Using an insertion instrument attachable to the distal end of a flexible endoscope as seen in US20180110407A1 could allow a procedure using an analogue flexible endoscope, but it would require 2 persons. The physician would in this case have one hand controlling the tip of the flexible endoscope as well as the insertion instrument and the other hand would support the eyepiece of the proximal end of the flexible endoscope. A clinician would be needed to operate the separate device that advances and pressurizes the balloon.

For the balloon dilation procedure to become accessible to a wider range of the population across the globe, the physicians need to be able to perform the procedure alone using standard low-cost equipment such as the analogue flexible endoscope, as this would allow for the procedure to be carried out in less equipped rooms in the hospital at lower cost and at higher availability. If the procedure could be carried out by a single physician using analogue endoscopes, any private practice clinic could perform it.

For the highest possible availability of the procedure, the cost of the necessary disposable devices must be lowered such that the overall cost of the procedure may be lowered. The main cost driver is currently the indirect cost of running a highly equipped room of a hospital or an advanced clinic occupying 2-3 staff members and the main cost savings will come from changing these requirements. Additional cost savings may come from reducing the necessary procedure duration, preparation time and from use of less expensive disposable instruments.

The current combination of multiple disposable devices also leads to excess garbage, which is environmentally undesirable. In an effort to improve all aspects of this procedure, the environmental footprint must be considered as well.

Finally, it would be a great advantage if the pain and discomfort of the procedure could be lowered, such that it may be performed without the use of general anesthesia and needles for local anesthesia, such that even people with a fear of general anesthesia and needle phobia would want to have the procedure done. Optimally, the procedure should be performed with a smaller cross-sectional area of the instrumentation and with fewer movements of the instruments inside the nose. Preferably, the endoscope and the insertion instrument would be handled by only one hand to reduce relative movements between the two instruments but configured in a way such that each of the inserted instruments can yield to the inner anatomy of the nose to cause the least possible patient discomfort. It would be crucial that an integrated one-hand operated device controlling both an endoscope and the insertion instrument could be operated without changing hand or finger grip position, as this would reduce the movement of the instruments inside the patient nose and hence would be less uncomfortable. Using a flexible endoscope that yields to the inner anatomy of the nasal passageway is preferred rather than using a stiff instrument such as the static endoscope that forces the soft tissue of the inner nose to yield, thereby leading to high patient discomfort.

U.S. Pat. No. 9,700,705 discloses a system for inserting and pressurizing a balloon catheter, having a handheld insertion instrument with a guiding tube into which a balloon catheter and a visualization device such as an endoscope may both be inserted and guided independently.

The pressurization device is not attached to the insertion instrument and there are no guiding means between the pressurization device and the insertion instrument. Hence, one hand must be on the insertion instrument and one other hand must be on the pressurization device to move the balloon relative to the insertion device and for inflation of the balloon. A third hand needs to hold the proximal end of the endoscope. Clearly, one physician and one assistant would be needed to handle this system. Having the endoscope inside the guiding tube may be advantageous for entry through an artificial passageway in the canine fossa as depicted. However, it may not be suitable for access through the nostril as the outer diameter of the stiff guiding tube would be much larger to include both an endoscope and the balloon catheter.

U.S. Pat. No. 10,034,681B2 discloses a system and a method for dilating the Eustachian tube, having a guide member with a hollow shaft portion and a handle portion and having a dilation catheter slidable relative to the guide member shaft with an expandable element disposed at the distal end and an actuator disposed at the proximal end. In one example, the actuation member comprises a bladder for inflation of the balloon, much like presented in EP3368139B1. However, it is not feasible to squeeze a bladder with a hand to generate the hydraulic pressure of 8 to 12 bar needed in the balloon to perform the dilation of the Eustachian tube or a Sinus passageway. In another example, a button is coupled with a plunger slidably disposed in a fluid reservoir defined in the actuator housing, such that pushing the button will move the plunger relative to the fluid reservoir to inflate the balloon. No guiding means are mentioned for guidance of the actuator or any parts of a syringe assembly relative to the guide member and it is clear that the only interface and guidance between the dilation catheter and the guide member is the coaxial placement of the dilation catheter shaft into the guide member shaft. It is not obvious how a user could conveniently operate a syringe coupled to or embedded into the actuator and also operate the guide member with one hand only to advance the balloon catheter and to inflate the balloon using only one hand without changing hand or finger grip position for initial advancement and subsequent inflation.

Balloon dilation procedures require a guiding tube or sheath for placing the distal end of the balloon catheter in the correct position in front of and aligned with the passageway to be dilated before it can be advanced into the passageway for dilation. For several decades, balloon catheters have been used for dilation of the blood vessels in the human body, and steerable sheaths and guidewires are well-known accessories used to reach specific passageways that are not directly accessible from just a straight or prebend guiding tube. For dilation of passageways accessible through the nose, such as the Eustachian tube or the Sinus passageways, it is also advantageous to have a steerable distal tip of the guiding tube. If the guiding tube may be inserted in a straight configuration through the nostril and bent into position when inside the nose, it may be less painful during the insertion. If the distal tip of the guiding tube is steerable, then it may be possible to dilate different passageways placed at different angles by using the same guiding tube.

U.S. Pat. No. 11,020,136B2 discloses deflectable guide catheters and methods, including methods for using deflectable guide catheters to perform transnasal procedures within the ear, nose, throat, paranasal sinuses or cranium. Some deflectable guide catheters of the present invention comprise a substantially rigid tube, a helical spring attached to and extending from the distal end of the substantially rigid tube, a tubular plastic inner jacket, and an outer plastic jacket substantially covering at least the helical spring member. The spring member is deflectable to cause the distal portion of the guide catheter to deflect to a curved configuration. In embodiments for transnasal use, the deflectable guide catheter may have a length of less than 25 cm.

U.S. Pat. No. 11,376,401B2 discloses an apparatus includes a body, an actuation assembly, and a guide catheter extending distally from the body. The guide catheter includes an open proximal end, an open distal end, a rigid proximal portion, a bendable distal portion, and a pull wire extending from the bendable distal portion to the rigid proximal portion. A proximal end of the pull wire is coupled with the actuation assembly. The actuation assembly is operable to translate the pull wire relative to the rigid proximal portion to thereby articulate the bendable distal portion.

All embodiments and descriptions in the mentioned prior art demonstrate deflectable catheter designs comprising a pull wire attached in one end to the most distal part of the deflectable portion and in the other end being attached to an actuator assembly arranged to create a pulling force in the pull wire. Most presented solutions require rotation of a knob to create the pulling force in the pull wire which would require two hands. Other actuator assemblies require pulling of an actuator in a proximal direction.

SUMMARY

It is an object to increase the availability of the procedure that involves primarily the dilation of the Eustachian tube, but also the Sinus passageways. Currently, only a fraction of patients seen in an ENT practice with Eustachian tube or Sinus passageway dysfunction ends up getting a balloon dilation even though many more could benefit from it. The present disclosure radically changes the procedure requirements such that it can be performed with less pain and fewer anesthetics, faster and at lower cost in hospitals and advanced clinics, but furthermore, the procedure can be performed in any private ENT practice, by one single doctor, and with available low-cost analogue flexible or static endoscopes.

It is also an object to provide better integration of the balloon catheter, the insertion instrument, the pressurization device, and the endoscope as this may lead to an improved procedure requiring less personnel and less expensive equipment, causing less patient discomfort.

As previously described, the procedure requires a dilatable balloon catheter, an insertion instrument with a hollow guiding tube for presenting the balloon adjacent to the opening of the Eustachian tube, means for advancing the balloon catheter out of the guiding tube and into the eustachian tube or other passageways, a pressurization device for pressurizing the balloon and an endoscope for visual confirmation of correct placement of the balloon. With all available equipment and in most prior art, at least one assistant is needed to assist the physician during the procedure.

Some of the aspects and possible implementations, aim to improve the procedure in numerous ways leading to less patient discomfort, less staffing, and less costly equipment.

In the following implementations and descriptions a "syringe assembly" comprises a syringe barrel having an internal cylindrical cavity with a fully open proximal end and a distal end with a fluid connection port, a movable sealing element arranged to move linearly inside the syringe barrel along its center axis and sealing against the inner cylindrical surface and a plunger rod being in connection with the movable sealing element such that linear motion of the plunger rod relative to the syringe barrel will provide an equal linear motion of the movable sealing element relative to the syringe barrel.

According to a first aspect there is provided a handheld insertion device for balloon dilation of the Eustachian tube or any other anatomic passageway of a person, the device comprising:

- a balloon catheter,
- a syringe assembly comprising several parts, the several parts comprising a syringe barrel, a sealing element and a plunger rod,
- a balloon catheter guiding tube for receiving and guiding the balloon catheter,
- a device body rigidly attached to a proximal end of the balloon catheter guiding tube,
- the balloon catheter having a distal inflatable part to be advanced out from the distal end of the balloon catheter guiding tube and a proximal part being fluidically connectable to the syringe assembly for inflation and pressurization of the balloon catheter,
- wherein the device body comprises guiding means for movement of one or more parts of the syringe assembly towards to the guiding tube, and wherein
- the balloon catheter is operably coupled to one or more parts of the syringe assembly for advancing the balloon catheter out from the distal end of the balloon catheter guiding tube by linear motion of the one or more parts of the syringe assembly.

By having guiding means for movement of the syringe assembly towards the guiding tube for advancing the balloon catheter, it becomes possible to operate the handheld device with one hand, without changing hand or finger grip position on the device whilst prior art devices require a two-handed operation or at least require changing hand or finger grip position during the procedure.

According to a possible implementation of the first aspect, the guiding means for movement of the syringe assembly towards the guiding tube are configured to guide the syringe assembly in a linear or slightly curved trajectory towards the guiding tube.

According to a possible implementation of the first aspect, the guiding means for movement of the syringe assembly are arranged in the interface between the one or more inner surfaces of an open cavity in the device body and one or more outer surfaces or one or more parts of the syringe assembly.

According to a possible implementation of the first aspect, the guiding means for linear motion of the syringe assembly relative to the guiding tube are arranged between the outer surface of the syringe barrel and the inner surface device body.

According to a possible implementation of the first aspect, the guiding means for linear motion of the syringe assembly relative to the guiding tube are arranged between the outer cylindrical surface of the syringe barrel and the inner cylindrical surface device body.

According to a possible implementation of the first aspect, the guiding means for linear motion of the syringe assembly relative to the guiding tube are arranged as one or more axial grooves on the outer surface of the syringe barrel and one or more protruding fins on the inner surface of an open part the device body.

According to a possible implementation of the first aspect, the guiding means for linear motion of the syringe assembly relative to the guiding tube are arranged as one or more axial grooves on the inner surface of an open part of the device body and one or more protruding fins on the outer surface of the syringe barrel.

According to a possible implementation of the first aspect, the guiding means linear motion of the syringe assembly relative to the device body are arranged as a rail on the external surface of the syringe barrel and an opposing rail track in the device body, such that the syringe assembly may be fully exposed and visible.

According to a possible implementation of the first aspect, the device is configured for dilating passageways accessible through the nostril of a human, such as the Eustachian tube and Sinus passageways.

According to a possible implementation of the first aspect, the device is configured for dilating passageways in the urinary system of a human accessible such as the ureter.

According to a possible implementation of the first aspect, the device is configured for dilating blood vessels of a human accessible such as the Coronary Artery.

According to a possible implementation of the first aspect, the syringe assembly is arranged to move linearly partly or fully inside a cavity of the device body.

According to a possible implementation of the first aspect, a syringe assembly may be placed relative to the device body in such way that the distal end of the syringe barrel having the fluid connection port is placed towards the balloon catheter guiding tube and in such way that the balloon catheter is in fluid connection with the distal end of the syringe barrel and attached directly or indirectly to the syringe barrel.

According to a possible implementation of the first aspect, a syringe assembly may be placed relative to the device body in a reversed position having the plunger rod placed towards the balloon catheter guiding tube and in such way that the balloon catheter is in fluid connection with the syringe barrel via a lumen in the plunger rod and where the balloon catheter is attached directly or indirectly to the plunger rod.

According to a possible implementation of the first aspect, the syringe assembly may be prefilled with liquid from device manufacturing, such that no device preparation is needed prior to the procedure other than unpacking the device. The prefilled liquid may be an exact amount of liquid required to fill and pressurize the balloon catheter to the correct pressure, when the plunger rod and the sealing element is placed at a predefined exact position relative to the syringe barrel.

According to a possible implementation of the first aspect, the device body and the guiding tube may define an instrument for multiple use into which a disposable custom single-use syringe assembly and balloon catheter may be inserted and operated.

According to a possible implementation of the first aspect, the device including a device body, guiding tube, balloon catheter, and syringe assembly may be preassembled and disposable for single use only.

According to a possible implementation of the first aspect, the device has a primary configuration, in which the syringe assembly and the balloon catheter are in a first position where the distal part of the balloon catheter is uninflated and fully retracted inside the guiding tube with the plunger rod retracted relative to the syringe barrel, the syringe barrel preferably being filled with water, a secondary configuration in which the syringe assembly and balloon catheter are in a second position where the distal part of the balloon is advanced out from the tip of the guiding tube and wherein the plunger rod is retracted relative to the syringe barrel, and a tertiary configuration in which the syringe assembly and balloon catheter are in the second position with the plunger rod inserted into the syringe barrel and the balloon catheter in an inflated configuration.

According to a possible implementation of the first aspect, the device comprising an end stop preventing further distal movement of the distal end of the syringe assembly, when the syringe assembly and the balloon catheter is in the second position.

According to a possible implementation of the first aspect, wherein the distal end of the syringe assembly may be lockable in a number of positions relative to the device body, such that the balloon advancement distance out from the distal end of the guiding tube is variable and lockable and wherein any locked position, having the balloon fully advanced, is to be understood as the second position of the syringe assembly and the balloon catheter.

According to a possible implementation of the first aspect, the device having a first thruster operably coupled to the distal part of the syringe assembly configured to move the syringe assembly and the balloon catheter from the first position to the second position and having a second thruster operably coupled to the proximal part syringe assembly configured to move the plunger relative to the syringe barrel for inflation and pressurization of the balloon catheter.

When the balloon is advanced out from the distal tip of the guiding tube and inserted into a passageway to be dilated, it is very important to hold this position of the advanced balloon steadily before and during inflation of the balloon. This is not a challenge when the physician is holding a balloon insertion device in position with a steady grip on the insertion device while an assistant is operating a separated pressurization device for inflation of the balloon. If the pressurization functionality is integrated into a one-hand operated insertion device, it is undesirable to have two different actuators, triggers or thrusters to engage, as this requires the operator to change hand or finger grip position on the device between advancement and inflation of the balloon catheter and because the change of hand or grip position on a one-hand operated device, is likely to cause a movement of the guiding tube and the advanced balloon while inserted into the passageway of the patient. When the balloon is successfully advanced, it is the natural next step to immediately inflate the inflatable part of the balloon catheter and in many ways, it would be preferred to advance the balloon by moving one movable member of the device with one finger and to inflate the balloon by continuing the movement of the one finger on the one movable member, as this would provide the least possible movement of the device during these procedure steps.

According to a possible implementation of the first aspect, the device comprising only one single thruster operably coupled to the proximal end of the syringe assembly, the single thruster being configured to first move the syringe assembly and the balloon catheter from the first position to the second position and subsequently to move the plunger relative to the syringe barrel for inflation and pressurization of the balloon catheter.

A balloon catheter may be damaged, if the balloon is mistakenly inflated partly or fully while retracted inside the guiding tube, and the balloon catheter may be damaged if the operator attempts to advance a balloon that is stuck inside the guiding tube due to partial inflation. With two different thrusters to advance and inflate the balloon respectively, the wrong thruster may be engaged initially, and the balloon may be partially inflated inside the guiding tube. Having a balloon insertion device with only one thruster for advancement and inflation of the balloon increases the risk of inflation of the balloon inside the guiding tube. To reduce the risk of damaging the expensive balloon catheters and to avoid a failed procedure attempt, it would be advantageous to have means for preventing inflation of the balloon until the balloon is fully advanced.

According to a possible implementation of the first aspect, the device comprising a locking arrangement for preventing movement of the plunger relative to the syringe barrel when the syringe assembly and the balloon catheter are in the first position or between the first position and the second position.

According to a possible implementation of the first aspect, wherein the locking arrangement comprises one or more resistance elements creating a resistance between the plunger and syringe barrel such that a second force F2 required to move the plunger relative to the syringe barrel is substantially higher than a first force F1 required to move the syringe assembly and the balloon catheter from the first position to the second position.

According to a possible implementation of the first aspect, wherein the resistance element is the sealing element that seals radially against the syringe barrel and where a second friction force F2 between the sealing element and the syringe barrel is significantly larger than a first friction force F1 between the syringe assembly and the balloon catheter relative to the device body and the guiding tube.

According to a possible implementation of the first aspect, wherein the resistance elements are one or more deformable elements arranged on either the plunger rod or the syringe barrel preventing movement of the plunger rod into the syringe barrel and wherein the second force F2 applied axially onto a part of the syringe assembly is needed to deform the deformable elements in a radial direction to an extent where the plunger rod can be inserted into the syringe barrel.

According to a possible implementation of the first aspect, wherein the resistance element is a valve configured to control the passage of liquid between the liquid in the syringe barrel and the balloon catheter lumen, and wherein the valve is closed when the hydrostatic pressure of the liquid in the syringe barrel is below a pressure limit and opens when the hydrostatic pressure of the liquid in the syringe barrel exceeds the pressure limit, wherein the second Force F2 applied to a part of the syringe assembly is needed to reach the pressure limit.

According to a possible implementation of the first aspect, wherein the resistance element is a flow restriction orifice between the fluid volume in the syringe barrel and the balloon catheter.

According to a possible implementation of the first aspect, wherein the locking arrangement comprises a first locking mechanism, wherein the first locking mechanism comprises a movable locking member, preferably in the form of a spherical locking member, the movable locking member having a locked position in which relative movement between the syringe barrel and the plunger rod is prevented and an unlocked position in which relative movement between the syringe barrel and the plunger rod is enabled.

According to a possible implementation of the first aspect, wherein the movable locking member is partially received in a recess in the plunger rod and partially received in a recess in the syringe barrel in the locked position, and wherein the movable locking member is partially received in the recess in the syringe barrel and partially received in a recess in the device body in the unlocked position, the recess in the device body being arranged to receive a portion of the movable locking member when the syringe assembly and balloon catheter are is in the second position.

According to a possible implementation of the first aspect, wherein the means for preventing inflation of the balloon when the balloon is inside the guiding tube, is a hydraulic lock preventing liquid from passing from the syringe barrel into the fluid connection port of the balloon catheter until the syringe assembly and the balloon catheter are in the second position and wherein 3 radial seal rings on the external surface of the syringe barrel are sealing against a cylindrical cavity inside the device body, and wherein a fluid port in the distal end of the syringe barrel goes radially through the wall of the syringe barrel between the most proximal radial sealing ring and the middle sealing ring, and wherein another fluid port placed between the middle radial sealing ring and the most distal radial sealing ring is connected to the balloon catheter and wherein one or more grooves in the inner surface of the cylindrical cavity will allow fluid to pass across the middle radial sealing ring, from the syringe barrel to the balloon catheter, only when the syringe assembly is in the second position with the inflatable part of the balloon catheter fully advanced out from the guiding tube.

According to a possible implementation of the first aspect, wherein a third force F3 exerted onto a part of the syringe assembly directly or via movable members of the device, is needed to pressurize the balloon catheter to a predefined hydrostatic pressure needed for successful dilation.

According to a possible implementation of the first aspect, the first, second, and third forces F1, F2, and F3 are exerted onto one end of the syringe-plunger assembly, directly or indirectly via other members of the device, from one and same finger or hand engagement interface thereby allowing the operator to advance the balloon, inflate the balloon and pressurize the balloon having the same hand or finger grip on the device throughout balloon advancement, balloon inflation, and balloon pressurization.

According to a possible implementation of the first aspect, the first force F1 is 0-5N, preferably the force F1 is 1-4N, more preferably, the first force F1 is 2-3N.

According to a possible implementation of the first aspect, the second force F2 is 2-8N, preferably the force F2 is 3-7N, more preferably, the second force F2 is 4-6N.

According to a possible implementation of the first aspect, the third force F3 is 4-40N, preferably the third force f3 is 7-25N, more preferably, the third force f3 is 10-20N.

For typical Eustachian tube or Sinus passageway balloon dilation procedures, the balloon needs to be dilated at 8-12 or e.g. exactly 10 bar over a period of several minutes, typically 2 minutes. Exerting an external force onto the plunger relative to the syringe barrel to achieve exactly 10 bar over 2 minutes may be strenuous and difficult. It would be preferred to have means in the device for holding the pressure during the dilation without applying any external force.

According to a possible implementation of the first aspect, wherein the proximal end of the syringe assembly is lockable in one or more positions relative to the distal end of the syringe assembly either directly or via other lockable members of the device.

According to a possible implementation of the first aspect, wherein a thruster connected to the proximal end of the syringe assembly is the lockable member being lockable in one or more positions relative to the device body.

According to a possible implementation of the first aspect, wherein a resilient element is positioned between the lockable member of the device and the sealing element sealing radially in the syringe barrel, the resilient element preferably comprising one or more of: a metal spring, a polymer spring, a gas spring or a spring comprising a resilient material.

According to a possible implementation of the first aspect, any resilient element placed between a movable and lockable member of the device and a movable sealing element inside a syringe barrel part of the device has a first state, and a second compressed state wherein the third force F3 applied directly or indirectly to a part of the syringe assembly is required to compress the resilient element to the second compressed state, such that the compressed spring applies the third force F3, directly or indirectly to the movable sealing element inside the syringe barrel, when the lockable member is locked even upon release of the external force.

According to a possible implementation of the first aspect, wherein the lockable member of the device is lockable in exactly one predefined position and wherein this position is locking the syringe assembly in a state where the balloon is fully advanced, and where the balloon is fully inflated and fully pressurized to a predetermined hydrostatic pressure and wherein the locking member is locking the resilient element is in its second compressed state.

According to a possible implementation of the first aspect, wherein a pressure relief valve is in fluid connection with the fluid chamber of the syringe barrel, and wherein the pressure relief valve is adjusted to the open when the hydrostatic pressure exceeds the predetermined hydrostatic pressure needed for the dilation procedure.

According to a possible implementation of the first aspect, wherein a lumen through the plunger rod forms part of the fluid connection between the fluid inside the syringe barrel and a pressure gauge.

According to a possible implementation of the first aspect, wherein a resilient element is placed on a liquid side of the movable sealing element inside the syringe barrel and operably connected such that the resilient element will be compressed when the plunger rod is moved into the syringe barrel and wherein the resilient element is configured to push back the movable plunger rod upon release of applied force to the plunger rod.

According to a possible implementation of the first aspect, wherein a resilient element is operably connected to the device body and a syringe assembly and where the resilient element will be either compressed or elongated when the syringe assembly is moved from the first position to the second position and wherein the resilient element will urge the syringe assembly back to the first position from the second position upon removal of applied external force.

According to a possible implementation of the first aspect, wherein a cylindrical cavity in the device body acts as the syringe barrel of the syringe assembly.

According to a possible implementation of the first aspect, wherein the proximal end of the balloon catheter is directly connected to a movable sealing element inside the syringe barrel.

According to a possible implementation of the first aspect, wherein the movable sealing element connected to the proximal end of the balloon catheter has a proximal radial sealing ring and a distal radial sealing ring and wherein a fluid connection port between the two radial sealing rings is in fluid connection with the lumen of the balloon catheter and wherein one or more grooves in the inner wall of the syringe barrel will create a liquid passage across the proximal radial sealing ring only when the proximal sealing ring is axially aligned with the grove or groves.

According to a possible implementation of the first aspect, the device body comprises endoscope support features placed in conjunction with a hand- or finger grip-portion of the device body to partly support a flexible or static endoscope, such that the endoscope is only fully supported when one or more fingers or any part of the hand of an operator is placed firmly on the grip-portion of the device body thereby pressing part of the endoscope against the support features and where such support features may be configured as an open groove along at least on a part of the external side of the device body, the groove being substantially parallel with the balloon catheter guiding tube, the groove being at least 1 mm deep, at least 2 mm wide and at least 10 mm long. Preferably the groove is 2 mm deep, 4 mm wide, and at least 50 mm long. Alternatively, the support features are arranged as one or more in-line holes or tubes arranged on a side of the device body, the holes or tubes preferably having an open area wider than 3 mm and higher than 3 mm. The holes or tubes have a center axis substantially parallel to the guiding tube. Alternatively, the support features are arranged as one or more forks arranged in line on a side of the device body, the forks preferably having an open area wider than 3 mm and higher than 1 mm. The forks have a center axis substantially parallel to the guiding tube.

According to a possible implementation of the first aspect, the device body comprises endoscope support features including elastic bands or elastic clips to fixate a part of an endoscope to the external surface of the device body.

According to a possible implementation of the first aspect, the device comprises a guidewire for confirmation of the correct placement inside an anatomic passageway prior to balloon insertion, the guidewire being arranged to move inside a lumen of the balloon catheter. Such guidewire components and procedures are well known in combination with balloon catheters and traditional balloon insertion devices and may be needed as part of the first aspect to allow balloon dilation of the sinus passageways.

According to a possible implementation of the first aspect, the device comprises an integrated digital endoscope as part of a disposable complete device connectable to an external monitor, having a camera chip or the tip of optical fibers and or a lens integrated as part of the balloon catheter guiding tube in a position close to the tip of the guiding tube, such that the field of view by default will cover the tip of the guiding tube.

According to a possible implementation of the first aspect, a single one-hand operated device integrates and combines the insertion instrument and the pressurization device in such way that the physician using only one hand and without changing grip on the device, can insert the guiding tube into the nostril, advance the balloon into the Eustachian tube or a Sinus passageway by pressing a movable member with one finger, inflate the balloon and pressurize the balloon by pressing same movable member further forward using the same finger. The integration reduces the number of disposable devices used for the procedure which is advantageous from an environmental perspective as well as a cost perspective. In one configuration, this aspect may be used in combination with a one-hand operated digital static endoscope such that the procedure may be performed by one physician with no assistant. The physician would hold and operate the integrated device using one hand and would operate the digital static endoscope using the other hand while looking at the monitor for navigation.

In one other and more advantageous configuration, the integrated device further includes endoscope support means The physician may in this case operate the integrated device and support a part of a flexible or static endoscope using one same hand. Consequently, the other hand of the operator is completely free to support and control the eyepiece of an analogue endoscope or the proximal part of any other analogue or digital endoscope. By integrating the pressurization device and the insertion device into one single device and by having means on the device body for supporting the endoscope, it is made possible for only one operator to perform this procedure easily and quickly and without the need for expensive digital monitoring systems, and with less pain for the patient. Having only one smaller disposable device, rather than 2 or 3 larger disposable devices, is faster in preparation time, lowers device costs, and is better for the environment.

According to a second aspect, there is provided a method for balloon dilation of the Eustachian tube, Sinus passageways or any other anatomic passageway accessible through the nostril of a person using a device according to the first aspect or any possible implementations thereof, the method comprising:

a) with one hand grasping the device, insert the guiding tube portion of the device into a patient nostril until located correctly at the opening of an anatomic passageway to be dilated,
b) with one finger of the one hand applying a first force F1 onto the proximal end of the syringe assembly of the device in a distal direction to advance the distal part of the balloon catheter out from the distal tip of the guiding tube and into the anatomic passageway to be dilated.
c) subsequently with the one same one finger of the same one hand, applying a second higher force sF2 to the same proximal end of the syringe assembly of the device in a distal direction for inflation of the inflatable part of the balloon catheter,
d) subsequently with the same one finger of the same one hand, applying a third even higher force F3 to the same proximal end of the syringe assembly of the device in a distal direction to pressurize the balloon catheter for dilation of the anatomic passageway,
e) optionally locking the proximal end of the syringe assembly relative to the distal end of the syringe assembly to hold required hydrostatic pressure without applying an external force,
f) optionally releasing the locked syringe assembly,
g) releasing the applied force applied to the proximal end of the syringe assembly for releasing the pressure in the balloon catheter after completed dilation, and
h) retraction of the deflated balloon.

According to a possible implementation of the second aspect, the method comprises rotating or bending the distal end of the guiding tube to point the distal tip of the guiding tube towards the passageway to be dilated.

According to a possible implementation of the second aspect, the method comprises advancing a guidewire into the passageway to confirm the placement.

According to a third aspect, there is provided a method for balloon dilation of the Eustachian tube or any other anatomic passageway accessible through the nostril of a person using a device according to the first aspect or any possible implementations thereof, the method comprising:

a) with one hand grasping the device, inserting a guiding tube portion of the device into the nostril until located correctly at the opening of an anatomic passageway to be dilated,
b) optionally rotating or bending the distal end of the guiding tube to point the distal tip of the guiding tube towards the passageway to be dilated,
c) optionally advancing a guidewire into the passageway to confirm the placement,
d) with one finger of the one hand, pushing a movable member of the device forward in a distal direction from a first position to a second position for advancement of the balloon out from the distal tip of the guiding tube and into the anatomic passageway to be dilated,
e) with the same one finger, pushing the same movable member further forward from the second position to a third position for inflation and pressurization of the balloon catheter,
f) optionally locking the same movable member relative the device body at a specific position or at a specific hydrostatic pressure, to hold the needed hydrostatic pressure in the balloon catheter without applying external force,
g) optionally bringing the same movable member into an unlocked state,
h) optionally pushing the same movable member backwards in a proximal direction from the third to the second position, to deflate the balloon,
i) optionally pushing the same movable member backwards in a proximal direction from the second position to the first position to retract the balloon out from the passageway and into the guiding tube,
j) retracting the guiding tube and the balloon catheter from the passageway and from the nostril after successful dilation.

According to a fourth aspect, there is provided a handheld insertion device for balloon dilation of the Eustachian tube or any other anatomic passageway accessible through the nose of a person, the device comprising: a balloon catheter, a balloon catheter guiding tube for receiving and guiding the balloon catheter, the balloon catheter having a distal inflatable part to be advanced out from the distal end of the balloon catheter guiding tube and a proximal part being fluidically connectable to an internal or external inflation and pressurization device for inflation and pressurization of the balloon catheter, an actuator operably coupled to the proximal end of the balloon catheter, a device body rigidly connected to a proximal end of the guiding tube, at least a portion of the guiding tube that extends from the proximal end of the guiding tube towards the distal end of the guiding to being straight, the device body being shaped and sized to be held in the hand of an operator, the device body being provided a substantially straight track that is configured for supporting and guiding part of the cylindrical shaft of a static or flexible endoscope, the straight track extending substantially parallel with the straight portion of the guiding tube.

According to a possible implementation of the fourth aspect, the straight track is arranged so that the endoscope shaft, when guided and engaged by the track, extends substantially parallel with the straight portion of the guiding tube and in close proximity to the guiding tube.

According to a possible implementation of the fourth aspect, the straight track comprises a straight groove in an outer surface of the device body, the groove preferably being at least 1 mm deep, 2 mm wide, and having a length of at least 10 mm.

According to a possible implementation of the fourth aspect, the straight track comprises a plurality of U-shaped, C-shaped or V-shaped guide elements that are arranged to form a straight track for guiding part of the endoscope shaft.

According to a possible implementation of the fourth aspect, the straight track comprises a plurality of guide plates or walls flanking at least a portion of the track, the guide plates or walls providing a guide surface facing the track, and the guide surface comprising at least one component that is straight and substantially parallel with the straight portion of the guiding tube.

According to a possible implementation of the fourth aspect, the track is configured to allow longitudinal displacement and rotation of the endoscope shaft relative to the device body and to limit lateral movement of the cylindrical object relative to the device body in all directions or in all but one direction.

According to a possible implementation of the fourth aspect, the device body and the track are configured such that a part of the hand of the operator holding the device can selectively apply pressure on the endoscope shaft thereby selectively impeding longitudinal displacement and rotation of the cylindrical object relative to the device body.

According to a possible implementation of the fourth aspect, the straight track is arranged on a distal grip-portion of the device body and wherein the straight track defines a first center axis being substantially parallel with the guiding tube center axis, the device body having a proximal elongate portion that includes an actuator for advancement and retraction of the balloon catheter, the proximal elongate portion of the device body having a second center axis.

According to a possible implementation of the fourth aspect, there is an angle between the first center axis defined by the straight track and the second center axis defined by the proximal elongate portion of the device body, such that the proximal elongate portion of the device body is distanced from the center axis of an endoscope shaft when supported by the straight track to allow space for a larger proximal end of the static endoscope, the angle preferably being between 5 to 90 degrees, the angle more preferably being 10 to 60 degrees, the angle preferably being 20 to 45 degrees.

According to a possible implementation of the fourth aspect, the actuator is engaged in a linear guiding track on the downfacing surface of the elongate proximal portion opposite the endoscope placement. Placing actuators of any kind on the downfacing surface of the device body is advantageous because the endoscope will be placed on the top surface and would conflict with actuators and finger movements on the top side of a device body.

According to a possible implementation of the fourth aspect, the device comprises an inflation and pressurization device for inflation and pressurization of the balloon catheter.

According to a possible implementation of the fourth aspect, the pressurization and inflation device comprises a syringe assembly comprising a syringe barrel, a plunger rod, and a sealing element.

According to the fourth aspect, an insertion instrument having a device body and a guiding tube, has support means on the hand or finger engagement portion of the device body for support of the middle part of the shaft of an endoscope, the middle part being approximately 100 mm. from the distal tip of the endoscope shaft, the support means being configured to partly support the endoscope, such that the endoscope is only fully supported when the physician has a firm grip on the hand or finger engagement portion of the device body and such that a slight release of the grip will allow an adjustment of the position of the endoscope relative to the guiding tube. In this aspect, a physician may operate the insertion instrument and support an analogue flexible endoscope near the patient nostril with one hand, while operating the proximal end of the endoscope and the eyepiece using the other hand while an assistant is operating the pressurization device. Another physician may choose to use this same aspect in combination with a digital static endoscope, operating the insertion instrument and the static digital endoscope with one hand while operating a one-hand operated pressurization device with the other hand, thus performing the procedure alone with no assistant. The advantages of the unique endoscope support features on the device body of the insertion instrument are that they allow for; freeing one hand to reduce staffing, smallest possible circumference of the instrumentation inserted into the nostril, co-guided instruments leading to fewer relative instrument movements inside the nose, all leading to least possible pain.

According to a fifth aspect, there is provided a method for balloon dilation of the Eustachian tube or any other anatomic passageway accessible through the nose of a person using a device according to the fourth aspect or any possible interpretation thereof, the method comprising:

- a. placing of an endoscope shaft onto or into the straight track on the device body of the balloon insertion device,
- b. with fingers or any part of one hand, grasping the grip-portion of the device body and pressing part of the endoscope shaft against the straight track on the device body to fully support at least part of the endoscope shaft,
- c. inserting the guiding tube of the insertion instrument and the endoscope shaft into the nostril of a person simultaneously,
- d. optionally adjusting the endoscope shaft relative to the guiding tube, by slightly releasing the grip on the part of the hand holding the endoscope shaft against the straight track while with the other hand rotating or translating the endoscope shaft further in or out,
- e. advancing the balloon out from the tip of the guiding tube and into the anatomic passageway to be dilated, once position is confirmed by the visual image presented by the endoscope,
- f. inflating the balloon to dilate the anatomic passageway, and
- g. deflating and retracting the balloon.

According to a sixth aspect, there is provided a device for guiding a balloon catheter through the nostril to the opening of the Eustachian tube, Sinuses or any other anatomic passageway of a person, the device comprising a device body connected to a stiff hollow balloon catheter guiding tube, a balloon catheter with an inflatable distal portion and a proximal portion with a fluid connection port, wherein the proximal portion is formed as a cylindrical element arranged to move linearly inside a cylindrical cavity of the device body and wherein one or more radial sealing elements on the cylindrical element are sealing against the inner surface of the cylindrical cavity of the device body, and wherein the balloon catheter is retracted inside the guiding tube when the cylindrical element is in a first proximal position and wherein the inflatable portion of the balloon catheter is fully advanced when the cylindrical element is in the second and most distal position relative to the cylindrical cavity of the device body.

According to a possible implementation of the sixth aspect, a thruster is connected to the cylindrical element inside the device body and wherein, a hermetically closed volume inside the cylindrical cavity of the device body proximal to the cylindrical element defines a gas spring, wherein the gas pressure in the gas spring is 1 atm when the cylindrical element is in the first most proximal position and wherein a vacuum is created in the gas spring, when the cylindrical element is moved in a distal direction by applying force to the thruster in a distal direction, and such that the gas spring vacuum will pull the cylindrical element and thereby the balloon catheter back in a proximal direction, when the force applied onto the thruster is released.

According to a possible implementation of the sixth aspect, a port opens between the gas chamber and the balloon catheter immediately after successful dilation, such that the vacuum in the gas chamber is partly used to first deflate the balloon and subsequently used for retracting the balloon into the catheter.

According to a possible implementation of the sixth aspect, a fluid connection port going radially through the device body wall is connectable to an external pressurization device and wherein the cylindrical element placed inside the cylindrical cavity of the device body acts as a valve for controlling passage of fluid from the fluid connection port through the cylindrical element and into the balloon catheter, and wherein the cylindrical element in the first position and any position between the first position and the second position is preventing fluid from passing into the balloon catheter and wherein the cylindrical element in the second position only, will allow fluid to pass from the fluid connection port and into the balloon catheter. Having such a valve function will prevent premature inflation of the balloon, while the balloon is still inside the guiding tube. Having such a valve function will also allow for automatic inflation of the balloon from an external fluid cartridge that is prepared and charged to release the needed volume of water at the needed hydrostatic pressure.

According to a possible implementation of the sixth aspect, a resilient element is placed between the distal end of the cylindrical element and the most distal end of the cylindrical cavity and wherein the resilient element is engaged just before the cylindrical element reaches the second position and wherein the resilient element must be compressed before the cylindrical element can reach the second position where the fluid connection is allowed between the connection port and the balloon catheter. Having this resilient element will create noticeable tactile feedback for the operator, such that the opening of the fluid connection is done deliberately.

According to a possible implementation of the sixth aspect, the thruster is connected to the cylindrical element through a rod, and wherein this rod is sealed against an internal cylindrical cavity integrated as part of the device body.

According to a seventh aspect, there is provided a system for inflating and pressurizing a balloon catheter, the system comprising: a balloon catheter, a syringe body having a distal syringe barrel section with a distal opening for connection with the balloon catheter, a proximal thruster guide section, and external hand or finger engagement geometries, a plunger with a distal plunger head having a radial sealing element for sealing against in the inner surface of the syringe barrel and a plunger rod, a thruster having a proximal end with a finger or hand engagement portion, and a thruster rod, and a spring element, wherein the plunger head of the plunger is inserted into the syringe barrel section of the syringe body and wherein the thruster rod is inserted into the thruster guide section of the syringe body and wherein the spring element is placed between said thruster and said plunger, such that external axial forces applied to said thruster in a distal direction are transferred to said plunger through said spring element, characterized in that the thruster and the syringe body have locking means for locking of the thruster in exactly one axial position relative to the syringe body.

According to a possible implementation of the seventh aspect, the locked position of the thruster relative to the syringe body holds the plunger in a specific position relative to the syringe barrel where the balloon is fully inflated and holds the spring in a specific compressed length such that the spring acts with a specific force onto the plunger head to thereby create a specific hydrostatic pressure inside the syringe barrel and the balloon needed for the dilation procedure.

According to the above implementation of the seventh aspect, there is no need for a pressure Gauge and there is no need for an adjustable plunger for the operator to operate. In some cases, the operator may misinterpret the dials or numbers on a pressure gauge resulting in too high or too low pressure being applied to the balloon. To reduce the risk of error, it is desirable to have only two modes for a pressurization device being the uninflated mode and the inflated and locked mode with the correct pressure. Such a system is possible when the attachable balloon is paired with the syringe assembly and the needed balloon inflation volume is known. However, for such a system, the tolerances on parts, spring stiffness, balloon catheter size, and water filling volume in the syringe barrel, may all contribute to tolerances on the pressure in the balloon for that one specific locked position. It would be advantageous to make the system in a way, where the filled water volume to be evacuated from the syringe barrel is always higher than the needed water volume in the balloon catheter and where a pressure relief valve having a fluid connection with the syringe barrel would let out water in case the hydrostatic pressure exceeds the specific pressure needed. This way, the single locked position cannot result in a hydrostatic pressure that is too low or too high. The closed water volume of the system would then be calibrated to the specific balloon attached, and the subsequent balloon inflations would be accurate on the inflation pressure for that one lockable position of the thruster.

According to a possible implementation of the seventh aspect, a pressure relief valve is in hydraulic connection with the water volume of the syringe assembly and wherein the pressure relief valve will open and evacuate water, when the hydrostatic pressure in the syringe barrel exceeds the specific pressure needed for the dilation procedure.

According to a possible implementation of the seventh aspect, the plunger rod has an external cylindrical diameter slightly smaller than the diameter of an internal cylindrical cavity of the thruster rod and wherein the plunger rod is configured to move axially inside said thruster rod cavity, and wherein a helical spring element is placed onto the plunger rod, and wherein external forces applied onto the thruster in a distal direction will be transferred from a distal surface on the thruster rod, through the helical spring to the plunger head, and wherein the helical spring will be compressed axially when an external force is applied onto the thruster and the pressure increases in the syringe barrel.

According to a possible implementation of the seventh aspect, two radial sealing elements are placed proximally on the plunger rod configured to seal radially against the inner surface of the cylindrical cavity inside the thruster rod, and wherein a first radial port on the surface of the plunger rod placed between said two radial sealing elements is in fluid connection with the syringe barrel volume through an internal axial lumen in the plunger, and wherein a second radial port in the thruster rod connects the inner surface of the cylindrical cavity in the thruster rod with the outer surface of the thruster rod, said second radial port being placed in an axial position proximal to the most proximal radial sealing element on the plunger rod only when the syringe assembly is in a first stage where the pressure in the syringe barrel is lower than a setpoint, and wherein increased pressure in the syringe barrel above the setpoint forces the plunger to move further in a proximal direction relative to the thruster beyond a point where the most proximal radial sealing element on the plunger rod passes the second radial port, thereby creating an open fluid connection from the outside surface of the thruster rod, through the second radial port and through the first radial port and through the axial lumen of the plunger to the syringe barrel volume. In this configuration, the same spring element is used in part to create a pressure relief function and in part to apply a force onto the plunger head when the thruster is locked.

According to a possible implementation of the seventh aspect, the thruster has an axial end-stop placed exactly at the locked position or slightly distal to the locked position.

According to a possible implementation of the seventh aspect, said locking means comprise one or more radial features on the external surface of the thruster rod and one or more opposing features on an internal surface of one or more radially flexible and deformable parts of the thruster guide section of the syringe body.

According to a possible implementation of the seventh aspect, said locking means comprise one or more internal axial ribs on an internal cylindrical surface of the thruster guide section of the syringe body and a two-parted thruster rod with a proximal part connected to the thruster engagement portion and a separate distal part, both parts having a cylindrical surface with a diameter slightly smaller than the diameter of the inner cylindrical surface of the thruster guide section of the syringe body, both parts having one or more axial groves aligned with said axial ribs, the proximal thruster rod part having a plural of angled cam surfaces at the distal end, the distal thruster part having a plural of oppositely matching angled cam surfaces on its proximal end, said angled cam surfaces configured to translate axial forces from the proximal thruster part to a rotating force in the distal thruster part, wherein the distal thruster part can rotate freely when is has passed the end of the internal axial ribs at a certain axial position, wherein every other cam surface of the distal thruster part has the one or more axial groves at the lower cam area and where every other cam surface of the distal thruster part has a locking surface in the lower cam area configured to lock against the distal end of the axial ribs and wherein external axial forces from the thruster finger engagement portion, are transferred from the proximal thruster part through the cam surfaces to the distal thruster part and from a distal surface on the distal thruster part through the spring element to the plunger, wherein said distal thruster part can toggle between a state where it can translate freely along the axial ribs and a state where it is locked axially against the distal end of the axial ribs.

According to a possible implementation of the seventh aspect, the balloon catheter and the pressurization device are preassembled and prefilled with liquid from manufacturing.

According to a possible implementation of the seventh aspect, the system includes a guiding tube for inserting the balloon catheter through the nostril of a person to dilate the Eustachian tube or any Sinus passageway and wherein the balloon catheter is configured to move inside the guiding tube.

According to a possible implementation of the seventh aspect, the system includes a guiding sheath for inserting the balloon catheter into a blood vessel of the body of a human and wherein the balloon catheter is configured to move inside the guiding sheath.

According to a possible implementation of the seventh aspect, the system includes a guiding sheath for inserting the balloon catheter into the urinary system of a human e.g. the Ureter and wherein the balloon catheter is configured to move inside the guiding sheath.

According to a possible implementation of the seventh aspect, the system includes a guiding sheath for inserting the balloon catheter into any passageway in the human body through a natural or artificial body opening.

According to an eighth aspect, there is provided a method for inflating and pressurizing a balloon catheter for dilation of a passageway in the body of a human, using a device according to the seventh aspect or any possible interpretation thereof, the method comprising:

a) Optionally retracting the thruster from the most distal position to the most proximal position while having the distal fluid connection port of the syringe body connected to a source of liquid, for pulling liquid into the syringe barrel,
b) optionally evacuating air from the liquid in the syringe barrel,
c) optionally mounting the balloon catheter to the catheter connection port of the syringe body,
d) grasping the device with one hand only and pressing the thruster in a distal direction into the syringe body until reaching a firm end-stop,
e) locking the thruster relative to the syringe body at the end-stop position,
f) unlocking the thruster
g) retracting the thruster to deflate the balloon.

According to a ninth aspect, there is provided a method for inflating and pressurizing a balloon catheter for dilation of a passageway in the body of a human, using a device according to the seventh aspect or any possible interpretation thereof, the method comprising:

a) Optionally retracting the thruster from the most distal position to the most proximal position while having the distal fluid connection port of the syringe body connected to a source of liquid, for pulling liquid into the syringe barrel,
b) optionally evacuating air from the liquid in the syringe barrel,
c) optionally mounting the balloon catheter to the catheter connection port of the syringe body,
d) grasping the device with one hand only and pressing the thruster in a distal direction into the syringe body until reaching a firm end-stop to automatically lock the thruster,
e) pressing the same thruster again in a distal direction to automatically unlock the thruster,
f) retracting the thruster to deflate the balloon.

According to a tenth aspect, there is provided a handheld insertion device for dilation of the Eustachian tube or Sinus passageways accessible through the nostril of a human, the device comprising: A balloon catheter having a distal inflatable balloon and a proximal fluid connection port, a guiding tube into which the balloon catheter can be inserted and guided, a device body attached to the guiding tube, and an actuator, wherein the guiding tube has a proximal rigid portion and a distal deflectable portion, wherein the guiding tube has one lumen for guiding of the balloon catheter and one lumen for a pull wire, and wherein a pull wire inside the guiding tube pull wire lumen in one end is attached to the distal end of the guiding tube and in the other end is rigidly attached to the device body to fixate the pull wire, and wherein the guiding tube can translate linearly relative to the device body along its own center axis, and wherein the actuator is operably connected to the guiding tube and wherein movement of the actuator in a distal direction results in movement of the guiding tube in a distal direction relative to the device body and relative to the fixated pull wire, thereby deflecting the deflectable portion of the guiding tube.

According to a possible implementation of the tenth aspect, the deflectable portion is resiliently biased to a straight configuration.

According to a possible implementation of the tenth aspect, the distal deflectable portion is deflectable in one plane of deflection only.

According to a possible implementation of the tenth aspect, the guiding tube of the device comprises a deflectable tube with the balloon catheter lumen and the pull wire lumen, having the most proximal end connected to the actuator of the device and having the most distal end attached to the pull wire, and wherein the deflectable tube is equally flexible in its full length, and wherein the guiding tube further comprises a stiff straight tube rigidly connected to the device body, and wherein the deflectable tube is guided for linear movement inside the stiff straight tube, such that the part of the deflectable catheter inside the stiff straight tube is prevented from deflecting and such that the part of the deflectable tube extending out from the distal end of the stiff straight tube may deflect when the actuator and thereby the whole deflectable tube is moved forward in a distal direction relative to the stiff straight tube, and relative to the pull wire.

According to a possible implementation of the tenth aspect, the guiding tube of the device comprises a deflectable tube with the balloon catheter lumen and the pull wire lumen and wherein the guiding tube of the device further comprises a stiff straight tube, the deflectable tube being attached and bonded to the stiff straight tube such that one distal portion of the deflectable tube is extending out from the distal end of the stiff straight tube and one proximal portion of the deflectable tube is placed inside the stiff straight tube, and wherein the pull wire is attached in one end to the most distal end of the deflectable tube and in the other end being rigidly attached to the device body, and wherein the stiff straight tube can translate linearly relative to the device body and wherein the actuator is attached to the proximal end of the stiff straight tube, such that movement of the actuator and thereby the stiff straight tube forward in a distal direction relative the device body and relative to the pull wire, will deflect the deflectable portion of the deflectable tube.

According to a possible implementation of the tenth aspect, a hub is bonded to the proximal end of the deflectable tube and wherein a resilient member is positioned between the hub and the device body such that the resilient member is either compressed or elongated when the deflectable tube is pushed forward in a distal direction.

According to a possible implementation of the tenth aspect, wherein any deflected position of the distal tip of the guiding tube is lockable by locking the actuator relative to the device body in several positions and wherein the lock preferably comprises a releasable one-way lock.

According to a possible implementation of the tenth aspect, the one-way lock comprises a serrated surface along the actuator and an opposing serrated releasable cam of the device body and wherein movement of the actuator in a distal direction is allowed by the serrated cam and wherein movement in a proximal direction is not allowed by the cam, and wherein the cam is releasable using a lever.

According to a possible implementation of the tenth aspect, a knob attached to the proximal end of the guiding tube may be rotated relative to the device body for rotation of the guiding tube.

According to a possible implementation of the tenth aspect, the device further comprises a second actuator attached to a guide wire placed inside a lumen of the balloon catheter, and wherein movement of the second actuator in a distal direction will cause the guidewire to be advanced out from the distal end of the deflectable guiding tube.

According to a possible implementation of the tenth aspect, the device further comprises a third actuator attached to the balloon catheter and wherein movement of the actuator in a distal direction will cause the inflatable portion of the balloon catheter to be advanced out from the distal end of the deflectable guiding tube.

According to a possible implementation of the tenth aspect, the device further comprises a fourth actuator attached to the plunger of a syringe assembly connected to the device body and where the syringe assembly has a fluid connection to the balloon catheter and where a movement of the actuator in a distal direction will cause the plunger to move relative to a syringe barrel for inflation of the inflatable part of the balloon.

According to these implementations of the tenth aspect, it may be possible to provide a device that is conveniently operated with one hand only and where one grip position of the hand is unchanged during the procedure and where one single finger e.g. the thumb may selectively push actuators in a distal direction for guiding tube deflection, guide wire advancement, balloon advancement, and balloon inflation. Having actuators that are all pushable in a distal direction and within reach of one finger e.g. the thumb may be the only possible way of operating all said functions in one single device with one single hand and without changing the grip position.

According to an eleventh aspect, there is provided a method for inserting and inflating a balloon catheter for dilation of the Eustachian tube, Sinus passageways, or any other passageways accessible through the nostril of the person, using a device according to the tenth aspect or any possible interpretation thereof, the method comprising:

a) optionally rotate the guiding tube of the device to a desired angle suitable for reaching the passageway to be dilated,
b) grasping the device with one hand only and inserting the straight guiding tube into the nostril of a person,
c) using the thumb to push a first actuator in a distal direction for deflection of the distal end of the guiding tube until aligned with the passageway to be dilated,
d) optionally using the same thumb of the same hand to push a second actuator in a distal direction for advancing a guidewire into the passageway,
e) using the same thumb of the same hand to push a third actuator in a distal direction for advancing the inflatable part of the balloon catheter out from the distal tip of the guiding tube, f) optionally using the same thumb of the same hand to push a fourth actuator in a distal direction for inflation of the inflatable part of the balloon catheter, g) deflate and retract the balloon when the dilation is completed.

According to a twelfth aspect, there is provided a handheld insertion device for dilation of the Eustachian tube or Sinus passageways accessible through the nostril of a human, the device comprising: A balloon catheter having a distal inflatable balloon and a proximal fluid connection port, a guiding tube into which the balloon catheter can be inserted and guided, a device body attached to the guiding tube, a first actuator connected to the proximal end of a mandrel, and a second actuator connected to the proximal end of the balloon catheter, wherein both actuators are linearly slidable along the device body, wherein the guiding tube has a proximal rigid section and a distal deflectable section, wherein the guiding tube has one lumen for guiding of the balloon catheter and one lumen for guiding the mandrel, the mandrel having a distal end that is curved and elastically flexible with a stiffness significantly higher than the deflectable distal portion of the guiding tube and significantly lower than the stiff proximal portion of the guiding tube, and wherein movement of the actuator from a first proximal position to a second distal position will move the curved tip of the mandrel from a retracted position inside the stiff portion of the guiding tube and into an advanced position partly or fully inside the deflectable distal portion of the guiding tube for partial or full deflection of said deflectable distal portion of the guiding tube.

According to a possible implementation of the twelfth aspect, the first actuator may be rotated to rotate the mandrel relative to the guiding tube, such the plane of the guiding tube deflection and the degree of deflection may be manipulated with one single actuator while the guiding tube is inside the nose of the patient.

According to a possible implementation of the twelfth aspect any deflected and rotated position of the distal tip of the guiding tube is self-locking, caused by high friction forces between the actuator and the track in which the actuator moves.

According to a thirteenth aspect, there is provided a handheld insertion device for dilation of the Eustachian tube or Sinus passageways accessible through the nostril of a human, the device comprising: A balloon catheter having a distal inflatable balloon and a proximal fluid connection port, a guiding tube with a curved and flexible distal end, into which the balloon catheter can be inserted and guided, a stiff straight tube surrounding a portion of the guiding tube, a device body for grasping the device, a first actuator for translating the guiding tube relative to the steel tube and a second actuator connected to the proximal end of the balloon catheter for advancement and retraction of the balloon, wherein both actuators are guided to slide linearly along the device body, and the first actuator in a first position has the curved and flexible distal end of the guiding tube retracted fully into the stiff straight tube and where the actuator in a second position has the curved and flexible distal end of the guiding tube fully or partly advanced out from the distal end of the stiff straight tube.

According to a possible implementation of the thirteenth aspect, the first actuator is connected to the guiding tube, and the stiff straight tube is rigidly connected to the device body, wherein a first proximal position of the actuator will have the curved and flexible distal end of the guiding tube fully retracted inside the stiff straight tube and wherein a second and more distal position of the actuator will have the curved and flexible distal end of the guiding tube fully or partly advanced out from the distal end the of stiff straight tube.

According to one implementation of the thirteenth aspect, the first actuator is connected to the stiff straight tube, and the guiding tube is rigidly connected to the device body, wherein a first distal position of the actuator will have the curved and flexible distal end of the guiding tube fully retracted inside the stiff straight tube and wherein a second and more proximal position of the actuator will have the curved and flexible distal end of the guiding tube fully or partly advanced out from the distal end the of stiff straight tube.

According to a possible implementation of the thirteenth aspect, a knob is connected to the proximal end of the guiding tube for rotation of the guiding tube.

According to a possible implementation of the thirteenth aspect, one single actuator may rotate and translate the guiding tube relative the stiff tube, such the plane of the guiding tube deflection and the degree of deflection may be manipulated with one single actuator while the guiding tube is inside the nose of the patient.

According to a possible implementation of the thirteenth aspect wherein any deflected and rotated position of the distal tip of the guiding tube is self-locking, caused by high friction forces between the actuator and the track in which the actuator moves.

Balloon insertion devices often has an actuator that can be pushed in a distal direction with a finger for advancing a guidewire in a distal direction and an actuator that can be pushed in a distal direction with a finger for advancing the balloon catheter in a distal direction. If the operator is to operate such a device with one hand only and without changing the grip position, it may be advantageous to have an actuator that can be pushed in a distal direction with a finger to deflect the distal end of the guiding tube while the guiding tube is inserted into the nose of a patient.

According to a fourteenth aspect, there is provided a handheld insertion device for balloon dilation of the Eustachian tube or any other anatomic passageway in the head of a person, the device comprising a pressurization device operably connected to a movable member, the movable member being configured for being moved by a finger of a hand of an operator holding the device, a balloon catheter, a guiding tube for receiving and guiding the balloon catheter, the balloon catheter having a distal inflatable part to be advanced out from the distal end of the balloon catheter guiding tube and a proximal part being fluidically connected to the pressurization device for inflation and pressurization of the balloon catheter, an actuator operably coupled to the balloon catheter and configured for advancing the distal inflatable part out from the distal end of the guiding tube, the actuator being operably coupled to the movable member, the movable member being configured to move in a substantially distal direction from a most proximal to an intermediate position and from the intermediate position to a most distal position, the actuator being configured to advance the distal inflatable part out from the distal end of the balloon catheter guiding tube when the movable member is moved from the most proximal position to the intermediate position, and the pressurization device being configured to inflate and pressurize the balloon catheter when the movable member is moved from the intermediate position to the most distal position.

These and other aspects will be apparent from the examples and embodiment(s) described below.

BRIEF DESCRIPTION OF THE DRAWINGS

In the following detailed portion of the present disclosure, the aspects, embodiments, and implementations will be explained in more detail with reference to the example embodiments shown in the drawings, in which:

FIG. 53B is a side view of the eleventh embodiment of the handheld insertion device in a tertiary configuration.

FIG. 54B is a sectional view of the eleventh embodiment of the handheld insertion device in a tertiary configuration.

FIG. 74 is a flowchart describing the balloon dilation procedure using the handheld insertion device according to embodiment 1 to 8 and the embodiment 11 and the embodiment 15 or any combination thereof.

FIG. 76 is a flowchart describing the procedure using the pressurization device according to FIG. 60A to 64C or any combinations thereof.

DETAILED DESCRIPTION

Figure 1:
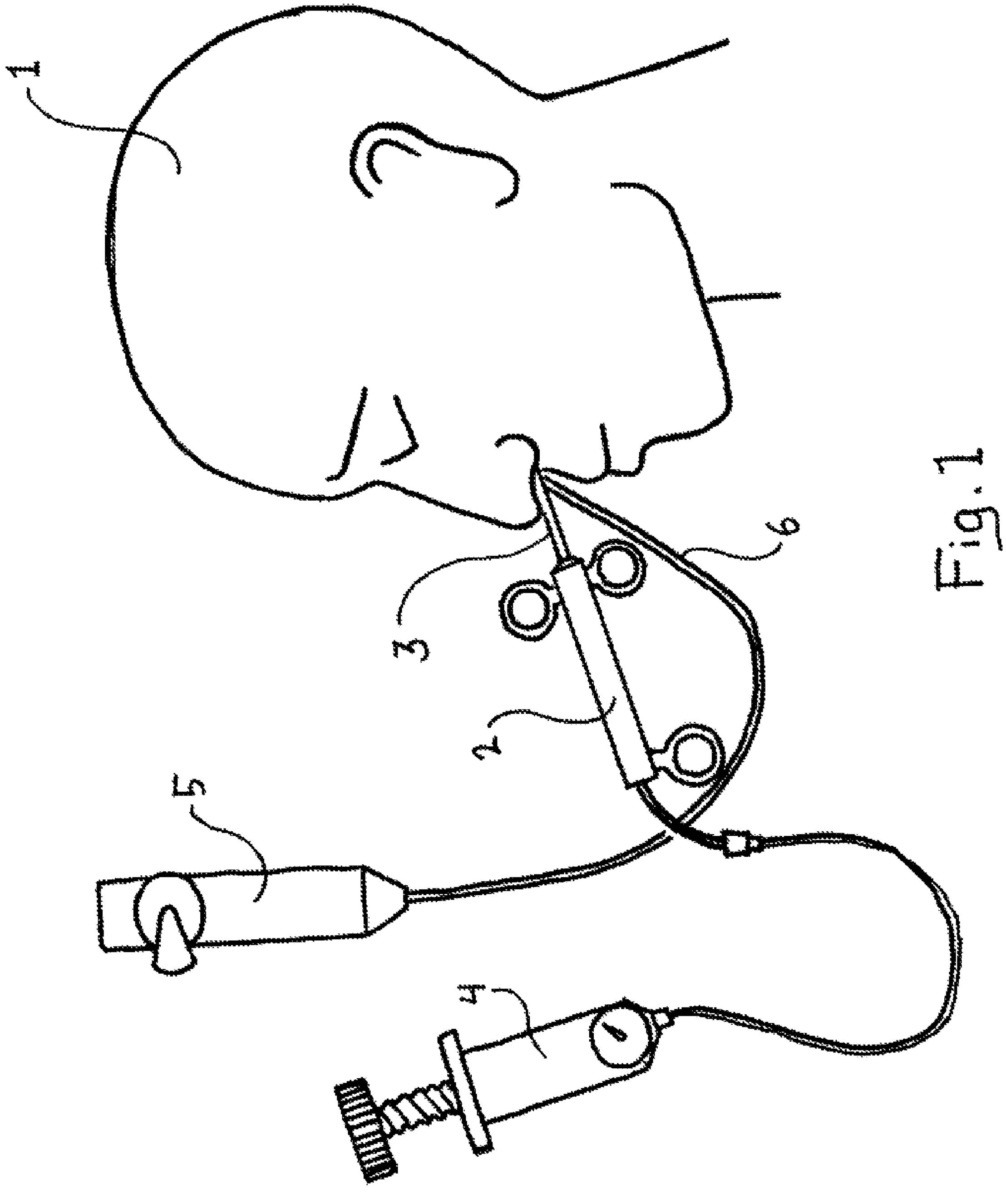
FIG. 1 illustrates a side view of a human patient's head and shows prior art instruments for dilation of the Eustachian tube inserted into the nose.

FIG. 1 illustrates a side view of a human patient's head 1 and shows prior art instruments for dilation of the Eustachian tube inserted into the nose. A typical insertion instrument 2 with a balloon catheter guiding tube 3 holding the balloon catheter inside. The proximal part of the balloon catheter comes out from the proximal part of the insertion instrument 2 and is connectable to the pressurization device 4 via a flexible tube. A flexible endoscope 5 is depicted having a flexible distal part 6 that is inserted into the same nostril. With depicted instruments, three people would be needed to perform the procedure. The physician (operator) would operate the insertion instrument 2 and would advance the balloon into the Eustachian tube using a slider on the insertion instrument. A first clinician (operator) would use two hands to hold and operate the pressurization device 4. A second clinician (operator) would hold and operate the flexible endoscope 5, having one hand on the proximal portion of the endoscope to control the movable tip of the scope and having the other hand supporting the flexible middle part of the endoscope 6 in the proximity of the nostril of the patient.

Figure 2:
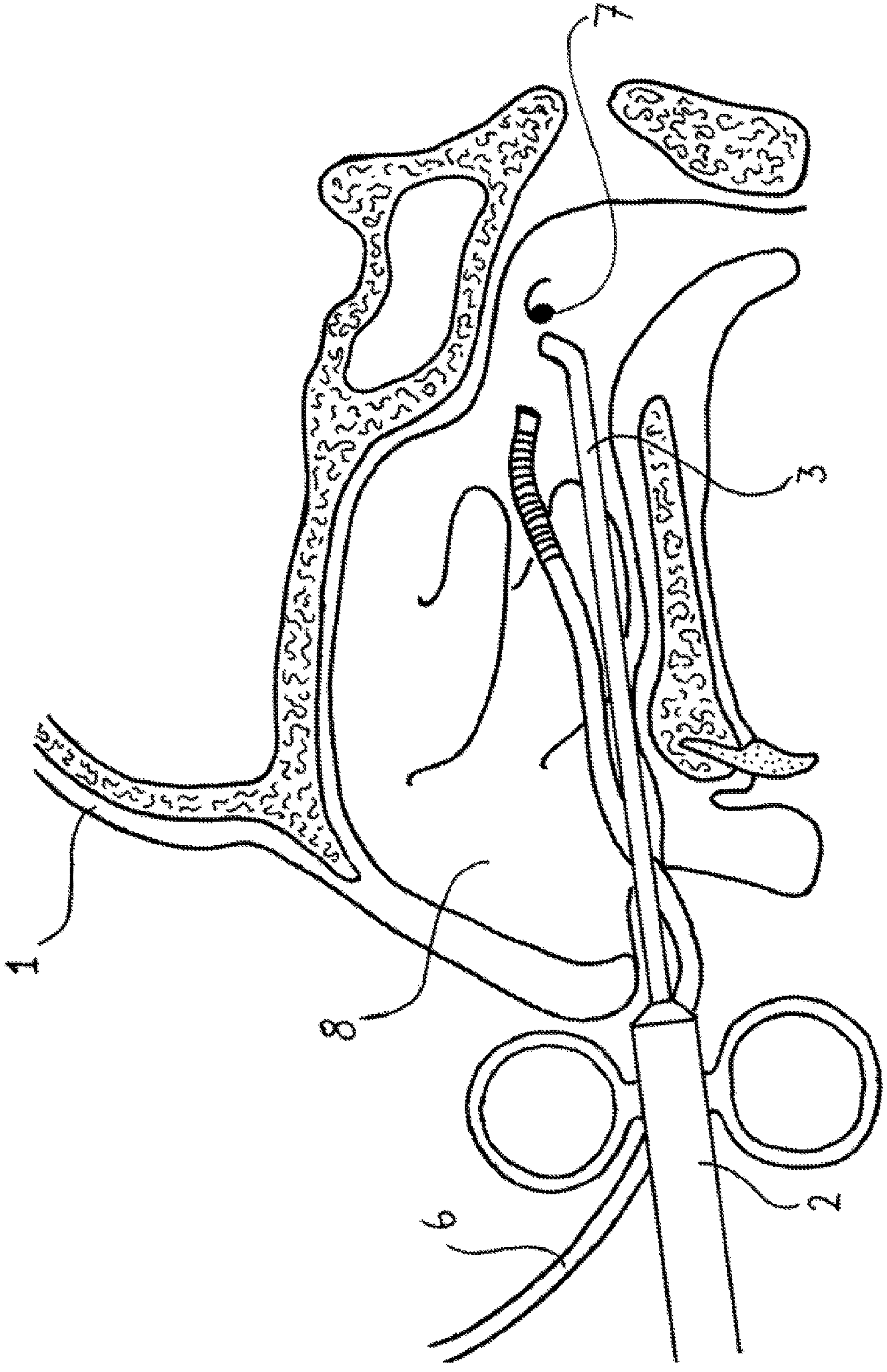
FIG. 2 shows a partial vertical section view through the right-side nasal passageway on a human head and depicts typical prior art instruments.

FIG. 2 shows a partial vertical sectional view through the right-side nasal passageway 8 on a human head 1 and depicts typical prior art instruments. In this section view, it can be seen how the guiding tube 3 of the insertion instrument 2 must be placed deep inside the nasal passageway 8 to reach the opening of the eustachian tube 7. A flexible endoscope 6 is depicted, and it is apparent that the tip of any endoscope must be adjacent to the tip of the guiding tube 3 to visually confirm the position of the guiding tube tip in front of the Eustachian opening 7 prior to insertion of the balloon.

Figure 3:
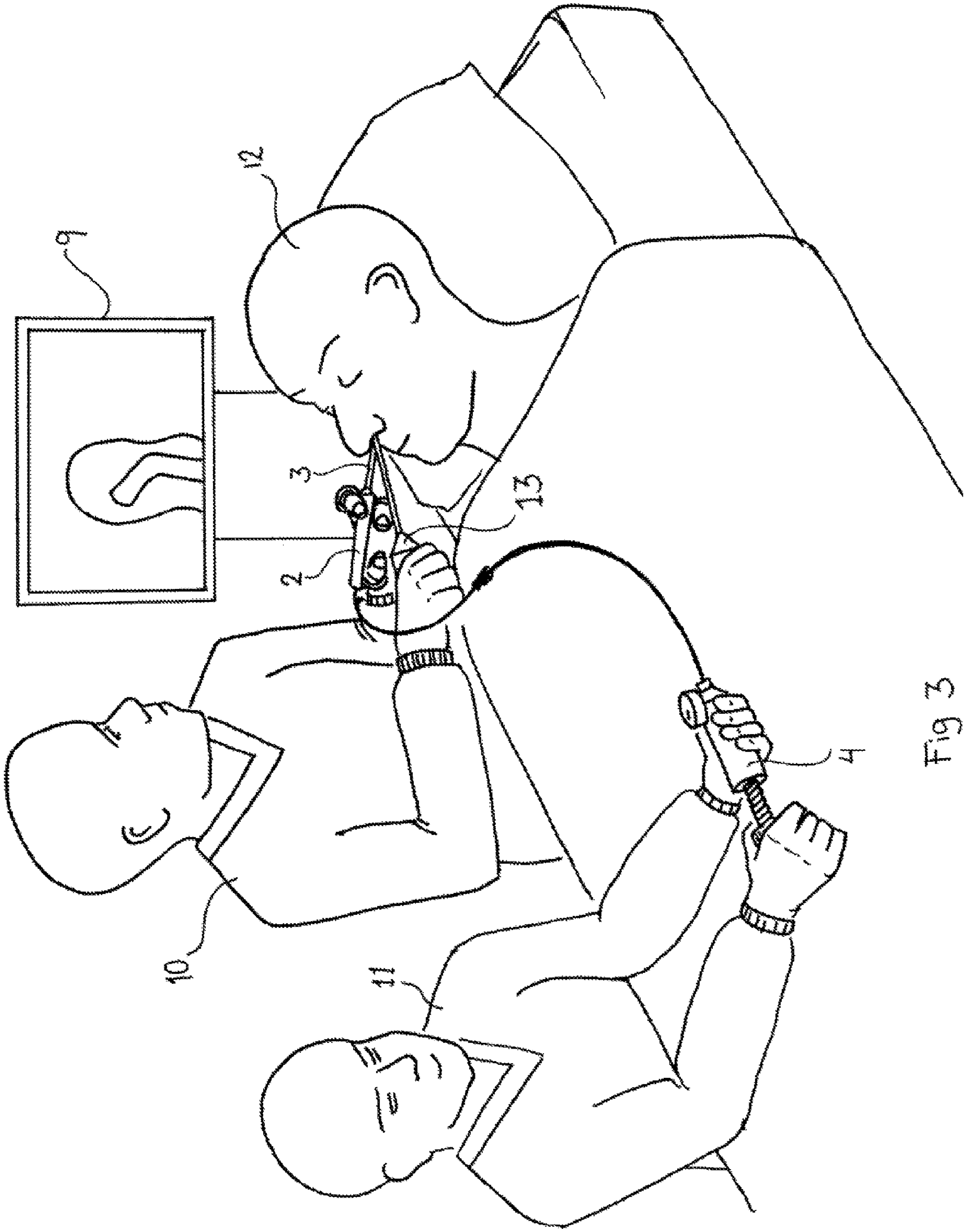
FIG. 3 shows the procedure performed on a fully sedated patient using prior art instruments including a stiff digital endoscope connected to a digital monitor.

FIG. 3 shows the procedure performed on a fully sedated patient 12 using a stiff (rigid) digital endoscope 13 connected to a digital monitor 7 for convenient visualization of the inside of the nose. A trained physician 10 can operate the stiff endoscope 13 with one hand while operating a typical prior art insertion instrument 2 with the other hand. A clinician (operator) 11 will operate a typical prior art pressurization device 4 using both hands. Operating both the insertion instrument 2 and the stiff endoscope 13 may be possible for the trained physician 10, but it will lead to higher discomfort for the patient and will require either full sedation or locally needle-injected anesthesia.

Figure 4:
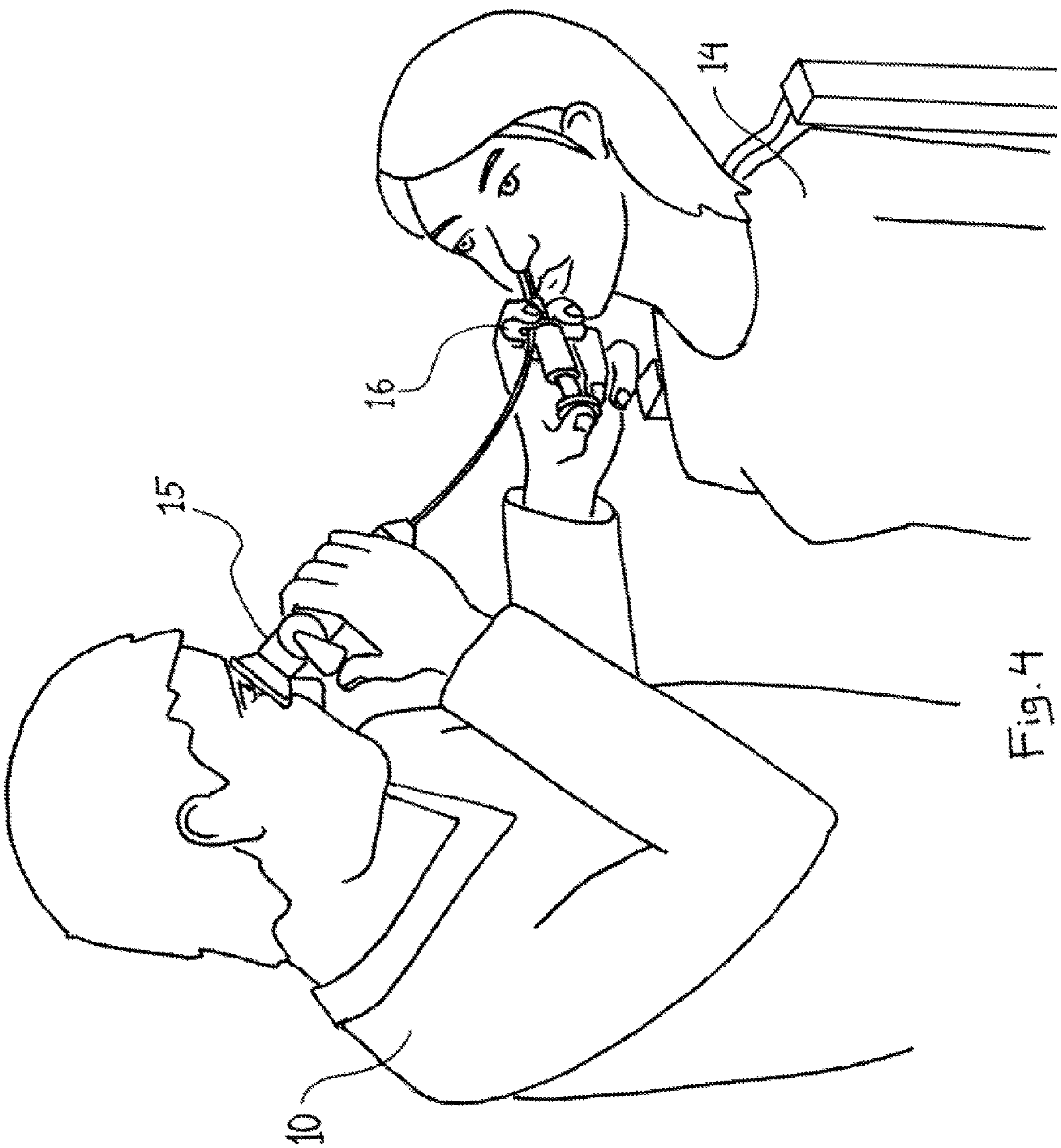
FIG. 4 shows the procedure performed with one configuration of the first embodiment by only one physician on a fully awake patient using an analogue flexible endoscope.

FIG. 4 shows the procedure performed with a handheld insertion device 16 according to an embodiment by only one physician (operator) 10 on a fully awake patient 14 using an analogue flexible endoscope 15. The physician 10 holds the device 16 with the first hand, the first hand also supporting the flexible portion of the analogue endoscope 15. The physician 10 holds the proximal portion of the flexible analogue endoscope 15 with the second hand. The physician 10 may hold the device 16 in the same finger-grip position during insertion into the nose, during advancing of the balloon and during inflation, pressurization, and deflation of the balloon, and finally during retraction out of the nose, and as such throughout the entire procedure. Controlling the tip of the guiding tube on the device 16 and the tip of the analogue flexible endoscope 15 using the same hand and with no changes in finger-grip position, will allow very little movement of the instruments inside the nose and will thereby cause very little discomfort for the patient 14 leading to an increased probability that patients will tolerate the procedure using only cotton pledgets soaked in local anesthetics and decongestants.

Figures 5A, 5B, 5C:
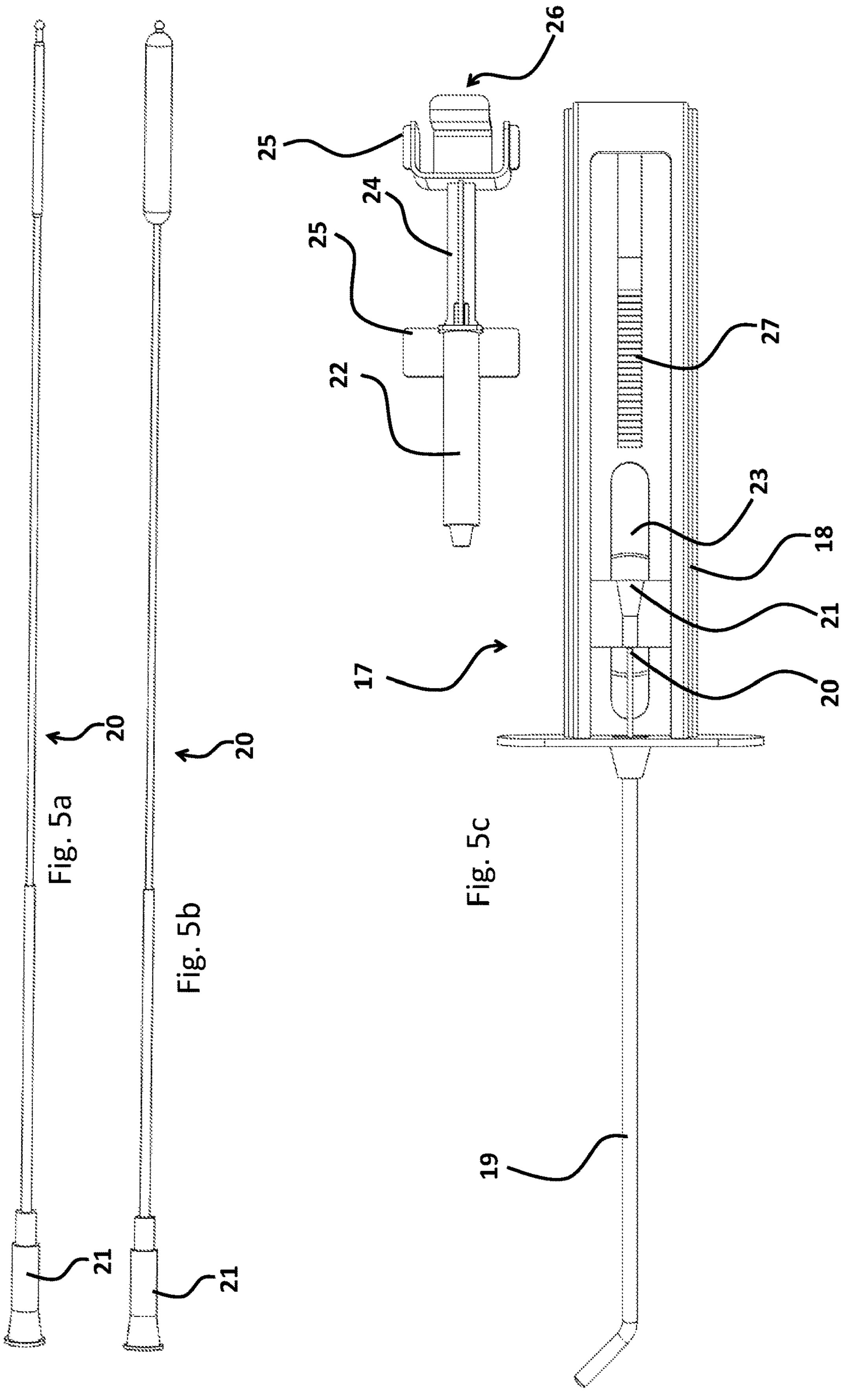
FIG. 5A is a side view of a balloon catheter with its proximal part comprising a fluid connection port, and its middle part comprising a catheter shaft and distal inflatable part comprising the balloon, with the inflatable part not being inflated.
FIG. 5B is a side view of a balloon catheter with its proximal part comprising a fluid connection port, and its middle part comprising a catheter shaft and distal inflatable part comprising the balloon, with the inflatable part being inflated.
FIG. 5C is a side view of a first embodiment of a handheld insertion device for balloon dilation in which a syringe assembly is not yet inserted into the device.

FIGS. 5*a* and 5*b* show an example of a balloon catheter 20 having a proximal fluid connection port 21 for connection with an inflation device, a medial catheter shaft, and a distal inflatable balloon. FIG. 5*a* shows the balloon in an uninflated state. FIG. 5*b* shows the balloon in an inflated state. The catheter shaft is a tubular element with a lumen that connects to the interior of the inflatable part. The proximal connector portion is configured for connection to an inflation and pressurization device. The inflatable part is configured to be inflated to a substantially cylindrical balloon with a predetermined diameter in the inflated state.

For balloon dilation of the Eustachian tube or Sinus passageways the inflated balloon size may be approximately 3-7 mm in diameter and 15-30 mm in length. Balloon catheters 20 may comprise a lumen for a guidewire. Any balloon catheter 20 in the following embodiments may be configured to include a guidewire lumen, a guidewire port and guidewire. The variants of available balloon catheters 20 with and without guidewire are well known to anyone in this field.

FIGS. 5*c*, 6A-C, 7A-B, and 8A-B show a first embodiment of the handheld insertion device 17 in which the pressurization device is integrated, thereby allowing a single physician to perform the procedure in combination with a digital static (rigid) endoscope. The physician (operator) will hold the static digital endoscope using one hand and hold the device 17 with the other hand. After preparation of the device, the physician will be able to hold the device 17 with one hand and with one finger grip position throughout instrument insertion, balloon advancement and balloon inflation and pressurization.

The device 17 comprises a device body 18 firmly attached to the balloon catheter guiding tube 19, the assembly may be single-use or multiuse and autoclavable. A balloon catheter 20 is preloaded into the device 17 in a first position. The balloon catheter 20 has a proximal connection part 21 with guiding means for linear guidance relative to the device body 18 and with a connection interface for sealing fluid connection to the syringe barrel 22. The connection part 21 has installed a manometer gauge 23. The connection part 21 facilitates fluidic connection between the balloon catheter 20, the syringe barrel 22, and the manometer gauge 23. The device including a modified syringe barrel 22 with a modified plunger rod 24 each having guiding means 25 to allow insertion into and linear guidance relative to the device body 18. In this embodiment, the guide means 25 comprise lateral fins extending from the syringe body, the tip of the fins being received in axially extending grooves in opposite internal side surfaces of the device body 18. Alternatively, the guiding means 25 may comprise transversely extending fins that are guided by the inner surface of the device body (not shown). The guiding means 25 can also be formed by a guide rail extending axially inside the device body engaging a groove in the outer surface of the syringe barrel or a groove in a part protruding from the syringe barrel, the protruding portion of syringe barrel may also be provided with an eyelet through which the guide rail extends (not shown). The device body 18 has a thumb/finger engagement interface formed by a recess or cavity 26 on one side through which an operator can monitor the plunger rod and syringe barrel positions and through which the thumb of an operator can access the thumb/finger interface part 26 of the plunger rod 24. The plunger rod 24 has one or more barbs configured to interlock with a linear ratchet counterpart 27 in the device body 18.

Figure 6A:
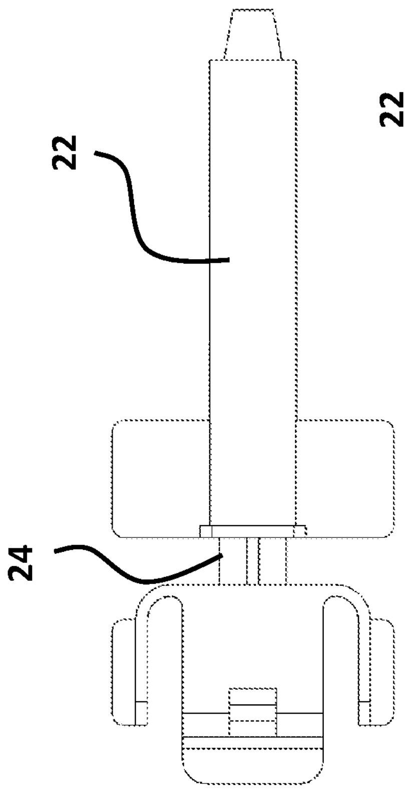
FIG. 6A shows the syringe assembly of FIG. 5C in a first preparation step wherein the plunger rod is in the bottom position.
Figure 6B:
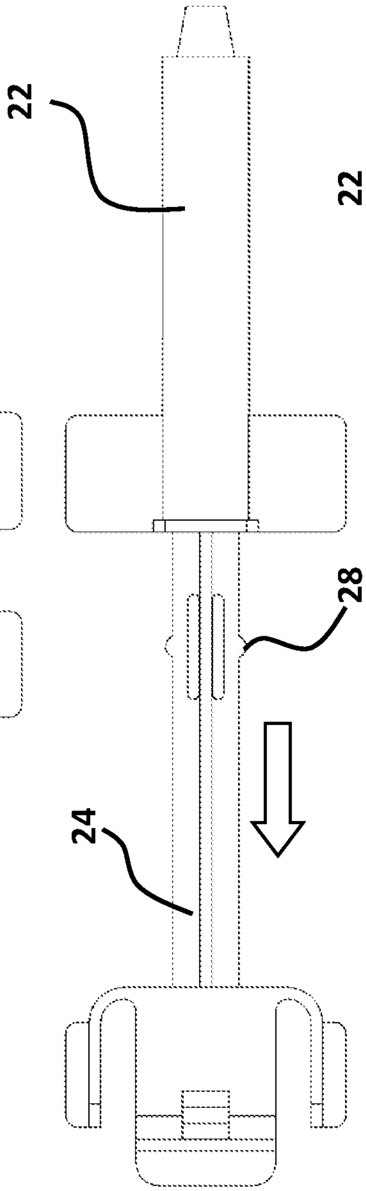
FIG. 6B shows the syringe assembly of FIG. 5C in a second preparation step wherein the plunger rod is in the top position after the operator has fully retracted the plunger rod thereby filling the syringe with a fluid such as water.
Figure 6C:
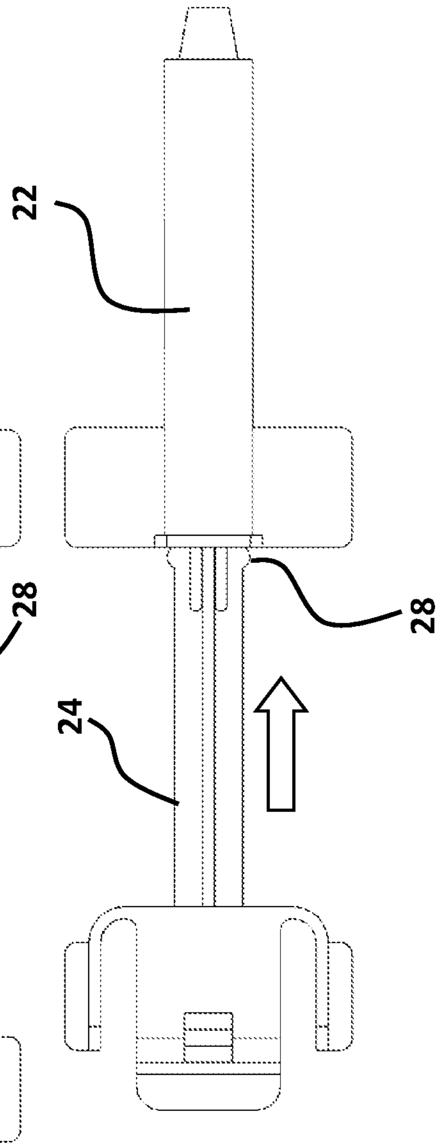
FIG. 6C shows the syringe assembly of FIG. 5C in a third preparation step wherein the plunger rod is in a final position after evacuation of air from the syringe barrel.

FIGS. 6A, 6B, and 6C show the syringe assembly with a syringe barrel 24 and plunger rod 22 in three different stages for preparation before insertion into the device body 18. FIG. 6A shows the initial first stage wherein the plunger rod 24 is in the bottom (fully inserted) position. FIG. 6B shows the plunger rod 24 in the top (fully retracted) position after the operator has fully retracted the plunger rod 24 thereby filling the syringe barrel 22 with a fluid such as water from a separate container. FIG. 6C shows a final position after evacuation of air from the syringe barrel 22. This final position of the plunger rod 24 relative to the syringe barrel 22 is felt by the operator as tactile feedback given by a sudden increase in resistance when pressing the plunger rod 24. There are bumps (protrusions) 28 on the plunger rod 24 in a certain position that protrudes beyond the inner diameter of the syringe barrel 22. Increased force on the plunger rod 24 will be needed to deform these bumps 28 such that the plunger rod 24 can be pressed further into the syringe barrel 22. These bumps 28 will hereby partly notify the operator of completed air evacuation and correct plunger rod positioning during preparation and will secondly act as a precaution to ensure that balloon advancement is performed prior to liquid evacuation and balloon inflation when a force is applied on the plunger rod 24, as the force required to advance the balloon is much lower than the force needed to move the plunger rod 24 further into the syringe barrel 22.

Figure 7A:
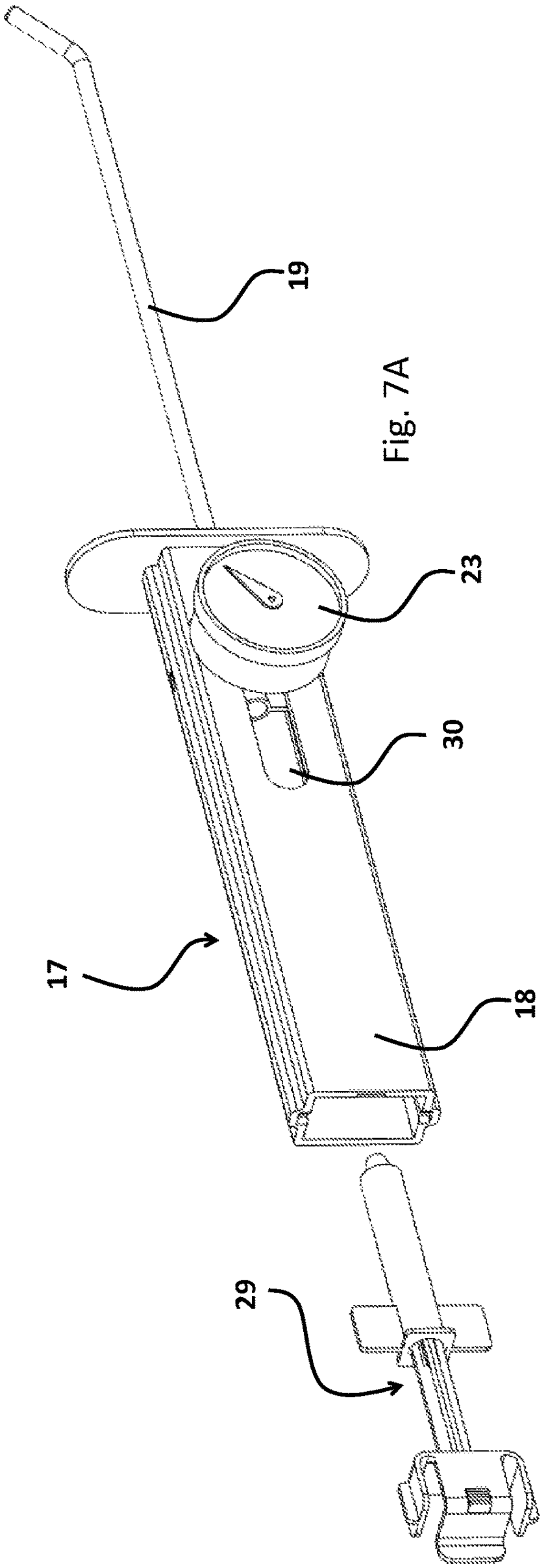
FIG. 7A shows a perspective view of the first embodiment of the handheld insertion device for balloon dilation of FIG. 5C in a fourth step where the prepared syringe assembly is ready to be loaded into the device body.

FIG. 7A shows a perspective view of device 17 where the prepared syringe assembly 29 is ready to be loaded into the device body 18. On one side of the device 17, a slot 30 in the device body 18 allows the manometer 23 to move forward and further allows the operator to monitor movement of the syringe assembly 29.

Figure 7B:
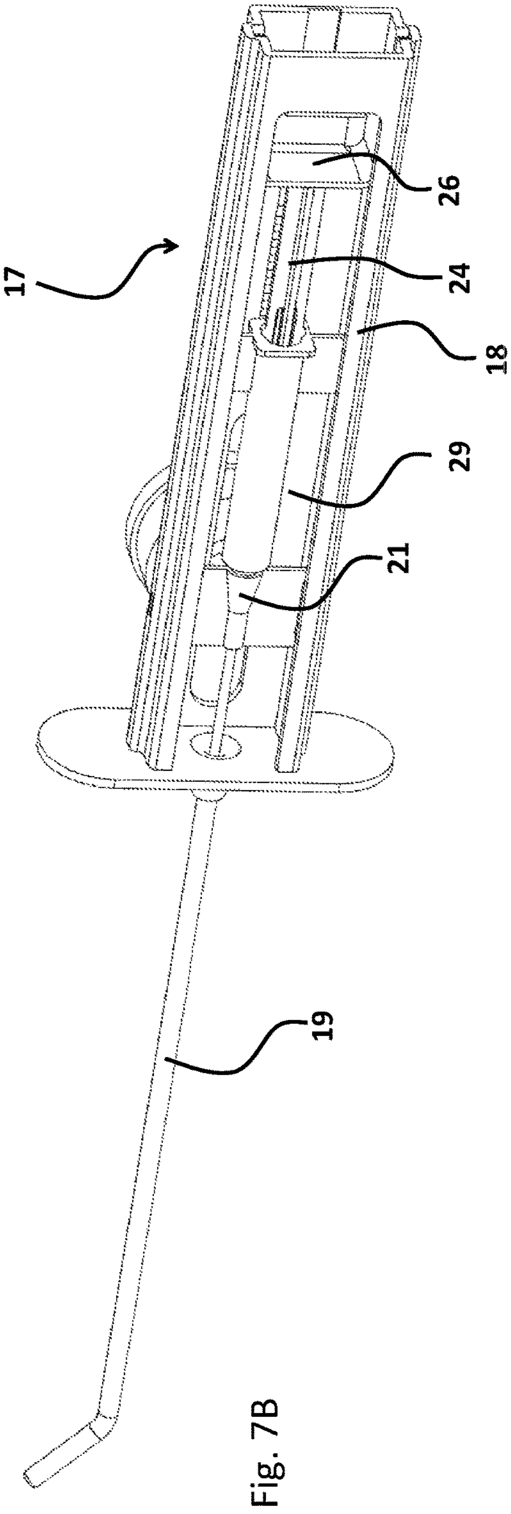
FIG. 7B is a perspective view of the handheld insertion device for balloon dilation of FIG. 5C in the primary configuration of the first embodiment in a fifth step, wherein the syringe assembly has been fully inserted into the device body and is connected to the balloon catheter proximal connection part.

FIG. 7B shows a perspective view of this embodiment of the device 17 where the syringe assembly 27 has been fully inserted into the device body 18 and is connected to the balloon catheter proximal connection part 21. The thumb/finger engagement interface 26 on the plunger rod 22 allows for push and pull using the thumb such that the balloon can be moved in and out when attempting to enter the Eustachian tube or other passageways to be dilated.

Figure 8A:
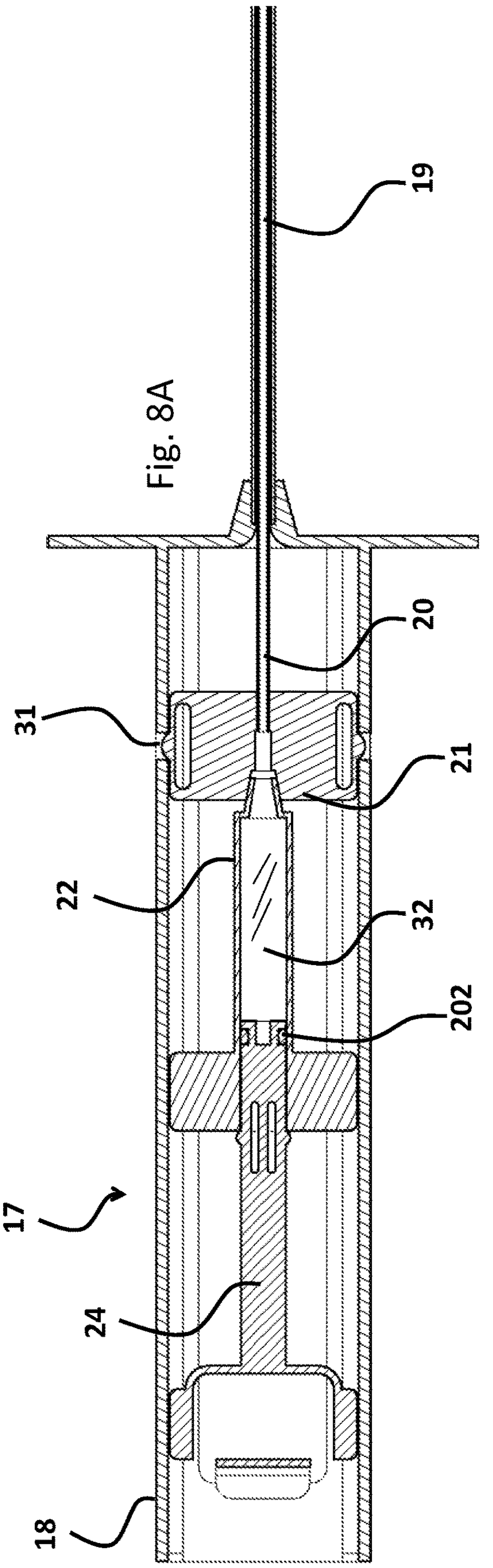
FIG. 8A is a sectional view of the handheld insertion device for balloon dilation of FIG. 5C in the primary configuration of the first embodiment in a sixth step, wherein the syringe-plunger assembly has been fully inserted into the device body and is connected to the balloon catheter proximal connection part.

FIG. 8A shows a section view of this embodiment of the device 17 in a first position where the device 17 is loaded and ready. The syringe barrel 24 with the plunger rod 22 is fully inserted into the device body 18 and has connected with the connection part 21 of the balloon catheter 20. The connection part 21 may have protruding bumps 31 interlocking with holes in the device body 18 to serve as tactile feedback indicating the correct start position of the assembly and to introduce a first force that needs to be overcome to initiate advancement of the balloon catheter 20. The force required to advance the balloon is to be significantly lower than the force needed to move the plunger rod 22 and thereby the movable sealing element 202 relative to the syringe barrel 24 for evacuation of fluid 32 from inside the syringe barrel 24 out and into the balloon catheter 20, hereby ensuring that the advancement of the balloon catheter 20 will happen prior to inflation of the balloon.

Figure 8B:
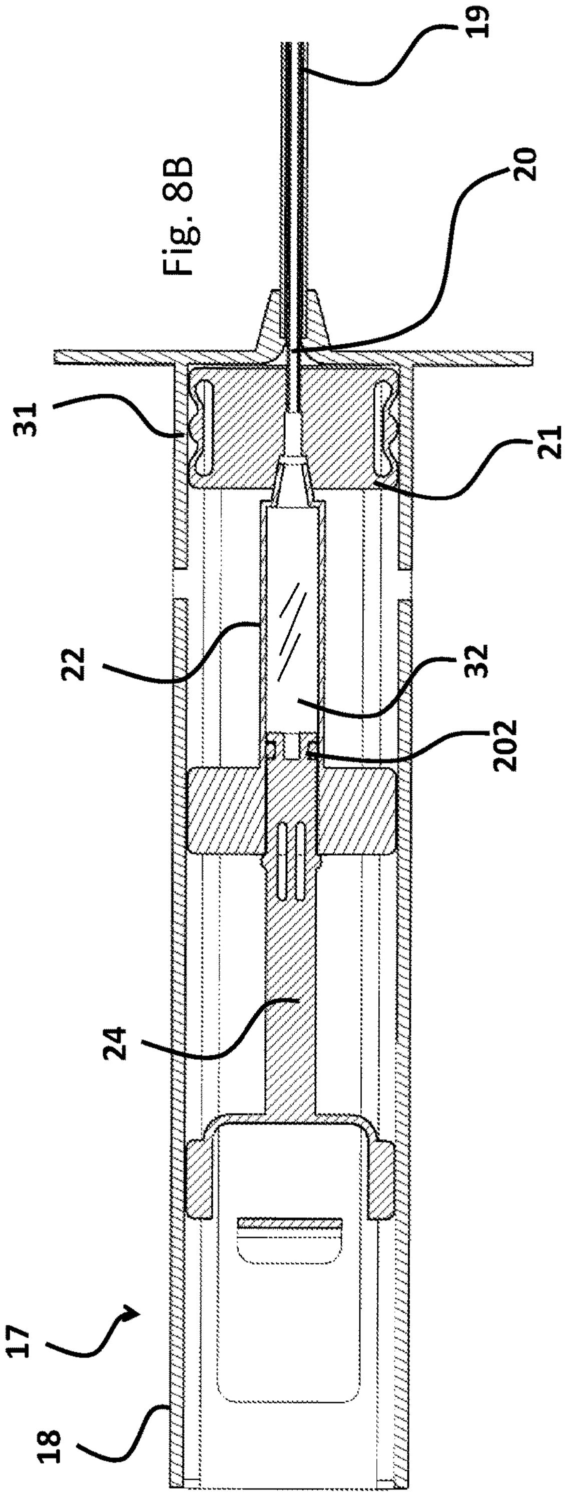
FIG. 8B is a sectional view of the handheld insertion device for balloon dilation of FIG. 5C in the secondary configuration in a seventh step, wherein the balloon catheter, the syringe barrel and the plunger rod have all been moved forward for full advancement of the balloon out of the guiding tube.

FIG. 8B shows a section view of this embodiment of the device 17 in a second position wherein the balloon catheter 20 with the connection part 21, the syringe barrel 24, and the plunger rod 22 have all been moved forward to a second position relative to the device body 18 for full advancement of the inflatable distal part of the balloon catheter 20 out of the guiding tube 19. It can be seen, that protruding bumps 31 of the connection part 21 have been deformed to allow movement relative to the device body 18, and the bumps 28 on plunger rod 24 have not yet deformed thereby keeping the plunger rod 24 and the movable sealing element 202 in an unchanged position relative to the syringe barrel 22. The balloon catheter 20 and the syringe assembly may be moved back and forward between fully retracted and fully advanced positions without any relative movement between the plunger rod 22 and the syringe barrel 24 and without having the plunger rod 22 interlocking with the ratchet locking features of the device body 18. As such, the operator can push and pull with their thumb on the plunger rod thumb/finger engagement interface 26 to push and pull the balloon catheter 20 in and out from the tip of the guiding tube 19 in attempting to insert it into the Eustachian tube or other passageways to be dilated.

Figure 9B:
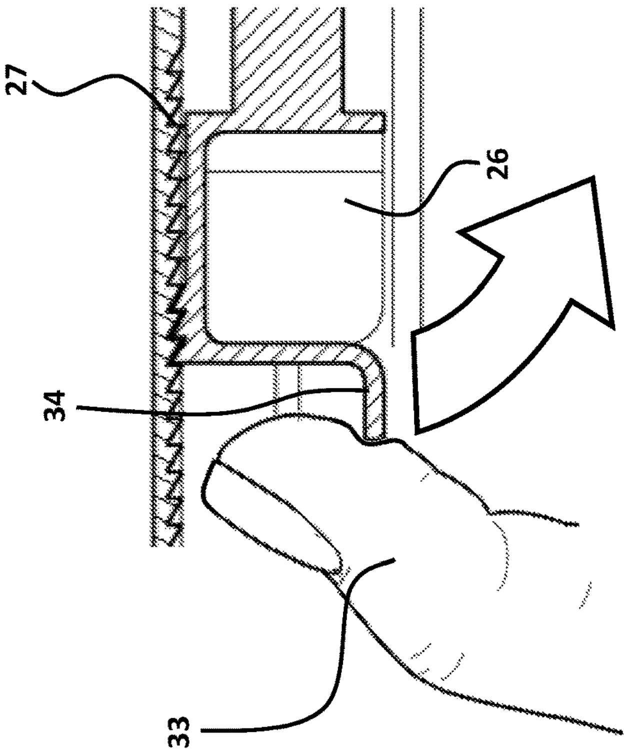
FIG. 9B is a close-up detailed sectional view of the linear ratchet lock between the plunger rod and the device body of the handheld insertion device for balloon dilation of FIG. 5C.
Figure 9A:
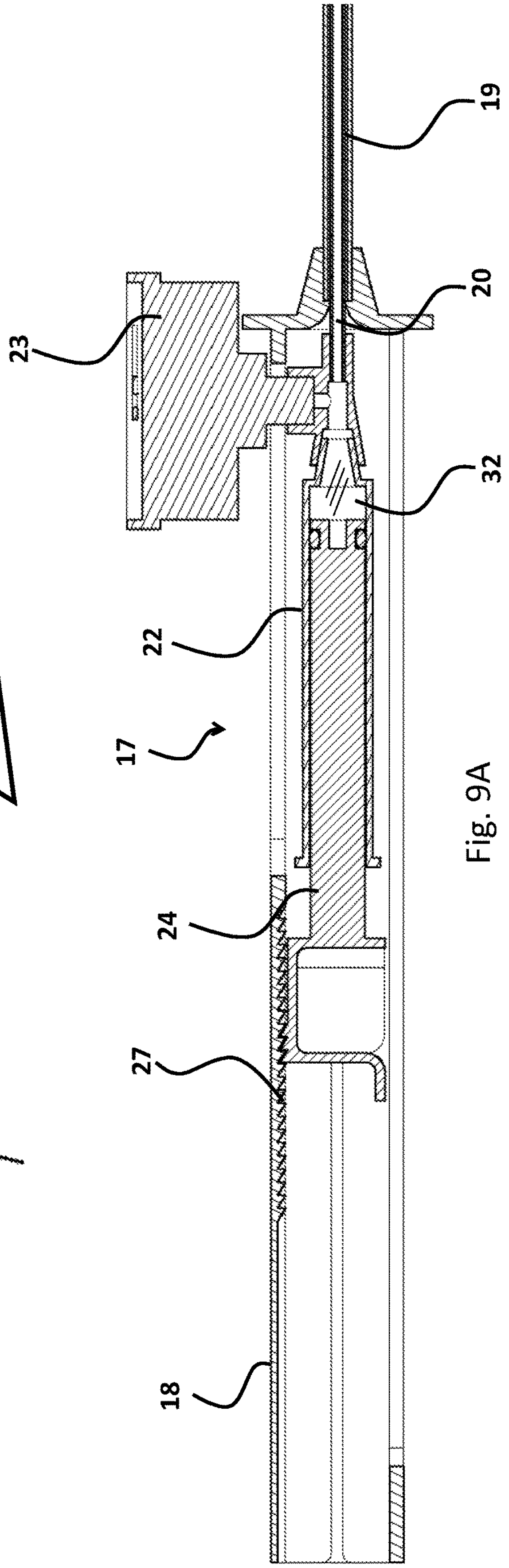
FIG. 9A is another sectional view of the handheld insertion device for balloon dilation of FIG. 5C in the tertiary configuration in an eighth step wherein the balloon is advanced and where the plunger has forced fluid out of the syringe barrel and into the balloon catheter for dilation of the balloon.

FIG. 9A shows another perpendicular sectional view of this embodiment of the device 17 in a third configuration wherein the balloon catheter 20 is advanced and where the plunger rod 22 is moved relative to (into) the syringe barrel 24 thereby evacuating fluid 32 out of the syringe barrel 24 and into the balloon catheter 20 for dilation of the balloon. In this sectional view, the fluid connection between the syringe barrel 24, the balloon catheter 20, and the manometer 23 can be seen. In this sectional view, it is illustrated how the plunger rod 22 and device body 18 are interlocking with a ratchet interface 27 to prevent reversal of the plunger rod 24 relative to the device body 18.

FIG. 9B shows a sectional detailed view of the linear ratchet lock 27 between the plunger rod 22 and the device body 24. For release of the ratchet lock 27, the operator will apply a force with their thumb 33 to the release lever 34 and pull the proximal end of the plunger rod 24 slightly outwards for release of the ratchet lock 27 thereby releasing the pressure in the balloon catheter 20.

Figure 10:
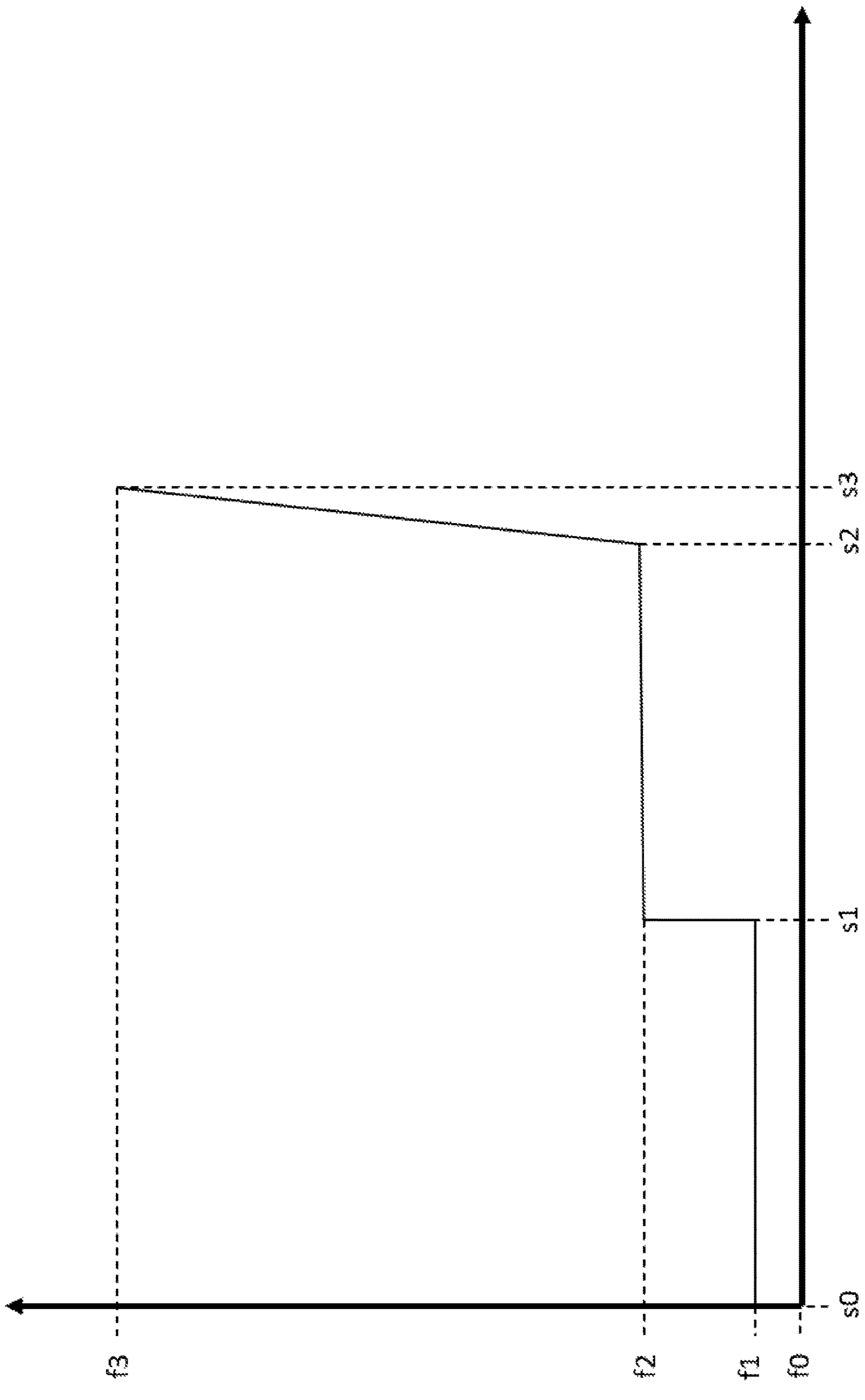
FIG. 10 shows a graph that illustrates the relationship between force (F) and distance (S) for the first embodiment of the handheld insertion device for balloon dilation of FIG. 5C, when the operator squeezes the device for advancement, dilation, and pressurization of the balloon.

FIG. 10 shows a graph that illustrates the relationship between force F and distance S when the operator squeezes the device 17 for advancement, dilation, and pressurization of the balloon. The graph illustrates the force and distance relations for the first and second embodiments of the device 17. The operator needs to overcome force f1 to initiate the advancement of the balloon catheter 20. The device 17 may have bumps that need to be deformed or friction between parts. When overcoming force f1, the operator may move the thumb/finger engagement part 26 from s0 to s1 thereby fully advancing the balloon. The operator will feel significant resistance when the balloon catheter 20 is fully advanced. The operator may retract the balloon catheter 20 and advance the balloon catheter 20 again several times as long as f2 has not been surpassed. When the operator has fully advanced the balloon catheter 20 and applies further force on the thumb/finger engagement part 26 surpassing force f2, then the plunger rod 24 will move relative to the syringe barrel 22 resulting in liquid being evacuated out from the syringe barrel 22 and into the balloon for inflation. Force f2 may be resulting from deformation of parts and or friction between the plunger rod 24 or the movable sealing element and the syringe barrel 24. Force f2 may be higher initially and drop slightly during movement of the plunger relative to the syringe. The difference between forces f1 and f2 is important because it acts as a precaution to avoid accidental inflation of the balloon while the balloon is still inside the guiding tube 19. Distance s2 of the thumb engagement part will be reached when the balloon is fully inflated. A relatively high force f3 needs to be applied to reach the rated balloon pressure for the dilation procedure. The system is hydraulically very stiff, and only a very small movement from s2 to s3 will be needed to reach the needed force f3. As the system is very stiff, possible ratchet positions (preventing the plunger rod 24 from reversing) will have a big impact on the resulting pressure. Furthermore, any small deformation of device parts or tissue may create sudden pressure loss and readjustment may be needed.

FIG. 11 to FIG. 18 show a second embodiment of the handheld insertion device 35. For this embodiment of the handheld insertion device 35, the procedure may still be performed by only one physician (operator) in combination with a digital static (rigid) endoscope. The physician will operate the device using one hand and will operate the static endoscope using the other hand, while looking at the digital monitor of the static endoscope for navigation.

Figure 11:
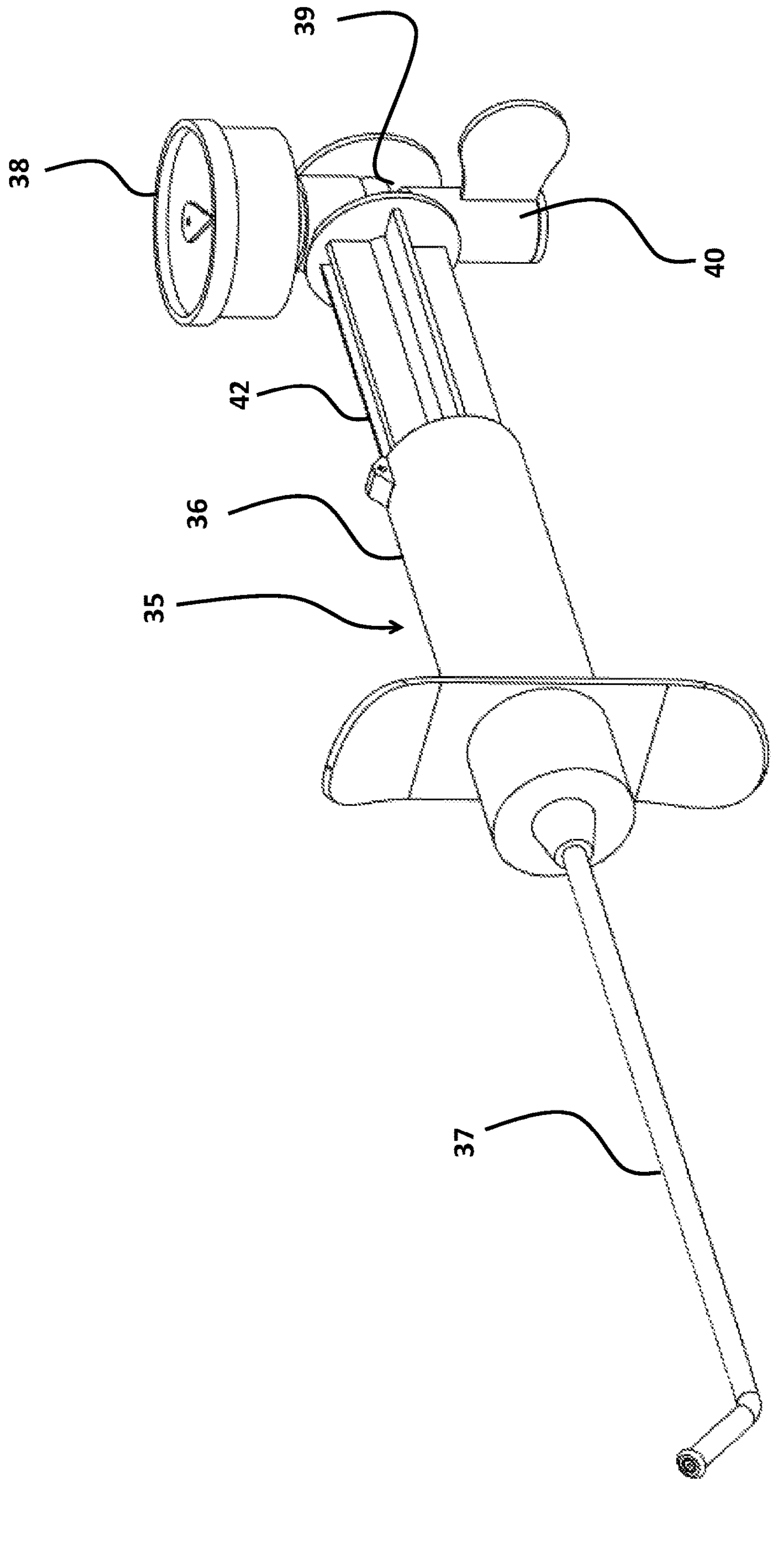
FIG. 11 is a perspective view of a second embodiment of the handheld insertion device for balloon dilation.

FIG. 11 shows a perspective view of this second embodiment of the handheld insertion device 35. In this embodiment, the handheld insertion device 35 comprises a device body 36 firmly connected to a balloon catheter guiding tube 37, an inverted syringe barrel 42 inserted partly and loosely into the device body 36, preferably with means for linear guidance (e.g. radial fins as shown, or other protrusions from the device body 36, the syringe barrel 42 being in fluid connection with a manometer gauge 38, the syringe barrel 42 further having a filling port 39, and a plug 40 that can seal the syringe barrel filling port 39.

Figure 12:
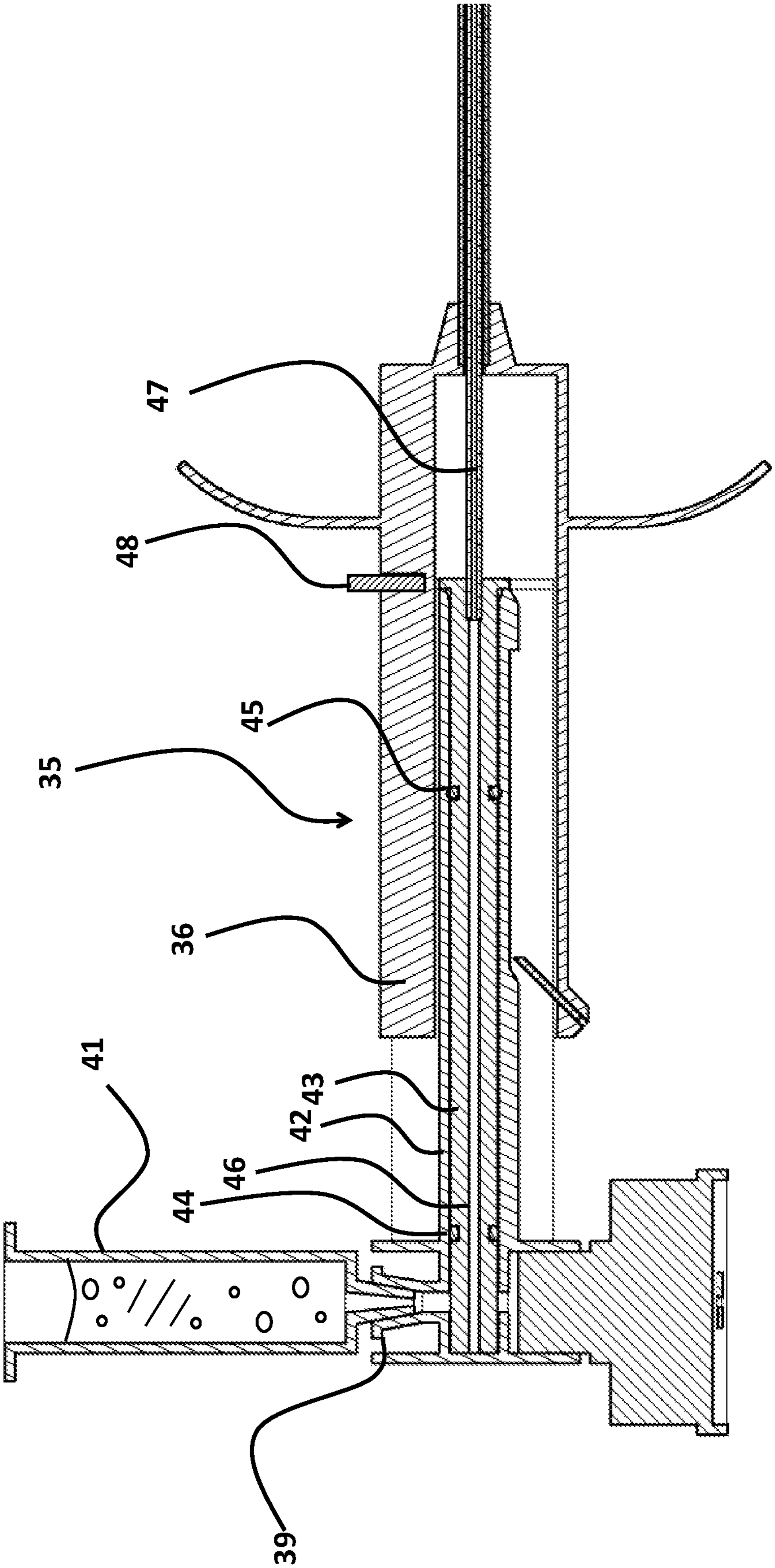
FIG. 12 is a sectional view of the handheld insertion device for balloon dilation of FIG. 11 in a first preparation step where an external waterfilled syringe is connected to the device.

FIG. 12 shows a sectional view of the handheld insertion device 35 in a first preparation step, wherein a waterfilled conventional syringe 41 is connected vertically upwards to the filling port 39 of the syringe barrel 42 of the device 35. The plunger rod 43 with a sealing element 44 and a resistance element 45 has an internal fluid connection lumen 46 and is connected directly to the balloon catheter 47. The plunger 43 is locked to the device body 36 by a locking part 48 and will not move relatively to the device body 36 during any preparation steps. In the first starting position, the plunger 43 is in the bottom position relative to the syringe barrel 42 of the device 35.

Figure 13:
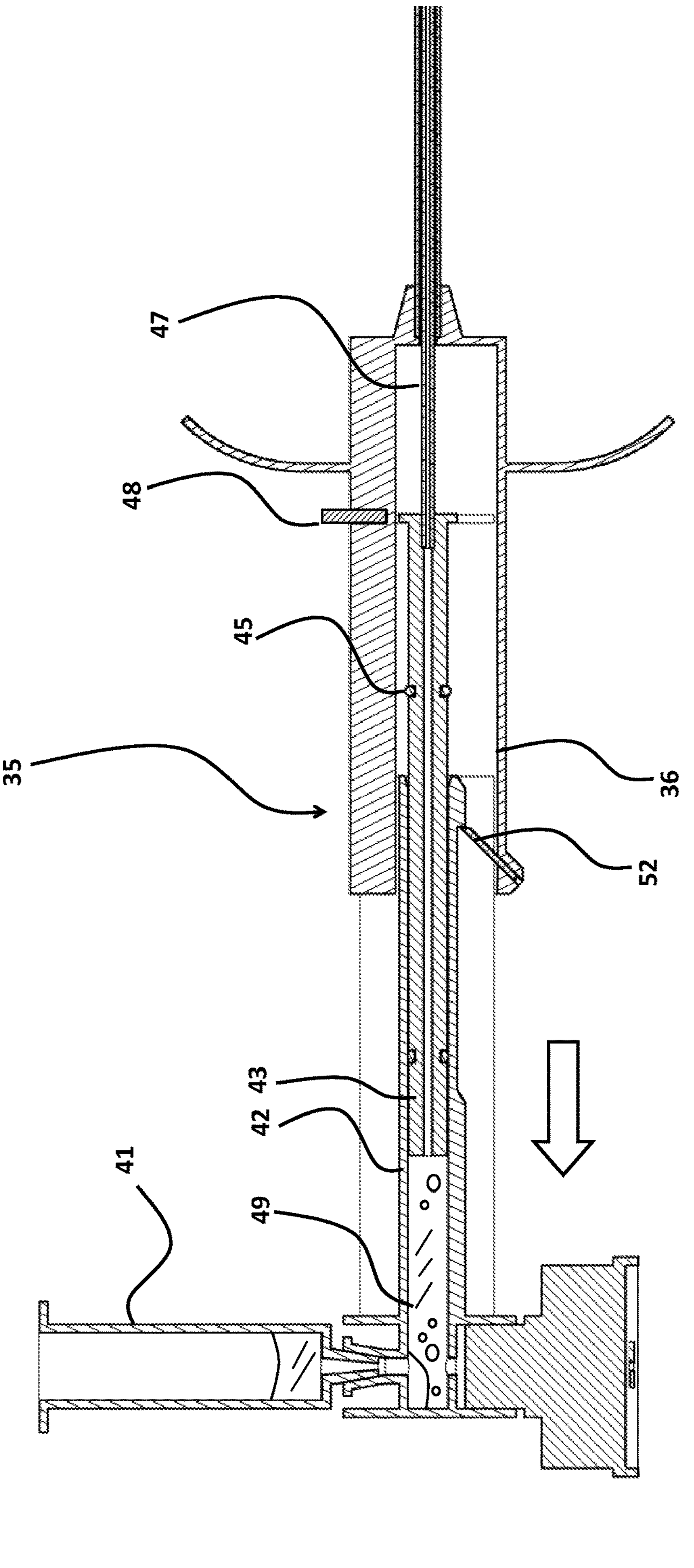
FIG. 13 shows the handheld insertion device for balloon dilation of FIG. 11 in a second preparation step wherein the internal syringe barrel is being filled with liquid.

FIG. 13 shows this second embodiment of the handheld insertion device 35 in a second preparation step, in which a portion of water or any liquid 49 is transferred from the regular syringe 41 to the syringe barrel 42 of the device 35, by pulling back the syringe barrel 42 of the device relative to the plunger rod 43, while the position of the plunger rod 43 relative to the device body 36 is unchanged because of the locking part 48. The movement of the syringe barrel 42 is restricted by the one-way locking part 52.

Figure 14:
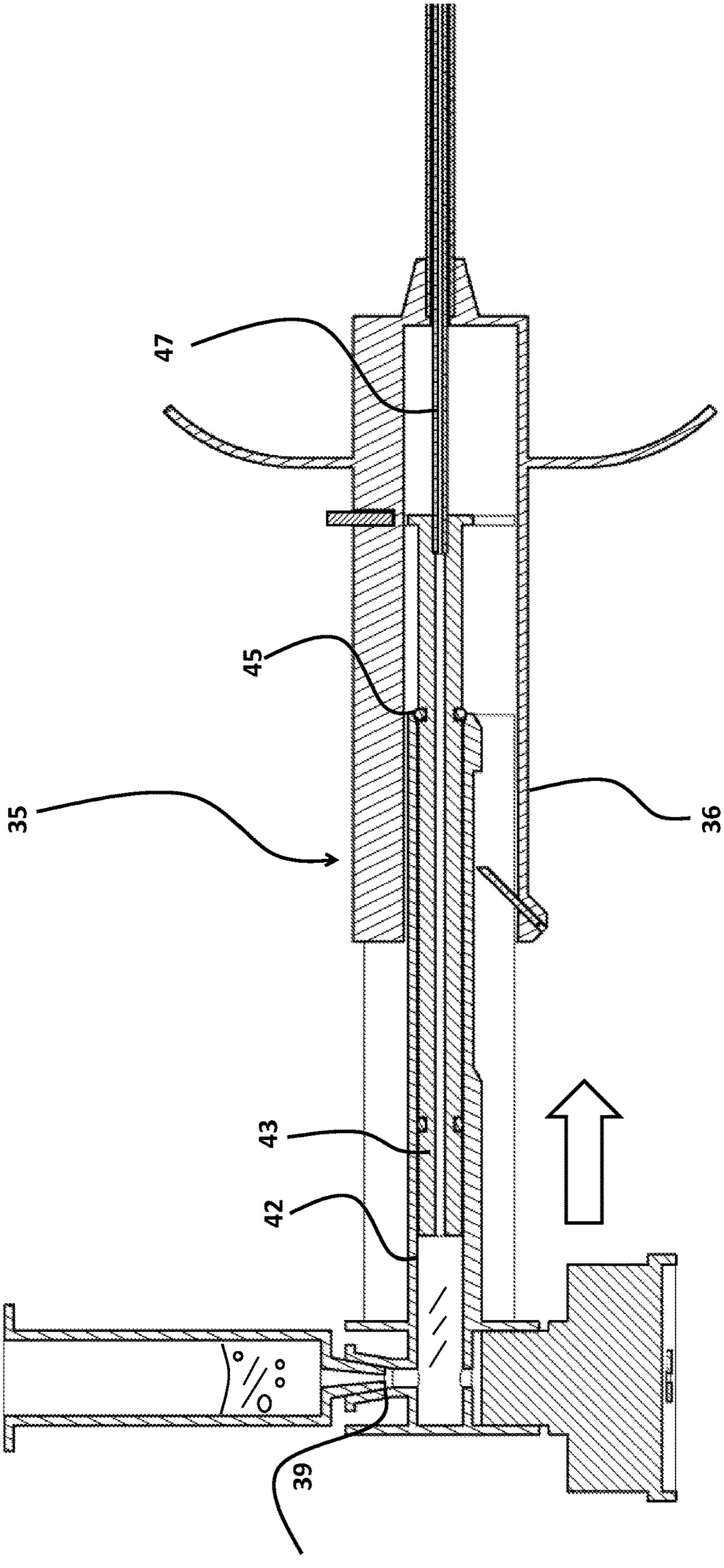
FIG. 14 shows the handheld insertion device for balloon dilation of FIG. 11 in a third preparation step wherein air is evacuated from the internal syringe barrel.

FIG. 14 shows the handheld insertion device 35 in a third preparation step, in which air is evacuated out of the syringe barrel 42 of the device 35 when the syringe barrel 42 is pressed back into the device body 36 until a certain position. Visual and tactile feedback will let the operator know when the syringe barrel 42 of the device 35 has been pressed sufficiently back in position. A resistance element 45 such as an O-ring or a protrusion on the plunger rod 43 is arranged in a position such that the insertion of the resistance element 45 into the syringe barrel 42 of the device 35 will create a sudden increase in resistance exactly when the plunger 43 is positioned correctly relative to the syringe barrel 42 of the handheld insertion device 35. During this stage, liquid will not enter the balloon catheter 47, as the inner orifice of the catheter 47 creates a higher flow resistance for water compared to the orifice of the open filling port 39.

Figure 15:
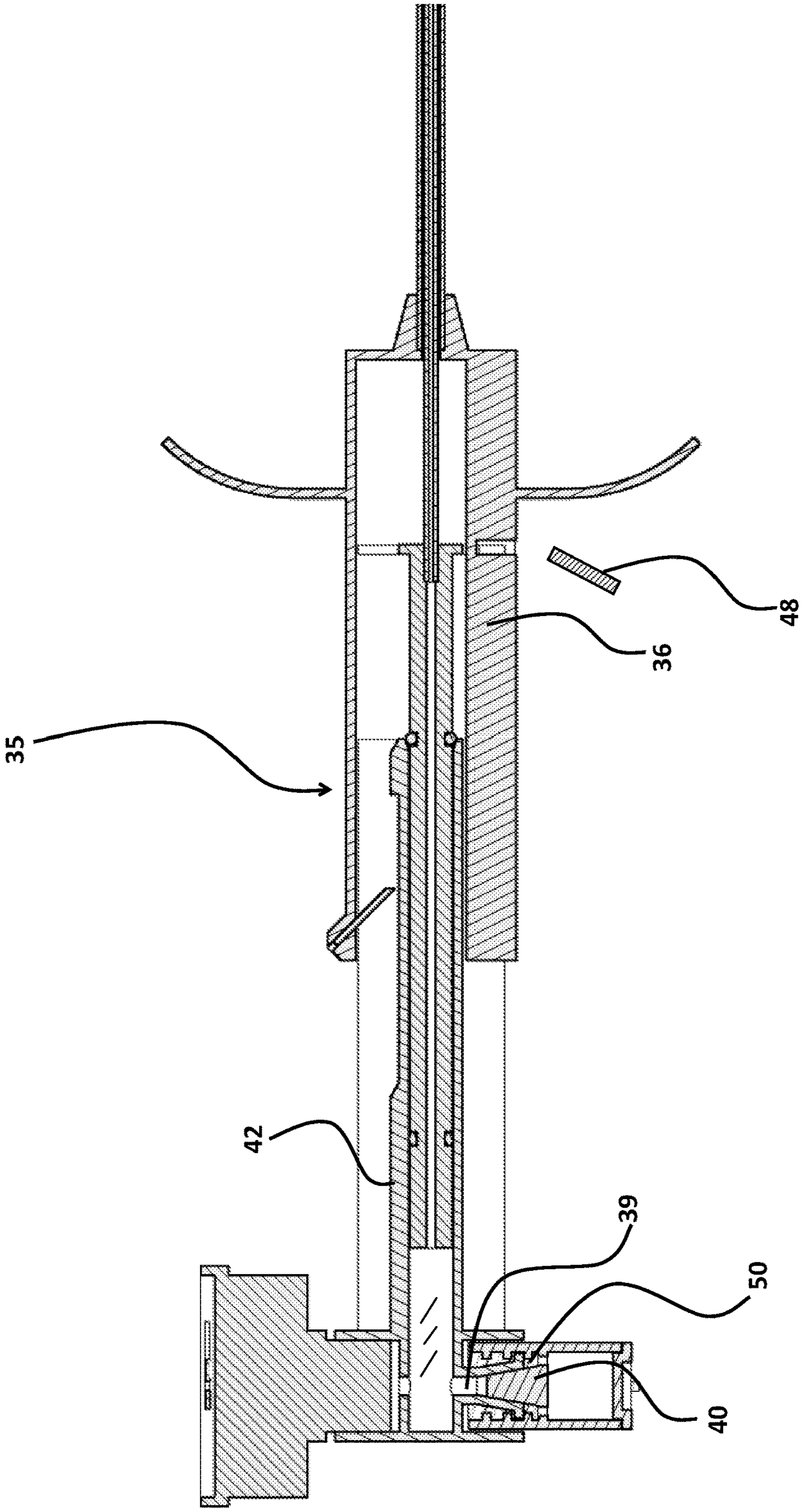
FIG. 15 shows the handheld insertion device for balloon dilation of FIG. 11 in a fourth preparation step where a filling port plug is mounted, and the device is in a primary configuration and ready to use.

FIG. 15 shows the handheld insertion device 35 after the final preparation step with a plug 40 mounted in the syringe barrel filling port 39 and the device 35 being ready for use, i.e. in a primary configuration. The interface between the syringe barrel 42 and the plug 40 may preferably be a threaded Luer-lock connection 50. The locking part 48 between the plunger rod and the device body 36 has been removed to allow movement of the parts.

Figure 16:
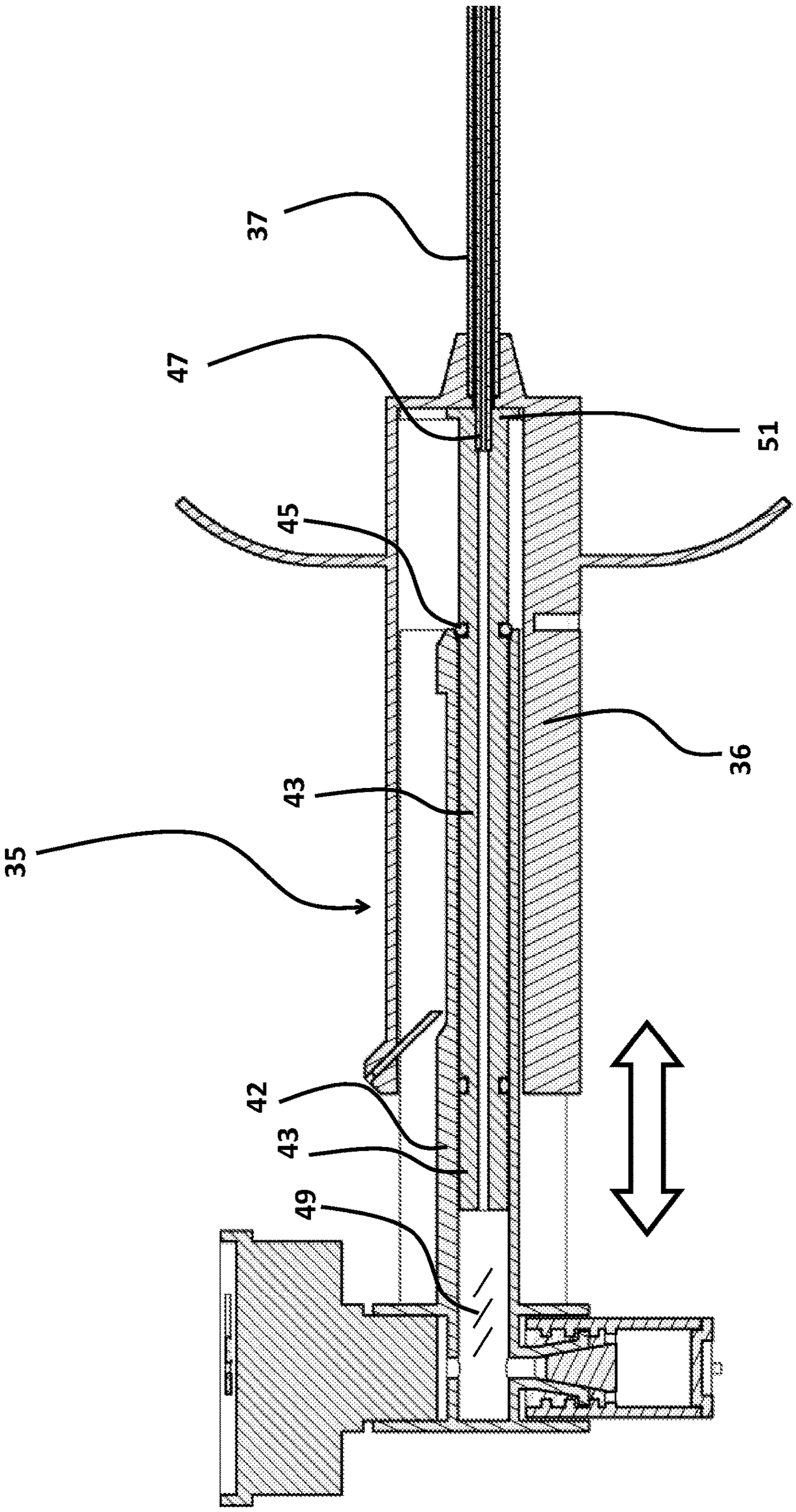
FIG. 16 shows the handheld insertion device for balloon dilation of FIG. 11 in a fifth step and secondary configuration wherein the balloon catheter, plunger rod, and syringe barrel have been pressed forward thereby advancing the balloon out from the tip of the guiding tube.

FIG. 16 shows the handheld insertion device 35 where the balloon catheter 47, the plunger rod 43, and syringe barrel 42 has been pressed forward relative to the device body 36 thereby advancing the balloon catheter 47 forward and out from the tip of the guiding tube 37, i.e. in a secondary configuration. The balloon catheter 47 may be moved back and forward after removing the locking part 48 between the device body 36 and the plunger rod 43 lock interface 51. To improve the grip on the device body 36 and to ease the push and pull finger movement, finger engagement may be configured differently e.g. finger engagement on the device 35 could be a recess or surface for engaging by the thumb and one or two recesses or surfaces for engaging by the front two fingers that hold the device 35. During this step, no liquid 49 will be evacuated from the syringe barrel 42 into the balloon catheter 20 because it requires significantly higher force to press the resistance element 45 on the plunger rod 43 into the syringe barrel 42 compared to the force required to move the balloon catheter 47 in and out of the guiding tube 37. Only when the balloon is fully advanced and the front part of the plunger rod 43 has impact with the bottom of the device body 36 and when the operator keeps adding force to the syringe barrel 42, will the syringe barrel 42 move beyond the resistance element 45 on the plunger rod 43 and liquid 49 will be forced into the balloon catheter 47 for inflation of the advanced balloon at the distal end of the balloon catheter 47.

Figures 17A, 17B:
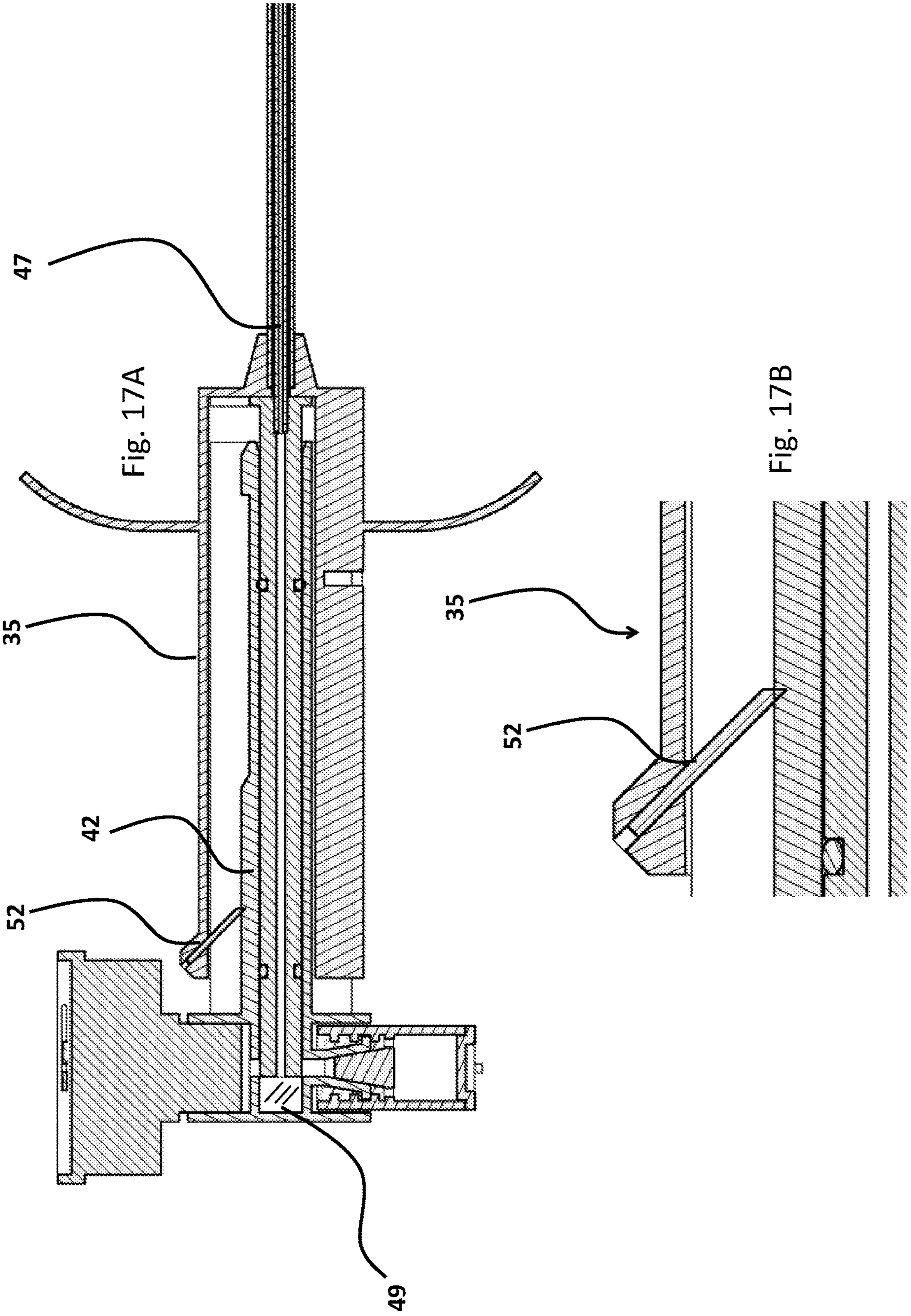
FIG. 17A shows the handheld insertion device for balloon dilation of FIG. 11 in a sixth step and tertiary configuration after evacuating liquid out from the syringe barrel and into the balloon catheter for inflation of the balloon.
FIG. 17B is a close-up detailed sectional view of the locking principle of the second embodiment of the handheld insertion device for balloon dilation of FIG. 11.

FIG. 17A shows the handheld insertion device 35 after evacuating liquid 49 out from the syringe barrel 42 and into the balloon catheter 47 for inflation of the balloon. A sharp element made, e.g. a blade or pin from a hard material such as steel acts as a one-way lock 52 by cutting into the softer material of the syringe barrel 42. Such a lock method may be preferable as it has infinite positions in contrast to any ratchet lock with a finite number of lockable steps.

FIG. 17B shows a close-up detail view of the one-way lock 52 of the second embodiment of the device 35.

Figure 18:
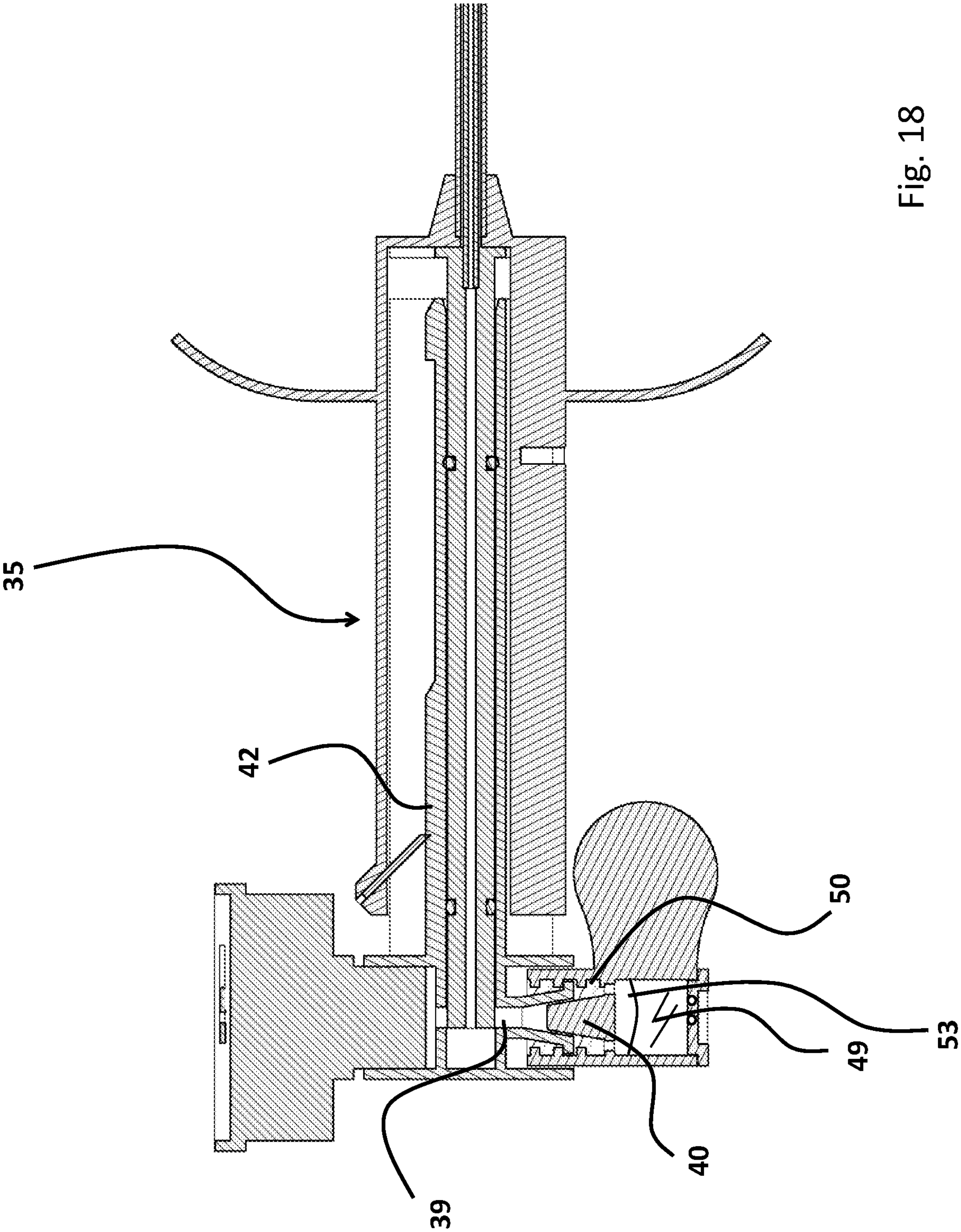
FIG. 18 shows the handheld insertion device for balloon dilation of FIG. 11 in a seventh step where pressure inside the balloon is released by opening of the plug.

FIG. 18 shows the second embodiment of the device 35 and illustrates how pressure inside the balloon catheter 20 is released in an alternative way, by partly opening a plug 40 that seals the filling port 39 of the syringe barrel 42. In this embodiment, the thumb of the operator is moved slightly to press the lever of the plug 40 forcing it to rotate e.g. 90 degrees thereby opening the plug thread 50 and releasing the pressure inside the syringe barrel 42. When releasing the pressure, a small liquid volume 49 needs to be evacuated out through the filling port 39, and to avoid spillage, the plug is configured to have a liquid collection reservoir 53. This method of releasing pressure may lead to less discomfort for the patient as there is no release of a mechanical preloaded element as for the release of e.g. a ratchet lock. Release of a loaded mechanical lock is likely to create a sudden noise and sudden movement of parts of the device and this can be unfortunate for a device that is placed partly into the patient's nose.

Figure 19:
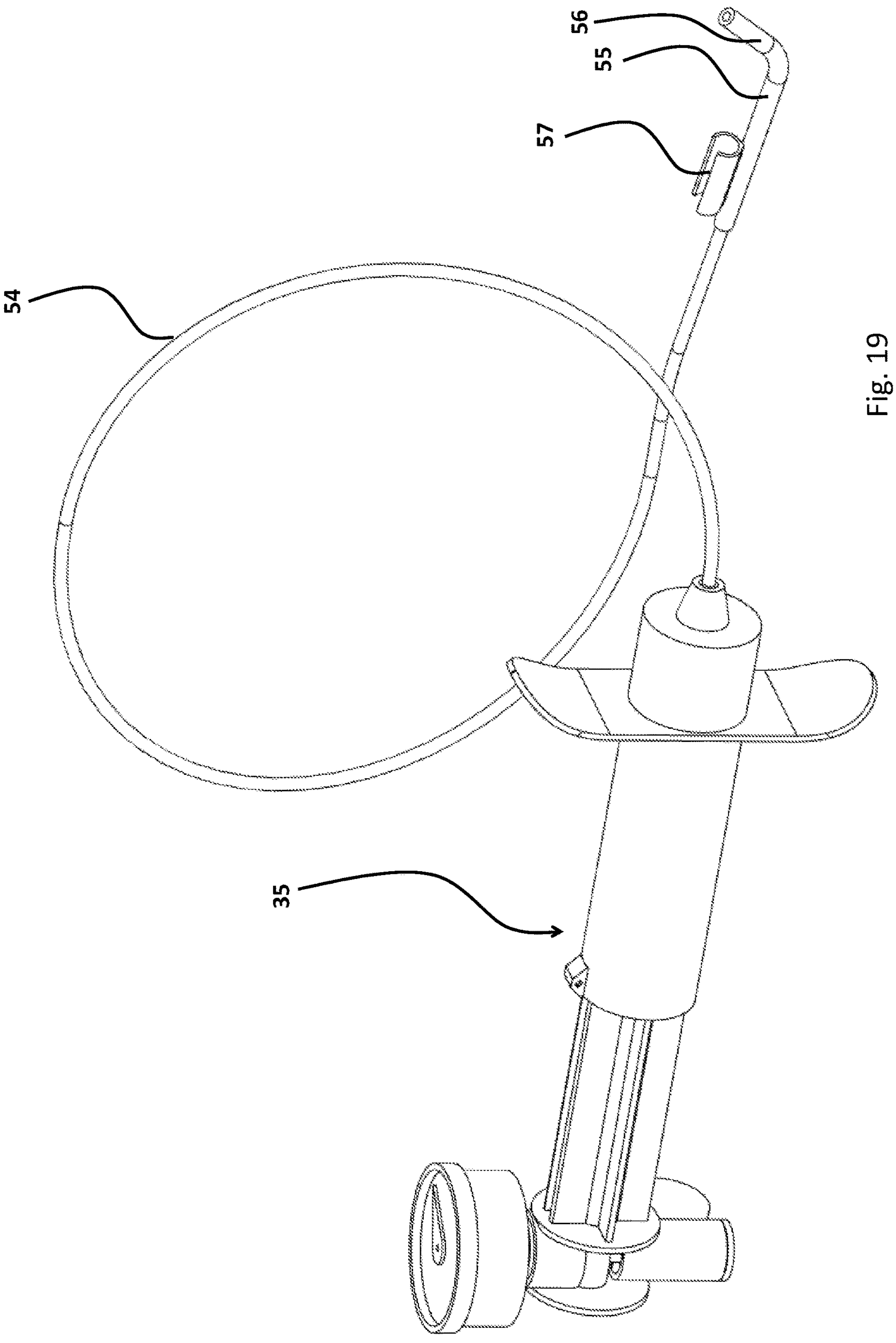
FIG. 19 is a perspective view of a variation of the second embodiment of the handheld insertion device for balloon dilation of FIG. 11 in which the hollow balloon guiding tube comprises a flexible proximal section and a stiff distal section and wherein the stiff distal section is connectable to the distal end of an endoscope.

FIG. 19 shows a perspective view of a variant of the handheld insertion device 35 according to the second embodiment in which the balloon guiding tube 54 comprises a flexible proximal section 54 and a stiff distal section 55, the stiff distal section 55 with a bent tip 56 having means 57 for temporary attachment to the distal cylindrical part of any endoscope.

Figure 20:
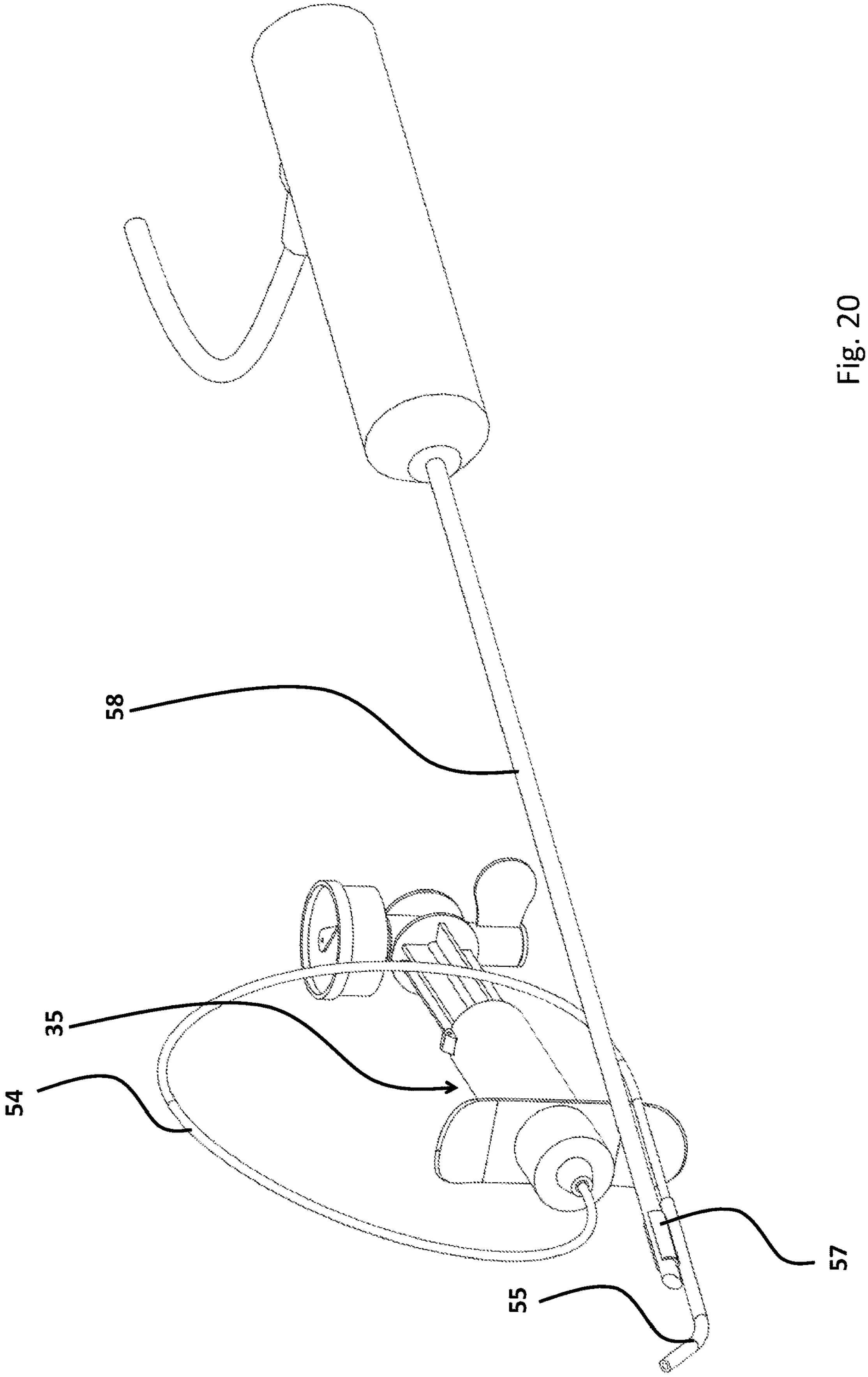
FIG. 20 shows a variant of the handheld insertion device for balloon dilation of FIG. 11 attached to a stiff endoscope.

FIG. 20 shows this variant of the second embodiment of the handheld insertion device 35 attached to a static (rigid) endoscope 58. This embodiment may be advantageous in use with any static endoscope digital or analogue. As the static endoscope 58 is a one-handed instrument, the physician may operate the static endoscope 58 and thereby also the distal section of the guiding tube 55 with only hand due to the attachment means 57. The physician (operator) may advance and pressurize the balloon catheter 20 using the handheld insertion device 35 on the other hand. In clinics with static endoscopes, this may be the preferred solution as any hand movements on the insertion and pressurization device are completely detached from the portion of the instruments located inside the nose. However, bundling of instruments inside the nose may lead to increased patient discomfort.

Figure 21:
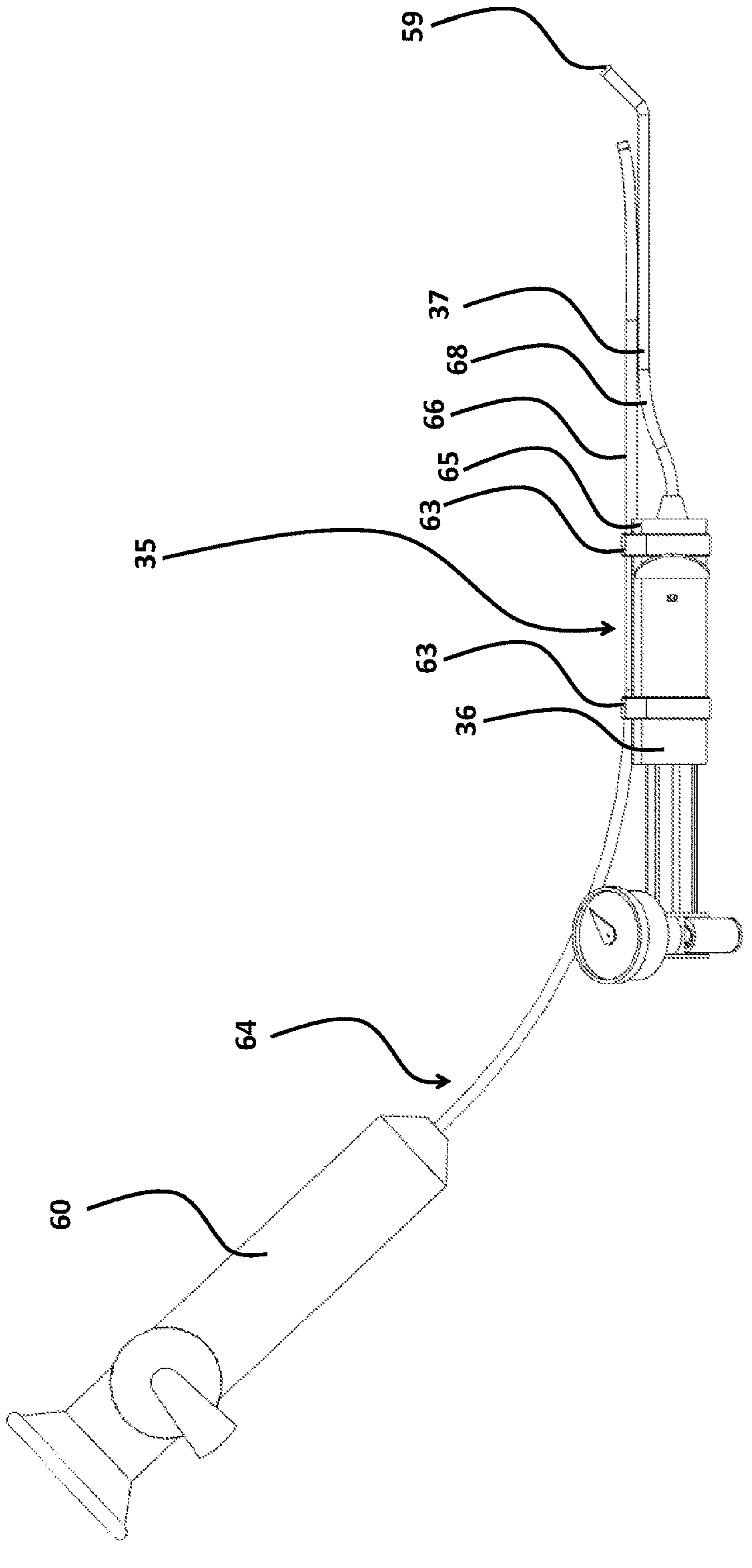
FIG. 21 is a side view of another variant of the handheld insertion device for balloon dilation of FIG. 11 with added means for attaching and supporting a flexible or static endoscope.

FIG. 21 shows a side view of another variant of the second embodiment of the handheld insertion device 35 with added means for attaching and supporting a flexible or static endoscope 64. An open grove 65 on one side of the device in combination with one or two rubber bands 63 acts as a flexible mount of the endoscope 64 onto the device body 36. Support features will allow at least rotation of the endoscope 64 along its own axis and translation parallel to its own axis relative to the device body 36 for adjustment of the field of view during the procedure. The open grove 65 forms a substantially straight track that is configured for supporting and guiding part of the cylindrical shaft of a static or flexible endoscope.

The attachment means may be separate rubber bands 63 or e.g. closable clips. In this embodiment, the physician may support the middle section of an endoscope 66 with the same hand that controls the device 35. Thereby, the other hand is completely free and can support the proximal end 60 of an analogue flexible endoscope 64 or any endoscope. This endoscope support feature hereby allows for the use of analogue flexible low-cost endoscopes and will enable the procedure to be performed more widely in private practices where digital endoscopes are not normally available. Hence, the endoscope support feature is a feature of the device 35. For the least possible patient discomfort, the distal end of the endoscope 66 and the guiding tube 37 must be placed closely together for the smallest possible combined circumference on the portion that enters through the nostril into the nose of the patient. This embodiment is shown with a bent guiding tube 37. The guiding tube 37 may come out from e.g. the center of the device body 36 and then have a soft s-shaped bend 68 to be positioned parallel to and close to the middle section of the endoscope 66 being supported onto the side of the device body 36. Having the smallest possible combined circumference of the two instruments will lead to less pain and discomfort for the patient. Having the two instruments co-guided will furthermore lead to less pain and discomfort for the patient as handling of the two instruments separately by two different hands or even two different operators will cause large relative movements between the two instruments. Flexible connection means between the two instruments at least 100 mm. from the distal tip 59 of the guiding tube 37 will further allow torsion between instruments such that the two instruments can stay over and under each other vertically inside the horizontally narrow nasal opening, even when the instrument assembly is rotated to locate the opening of the eustachian tube. In this embodiment, the instruments will yield to the anatomy and soft tissue of the nose rather than forcing the soft tissue to yield as seen in embodiments where instruments are bundled rigidly at the distal end of the endoscope. For these reasons, this embodiment is more advantageous compared to instrument bundling examples as seen in FIG. 20 and in US 2018/0110407 A1.

Figure 22:
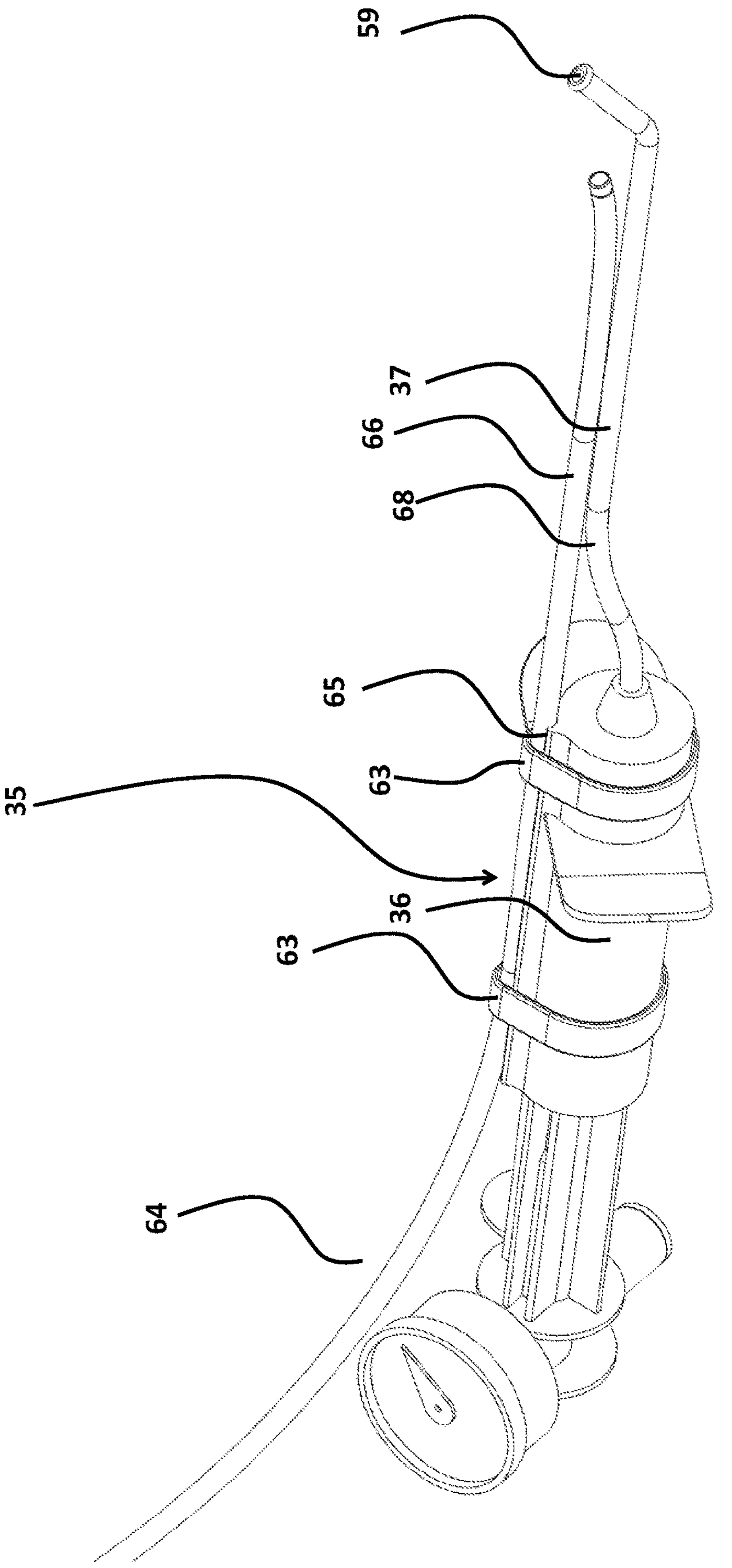
FIG. 22 is a perspective view of the other variant of the handheld insertion device for balloon dilation of FIG. 11 in the primary configuration.

FIG. 22 shows a perspective view of this variation of the second embodiment of the handheld insertion device 35. This variation of the second embodiment of the handheld insertion device 35 has a prefilled syringe ready to use inside the device body 36, having other means for ensuring correct pressure and other means for locking and holding the pressure. The device body 36 further has alternative means for supporting an endoscope. One advantage of this second embodiment is that there are no preparation steps. The device is ready to use once unpacked. A second advantage is that it has a simpler way of ensuring correct pressure in the balloon throughout the procedure. A third advantage of this variation of the second embodiment of the handheld insertion device 35 is that the attachment of an endoscope to the device body is more convenient and allows better positioning adjustment throughout the procedure.

Figure 23:
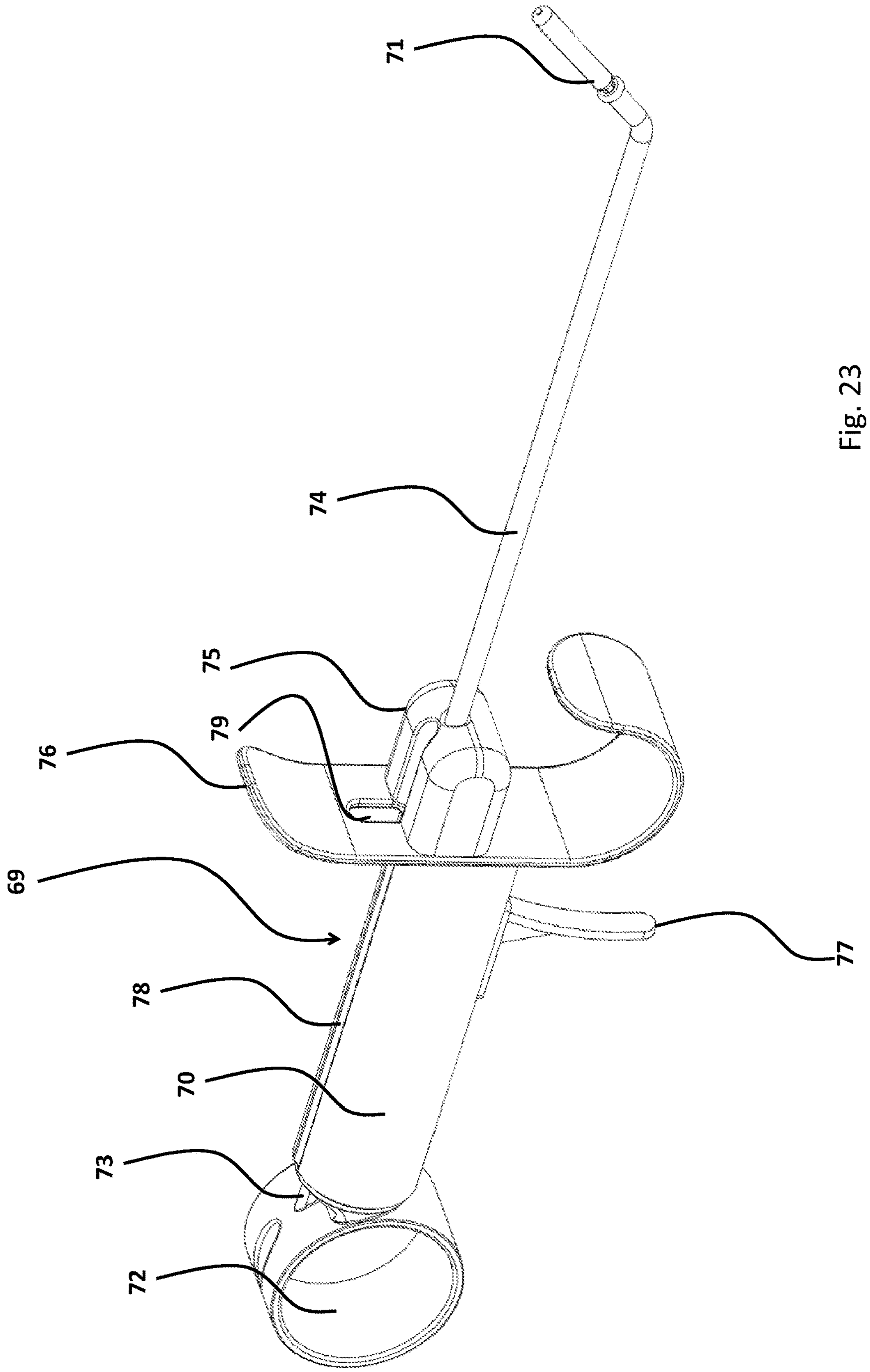
FIG. 23 shows a third embodiment of the handheld insertion device for balloon dilation in perspective view.

FIG. 23 shows a third embodiment of the handheld insertion device 69 in perspective view. The handheld insertion 69 device is depicted after advancement and inflation of the balloon 71. A thumb engagement interface 72 (e.g. a thumb ring as shown, or a thumb plate or other suitable surface or recess along the thumb to apply a pushing or pulling force onto the actuation member 73) is an integrated part of an actuation member 73. The actuation member 73 is to be pressed into the device body 70 for advancement and subsequently inflation and lastly pressurization of the balloon 71. A guiding tube 74 is attached to the device body 70 via a guiding tube connection part 75 that acts as part of the device body 70. The device body 70 has a finger engagement interface 76 at the front of the device such that two fingers may provide counterforce when pressing the actuation member 73 into the device body 70 using the thumb. Both front and rear finger engagement interfaces enable pushing of the actuation member 73 into the device body 70 and pulling of the actuation member 73 out from the device body 70. A trigger 77 is located on the underside of the device's body 70 and serves the purpose of releasing the pressure from the balloon 71. The intention is, that the index and middle finger are placed on the two-finger engagement interfaces 76 (e.g. a finger ring, or a finger engagement plate 76 as shown or other suitable surface or recess allowing the fingers to apply a proximately directed or distally directed force to the device body 70) at the front of the device having the index finger over the guiding tube 74 and having the middle finger under the guiding tube 74. The intention is, that the ring finger can be used to release the pressure after dilation by pressing the trigger 77. The endoscope support features comprise a groove 78 along the device body 70 parallel to the guiding tube 74 and a slot 79 in the finger engagement portion that protrudes out from the device body 70. The support features partly support an endoscope in such a way that an endoscope is only fully supported when the finger of the operator is placed firmly on the finger engagement interface pressing the endoscope down against the support features.

Figure 24:
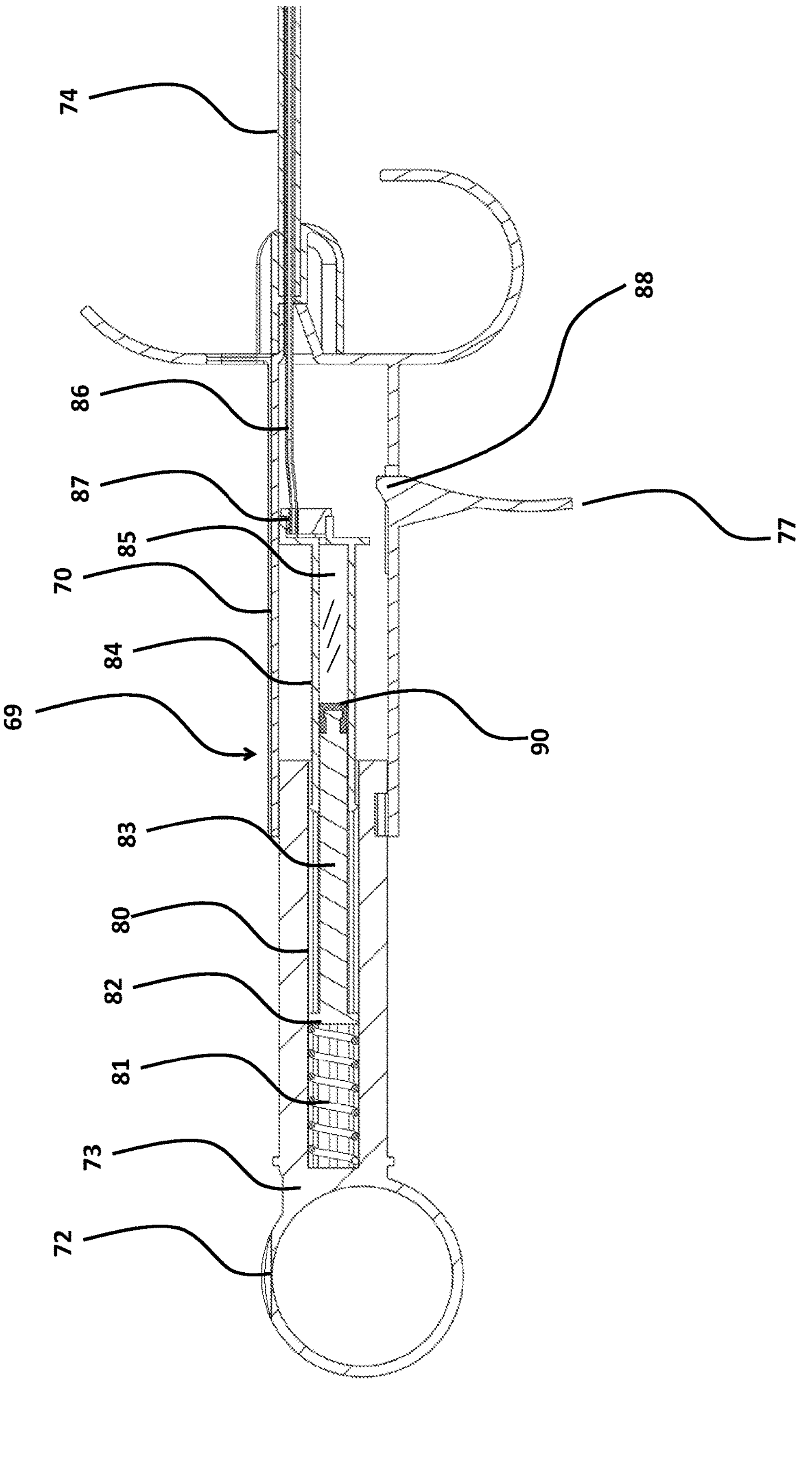
FIG. 24 is a cross-sectional view of the handheld insertion device for balloon dilation of FIG. 23 in a first step and primary configuration where the device is unpacked and ready to use.

FIG. 24 shows a cross-sectional view of this the third embodiment of the handheld insertion device 69 in a first stage and primary configuration where the device 69 is unpacked and ready to use. The actuation member 73 with a thumb engagement interface 72 fits loosely into the device body 70 and is guided for linear movement relative to the device body 70 having means to prevent rotation such that the only possible movement is translation parallel to the axis of the guiding tube 74. The actuation member 73 has an internal cylindrical cavity 80 that houses a metal coil spring element 81. Furthermore, the end of the plunger rod 82 fits inside the cylindrical cavity 80 and has an end-geometry towards the spring 81 that allows for compression of the spring 81 and guidance inside the cylindrical cavity 80. The other end of the plunger rod 83 is located inside the syringe barrel 84 and is attached to a sealing element 90 that seals the prefilled liquid portion 85. The syringe barrel 84 has guiding means to move linearly inside the device body 70 such that it is locked from any rotation and can translate only parallel to the guiding tube 74. The balloon catheter 86 is mounted onto the syringe barrel 84 via a catheter connection part 87. The balloon catheter 86 is connected to the syringe barrel 84 off-center to allow the balloon catheter guiding tube 74 to get as close to the side wall of the device body 70 as possible. The trigger 77 is in this embodiment an integrated part of the injection-molded device body 70 and has a finger engagement protrusion and lock engagement geometry 88 for interlocking with the actuation member 73.

Figure 25:
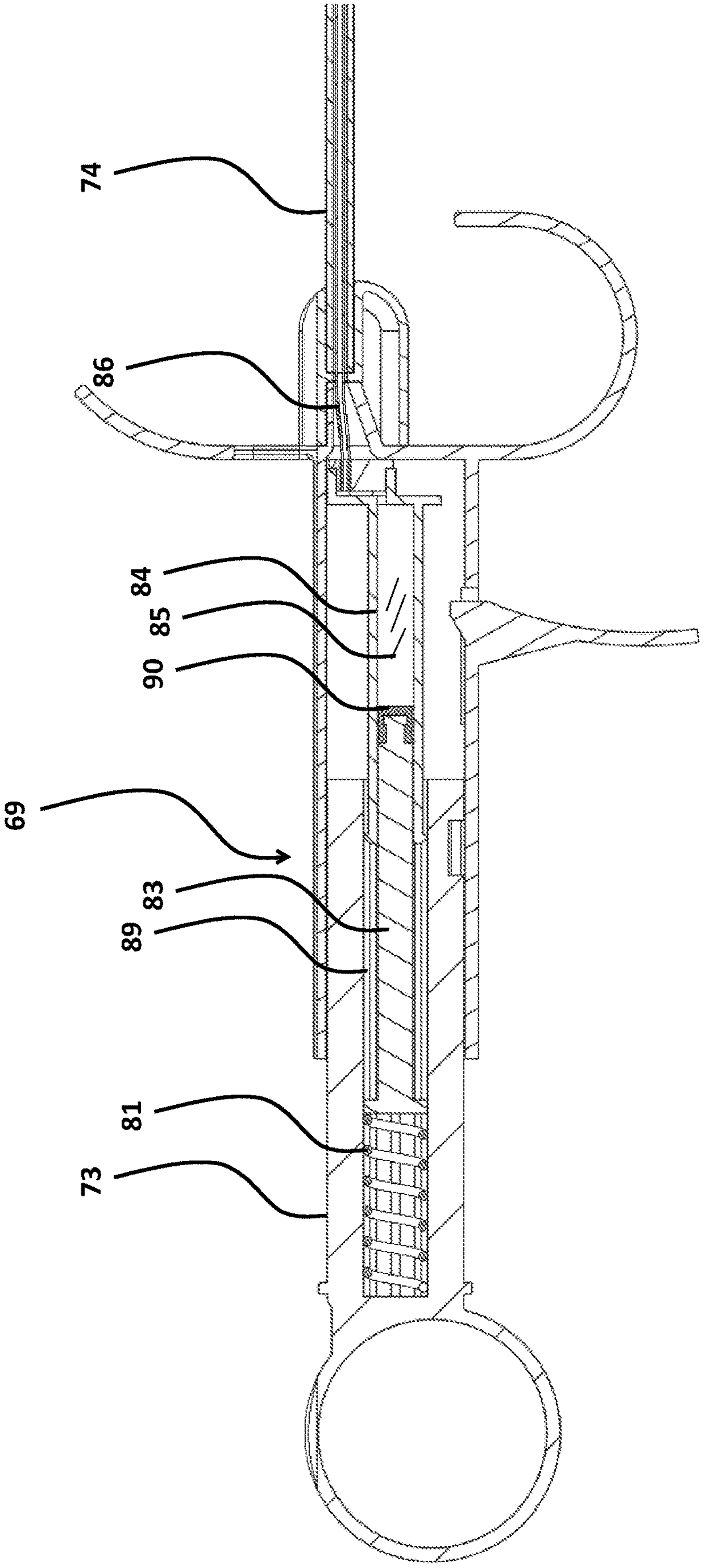
FIG. 25 is a cross-sectional view of the handheld insertion device for balloon dilation of FIG. 23 in a second step and secondary configuration where the actuation member, the spring, the syringe assembly, and the balloon catheter has moved from a first position to a second position corresponding to a fully advanced balloon.

FIG. 25 shows a cross-sectional view of this third embodiment of the handheld insertion device 69 in a second stage where the actuation member 73, the spring 81, the syringe assembly 89, and the balloon catheter 86 have moved forward to an end stop corresponding to a fully advanced balloon. This complete assembly may be moved forward and backward several times for advancement and retraction of the balloon in and out of the guiding tube 74. The sealing element 90 on the plunger rod 83 has a high friction force against the inner cylindrical wall of the syringe barrel 84 ensuring that the assembly can move back and forward without any relative movement between the syringe barrel 84 and the plunger rod 83 resulting in premature inflation of the balloon.

Figure 26:
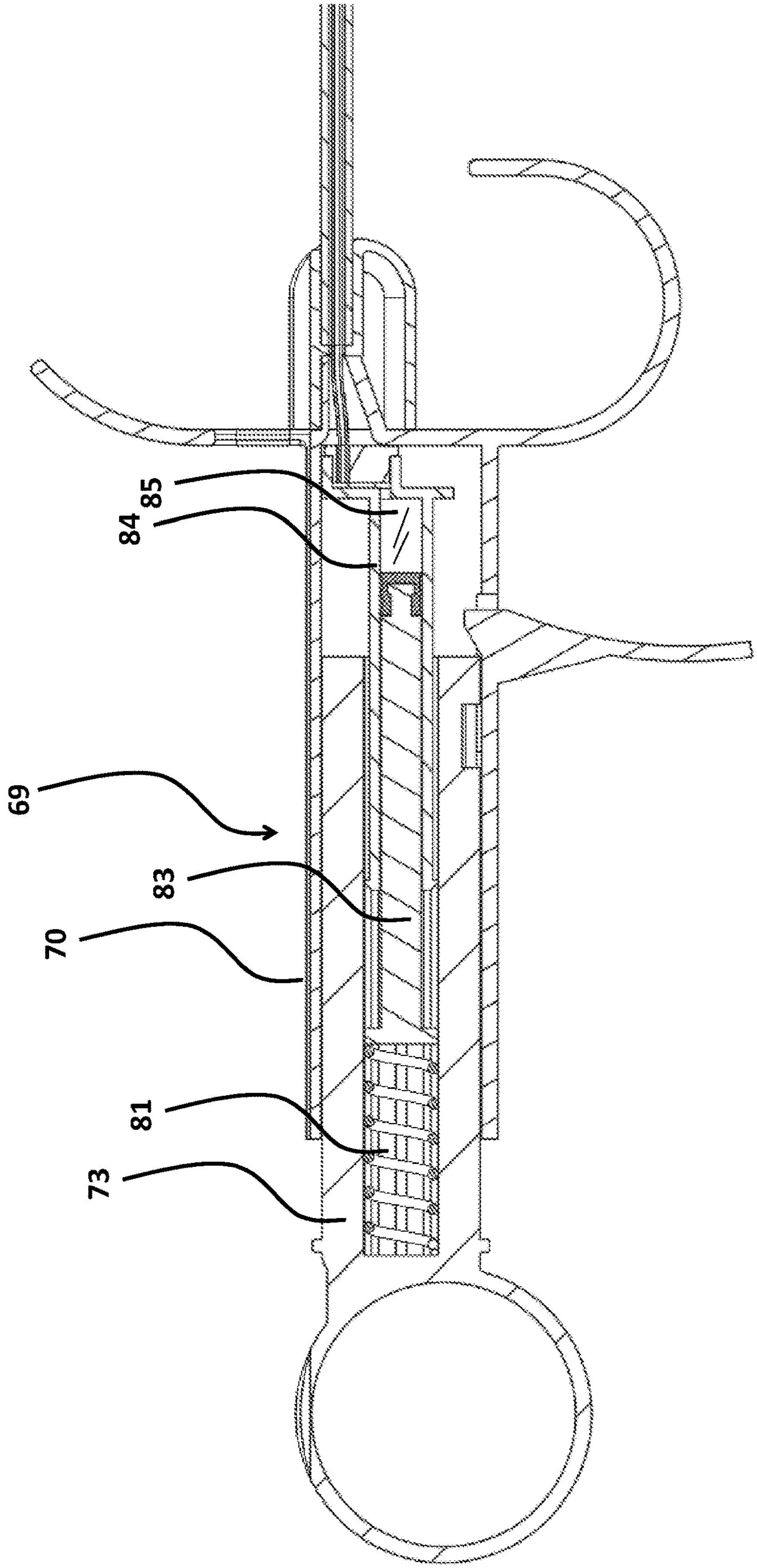
FIG. 26. Is a cross-sectional view of the third embodiment of the handheld insertion device for balloon dilation of FIG. 23 in a third step and tertiary configuration where the actuation member, the spring, and the plunger rod have moved forward resulting in evacuation of liquid from the syringe barrel and into the fully dilated balloon.

FIG. 26 shows a cross-sectional view of this third embodiment of the handheld insertion device 69 in a third stage where the actuation member 73, the spring 81, and the plunger rod 83 have moved forward relative to the device body 70 and the syringe barrel 84 resulting in evacuation of liquid 85 from the syringe barrel 84 and into the fully dilated balloon. The spring element 81 has not yet been compressed as the force required to fill the balloon is far lower than the force required to compress the spring 81.

Figure 27:
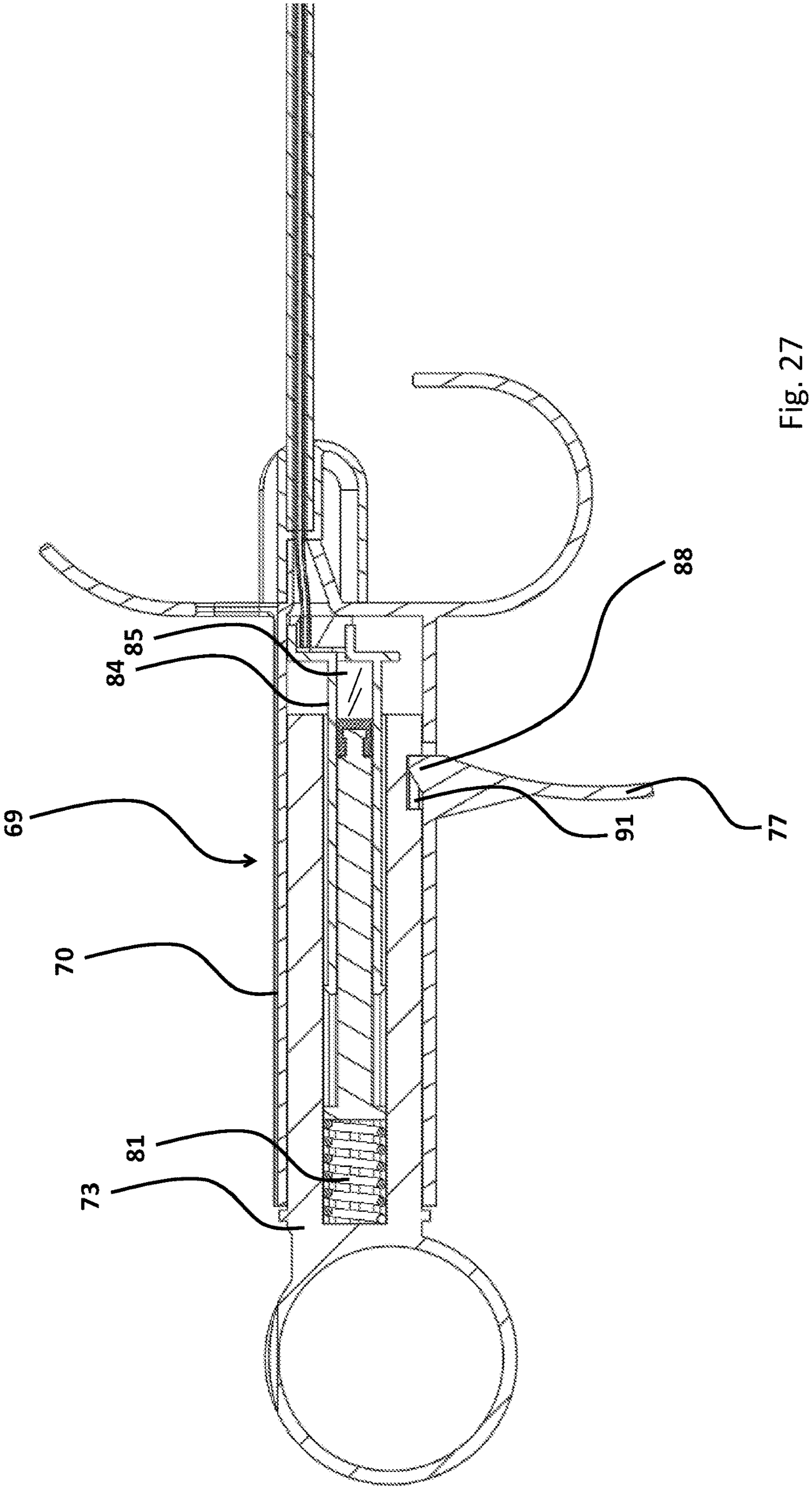
FIG. 27 is a cross-sectional view of the handheld insertion device for balloon dilation of FIG. 23 in a fourth step where the actuation member is moved further forward to a locked position resulting in compression of the spring element.

FIG. 27 shows a cross-sectional view of this third embodiment of the handheld insertion device 69 in a fourth stage where the actuation member 73 is moved further forward relative to the device body 70 resulting in compression of the spring 81 since the balloon is fully inflated and non-flexible. The actuation member 73 is pressed and moved further into the device body 70 until it reaches a predefined end-stop to ensure that the correct pressure in the balloon is obtained. The trigger locking geometry 88 will engage with a counter-lock 91 on the actuation member 73 and the applied external force from the operator can be released. Because the syringe barrel 84 is prefilled with a known volume of liquid 85 and because the inner volumes of the components are known, it is possible to define a given spring force a thereby a given balloon pressure for a certain position of the actuation member 73 relative to the device body 70 resulting in a certain spring compression. An advantage of this solution is that there is no need for a pressure gauge. As the liquid 85 is preloaded with a spring element 81, the balloon pressure will not fall significantly at any small leakage or deformation of components or tissue. Consequently, the pressure is held steady during the procedure and there is no need to monitor or readjust the pressure. After successful dilation of the anatomic passageway, the operator may apply pressure to the actuation member 73 using the thumb and subsequently pull the trigger 77 to release the locking geometry 88 from the counter-lock 91 and thereby releasing the pressure in the balloon.

Figure 28:
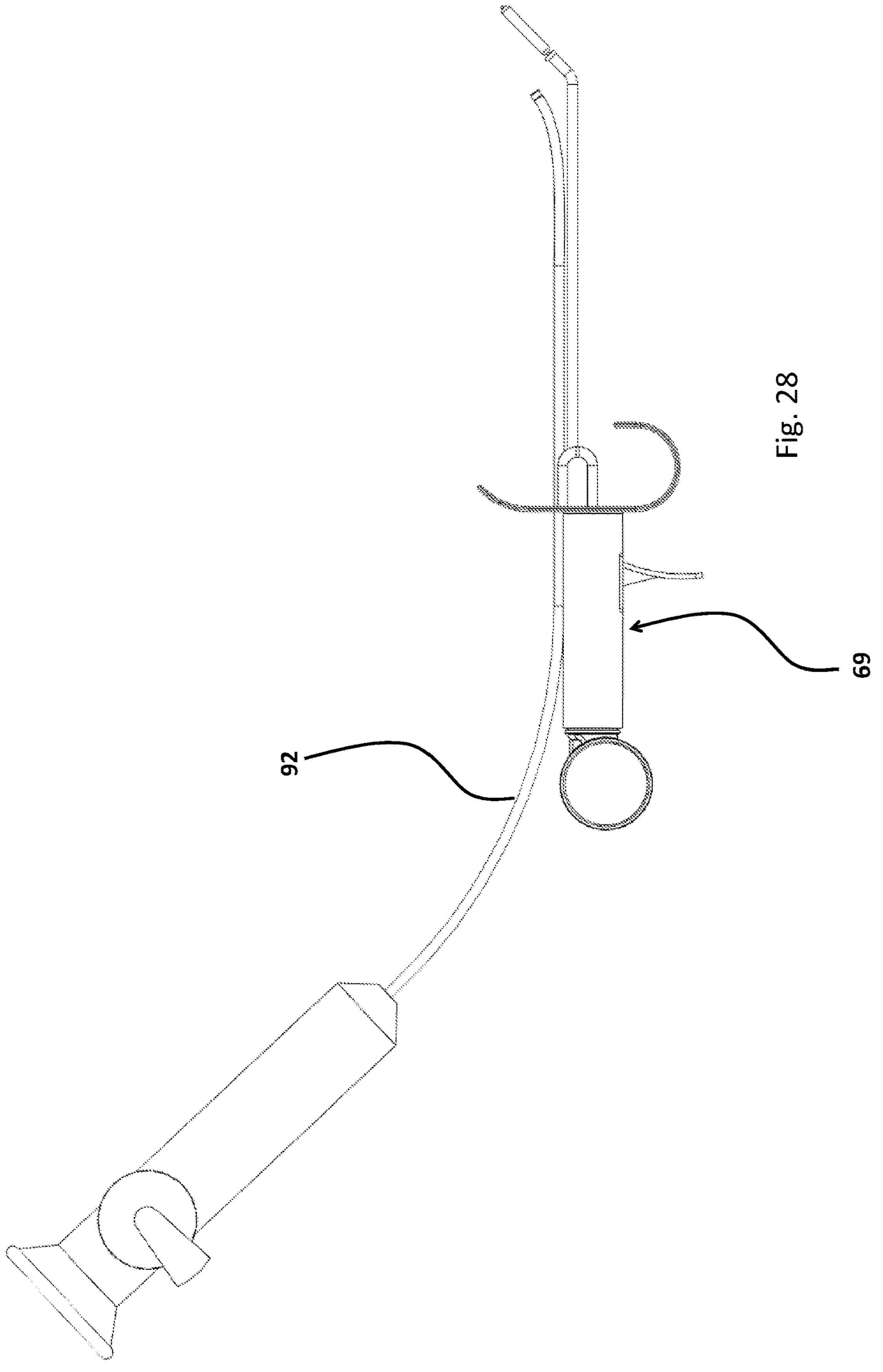
FIG. 28 is a side view of the handheld insertion device for balloon dilation of FIG. 23 in combination with an analogue flexible endoscope.

FIG. 28 shows a side view of this third embodiment of the handheld insertion device 69 in combination with an analogue flexible endoscope 92.

Figure 29:
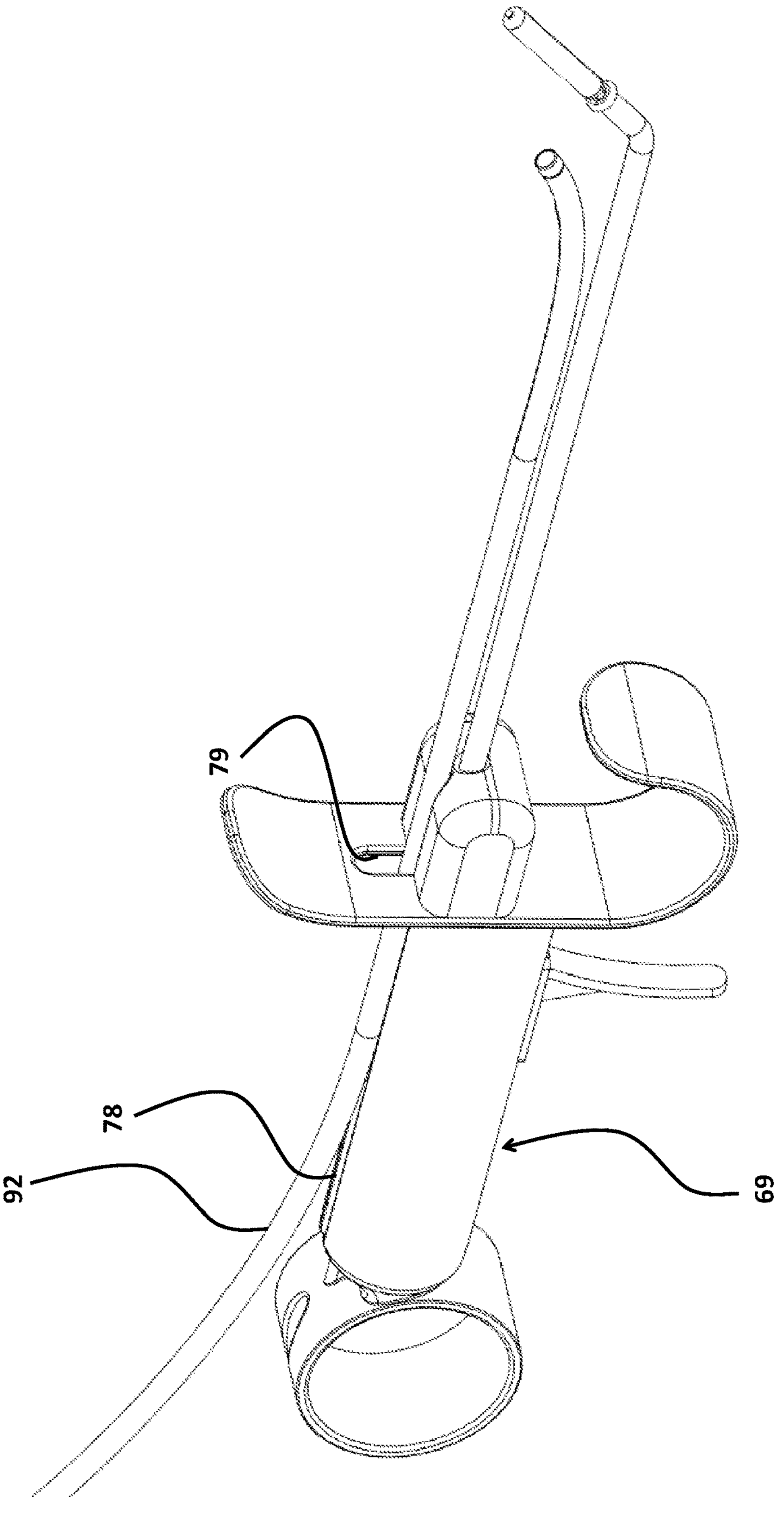
FIG. 29 is a perspective view of the handheld insertion device for balloon dilation of FIG. 23 in combination with an analogue flexible endoscope.

FIG. 29 shows a perspective view of this third embodiment of the handheld insertion device 69 in combination with an analogue flexible endoscope 92. Support features on the device body such as the groove 78 and the slot on the protruding finger engagement interface 79 are not enough to support the endoscope. In fact, the endoscope is only fully supported when the operator holds on to the device thereby pressing at least part of the endoscope down against the groove 78. The operator may adjust the force applied on the part of the endoscope to allow some adjustments of the position of the endoscope 92 during the procedure.

Figure 30:
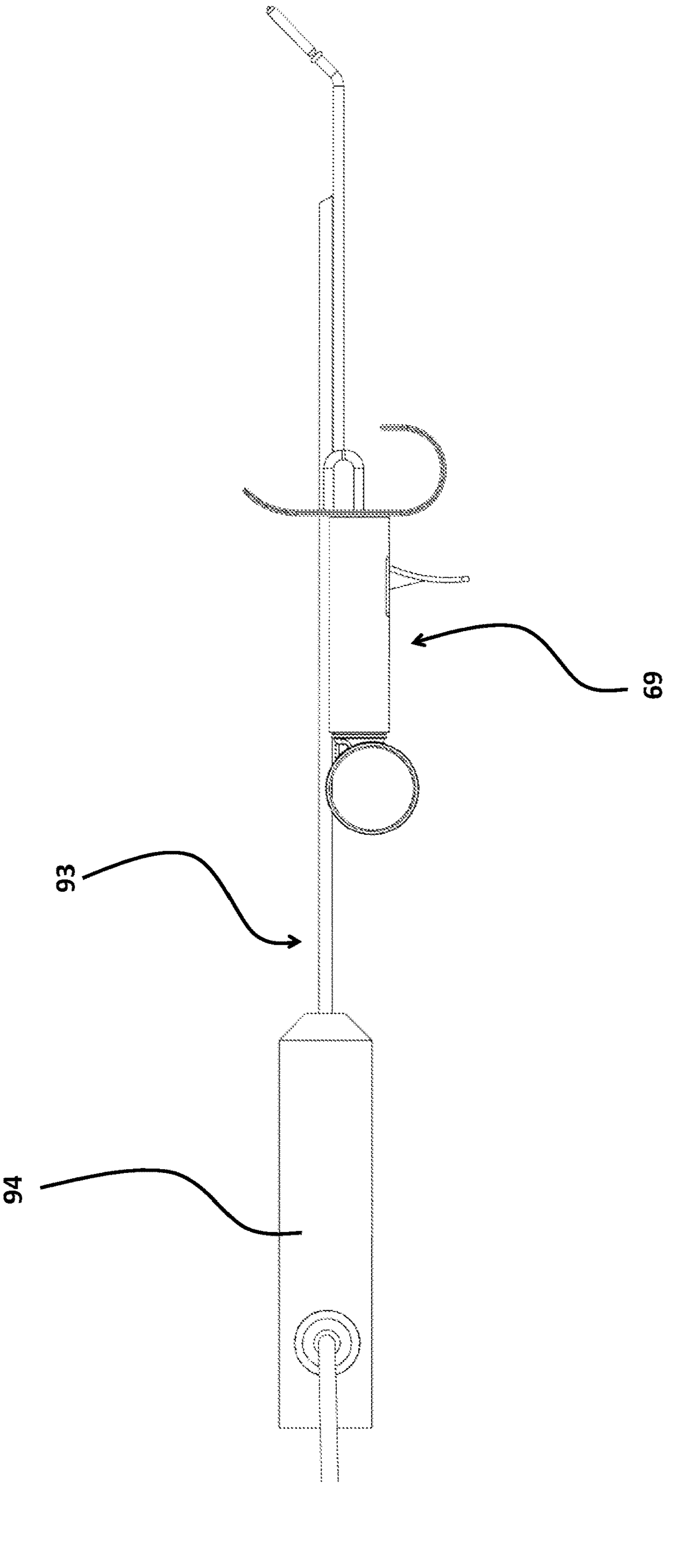
FIG. 30 is a side view of the handheld insertion device for balloon dilation of FIG. 23 in combination with a digital static endoscope.

FIG. 30 shows a side view of this third embodiment of the handheld insertion device 69 in combination with a digital static endoscope 93. The operator may operate the device with one hand and support and adjust the proximal part of the endoscope 94 using the other hand.

Figure 31:
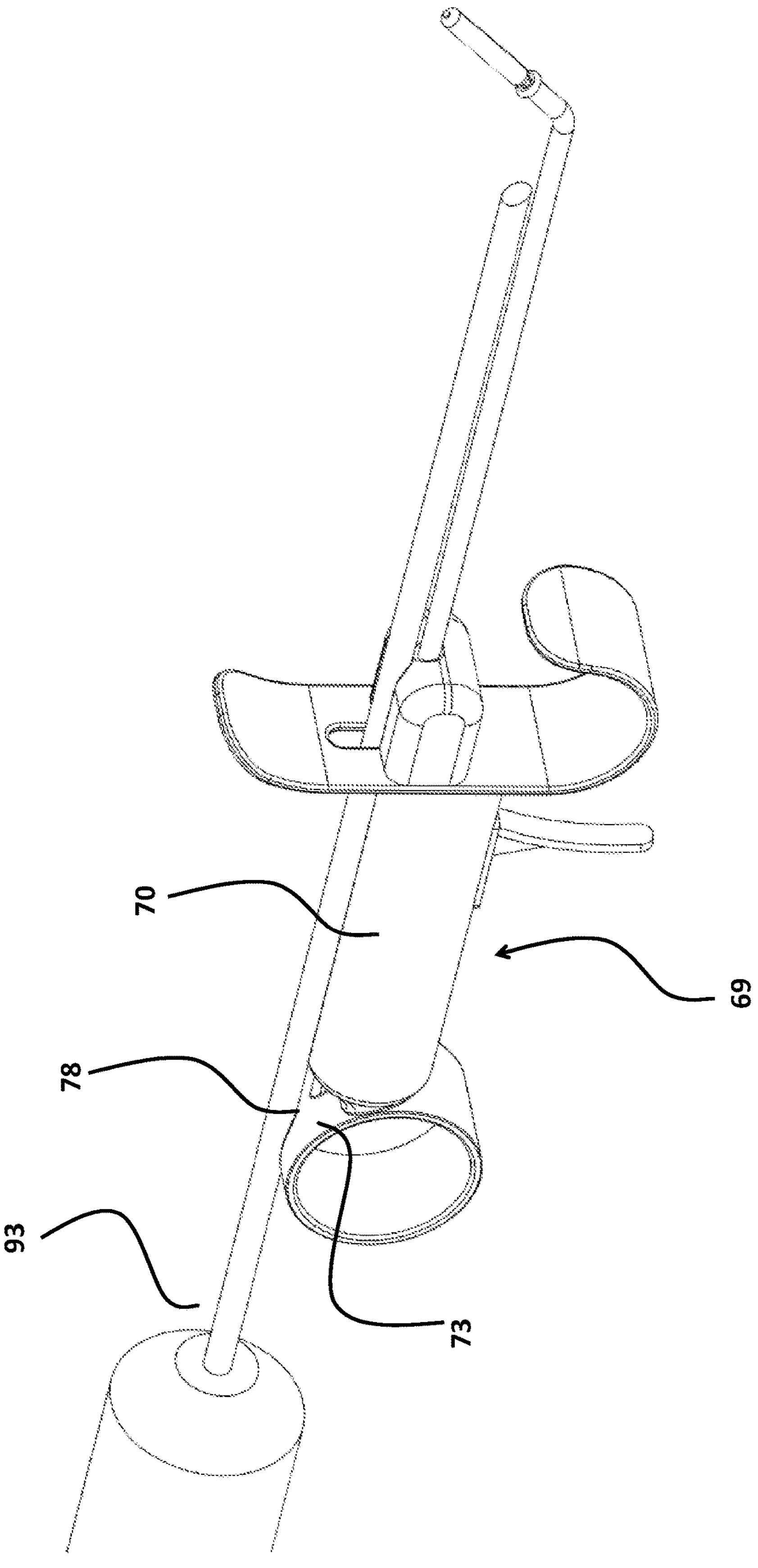
FIG. 31 is a perspective view of the third embodiment of the handheld insertion device for balloon dilation of FIG. 23 including support features in combination with a digital rigid endoscope.

FIG. 31 shows a perspective view of this third embodiment of the handheld insertion device 69 in combination with a static endoscope 93. The endoscope support groove 78 is both on the device body 70 and as well on top of the actuation member 73 such that the thumb can support the weight of the proximal part of the static endoscope, should the operator need to free one hand temporarily. The endoscope support groove 78 forms a substantially straight track that is configured for supporting and guiding part of the cylindrical shaft of the flexible endoscope 92.

FIGS. 32-35 show a fourth embodiment of the first aspect of the handheld insertion device 95. This fourth embodiment has many similarities to the third embodiment but is based on an internal gas spring system and has alternative endoscope support means.

Figure 32:
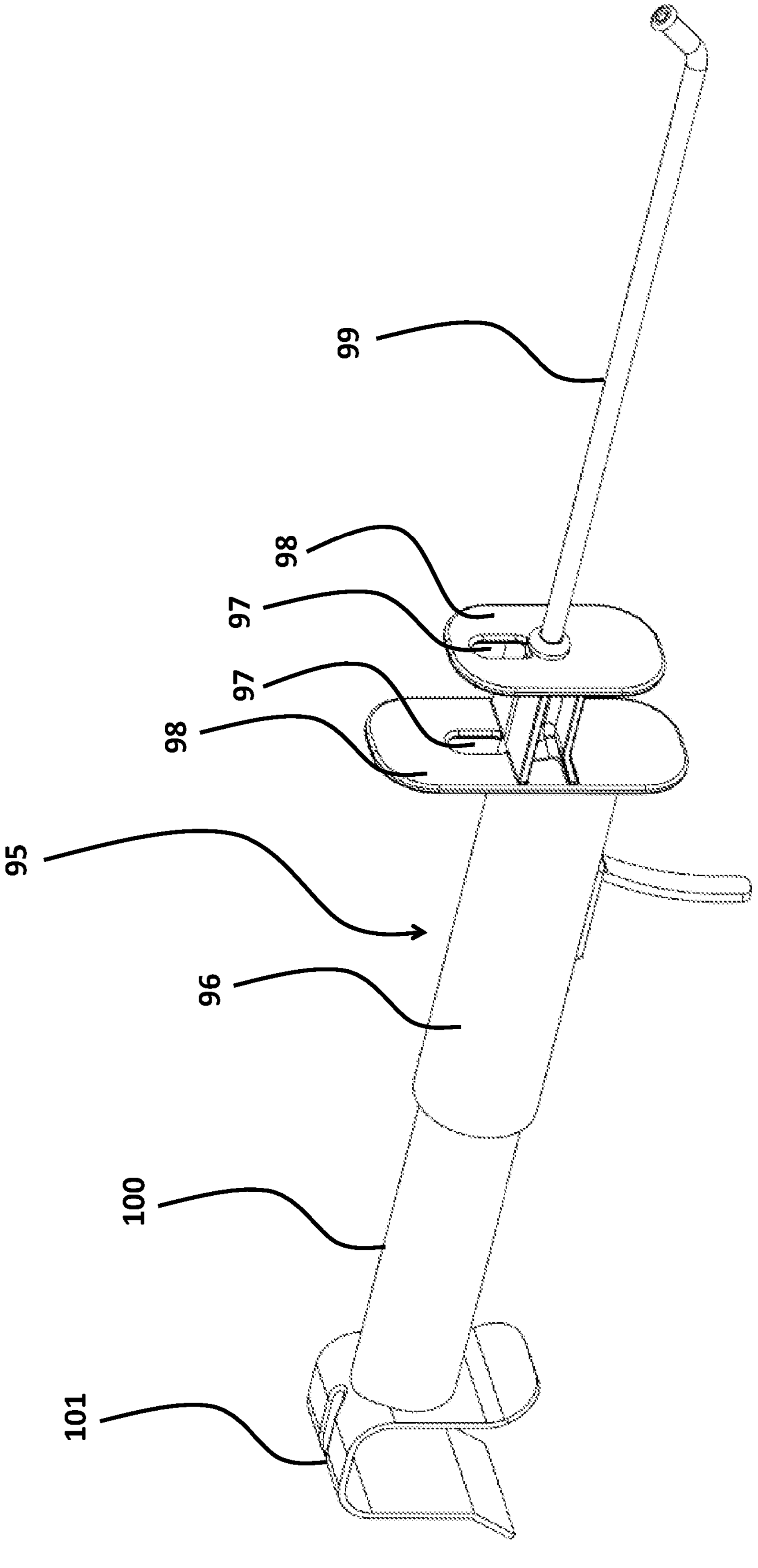
FIG. 32 is a perspective view of a fourth embodiment of the handheld insertion device for balloon dilation.

FIG. 32 shows a perspective view of this fourth embodiment of the handheld insertion device 95 in a first stage where the device 95 is unpacked and ready to use. Endoscope support means on the device body 96 are arranged as two slots 97 in two protruding finger engagement interfaces 98 placed over the guiding tube 99. As for the preceding embodiment, the endoscope is only fully supported when the operator has a firm grip on the device and uses a finger to press a part of the endoscope down against the bottom of the slots 97. One slot may be larger than the other slot to allow slight angular movement of the endoscope. An actuation member 100 with an alternative thumb engagement interface 101 is arranged to fit loosely inside the device body 96 having guiding means for linear translation movement relative to the device body 96, such that only translation parallel to the guiding tube 99 is possible.

Figure 33:
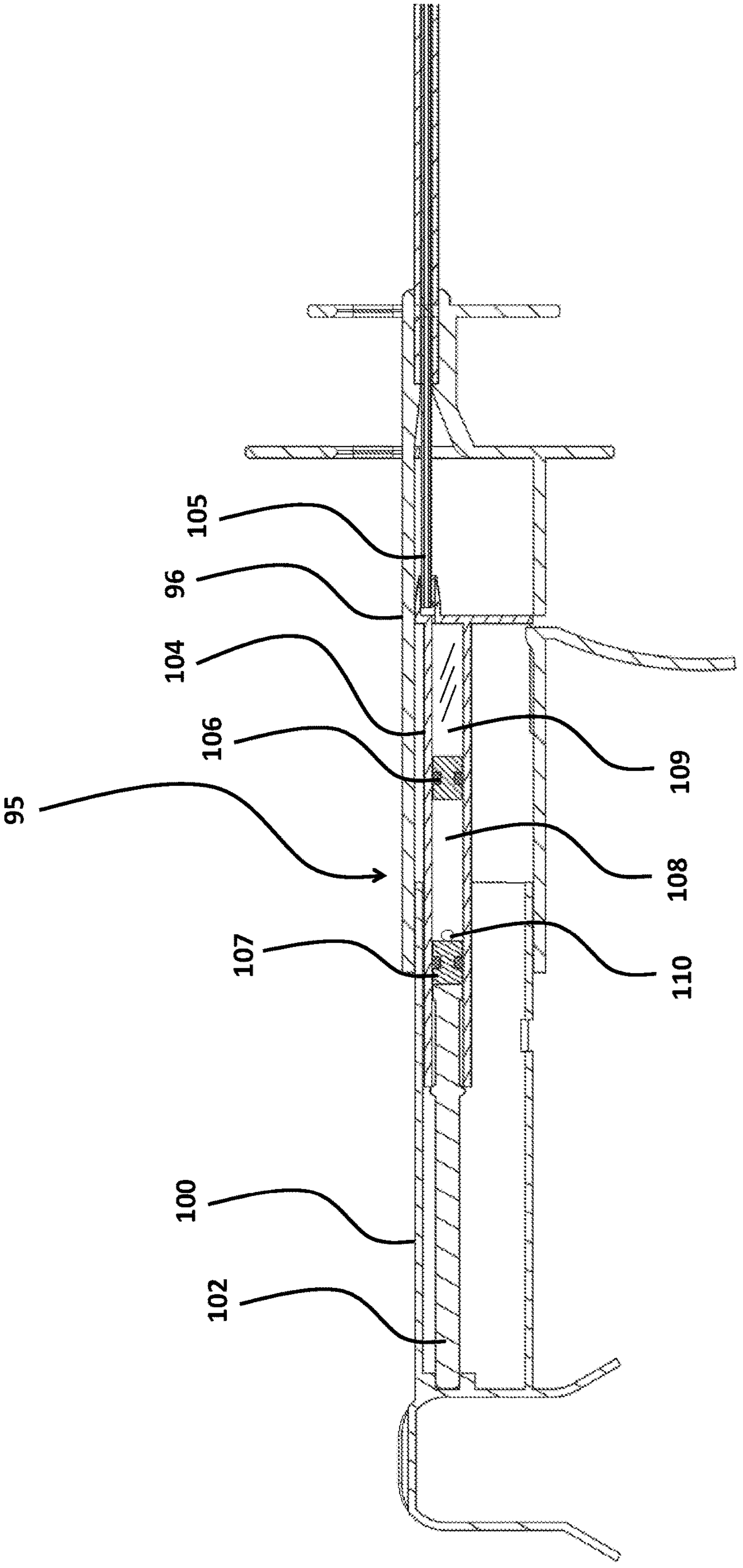
FIG. 33 is a sectional view of the handheld insertion device for balloon dilation of FIG. 32 in a first step and primary configuration where the device is unpacked and ready to use.

FIG. 33 shows a sectional view of this fourth embodiment of the handheld insertion device 95 in a first stage where the device 95 is ready to use. The actuation member 100 is attached to the proximal part of a plunger rod 102 inside the device 95 in order to transfer force from the operator via the actuation member 100 and via the plunger rod 102 to a rear sealing element 107 at the distal end of the plunger rod 102 inside the syringe barrel 104. The syringe barrel 104 is placed inside the device body 96 and has guiding means for linear translation movement relative to the device body 96. The balloon catheter 105 is mounted directly on the distal tip of the syringe barrel 104. Inside the syringe barrel 104 are two movable sealing elements, wherein a front sealing element 106 is placed towards the balloon catheter 105, and a rear sealing element 107 is placed towards the plunger rod 102. Inside the syringe barrel 104 and between the front sealing element and the attached balloon catheter is a prefilled and exact liquid volume. Between the two sealing elements is entrapped air 108, the entrapped air 108 acting as a gas spring to provide a spring-loaded force acting on the front sealing element 106 when the plunger rod 102 and the rear sealing element 107 is moved forward to a locked position relative to the device body 96. A small ventilation hole 110 placed as close to the rear seal element 107 as possible may ensure that no negative or positive pressure has built up in the entrapped air 108 prior to use of the device as a function of temperature changes. When the rear seal 107 moves past this ventilation hole 110, the chamber will be sealed, and the entrapped air 108 inside can be compressed as a spring element.

Figure 34:
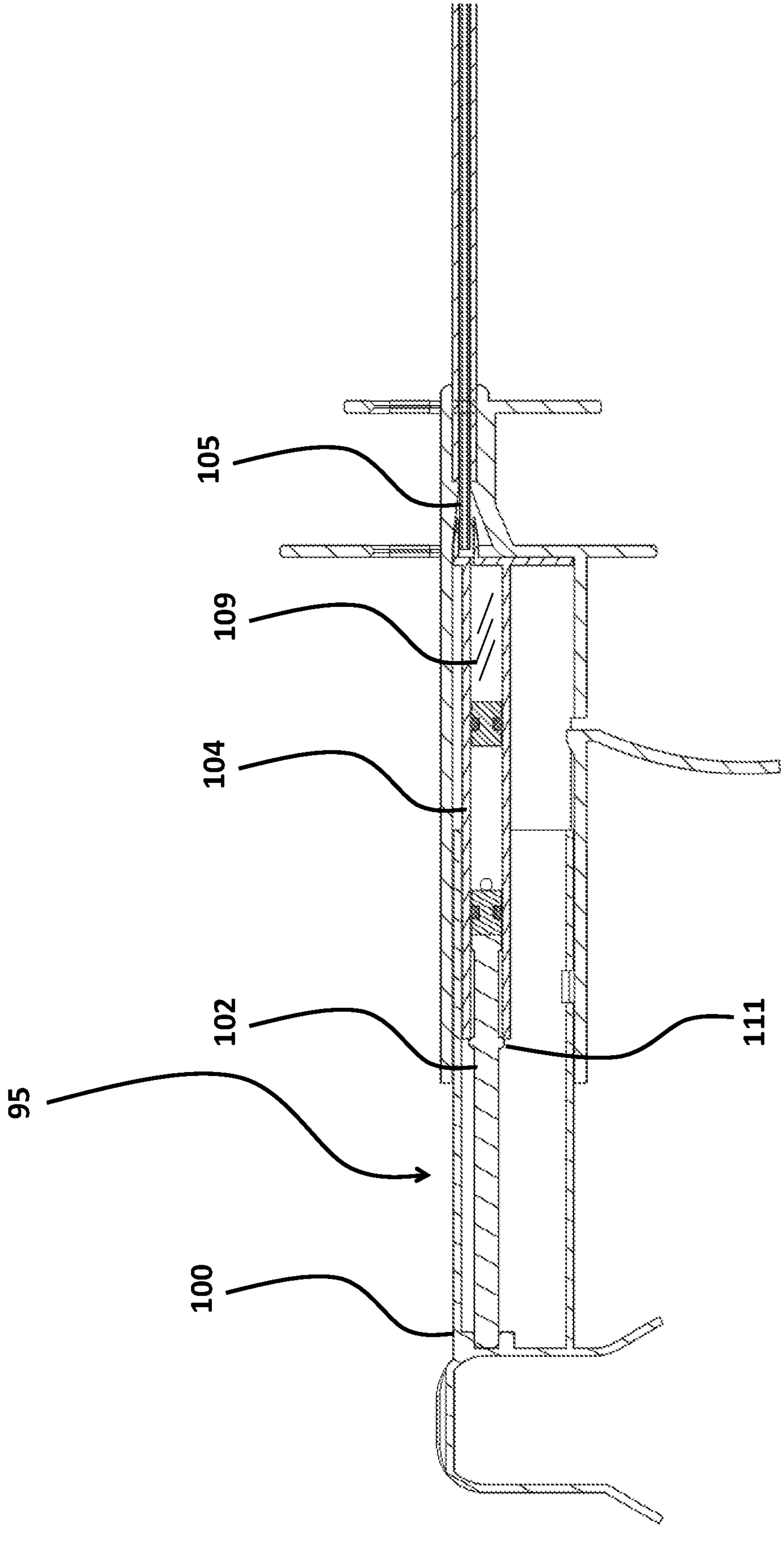
FIG. 34 is a sectional view of the handheld insertion device for balloon dilation of FIG. 32 in a second step and secondary configuration where the balloon catheter is moved from a first position to a second position.

FIG. 34 shows a sectional view of this fourth embodiment of the handheld insertion device 95 in a second stage where the actuation member 100, the plunger rod 102, the syringe barrel 104, the rear sealing element 107, and the front sealing element 106 and the balloon catheter 105 as an assembly have all been moved forward from a first position to a noticeable end stop at a second position corresponding to fully advanced balloon. A significantly higher force on the actuation member 100 will be required to push the plunger rod 102 further into the syringe barrel 104 for balloon inflation, as protruding bumps, 111 on the plunger rod 102 extend further out than the inner diameter of the syringe barrel 104. This full assembly may be pushed and pulled back and forward relative to the device body 96 several times before the operator wishes to proceed to inflate the balloon. The protruding bumps 111 on the plunger rod 102 need to be deformed requiring significantly higher force, before the plunger rod 102 can be moved further into the syringe barrel 104.

Figure 35:
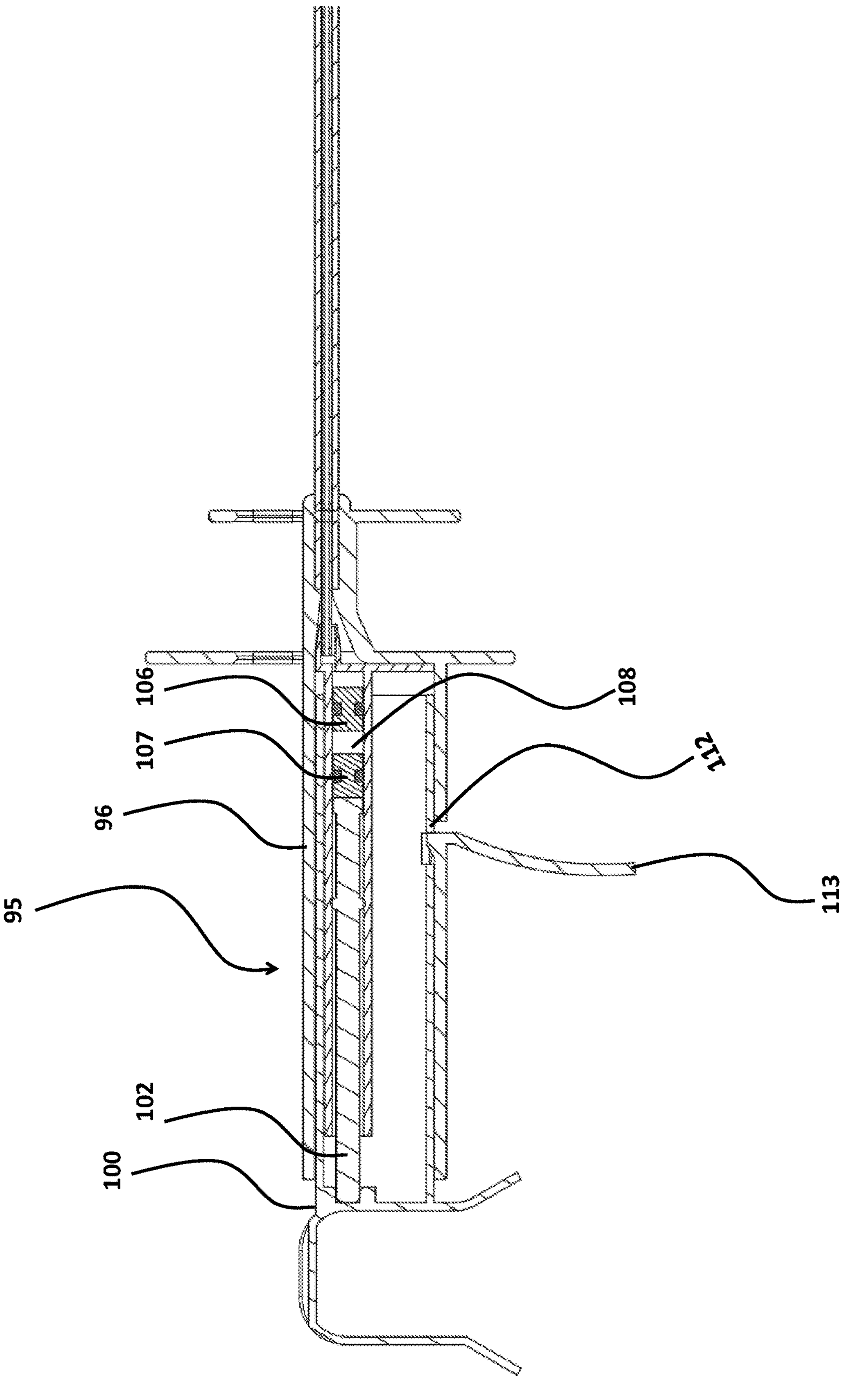
FIG. 35 is a section view of the handheld insertion device for balloon dilation of FIG. 32 in a third step and tertiary configuration where the actuation member has moved forward to a locked position corresponding to a fully inflated balloon and fully pressurized balloon.

FIG. 35 shows a sectional view of this fourth embodiment of the handheld insertion device 95 in a third stage where the actuation member 100, the plunger rod 102, and both sealing elements 106, 107 have moved forward to a position relative to the syringe barrel 104 corresponding to a fully inflated balloon and fully pressurized balloon. In this position, a necessary liquid volume has been evacuated into the balloon for inflation and the entrapped air 108 is compressed. The operator will press the actuating member 100 all the way into the device body 96 until a geometric hard stop. When releasing the actuation member 100, the actuation member 100 may move back slightly to the locked position where the lock 112 between the device body 96 and the actuation member 100 is engaged. The entrapped air volume 108 has been reduced corresponding to the pressure needed in the balloon e.g., the air volume has been compressed to $1/10$ of the original volume corresponding to a pressure increase from 1 bar to 10 bar. After successful dilation of the anatomic passageway, the operator may engage the trigger 113 to release the lock 112 that holds the actuation member 100 locked in position relative to the device body 96.

Figure 36:
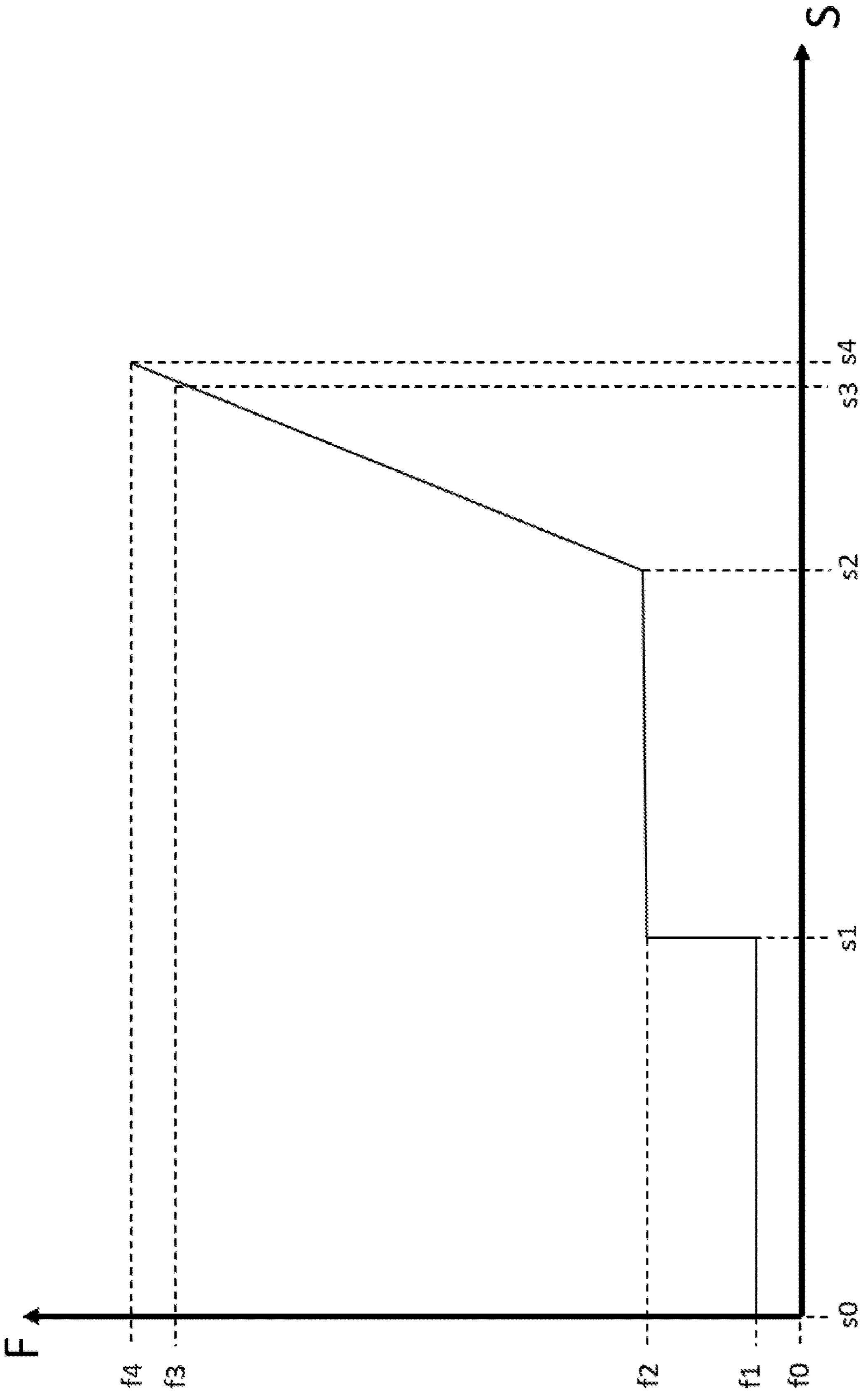
FIG. 36 shows a graph of the relationship between applied force on the actuation member and the travel distance of the actuation member relative to the device body and describes both third and fourth embodiments of the handheld insertion device for balloon dilation of FIGS. 23 and 32.

FIG. 36 shows a graph of the relationship between applied force on the actuation member and the travel distance of the actuation member relative to the device body and describes both third and fourth embodiment of the handheld insertion device. A certain force f1 must be overcome to initially move the actuation member for advancement of the balloon. The force f1 should be as low as possible and is mainly friction between parts. The operator may move the actuation member back and forth between s1 and s2. A force higher than f2 needs to be applied to further move the actuation member relative to the device body and thereby start moving the plunger and sealing elements relative to the syringe barrel resulting in balloon inflation. Force f2 is mainly given by friction of sealing elements inside the syringe and deformation of any deformable elements such as protruding bumps. Distance s2 is reached when the balloon is fully inflated without meeting significant resistance. The actuation member is geometrically restricted from moving beyond s4 and force f4 is thereby the maximum force that the operator can apply onto the inner seal element inside the syringe barrel. Hence, the operator cannot accidentally exceed the allowed pressure for the balloon. When the actuation member is released by the operator, the actuator member will move back slightly to distance s3 in a locked position resulting in force f3. Force f3 is in this case only applied by the internal spring element of the device and f3 on the sealing element inside the syringe barrel provides the needed pressure inside the balloon. Any small leakage or small deformation of parts or tissue that increases the internal pressurized volume will lead to an insignificant pressure drop because the system has a spring element and is less stiff. In contrast, FIG. 10 described the first embodiment of the handheld insertion device, where there was no spring element, where the system was very stiff, and where any small deformations leading to internal volume increase would cause significant pressure decrease, requiring pressure monitoring and readjustment.

FIGS. 37 to 42 show a fifth embodiment of handheld insertion device 114 in which several spring return functionalities are integrated for improved ergonomics and for convenient reusability of the device in cases of two-sided procedures on one patient.

Figure 37:
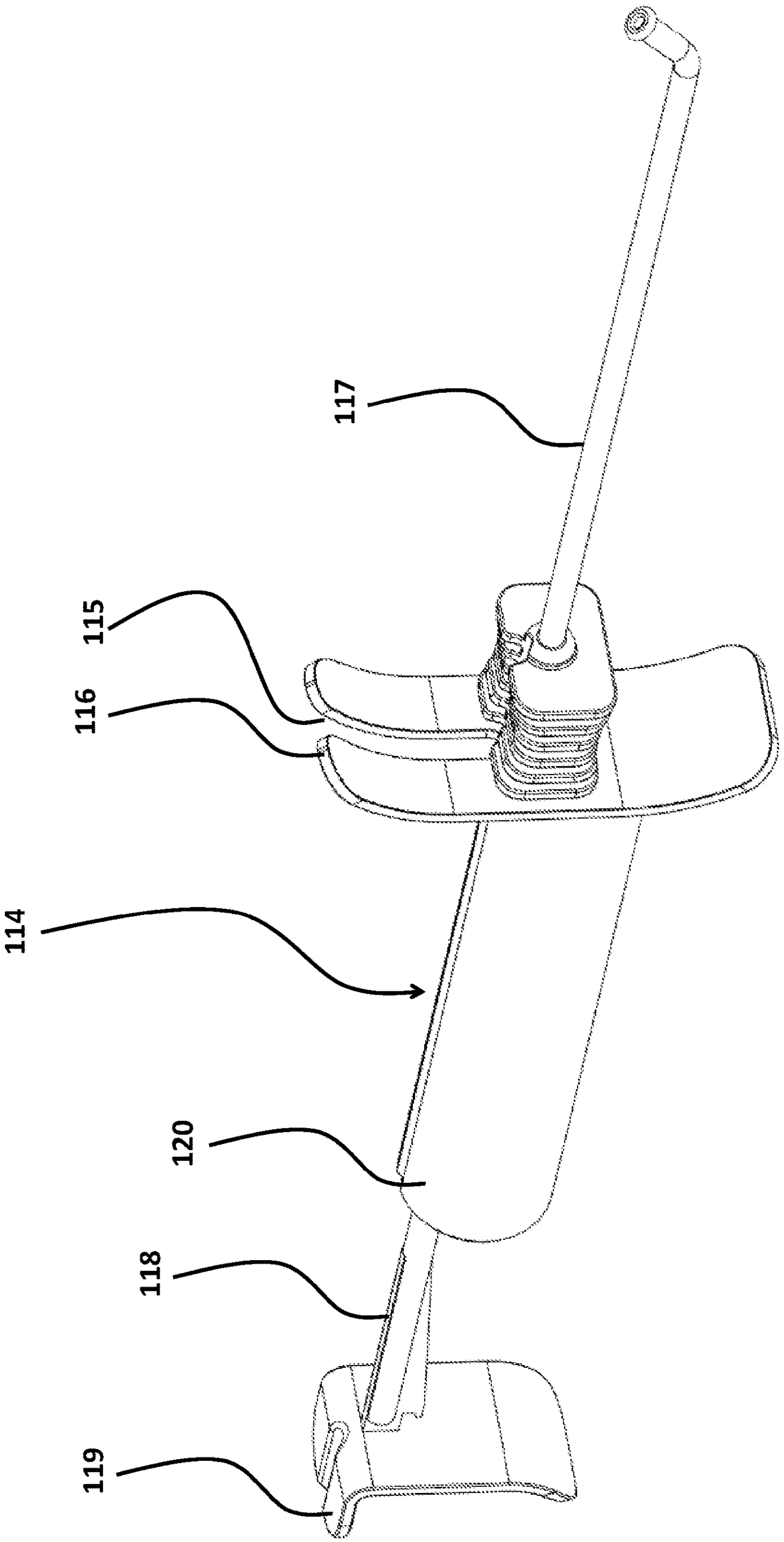
FIG. 37 is a perspective view of a fifth embodiment of the handheld insertion device for balloon dilation.

FIG. 37 shows a perspective view of this fifth embodiment of the handheld insertion device 114 in a first stage where the device is unpacked and ready to use. The device is prefilled with water in the internally placed syringe assembly and no preparation steps are necessary. The device has alternatively shaped support means for supporting an endoscope onto the device body, where an open slot 115 is a part of the finger engagement interface 116 placed above the guiding tube 117 for a faster and more convenient placement of the endoscope rather than penetrating a hole or slots. A plunger rod 118 with a thumb engagement interface 119 is arranged to be fixed and guided for linear translation movement into the device body 120 for advancement, inflation, and pressurization of the balloon.

Figure 38:
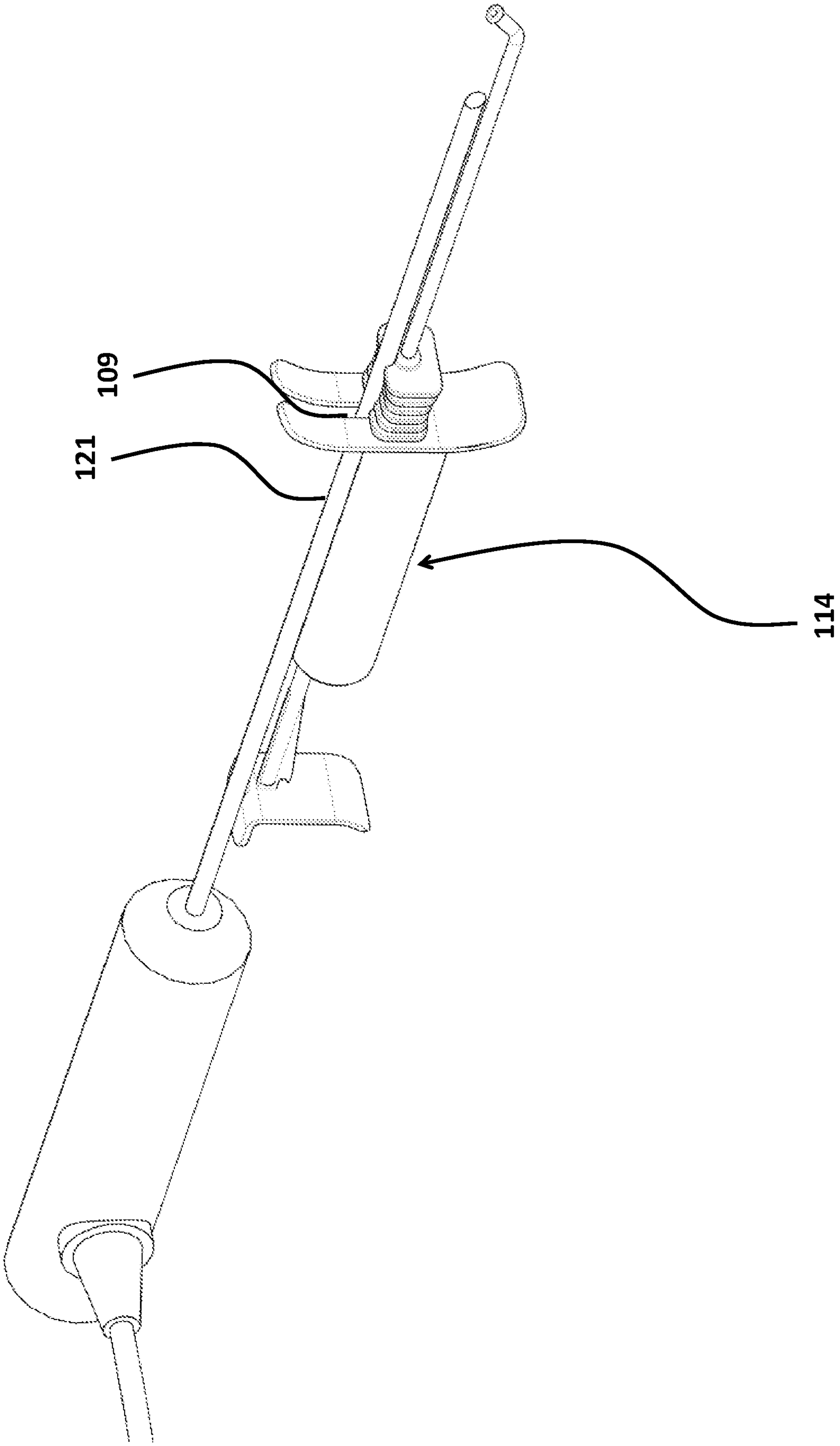
FIG. 38 is a perspective view of the handheld insertion device for balloon dilation of FIG. 37 in combination with a rigid endoscope.

FIG. 38 shows a perspective view of this fifth embodiment of the handheld insertion device 114 in combination with a static endoscope 121. The endoscope 121 is not supported sufficiently by the support means of the handheld insertion device 114 alone. However, the endoscope is fully supported, when the operator has a firm grip on the device 114 pressing a part of the endoscope down against the bottom of the device body and the open slot 109. The operator may use one hand to operate the device 114 and the other hand may support and adjust the position of the static endoscope 121. The open slot 109 forms a substantially straight track that is configured for supporting and guiding part of the cylindrical shaft of the static endoscope 121.

Figure 39:
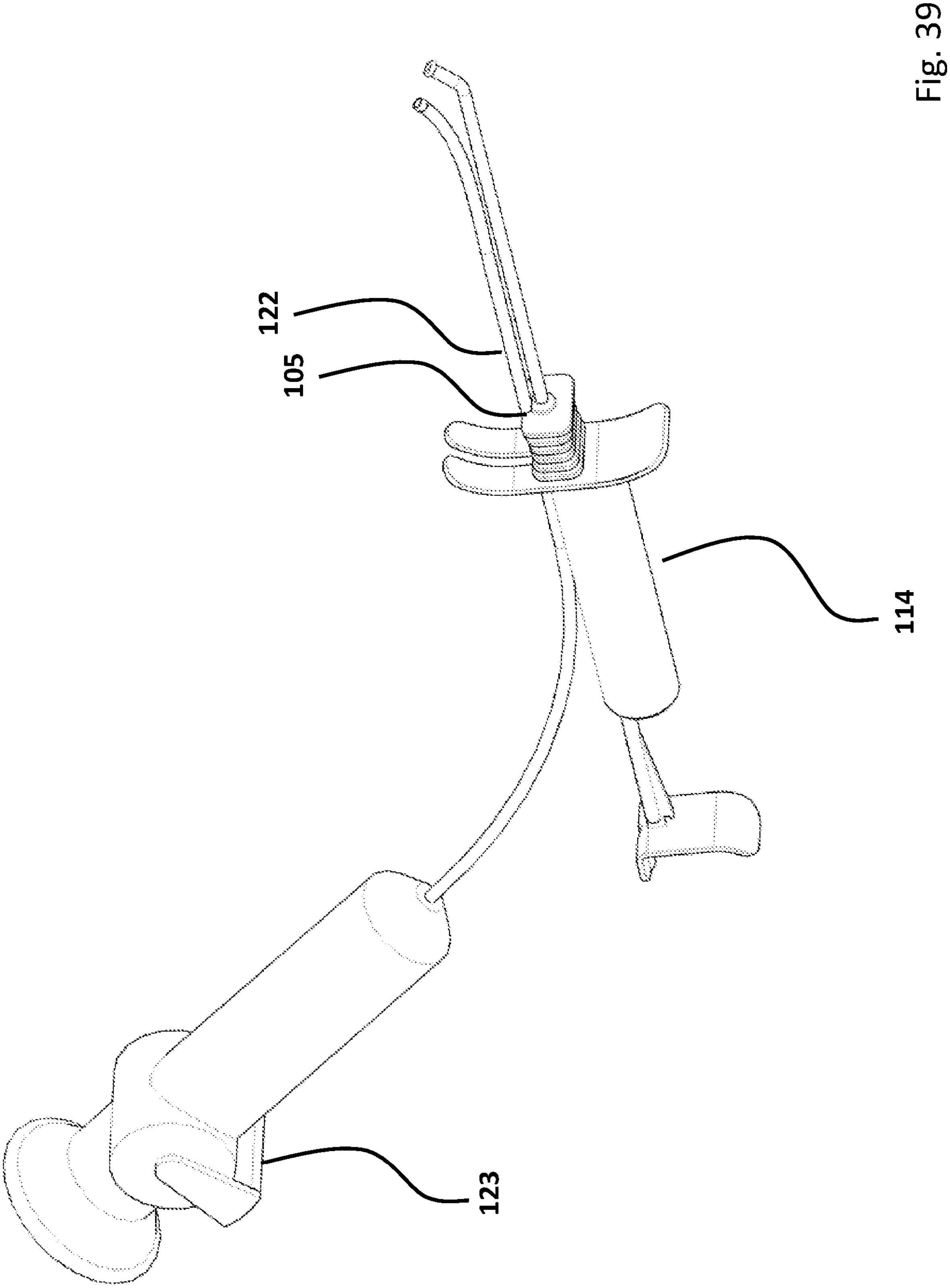
FIG. 39 is a perspective view of the handheld insertion device for balloon dilation of FIG. 37 in combination with a flexible analogue endoscope.

FIG. 39 shows a perspective view of the fifth embodiment of the handheld insertion device 114 in combination with a flexible analogue endoscope 122. The endoscope 122 is not supported sufficiently by the endoscope support means of the device 114 alone. However, the endoscope 122 is fully supported, when the operator has a firm grip on the device 114 pressing a part of the endoscope down against the device body and the bottom of the open slot 109. The operator may use one hand to operate the device 114 and the other hand may support and adjust the proximal part of the flexible endoscope 123.

Figure 40:
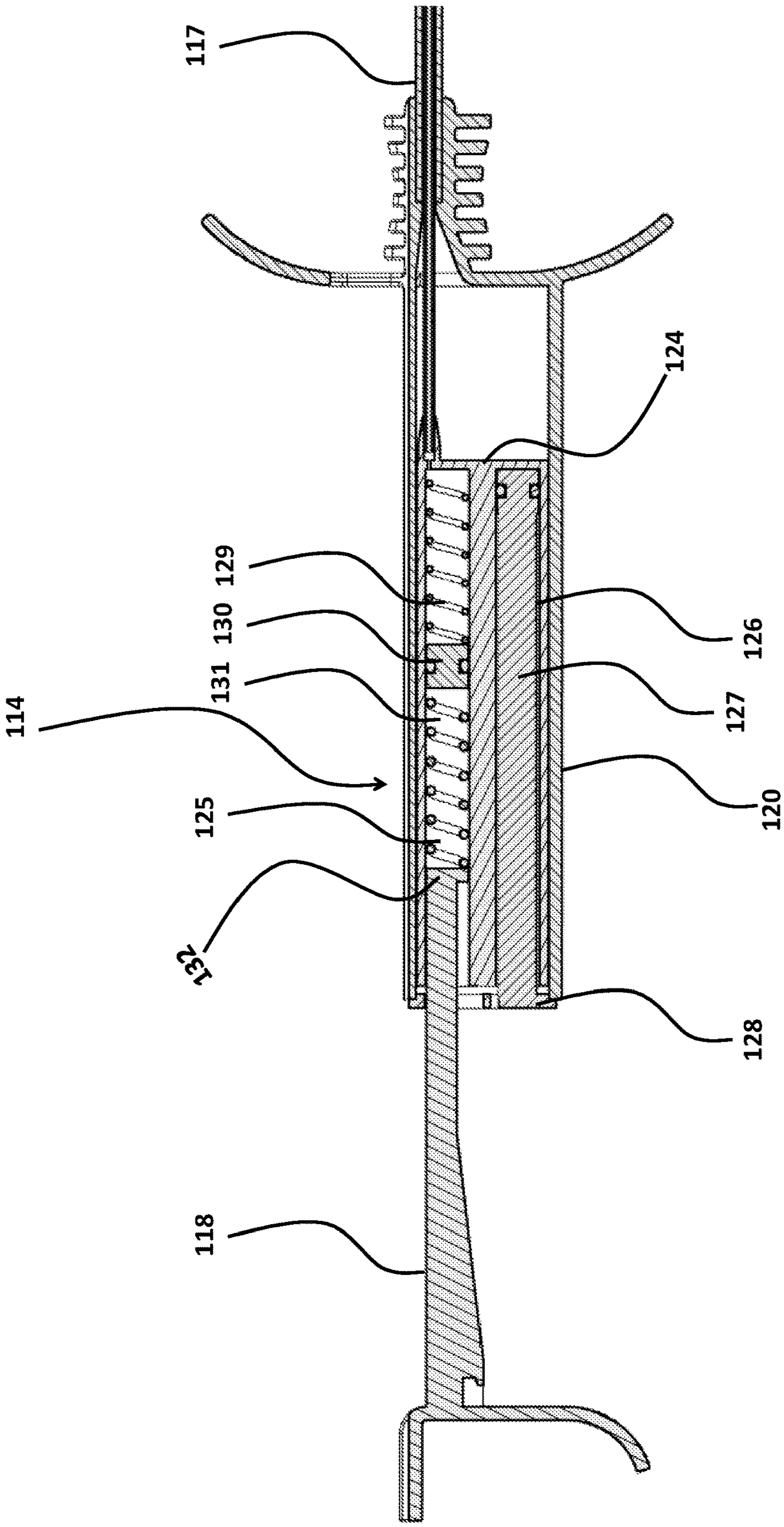
FIG. 40 is a sectional view of the handheld insertion device for balloon dilation of FIG. 37 in a first step, wherein the device is unpacked and ready to use.

FIG. 40 shows a sectional view of this fifth embodiment of the handheld insertion device 114 in a first stage, wherein the device 114 is unpacked and ready to use. A double syringe barrel body 124 is located inside the device body 120 and has guiding means for strictly translatory movements parallel to an axis defined by the cylindrical guide tube 117 and relative to the device body 120. The guiding means may comprise a snug or tight fit of the double syringe body 124 inside the device body 120. The double syringe barrel body 124 comprises an upper syringe barrel 125 prefilled with a specific water volume for balloon pressurization and a lower gas spring syringe barrel 126. The gas spring syringe barrel has a gas spring plunger rod 127 that is connected to and held back by the back-end geometry 128 connected to the rear end of the device body 120. The gas spring assembly provides a spring return functionality such that the operator no longer needs to pull back the actuation member for retraction of the balloon. Any change in force direction during pushing and pulling on an actuation member will result in movement of the overall device and will result in discomfort for the patient. Furthermore, it can be challenging to make a pulling motion with the thumb if the device is not suited well for the size of the hand of the operator. For these reasons, it is much better for the operator and for the procedure if the actuation member has a spring back function. As illustrated in this embodiment, the gas spring 126 is arranged to be a vacuum gas spring as this provides a preferred characteristic for the spring. The upper syringe barrel 125 contains a front spring 129, a sealing member 130, and a rear spring 131. The plunger rod 118 has an interface 132 against the rear spring 131 and transfers the force applied by the operator to one end of said rear spring 131. In the assembled and prepared device, the springs are pre-tensioned by the plunger rod 118 which is held in a position relative to the double syringe barrel 114 causing this pretension of both springs. The gas spring 126 requires significantly less force to fully retract compared to the force required to further compress the pre-tensioned springs 129, 131. The front spring 129 has a significantly lower stiffness compared to the rear spring 131.

Figure 41:
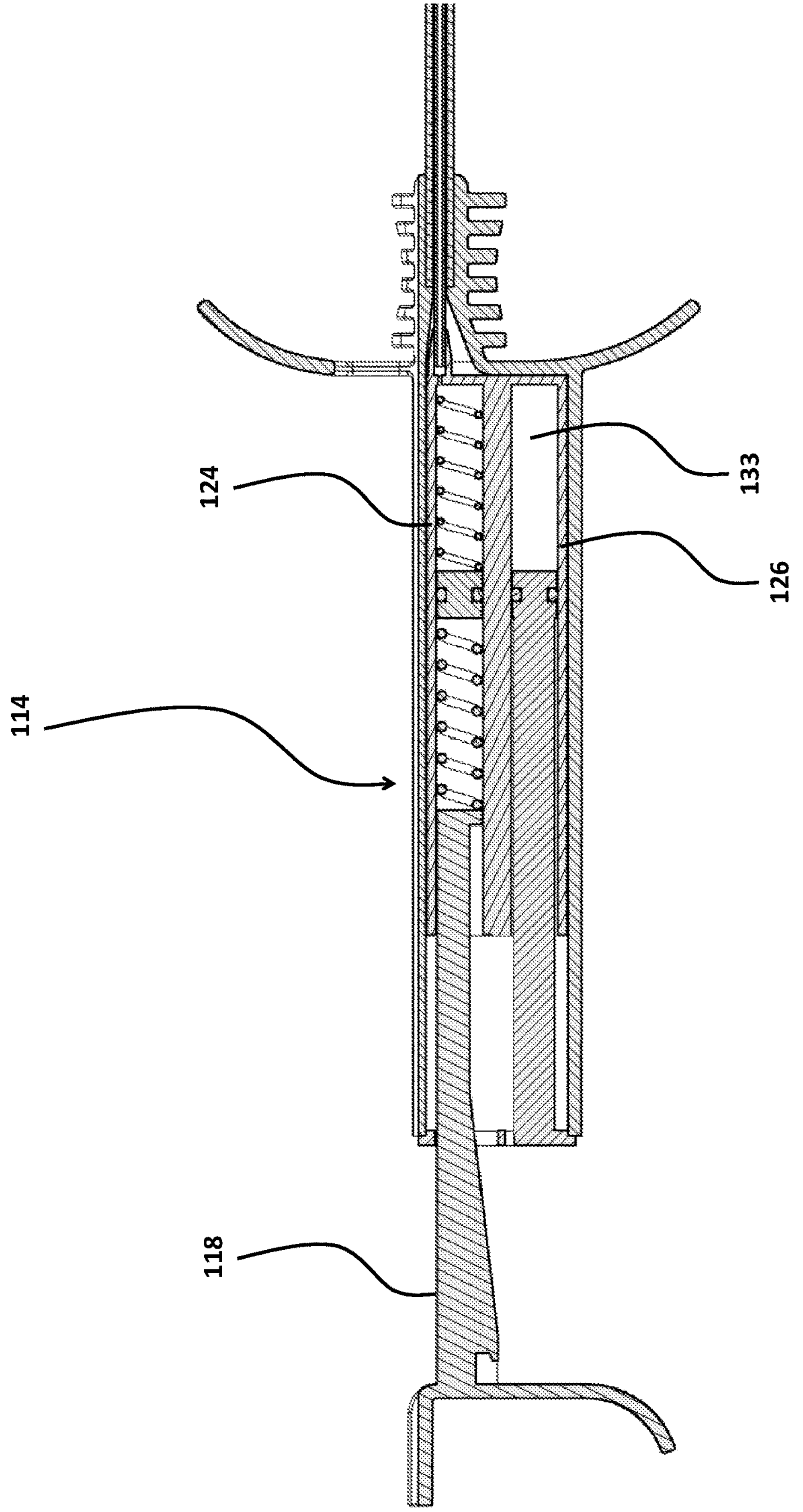
FIG. 41 is a sectional view of the handheld insertion device for balloon dilation of FIG. 37 in a second step, wherein the balloon catheter has moved from a first position to a second position.

FIG. 41 shows a sectional view of this fifth embodiment of the handheld insertion device 114 in a second stage, wherein the plunger rod 118 and the double syringe barrel body 124 assembly are moved forward to an end-position corresponding to a fully advanced balloon. A vacuum volume 133 is created inside the gas spring syringe 126 and a release of the plunger rod 118 will thereby cause a retraction of the assembly and a retraction of the balloon. This may be repeated several times until the balloon is advanced in the correct location.

Figure 42A:
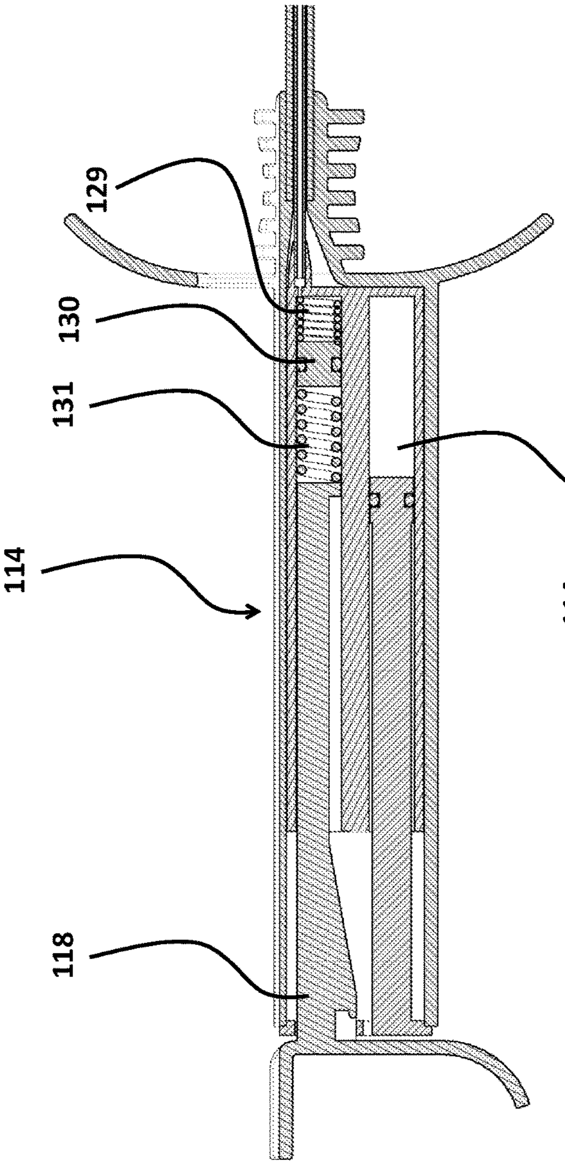
FIG. 42A is a sectional view of the handheld insertion device for balloon dilation of FIG. 37 in a third step, wherein the actuation member is pushed forward to an end stop.

FIG. 42A shows a sectional view of this fifth embodiment of the handheld insertion device 114 in a third stage, wherein the plunger rod 118 is pushed all the way to an end stop position. In this end stop position, the balloon is fully inflated and pressurized and the front spring 129 and the rear spring 131 are both compressed. At any time can the operator release the force on the plunger rod 118 to revert to previous stages. The stiffest spring in the system will always be decompressed first when the compression force is gradually released. When releasing the force, the rear spring 131 will be decompressed to release the pressure in the balloon, and at a further release of force, the front spring 129 will decompress, pushing back the sealing element 130 to pull out the liquid from the balloon, and at a further release of force, the gas spring 126 will revert to its original position and will retract the balloon. It is important that the balloon is deflated prior to retraction as the balloon needs to be fully deflated to re-enter the guiding tube.

Figure 42B:
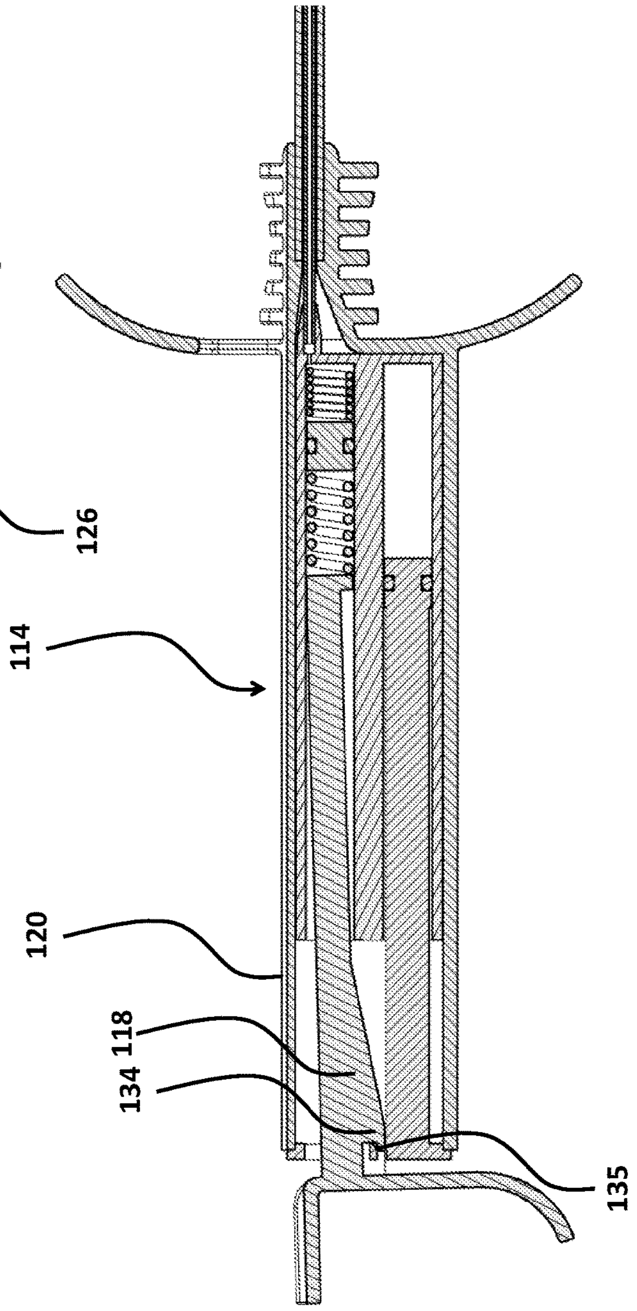
FIG. 42B is a sectional view of the handheld insertion device for balloon dilation of FIG. 37 in a fourth step, wherein the actuation member is locked in a final position relative to the device body corresponding to a fully inflated and pressurized balloon.

FIG. 42B shows a sectional view of the fifth embodiment of the handheld insertion device 114 in a fourth stage, wherein the plunger rod 118 is locked in a final position relative to the device body 120. In this embodiment, the locking feature 134 requires the operator to make a slight downward movement of the plunger 118 to wiggle it into an angle where it can interlock with the end-cap 135 that is rigidly connected to the device body 120. For release of the plunger rod 118, the operator may push and lift the plunger rod 118 upwards. When the operator has to press the spring-loaded plunger rod 118 prior to releasing the lock, there will be no sudden release of energy resulting in sudden movements or sudden noises.

Figure 43:
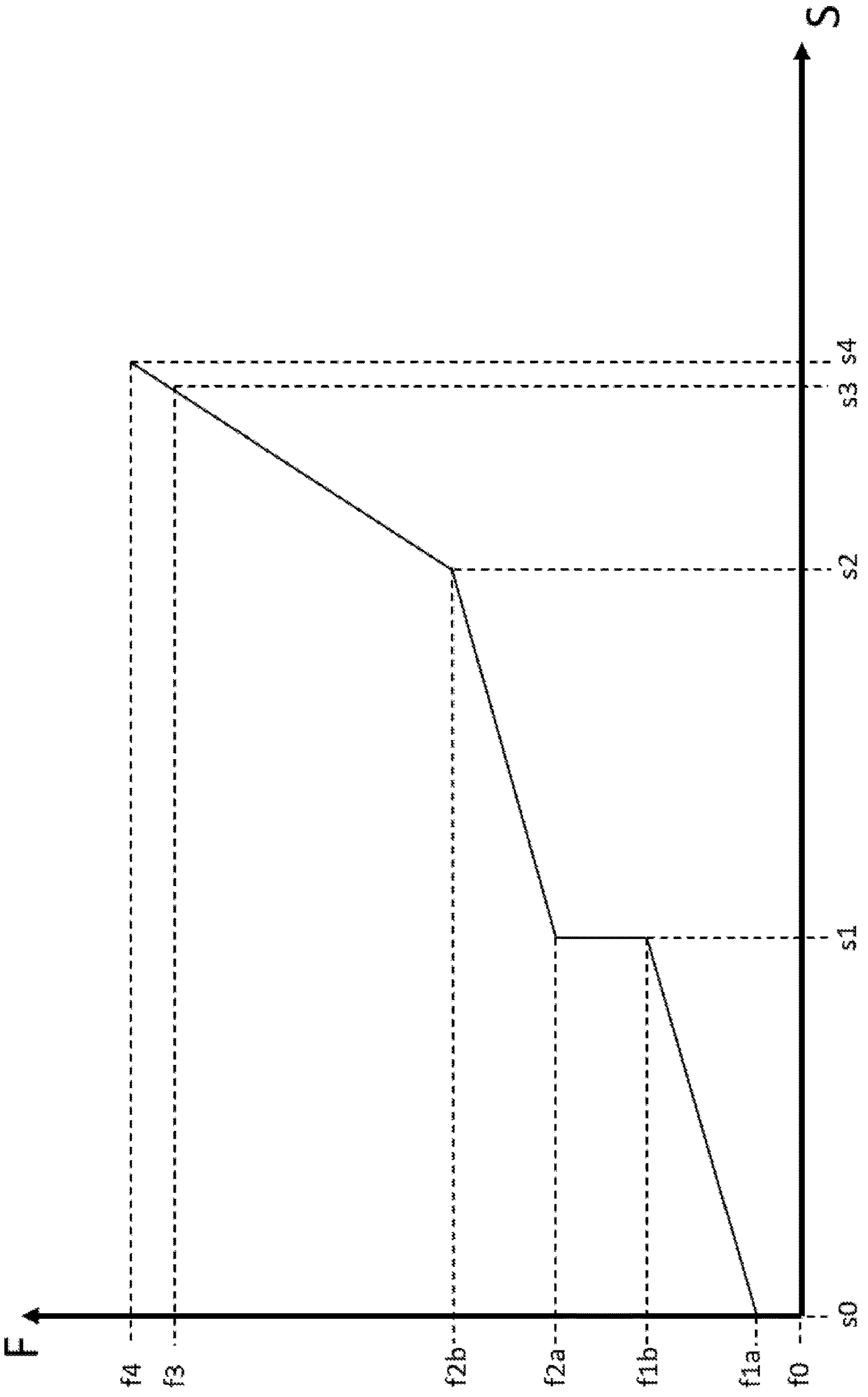
FIG. 43 shows a graph of the relationship between applied force on the actuation member and the travel distance of the actuation member relative to the device body and describes the he handheld insertion device for balloon dilation of FIG. 37.

FIG. 43 shows a graph of the relationship between applied force on the plunger rod and the travel distance of the plunger rod relative to the device body and describes the fifth embodiment of the handheld insertion device. An initial force f1*a* is required to start moving the plunger rod and due to the gas spring, the required force will gradually increase as a function of the stiffness of the spring. Force f1*b* will be required to reach position s1 where the balloon is fully advanced. A much higher force f2*a* will be needed for further movement. The difference between f1*b* and f2*a* acts as tactile feedback for the operator to know that the balloon is fully advanced, and to ensure that the balloon is not inflated prematurely. The operator may release the force on the plunger rod to retract the balloon at any time. Applying force f2*a* will initiate the inflation of the balloon but the front spring element needs to be compressed for further movement and the force needed will be a function of the stiffness of the front spring. When force f2*b* is applied to the plunger rod, the actuation member has moved to position s2 and the balloon is fully inflated but not pressurized. Applying further force will initiate pressurization of the balloon and at position s4 and force f4, the plunger rod is at its end position and can move no further. This acts as a safety precaution to avoid rupture of the balloon. When the operator moves the plunger rod back to the locked position s3, the required and correct force f3 provides the correct pressure in the balloon. After successful dilation, the operator may unlock the plunger rod and gradually release the applied force for de-pressurization, deflation, and retraction of the balloon. The procedure may conveniently and promptly be repeated on the other side or for other anatomic passageways on the same patient. All other prior art devices are made for only one-sided procedures and cannot easily be reused.

FIGS. 44-47 show a sixth embodiment of the handheld insertion device. In this embodiment, the syringe barrel and the device body are integrated into one single body and represent the most compact and low-cost device design. The device has a unique hydraulic lock that prevents premature inflation of the balloon during advancement and retraction of the balloon. This embodiment of the device may be combined with endoscope support features as seen in other embodiments and may be combined with a spring element to avoid pressure gauge and ratchet lock as for other embodiments.

Figure 44:
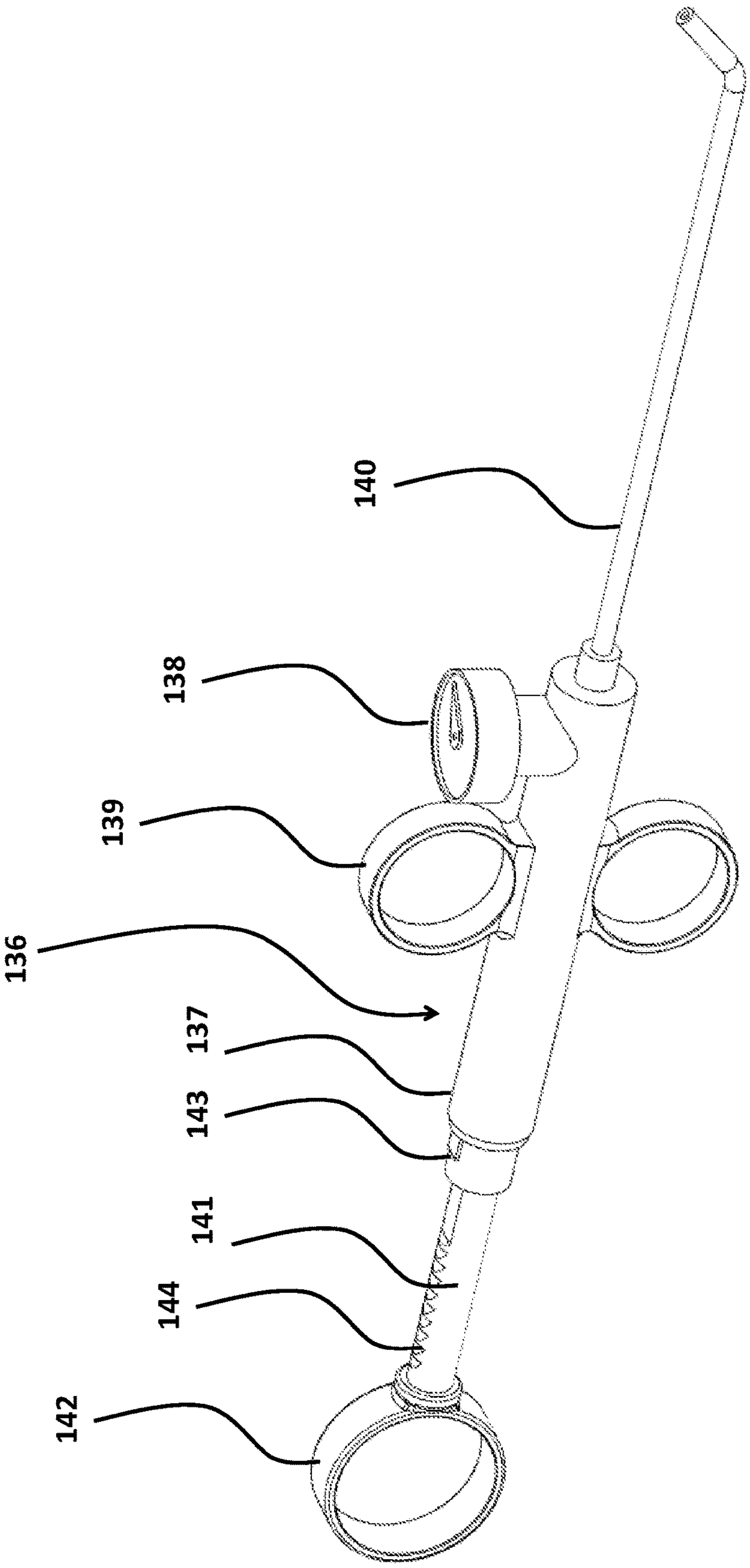
FIG. 44 is a perspective view of the sixth embodiment of the handheld insertion device for balloon dilation.

FIG. 44 shows a perspective view of this sixth embodiment of the handheld insertion device 136 in a first stage where it is unpacked and ready to use. The device body 137 has a threaded interface to fit a pressure gauge 138. The device body 137 has ring-shaped finger engagement interfaces 139 for two fingers. The guiding tube 140 is fixed rigidly to the front of the device body 137. A plunger rod 141 is connected to a ring-shaped thumb engagement interface 142 at the proximal end while the distal end of the plunger rod holds a sealing element that seals against the inside of the integrated syringe barrel in the device body 137. A locking element 143 is rigidly attached to the end of the device body and serves the purpose of guiding the plunger rod 141 as well as having a ratchet lock interface 144 against the plunger rod 141.

Figure 45:
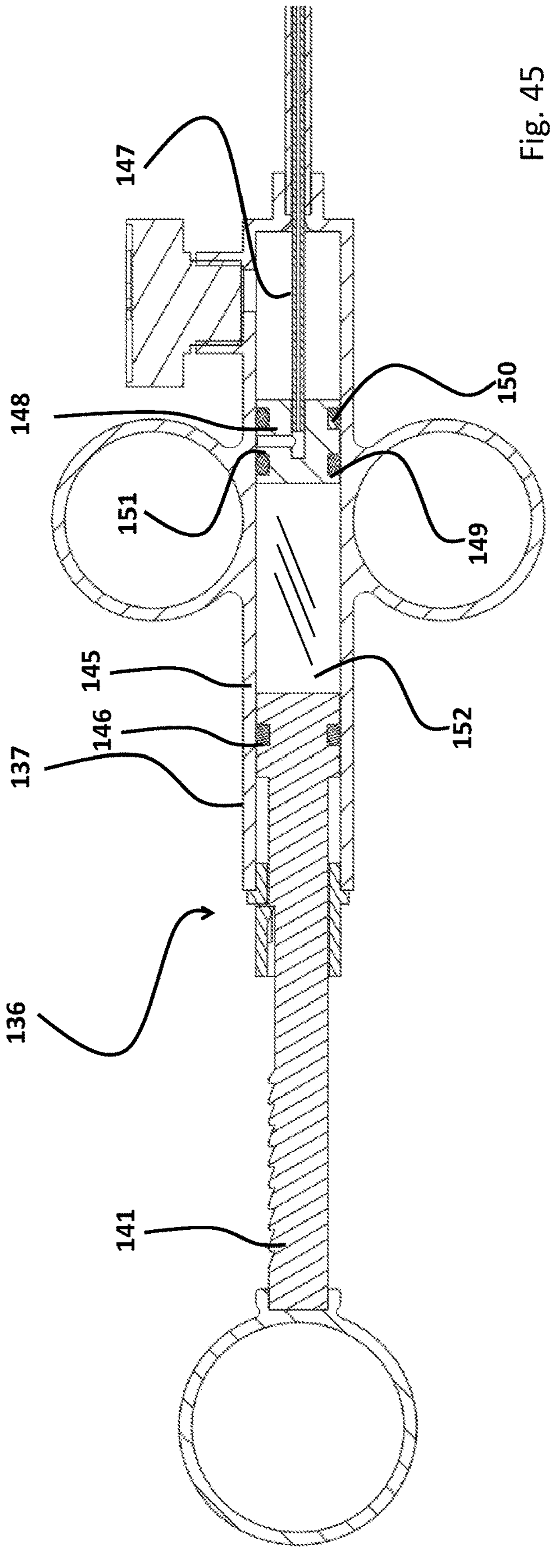
FIG. 45 is a sectional view of the handheld insertion device for balloon dilation of FIG. 44 in a first step and primary configuration where the device es unpacked and ready to use.

FIG. 45 shows a sectional view of this sixth embodiment of the handheld insertion device 136 in a first stage where it is unpacked and ready to use, i.e. in a primary configuration. Inside the device body 137, is a cylindrical cavity acting as an integrated internal syringe barrel 145. The plunger rod 141 has a sealing element 146 for sealing inside the syringe barrel 145. The proximal end of the balloon catheter 147 is connected directly to a dual seal element 148 placed inside the internal syringe barrel 145. The dual seal element 148 has two sealing rings, a rear sealing ring 149 towards the plunger rod, and a front sealing ring 150 towards the guiding tube. A fluid connection channel 151 placed between the two sealing rings connects the outer circumference of the sealing element 148 with the lumen of the balloon catheter 147.

In this first stage, there is a prefilled liquid 152 between the plunger rod sealing element 146 and the dual seal element 148, this confined volume being completely enclosed and sealed from ambient air. Any movement of the plunger rod 141 will result in a corresponding movement of the dual seal element 148 and thereby a corresponding movement of the balloon catheter 147 as forces are transferred through the incompressible prefilled liquid 152.

Figure 46:
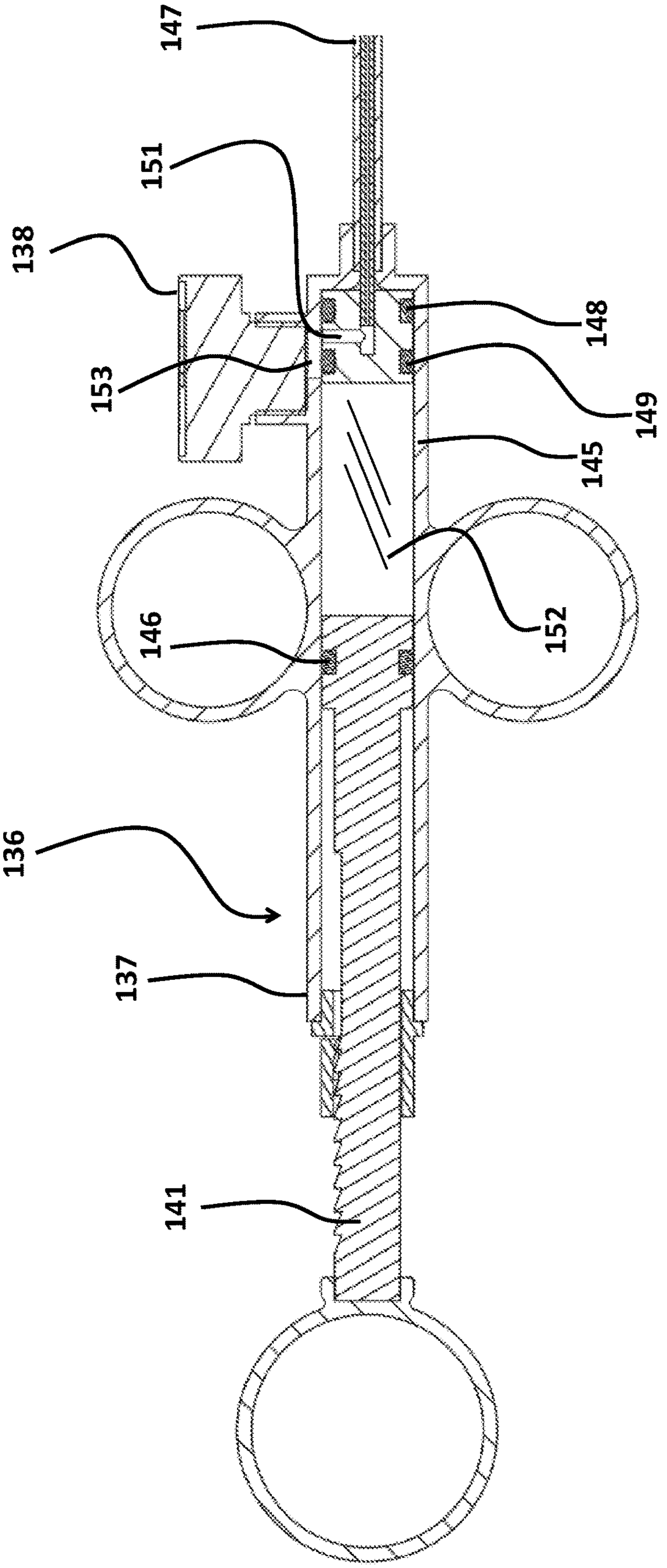
FIG. 46 is a sectional view of the sixth configuration of the handheld insertion device for balloon dilation of FIG. 44 in a second step and secondary configuration, where the balloon catheter has moved from a first position to a second position.
Figure 47:
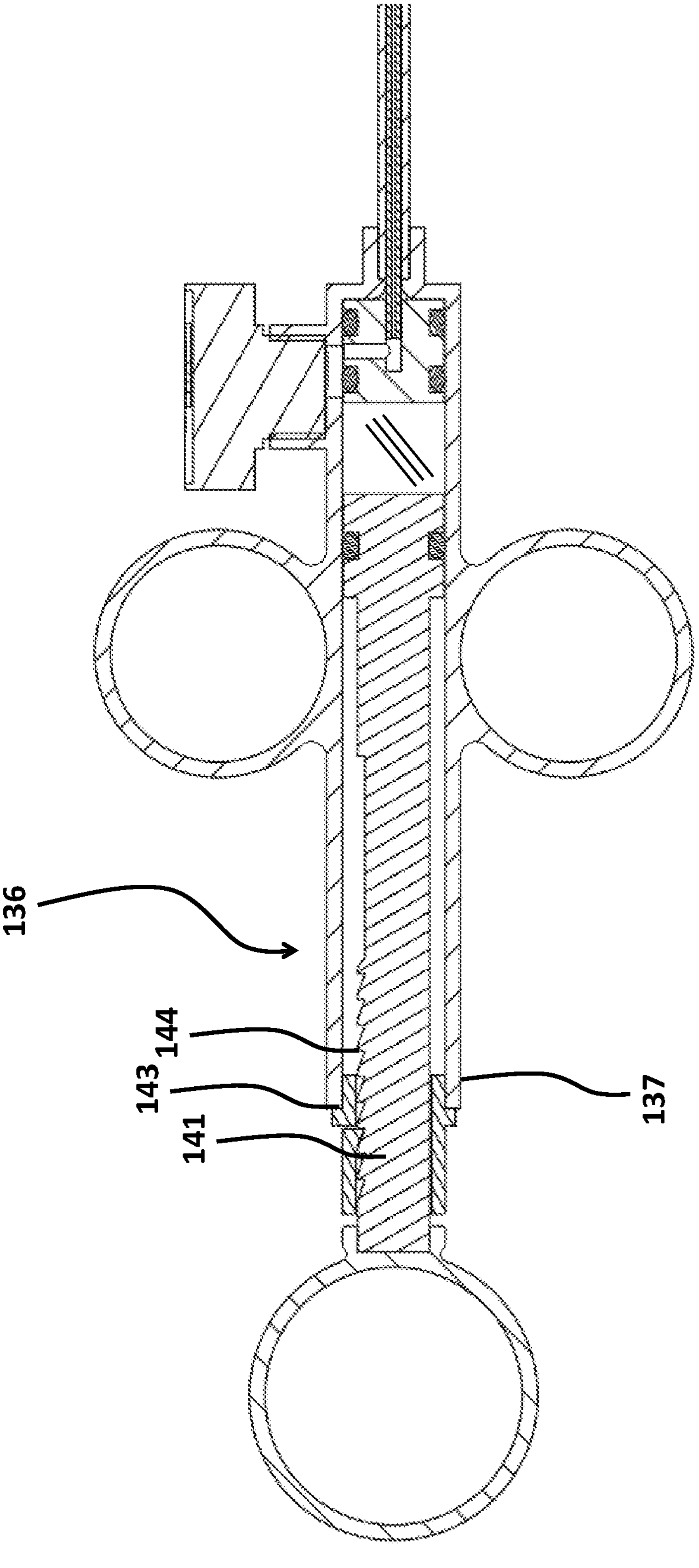
FIG. 47 shows a sectional view of the handheld insertion device for balloon dilation of FIG. 44 in a third step and tertiary configuration, where the plunger has been moved forward to a final locked position in which the balloon is fully inflated and pressurized.

FIG. 46 shows a sectional view of this sixth embodiment of the handheld insertion device 136 in a second stage i.e. in a secondary configuration, where the plunger 141 has been pressed into the device body 137 until the dual seal element 148 has reached an end stop at the bottom of the internal syringe barrel 145 and where the balloon is fully advanced. In this position of the dual seal element 148, the rear seal ring 149 has passed a groove 153 in the inner wall inside the internal syringe barrel 145 such that prefilled liquid 152 may pass from the volume between the plunger seal 146 and the rear seal ring 149 and into the fluid connection channel 151 of the dual seal element 148 and further into the lumen of the balloon catheter 147. In fact, when the dual seal element 148 is in the bottom position, the liquid volume 152 is connected to the balloon catheter 147 and any further movement of the plunger rod 141 will result in filling of the balloon. In previous embodiments, differences in applied forces were the method of avoiding premature filling of the balloon during movement of the balloon. In this embodiment, a hydraulic lock prevents any filling of the balloon before the balloon is fully advanced. For manufacturing purposes, it may be advantageous to combine the position of the grove 151 with the threaded interface for the pressure gauge 138.

FIG. 46 shows a sectional view of this sixth embodiment of the handheld insertion device 136 in a third stage, where the plunger rod 141 has been moved forward to a final position in which the balloon is fully inflated and pressurized i.e. in a third configuration. The ratchet interface 144 on the plunger rod 141 and the locking element 143 lock the position of the plunger 141 relative to the device body 137 and hold the pressure throughout the procedure. The operator may monitor the pressure and readjust the pressure if needed. For disengagement of the ratchet lock, the plunger 141 may be rotated 90 degrees. The device is not reusable in this embodiment.

Figure 48:
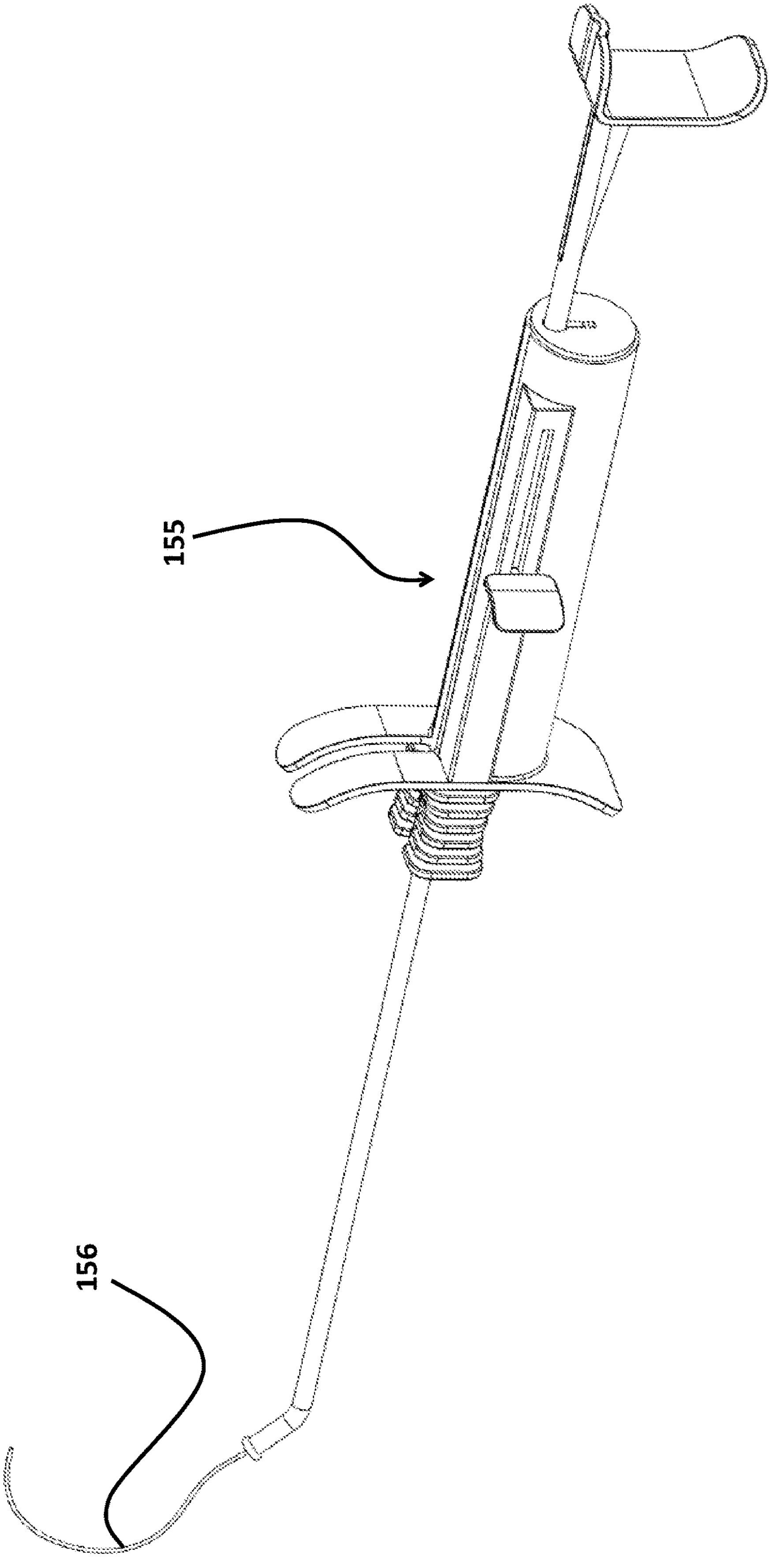
FIG. 48 shows a perspective view of a seventh embodiment of the handheld insertion device for balloon dilation similar to the fifth embodiment in which the device further comprises an illuminating guidewire.

FIG. 48 shows a perspective view of a seventh embodiment of the handheld insertion device 155 similar to the fifth embodiment in which the handheld insertion device further comprises an illuminating guidewire 156 used to confirm the placement prior to advancement and inflation of the balloon. Such a guidewire 156 feature may be preferred for dilation of any sinus passageways. In such an embodiment, the operator would firstly advance the guidewire 156 into the sinus cavity for placement confirmation, and then secondly advance the balloon out and around the guidewire 156 before inflation and pressurization. Guidewires on insertion instruments are well known and widely used but would be a mandatory and unique part of the fully integrated handheld insertion device 155 if used on sinus dilations. The guidewire feature 156 could be combined with any preceding embodiments.

Figure 49:
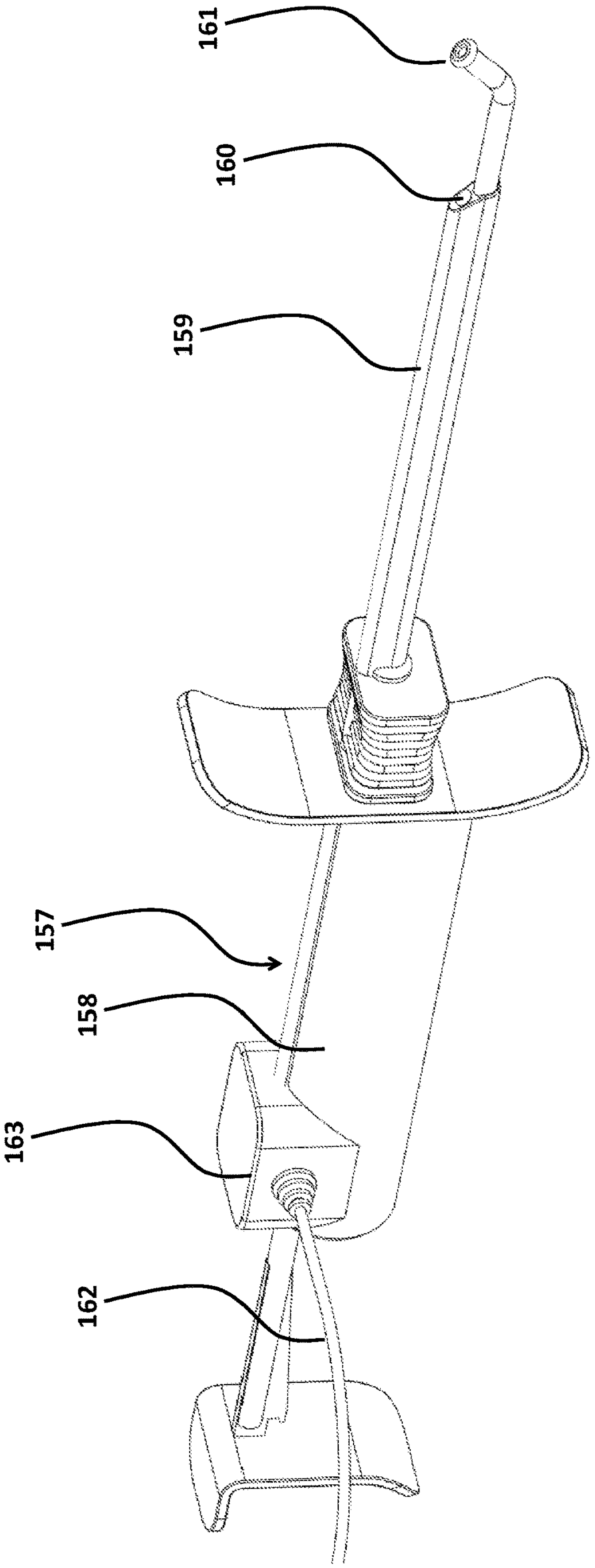
FIG. 49 is a perspective view of an eighth embodiment of the handheld insertion device for balloon dilation similar to the fifth embodiment in which the device body has an integrated digital endoscope with a camera lens.

FIG. 49 shows a perspective view of an eighth embodiment of the handheld insertion device 157 similar to the fifth embodiment in which the device body 158 has an integrated digital endoscope 159 with an image sensor 160 placed near the tip of the guiding tube 161 and a cable 162 with a plug coming out from a portion of the device body 158 for connection to a digital monitor. The integration of a digital endoscope 159 can be combined with any preceding embodiments of the device.

Figures 50A, 50B:
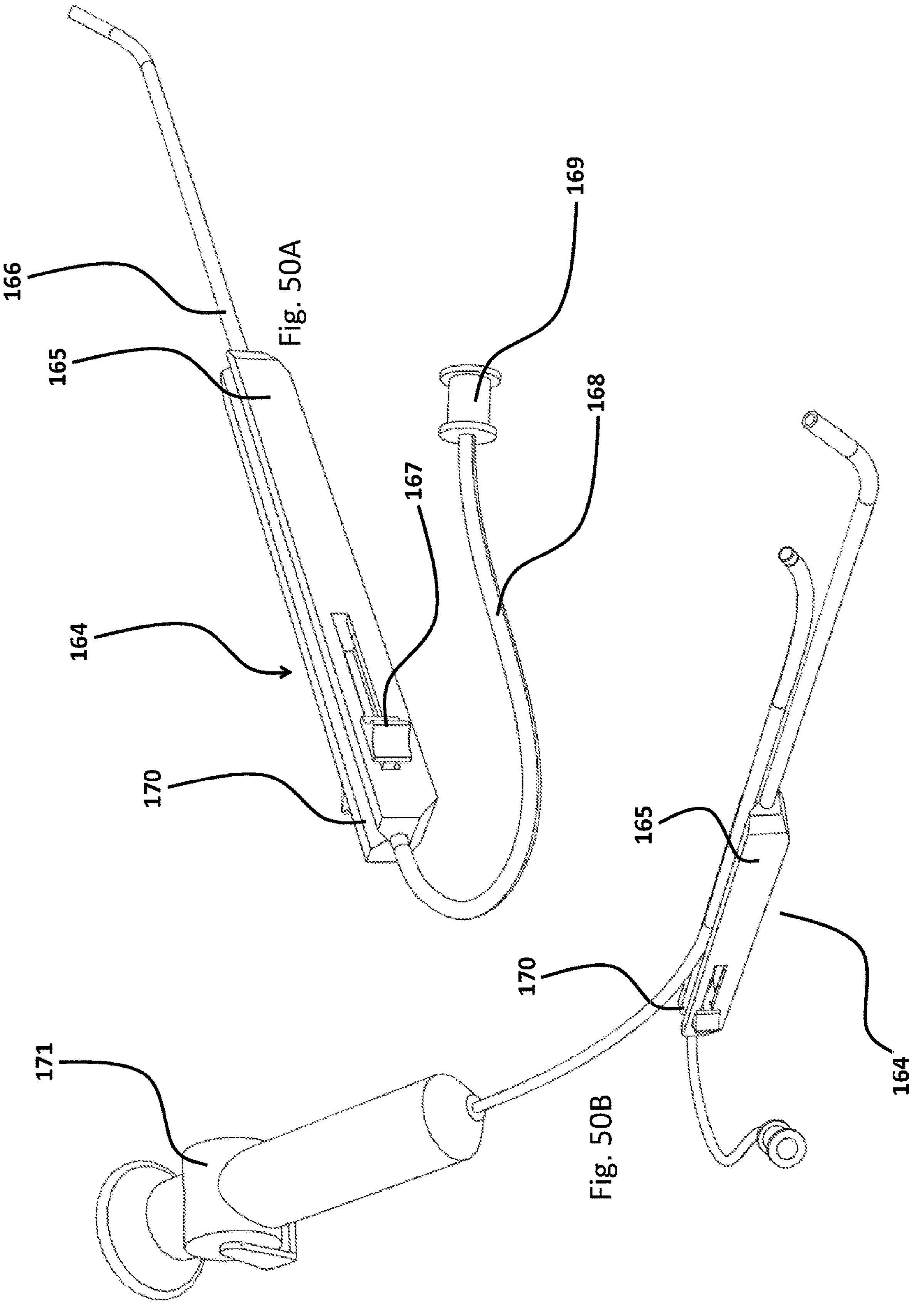
FIG. 50A is a perspective view of a ninth embodiment of the handheld insertion device for balloon dilation.
FIG. 50B shows a perspective view of the handheld insertion device for balloon dilation of FIG. 50A with a flexible endoscope.

FIG. 50A shows a perspective view of a ninth embodiment of the handheld insertion device 164. A device body 165 is connected to a guiding tube 166. A slider 167 placed on the device body 165 is connected to an internal balloon catheter such that forward movement of the slider 167 will move the balloon catheter forward to an advanced position out of the guiding tube 166. A proximal end of the balloon catheter 168 extends out from a hole in the device body 165 and has a connection part 169 for connection with an external pressurization device. The device body 165 has an open groove 170 along one side of the device body 165 parallel to the guiding tube 166 for partly supporting an endoscope. The open groove 170 is in this example shaped as a "V" and has a depth to support at least the lower ⅓ of a cylindrical element having a diameter of 3-4 mm. such as the thin cylindrical flexible part of a flexible endoscope or a thin cylindrical stiff part of a static endoscope. The open groove forms a substantially straight track that is configured for supporting and guiding part of the cylindrical shaft of a static or flexible endoscope and may have other shapes and sizes.

FIG. 50B shows a perspective view of this ninth embodiment of the handheld insertion device 164 and depicts an endoscope 171 placed in conjunction with the open groove 170 of the device body 165. Is it obvious that an endoscope is not fully supported by the open groove 170 on the device body 165 alone, but the endoscope will be fully supported when an operator, with one hand, has a firm grip on the device body 165 while pressing part of the cylindrical thin part of the endoscope 171 down against the open groove 170 while the other hand supports the proximal part of the endoscope. An assistant may operate a connected separate pressurization device.

Figures 51A, 51B:
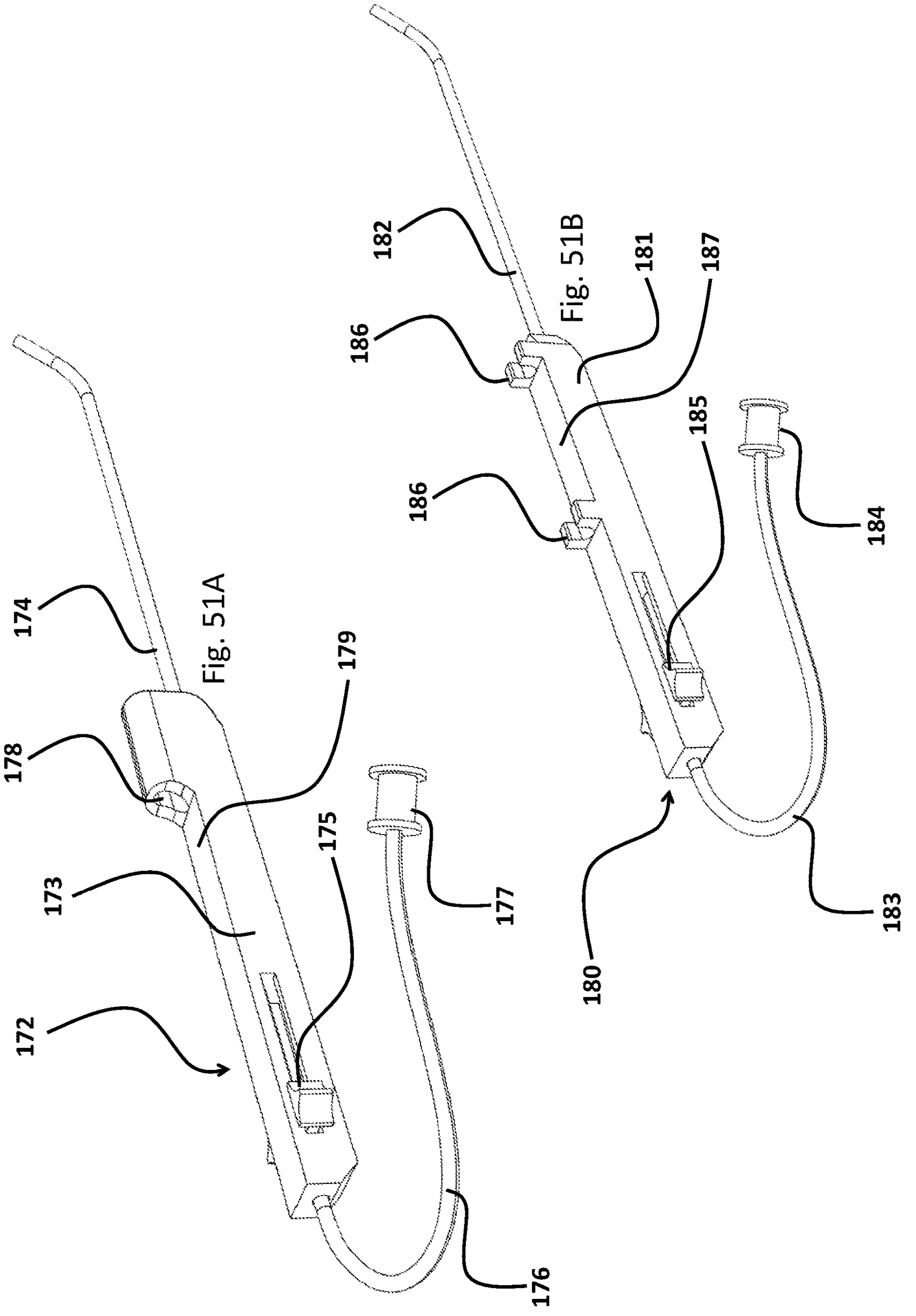
FIG. 51A is a perspective view of a variation of the ninth embodiment.
FIG. 51B is a perspective view of another variation of the ninth embodiment.

FIG. 51A shows a perspective view of the ninth embodiment of the handheld insertion device 164, but with other means for endoscope support. A device body 173 is connected to a guiding tube 174. A slider 175 placed on the device body 173 is connected to an internal balloon catheter such that forward movement of the slider 175 will move the balloon catheter forward to an advanced position out of the guiding tube 174. A proximal end of the balloon catheter 176 extends out from a hole in the device body 173 and has a connection part 177 for connection with an external pressurization device. The device body 173 has a tubular hole 178 placed on the top side and at the distal end towards the guiding tube 174. The tubular hole in this example has a width of 5 mm a height of 10 mm and a length of 25 mm, but the tubular hole may have other sizes and shapes. Most importantly, the tubular hole is wider than 4 mm and higher than 4 mm and has a length longer than 10 mm. The thin cylindrical part of a flexible or static endoscope may be inserted into the tubular hole to partly support the endoscope. The tubular hole is bigger than the thin cylindrical part of endoscopes that have diameters of 3-4 mm and does not fully support an endoscope. The length of the tubular hole provides angular restriction for the endoscope and keeps it parallel to the guiding tube. The operator may insert an endoscope through the tubular hole to a desired position where the field of view covers the tip of the guiding tube 174 and the operator may hold the device body with one hand while pressing part of the endoscope down against the top surface 179 of the device body 173 with one or more fingers or part of the hand for fully supporting the endoscope in the desired position. The tubular hole forms a substantially straight track that is configured for supporting and guiding part of the cylindrical shaft of a static or flexible endoscope.

FIG. 51B shows a perspective view of a variation of the ninth embodiment, but with other means for endoscope support. A device body 181 is connected to a guiding tube 182. A slider 185 placed on the device body 181 is connected to an internal balloon catheter such that forward movement of the slider 185 will move the balloon catheter forward to an advanced position out of the guiding tube 182. A proximal end of the balloon catheter 183 extends out from a hole in the device body 181 and has a connection part 184 for connection with an external pressurization device. The device body 181 has two forks 186 placed with a distance of approximately 50 mm, the forks having a centered gap with a width of 5 mm. The thin cylindrical part of a flexible or static endoscope may be placed in the gap between the two fingers of the forks such that the tip of the endoscope is positioned adjacent to the tip of the guiding tube 182. The operator may place an endoscope between the two fingers of the two forks in a desired position where the field of view covers the tip of the guiding tube 174 and the operator may hold the device body with one hand while pressing part of the endoscope down against the top surface 187 of the device body 181 with one or more fingers or part of the hand for fully supporting the endoscope in the desired position. The two forks 186 form a substantially straight track that is configured for supporting and guiding part of the cylindrical shaft of a static or flexible endoscope.

Figures 52A, 52B, 52C:
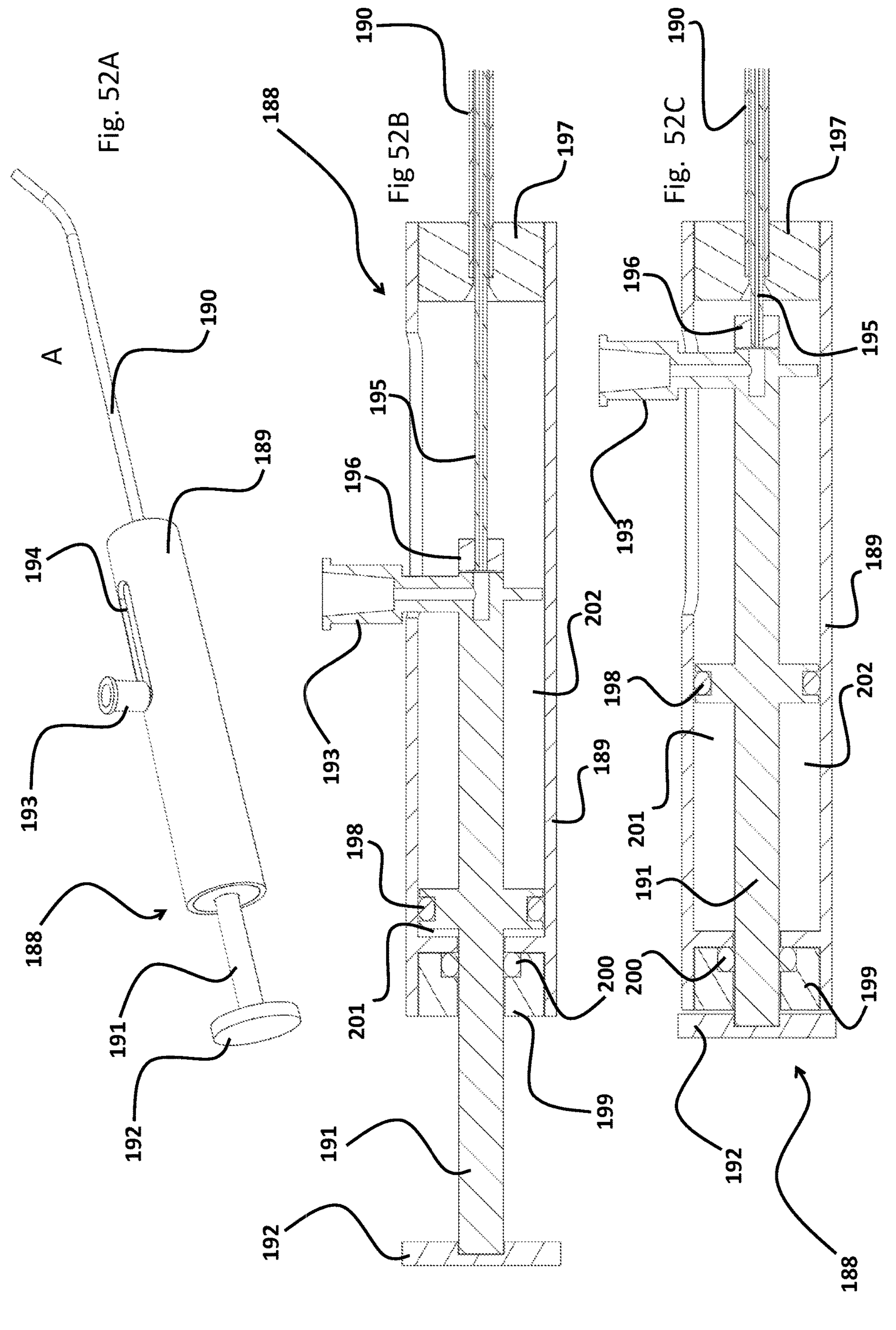
FIG. 52A is a perspective view of a tenth embodiment of the handheld insertion device for balloon dilation.
FIG. 52B is a sectional view of the handheld insertion device for balloon dilation of FIG. 52A in a primary configuration where the balloon catheter is in a first position fully concealed inside the guiding tube.
FIG. 52C is a sectional view of the handheld device for balloon dilation of FIG. 52A in a secondary configuration where the balloon catheter is in a second position fully advanced out of the tip of the guiding tube.

FIG. 52A shows a perspective view of a tenth embodiment of the handheld insertion device. A balloon insertion device 188 has a device body 189 connected to a guiding tube 190 into which a balloon catheter 195 is inserted. An advancement actuator 191 connected with a thumb engagement interface 192 is placed partly inside the device body 189 and is connected to the balloon catheter 195 for advancement and retraction of the balloon catheter 195. A fluid connection port 193 protrudes out form the device body 189 through a slot 194 in the device body 189.

FIG. 52B shows a sectional view of the tenth embodiment of the handheld insertion device in a first step, where the balloon in a first position is retracted inside the guiding tube 190. The advancement actuator 191 has a sealing element 198 (e.g. an O-ring) that seals against a cylindrical inner cavity 202. The advancement actuator further seals against a sealing element 200 (e.g. an O-ring) held in place by an end-cap 199. A confined air volume 201 is sealed by the two seals 200 and 198. A balloon catheter 195 is connected to the advancement actuator 191 by the proximal connection part 196. The guiding tube 190 is connected to the device body 189 via a front-cap 197.

FIG. 52C shows a sectional view of a tenth embodiment of the handheld insertion device 188 in a second step, where the balloon in a second position is fully advanced out of guiding tube 190. The advancement actuator 191 is pushed all the way to an end stop for full advancement of the balloon catheter 195. The confined air volume 201 has increased correspondingly and thus has a pressure much lower than ambient pressure. Release of force applied to the advancement actuator 191 will result in a retraction of the actuation member 191 and the balloon catheter 195 as a result of the pressure difference across the sealing element 198. The balloon may be advanced and retracted conveniently without the need to pull with the thumb. Alternating pushing and pulling motion on an insertion device may lead to movements of the device placed partly inside the nose, hence this solution provides a less uncomfortable procedure.

Figures 53A, 53B, 53C:
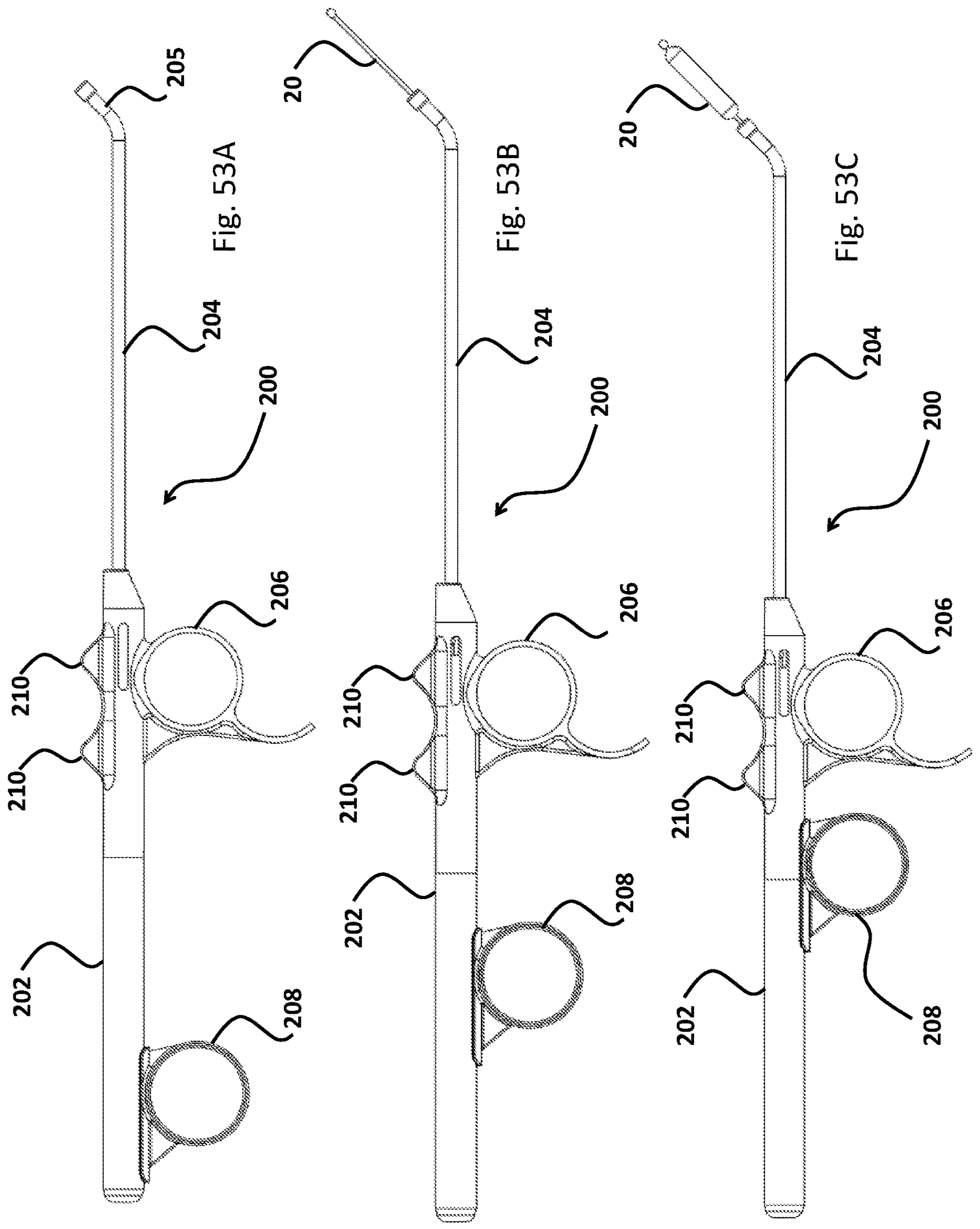
FIG. 53A is a side view of an eleventh embodiment of the handheld insertion device in a primary configuration.
FIG. 53B is a side view of the eleventh embodiment of the handheld insertion device in a secondary configuration.
FIG. 53C illustrates the handheld insertion device 200 of FIG. 53B with the inflatable part of the balloon catheter 20 protruding from the distal end of the insertion device.

FIG. 53A shows an eleventh embodiment of the handheld insertion device 200. In this embodiment the device body 202 is provided with a static handle to 206 that is integral with the device housing 202 for being engaged by one or more fingers of the operator and with a longitudinally displaceable handle 208, which is operably connected to the components inside the device body 202. The balloon catheter guiding tube 204 extends from the device body 202 as a prolongation of the oblong shape of the device body 202. The balloon catheter guiding tube 204 is shown with bent a tip (distal end) 205, but it should be understood that the balloon catheter guiding tube tip 205 could just as well be straight. In FIG. 53A the handheld insertion device 200 is in a primary configuration, with the balloon catheter 20 in the catheter guiding tube 204.

FIG. 53B shows a handheld insertion device 200 of the eleventh embodiment with the inflatable part of the balloon catheter 20 protruding from the distal end of the insertion device, with the inflatable part of the balloon catheter 20 not being inflated. The longitudinally displaceable handle 208 has been pushed forward to an intermediate position by the action of the thumb of the operator, thereby pushing the inflatable part of the balloon catheter 20 out of the catheter guiding tube 204. In FIG. 53A the handheld insertion device 200 is in a secondary configuration, with the inflatable portion distal of the balloon catheter 20 protruding from the catheter guiding tube 204.

FIG. 53C illustrates the handheld insertion device 200 of FIG. 53B with the inflatable part of the balloon catheter 20 protruding from the distal end of the insertion device, with the inflatable part of the balloon catheter 20 being inflated, by the operator having pushed the longitudinally displaceable handle 208 forward from an intermediate position and the device handheld insertion device 200 having assumed a tertiary configuration.

Figures 54A, 54B, 54C:
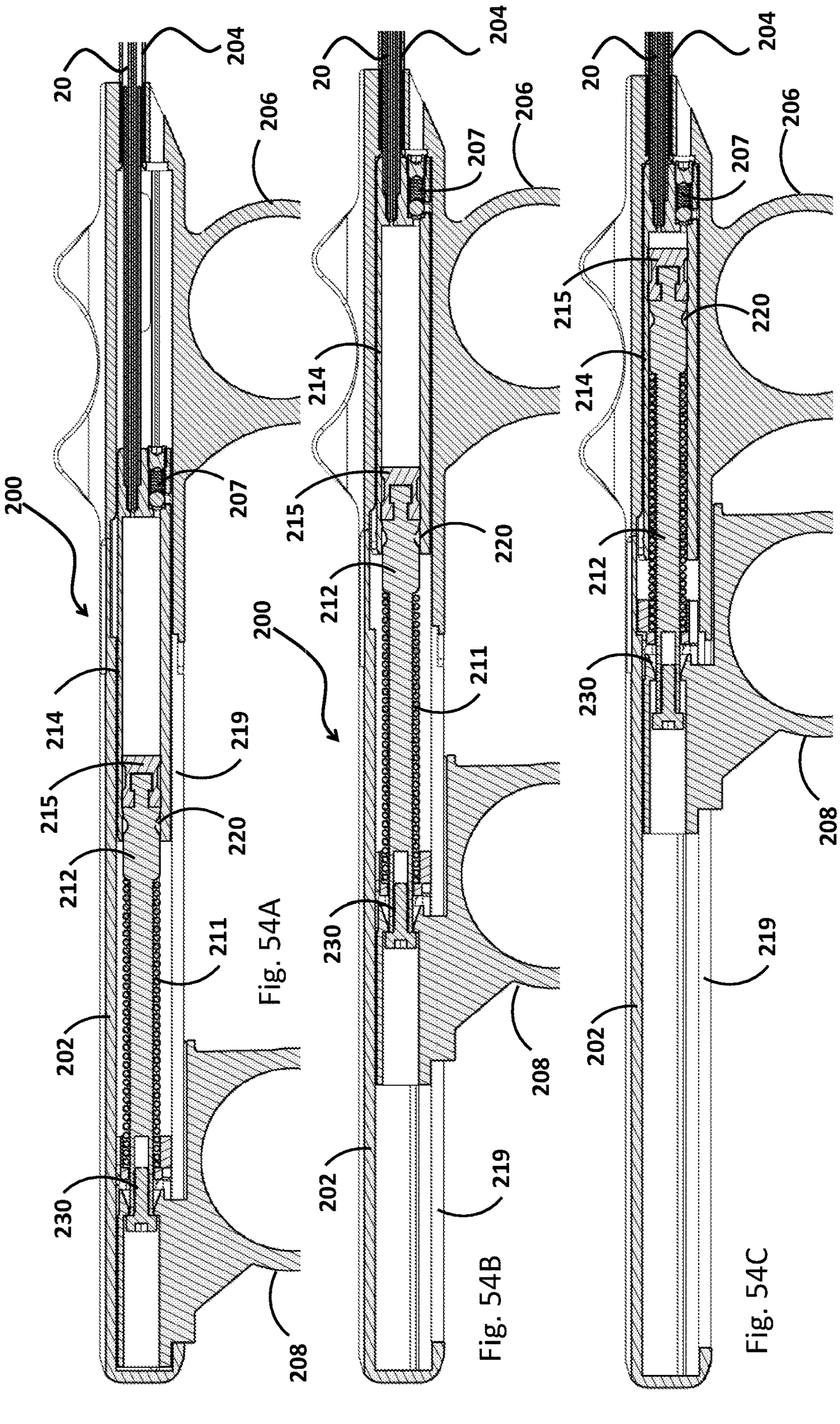
FIG. 54A is a sectional view of an eleventh embodiment of the handheld insertion device in a primary configuration.
FIG. 54B is a sectional view of the eleventh embodiment of the handheld insertion device in a secondary configuration.
FIG. 54C is a sectional view of the handheld insertion device 200 in the tertiary configuration of the device of FIG. 54A.

FIG. 54A is a sectional view of the handheld insertion device 200 in the primary configuration of FIG. 53A. The longitudinally displaceable handle 208 is in its fully retracted position and protrudes from the device body 202 through an elongated slit 219 device body 202. The longitudinally displaceable handle 208 is connected to the plunger rod 212 via a second locking mechanism 230 which in turn acts on the helical spring 211. The longitudinally displaceable syringe barrel 214 is received in the device body 202. The plunger out sooner 12 is in this embodiment provided with a sealing element 215 that sealingly engages the inner surface of the syringe barrel 215. The plunger rod 212 is in a range of positions longitudinal of the syringe 214 relative to the device housing barrel prevented from moving relatively to the syringe barrel 214 by a first locking mechanism 220 (shown in detail in FIG. 55A-C). A pressure relief valve 207 limits the maximum pressure in the syringe barrel and will be described in further detail below.

FIG. 54B is a sectional view of the handheld insertion device 200 in the secondary configuration of FIG. 54B. The longitudinally displaceable handle 208 is an intermediary position, having been pushed this position by the action of an operator on the longitudinally displaceable handle 208. Since the syringe barrel 214 is locked to the plunger rod 212, which in turn is connected to the longitudinally displaceable handle 208 via the helical spring 211, the syringe barrel 214 has moved in unison with the plunger rod 212 towards the distal end of the handheld insertion device 200. The proximal end of balloon catheter 20 is connected to the distal end of the syringe barrel 214 and therefore, the balloon catheter 20 has been advanced and the inflatable part of the balloon catheter 20 now protrudes from the tip of the catheter guiding tube 204. In this position of the syringe barrel 214 relative to the device body 202, the first locking mechanism 220 no longer prevents relative movement between the plunger rod 212 and the syringe barrel 214. Thus, when an operator pushes the longitudinally displaceable handle 208 further towards the distal end of the handheld insertion device 200, the plunger rod 212 will move into the syringe barrel 214 and force the water in the syringe barrel into the balloon catheter 20, thereby inflating the balloon catheter 20.

This is shown in FIG. 54C and the handheld insertion device 200 has now assumed its tertiary configuration.

Figures 55A, 55B, 55C:
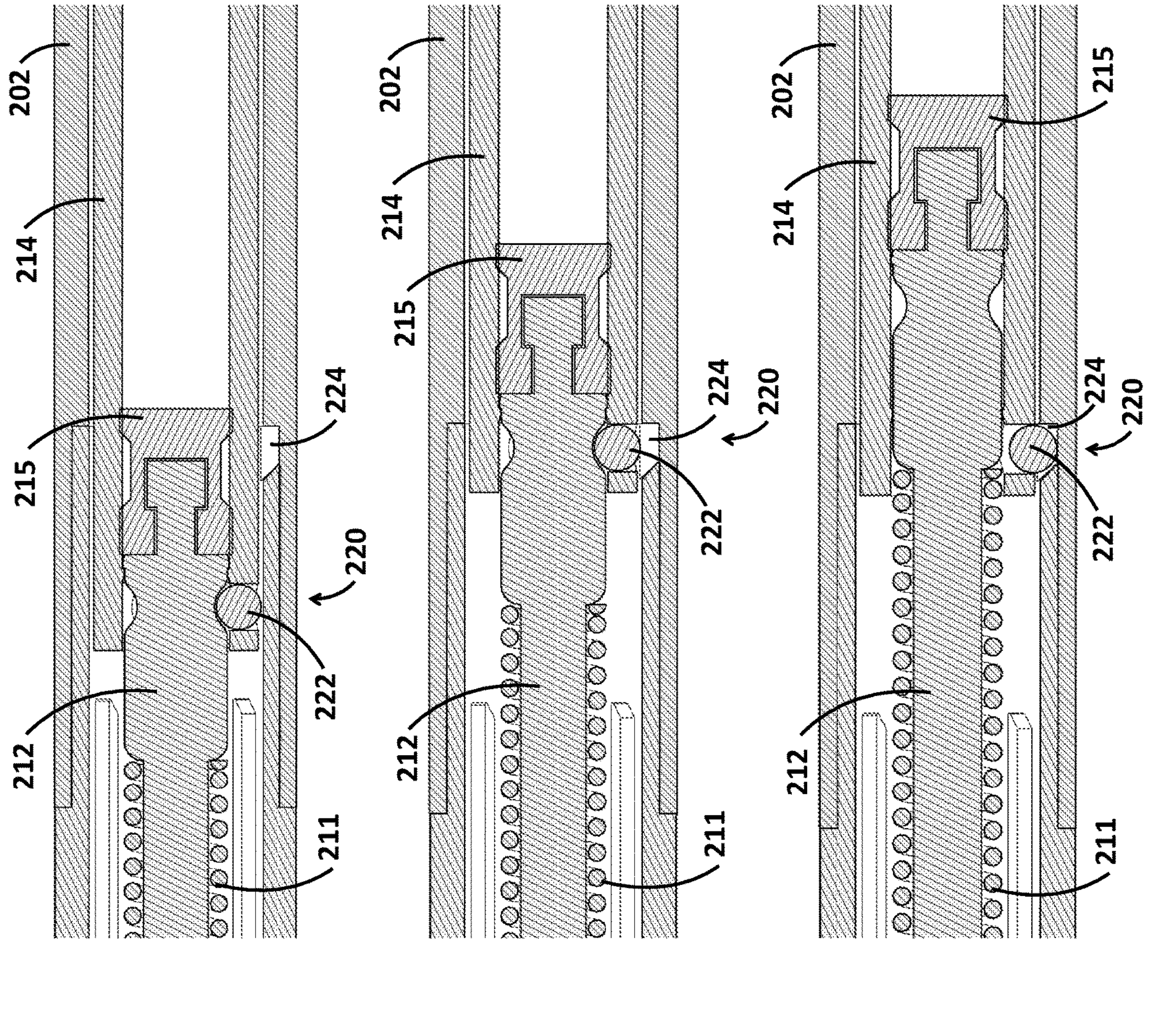
FIGS. 55A-C are detailed sectional views of a first locking mechanism used in the eleventh embodiment of the handheld insertion device in various states.

FIG. 55A shows the first locking mechanism 220 in greater detail with the handheld insertion device 200 in the first configuration. A locking member 222, in this embodiment the ball-shaped locking member, is received in a radial bore syringe barrel 214 with a portion of the locking member 222 protruding into an annular groove in the plunger rod 212. In all but one longitudinal position of the syringe barrel 214 relative to the device body 202 the locking member 222 cannot disengage from the annular groove in the plunger rod 212, except when the syringe barrel 214 is fully forwarded to the distal end of the device body 202 where the position of the locking member 222 coincides with the recess 224 in the device body 202 that allows the locking member 222 to move radially outward into the device body 202 to thereby disengage the annular groove in the plunger rod 212 as shown in FIG. 55B. FIG. 55C illustrates the locking member 222 having moved radially outward, thereby unlocking the plunger rod 212 from the syringe barrel 214 and allowing the plunger rod 212 to move into the syringe barrel 214 to expel the water in the syringe barrel 214 from the syringe barrel 214 and into the balloon catheter 20 for inflating the balloon catheter 20.

When the plunger rod 212 is retracted from the position shown in FIG. 55C, the locking member 222 will reengage when the annular groove in the plunger rod is axially aligned with the locking member 222 and the recess 224 (as shown in FIG. 55B), due to the recess 224 being beveled on its proximal side, thereby forcing the locking member 222 into the annular groove of the plunger rod 212. For further retraction of the piston rod 212, the syringe barrel 214 will move in unison with the piston rod to 212, as shown in FIG. 55A, thereby causing the inflatable portion of the balloon catheter 22 to be retracted into the catheter guiding tube 204. Thus, the syringe barrel 214 and thereby the balloon catheter 20 cannot be retracted before the balloon is deflated, thereby preventing damaging the inflatable part of the balloon catheter 20.

Figures 56A, 56B, 56C, 56D:
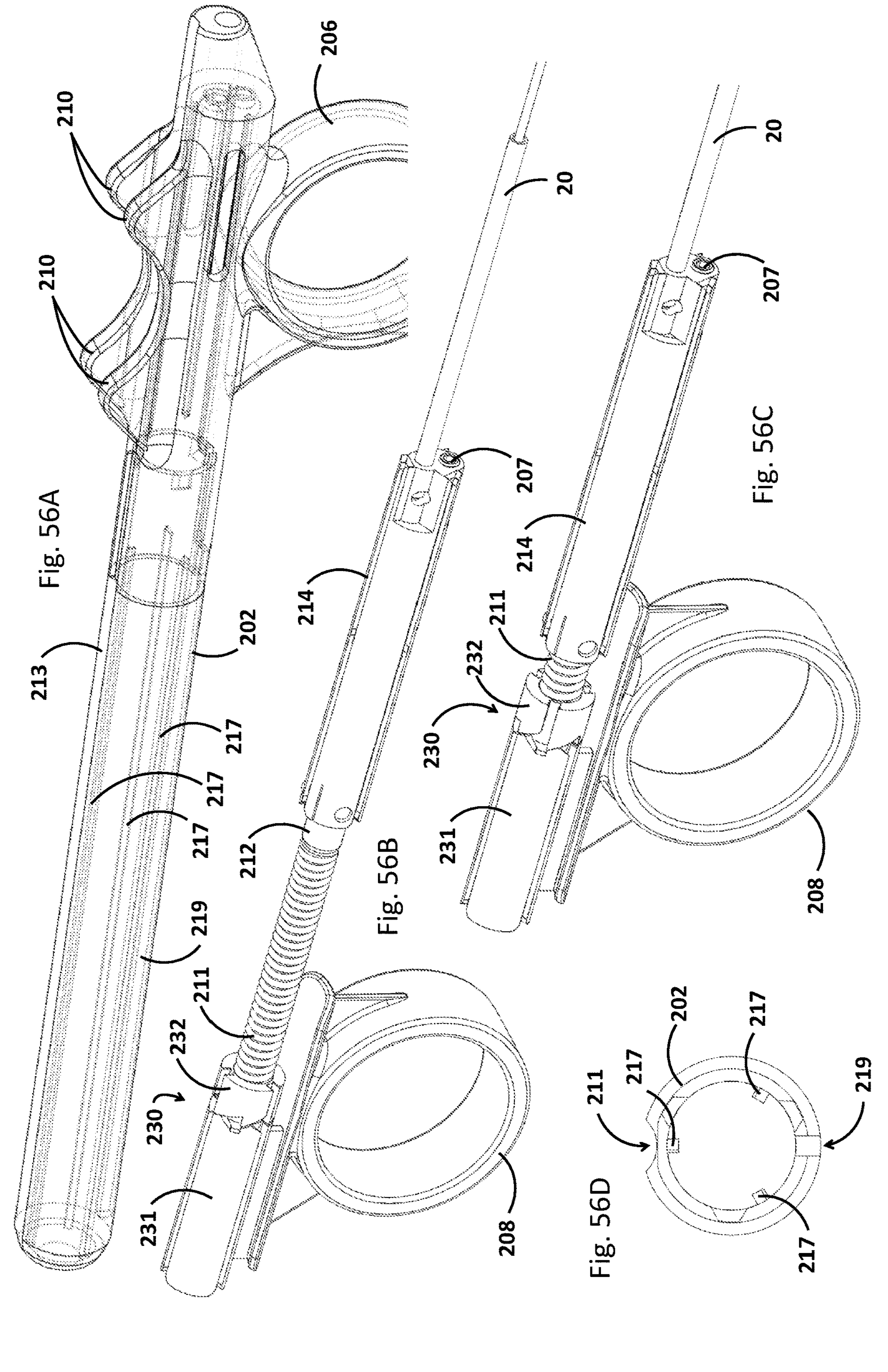
FIG. 56A is an elevated transparent view of the device body of the eleventh embodiment of the handheld insertion device.
FIG. 56B is an elevated view of the inner components of the handheld insertion device of the eleventh embodiment in a primary configuration.
FIG. 56C is an elevated view of the inner components of the handheld insertion device of the eleventh embodiment in a secondary configuration.
FIG. 56D is a sectional view through the tubular portion of the device body of the handheld insertion device of the eleventh embodiment.

FIG. 56A is an elevated transparent view of device body 202. FIG. 56B is an elevated view of the longitudinally displaceable handle 208, the plunger rod 212, the syringe barrel 214 with the balloon catheter 20 connected to the distal end of the syringe barrel 514, in the primary configuration with the plunger rod 212 fully retracted. In FIG. 56C the plunger rod 212 is fully inserted into the syringe barrel 214. A second locking mechanism 230 comprises a first cylindrical cam body 231 that moves in unison with the longitudinal movable handle 208 and is preferably an integral part thereof. The first cylindrical cam body 231 interacts with a second cylindrical cam body 232 that has a common axis with the first cylindrical cam body 232 and is arranged rotatable along the common axis. The first cylindrical cam body 231 is provided with a plurality of cam surfaces interacting with a plurality of cam surfaces on the second cylindrical cam body 232 to impart unidirectional rotational movement of the second cylindrical cam body 232. Both the first cylindrical cam bod 231 and the second cylindrical cam body 232 are provided with three circumferentially preferably evenly distributed axial slits in their outer surface that interact with three radially inwardly directed longitudinally extending axial ribs 217 in a bore in the device body 202 in which they are received. The thee longitudinally extending axial ribs 217 prevent the second cylindrical cam body 232 from rotating until it has passed the distal end of ribs 217, which is when the longitudinal movable handle 208 is in its most forward position, i.e. in the tertiary configuration as shown in FIG. 56C. Unidirectional rotational movement of the second cylindrical cam body 232 relative to the first cylindrical cam body 231 toggles the second locking mechanism 230 between locked and unlocked states, and the helical spring 211 biases the second cylindrical cam body 232 towards the first cylindrical cam body 231. FIG. 56D shows the second cylindrical cam body 232 rotated into a locked angle position. The locking element has rotated into a locked angle position. In the locked state, the second locking mechanism 230 prevents the second cylindrical cam body 232 from moving from its distal position in a proximal direction, thus keeping pressure on the plunger rod 212 via the helical spring 211, and in the unlocked state, the second locking mechanism 230 allows second cylindrical cam body 232 and thus the plunger rod 212 to move from its distal position in a proximal direction for allowing deflation and retraction of the balloon catheter 20. When the operator pushes the longitudinally movable handle 208 all the way forward so that the handheld insertion device 200 assumes its tertiary position, the second locking mechanism 230 will automatically lock and thereby keep pressure on the plunger rod 212 via the helical spring 211. The helical spring 211 assists in ensuring that the pressure in the balloon catheter 20 is substantially maintained. A renewed pressure by the operator on the longitudinally movable handle 208 will impart another rotation of the second cylindrical cam body 232, thereby moving the second locking mechanism 230 to the unlocked state and allowing retraction of the plunger rod 212.

In FIG. 56A a longitudinally extending groove 213 for providing a track for guiding an elongated cylindrical object along the length of the handheld insertion device 200, such as the insertion tube or a flexible or rigid endoscope.

FIG. 56D shows a cross-sectional view of device body 202 showing the internal longitudinally axial ribs 217, arranged 120° apart in the bore in which the cylindric locking parts 231 and 232 are guided and the longitudinal slit 219 in the device for allowing the longitudinally movable handle 208 to extend into the device body 202 to connect to the first cylindrical locking part 231.

Figure 57:
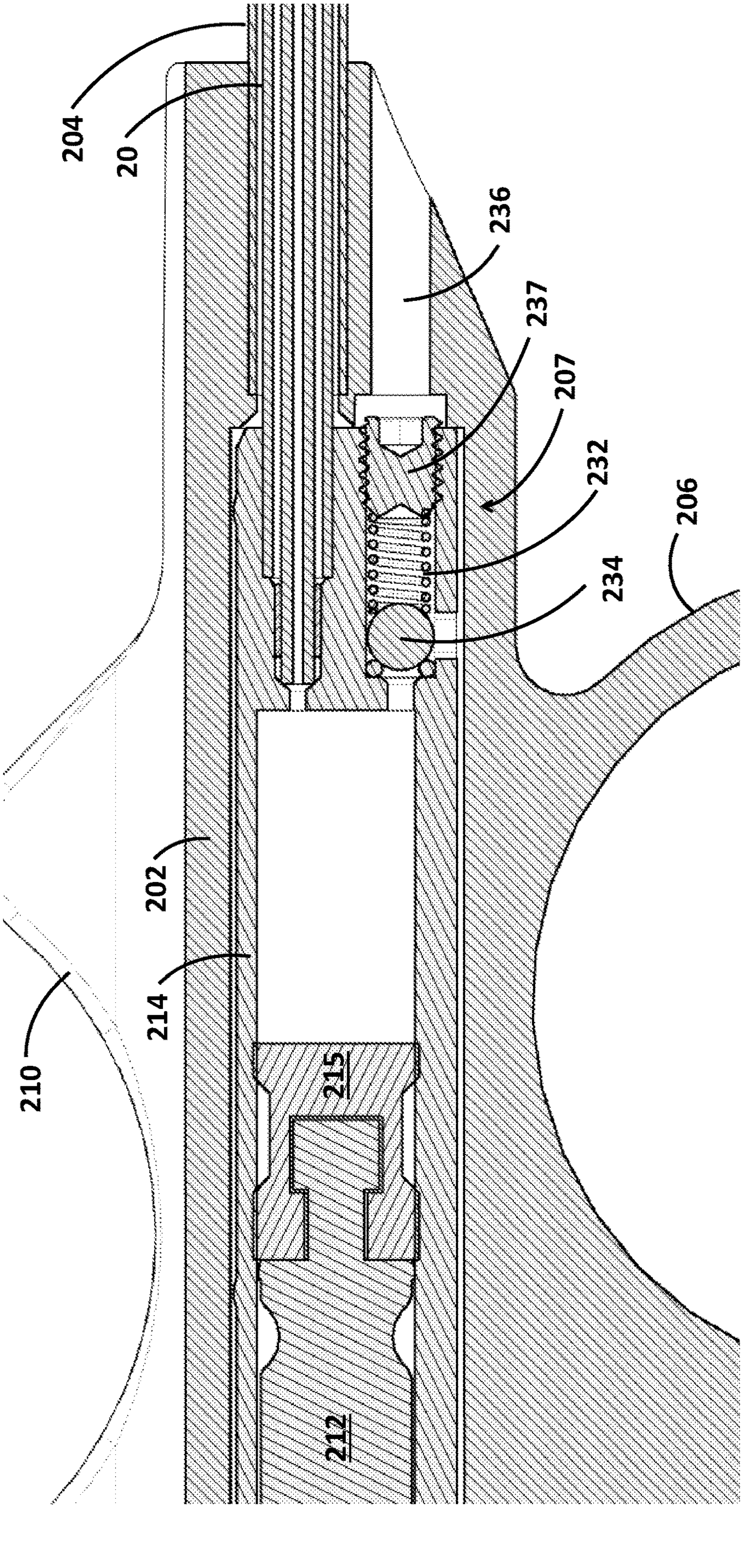
FIG. 57 is a detailed sectional view of a relief valve used in the eleventh embodiment of the handheld insertion device.

FIG. 57 is a detailed sectional view showing the distal end of the syringe barrel 214 in its most distal position in the device body 202, i.e. the handheld device 200 is in its tertiary configuration. The pressure relief valve 207 prevents overinflating of the balloon catheter 20. With only one locking position axially for the plunger rod 202 and no pressure gauge in this embodiment, axial tolerances of components, stiffness tolerances of spring, tolerances on balloon size and water filling tolerances influence the resulting pressure in the balloon catheter 20. The pressure relief valve 207 set at balloon operating pressure and a deliberately overfilled syringe barrel 214 eliminates or at least reduces the need for strict tolerances. Water evacuates through the pressure relief valve 207 at e.g. 10 bar continuously until the second locking mechanism 230 engages. The pressure relief valve 207 which in the present embodiment comprises a spring-loaded ball-shaped valve member 234, limits the maximum pressure in the syringe barrel 214. A spring, in the present embodiment the helical spring 232 urges the spring-loaded valve member 234 to a seat formed in the syringe barrel 204 and an adjustment screw 237 on the end of the helical spring 232 opposite to the valve member 234 allows for adjustment of the pressure at which the relief valve 207 opens. Thus, over-pressurization by the operator using excessive force on the longitudinally displaceable handle 208 is avoided.

Figure 58:
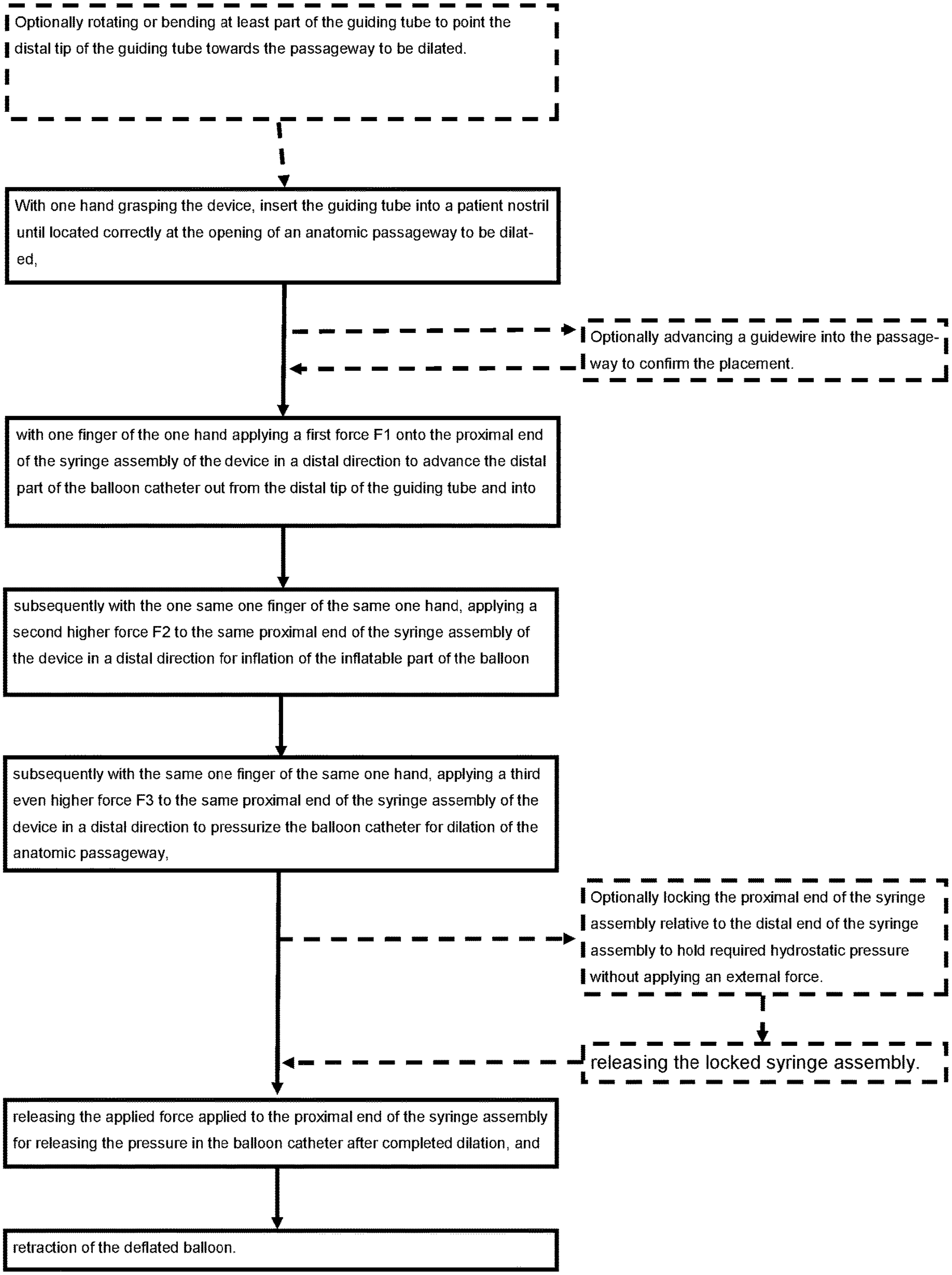
FIG. 58 is a flowchart describing the balloon dilation procedure using the handheld insertion device according to embodiment 1 to 8 and the embodiment 11 and the embodiment 15 and any combination thereof.

FIG. 58 shows a flowchart describing the balloon dilation procedure using the handheld insertion device according to embodiments 1 to 8 and embodiment 11 and embodiment 15 and any combinations thereof. The method comprises; optionally bending and or rotating at least part of the guiding tube to align it with the anatomic passageway. With one hand grasping the device inserting the guiding tube portion of the handheld insertion device into the nostril of a patient guided by an endoscope until located correctly at an opening of an anatomic passageway to be dilated. Preferably one operator handles both the endoscope and the handheld insertion device. The operator may optionally advance a guidewire through a lumen inside the balloon catheter out from the distal end of the guiding tube and into the passageway to confirm positioning.

Subsequently, the operator applies a first force f1 to a movable member, i.e. the thruster or handle of the handheld insertion device to advance the balloon catheter so that the balloon part extends from the catheter guiding tube into the anatomic passageway. Subsequently, the operator applies a second higher force f2 to the same movable member of the handheld insertion device for inflation of the inflatable part of the balloon catheter. Subsequently, the operator applies a third even higher force f3 to the same movable member of the handheld insertion device to pressurize the balloon catheter and thereupon the device automatically locks the movable member relative to the device body in this state, to hold the required pressure without applying external force by the operator. After the pressurized balloon has been applied to the anatomic passageway, the operator may optionally release the interlock between the movable member (plunger rod/handle) and the device body, e.g. by applying renewed pressure to the thruster/handle for pressure release after completed dilation, and next the operator will release the applied force to the thruster or movable member and retract the deflated balloon. In the flow chart illustration, the dashed lines of any boxes indicate optional procedure steps.

Figure 59:
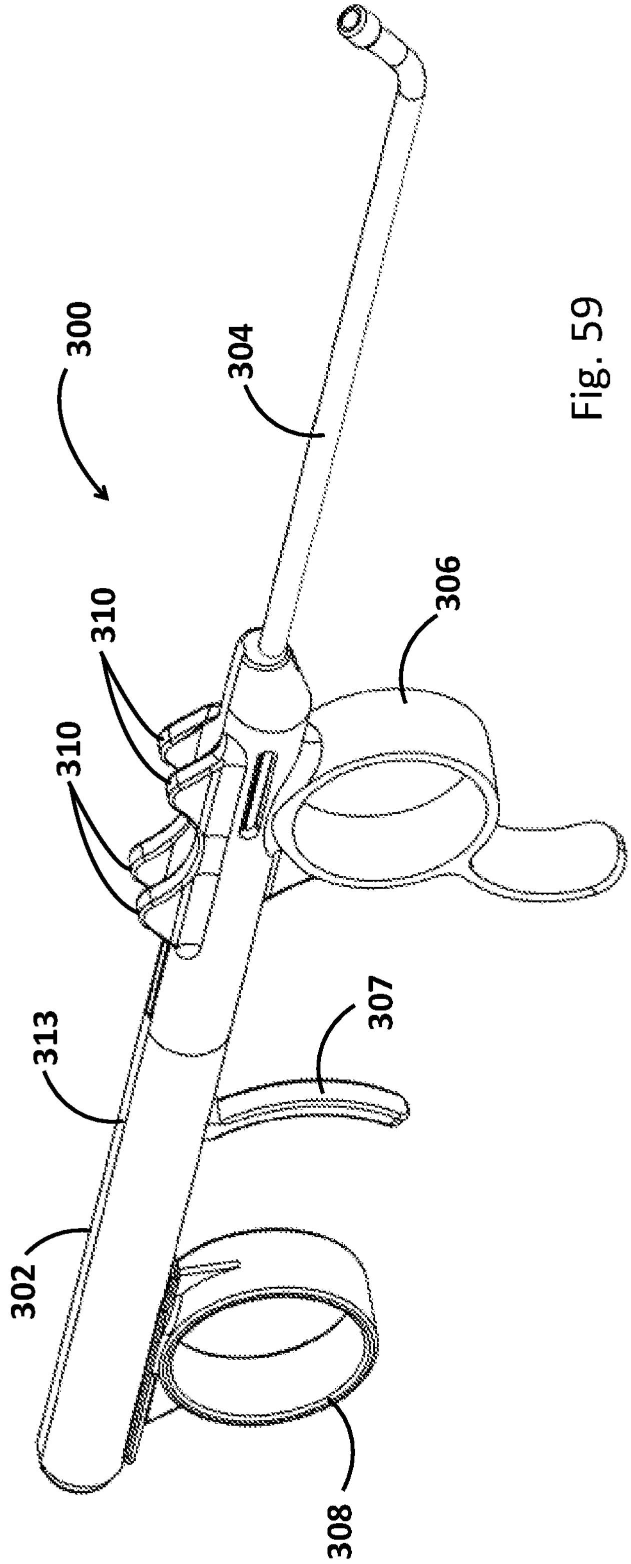
FIG. 59 is a perspective view of a twelfth embodiment of the handheld insertion device.

FIG. 59 is an elevated view of a handheld insertion device according to a twelfth embodiment having two (separate) thrusters/handles 307 and 308. The device body 302 is provided with a longitudinally extending groove 313 combined with pairs of guide plates 310 flanking the groove 313 for providing a track for guiding an elongated cylindrical object along the length of the handheld insertion device 300, such as the insertion tube or a flexible or rigid endoscope. A syringe barrel with a plunger rod and a sealing element inserted therein are arranged in the device body 302 in a way similar to the illustration in FIGS. 54*a*-54*c*. A catheter guiding tube 304 is connected with its proximal end to the distal end of the device body 302. The distal thruster 307 is operably coupled to the syringe barrel for linear movement of the syringe assembly and the balloon catheter 20 from the first (retracted) position to the second (extended) position. The proximal thruster 308 is operably coupled to the plunger rod for pressing the plunger rod into the syringe barrel, only once the syringe assembly is in the second (inserted/distal) position. Having separate thrusters/handles 307,308 may provide improved feeling of control over the two different procedure steps.

Figures 60A, 60B, 60C:
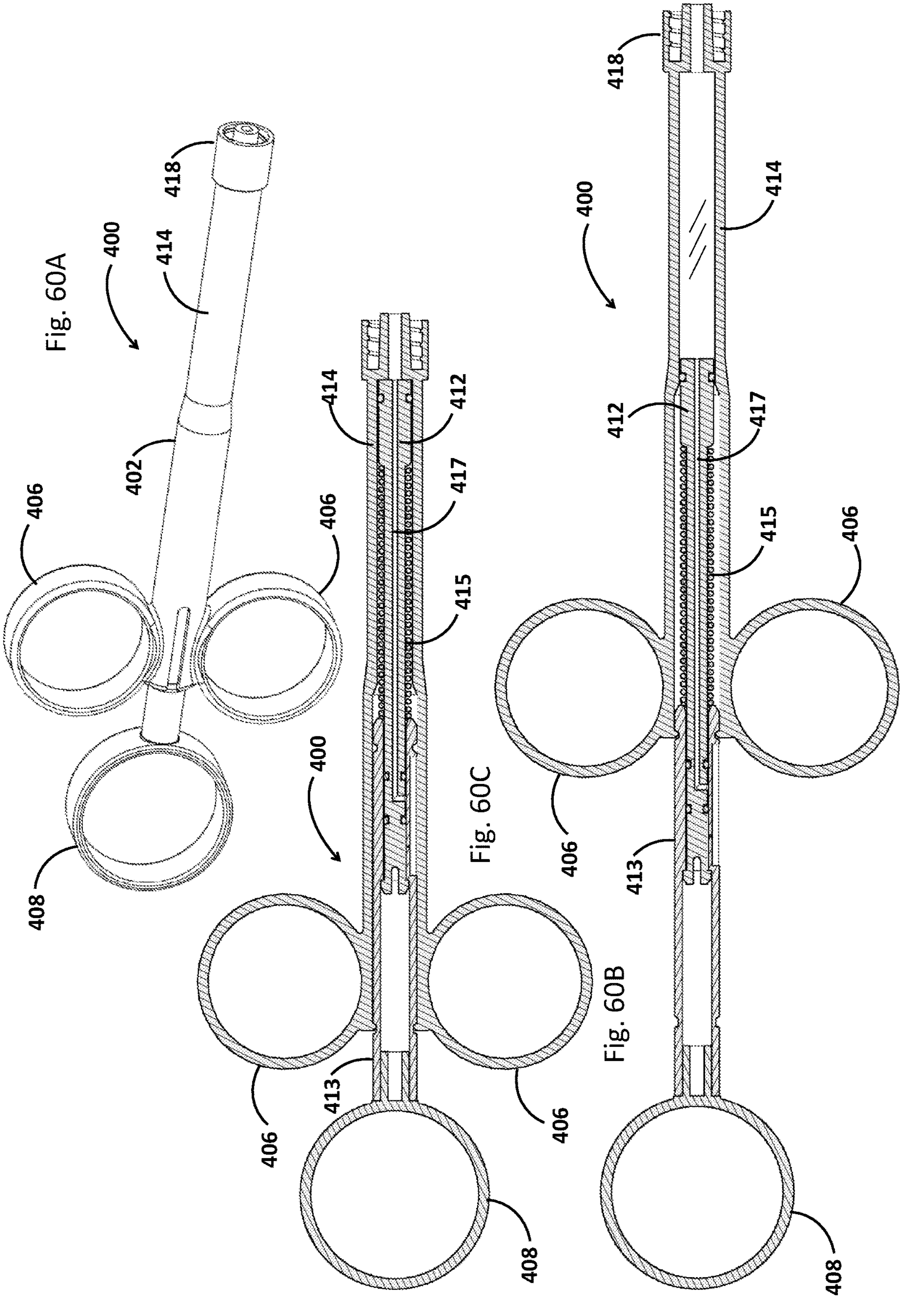
FIG. 60A is a perspective view of a first embodiment of a handheld balloon catheter pressurization device.
FIGS. 60B and C are sectional views of the first embodiment of the handheld balloon catheter pressurization device in different configurations.

FIG. 60A is a perspective view of a first embodiment of a handheld pressurization device 400 for Luer-Lock connection with a separate balloon catheter that may be operated in a separate balloon catheter insertion device. The handheld pressurization device 400 comprises a device body 402 that also forms a syringe barrel 414. Two rings 406 are also part of the device body 402 and provided for being engaged by the fingers of an operator. A plunger rod 412 is inserted in the syringe barrel 414, the proximal end of the plunger rod 414 is connected via a thruster rod 413 that is at its proximal end provided with a ring 408 for engagement by the thumb of an operator. In FIG., 60A the plunger rod 412 is fully inserted into the syringe barrel 414, i.e. the configuration of the device 400 when the fluid chamber in the syringe barrel has its smallest volume ready for aspiration of liquid (water) into the balloon catheter through the Luer lock connection 418.

FIG. 60B is a sectional view of the handheld pressurization device 400, like in FIG. 60A in the first configuration with the plunger 412 fully inserted in the syringe barrel 414 ready to be filled with liquid by retraction of the plunger. A first annular groove at the proximal end of the thruster rod 413 is aligned with locking protrusions on a flexible proximal portion of the syringe body 402. The finger rings 406 on the syringe body are moved outwards radially by the operator for the release of this lock to allow for retraction of the thruster rod 413. A helical spring 415 transmits axial force between the thruster rod 413 and the plunger rod 412, and the plunger rod 414 is slidable received in a bore in the thruster rod 413 to allow for axial displacement of the plunger rod 412 relative to the thruster rod 413. A helical spring 415 is operably arranged between the thruster rod 413 and the plunger rod 412. An axial relief conduit 417 that connects fluidically to the chamber in the syringe barrel 414 is arranged in the plunger rod 412 and has a proximal radial section that opens to the radially outer surface of the plunger rod 412. The function of the relief conduit 417 is explained below.

FIG. 60C is a sectional view of the handheld pressurization device 400 in a secondary configuration with the plunger rod 412 inserted in the syringe barrel 414 but in a retracted (proximal) position so that the fluid chamber in the syringe barrel 414 has its largest volume after aspiration of the liquid. i.e. when it has filled with liquid, and the handheld pressurization device 400 is ready to be connected to the proximal end of the balloon catheter via the Luer lock. A second circumferential groove distally on thruster rod 413 is aligned with the locking edges protrusions of the syringe body 402 for tactile feel of the correct position and to introduce an axial resistance before initiating the balloon of the balloon catheter.

Figure 61:
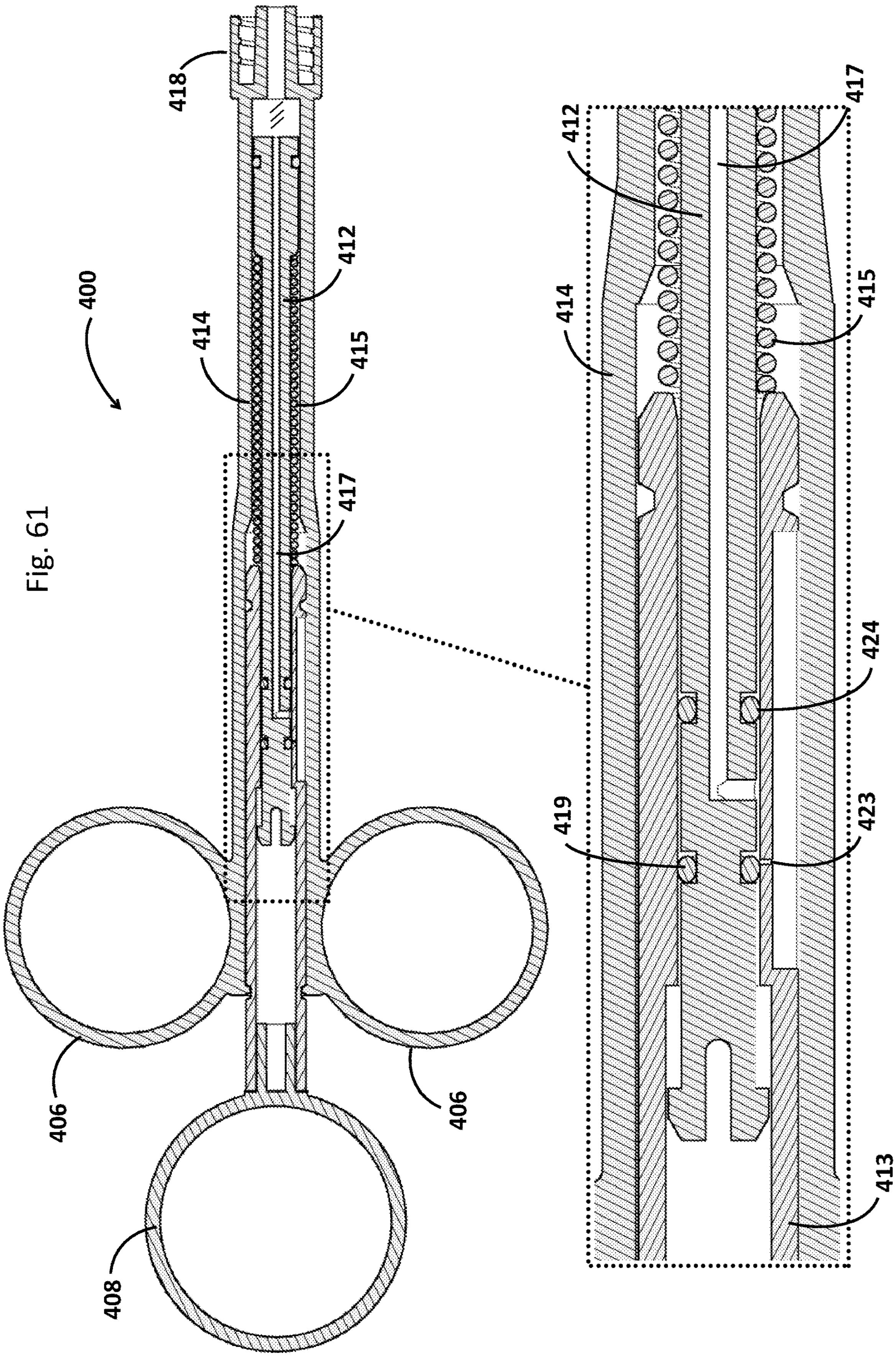
FIG. 61 is a detailed sectional view of a pressure relief system used in the first embodiment of the handheld balloon catheter pressurization device.
Figure 62:
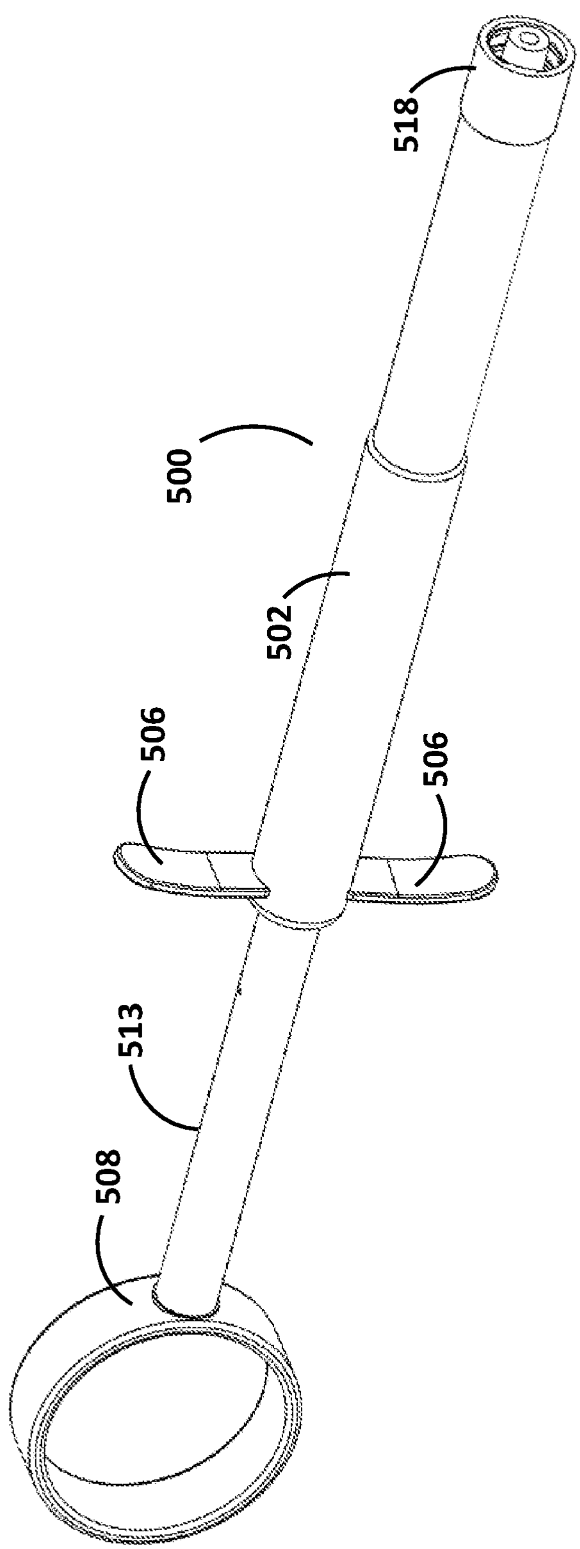
FIG. 62 is a perspective view of a second embodiment of a handheld balloon catheter pressurization device.

FIG. 61 is a sectional view of the handheld pressurization device 400 in tertiary configuration with thruster rod 413 locked relative to the syringe body 402, the pressure in the syringe barrel above a pressure setpoint, the helical spring 415 compressed to a point where the plunger rod 412 has moved proximally into the bore in the thruster rod 413 to an axial position where a most proximal radial seal 419 (O-ring) on the plunger rod 412 has passed a radial port 423 in the thruster rod 413, thereby creating an open fluidic connection between the chamber in the syringe barrel 414 and ambient via relief conduit 417, hence evacuating water until plunger rod 412 has moved distally to a position where the most proximal radial sealing element 419 is no longer placed in a proximal position relative to the radial port 423 in the thruster rod 413. This arrangement forms a pressure relief valve with relatively few parts. Water is evacuated into a cavity between the thruster rod 413 and the thruster guide section of the syringe body 402. A distal sealing element (O-ring) 424 prevents the liquid (water) from flowing distally into the clearance between the thruster rod 413 and the plunger rod 412. The exact water volume needed to fill the balloon catheter and potential extension tubes, may in many cases not be known. The present embodiment relies on deliberate overfilling of the syringe chamber compared to the expected water volume needed in balloon catheter and tubing. The pressure relief function is generally always used", and a varying portion of water will be released out and into a cavity of the device.

Figure 63A:
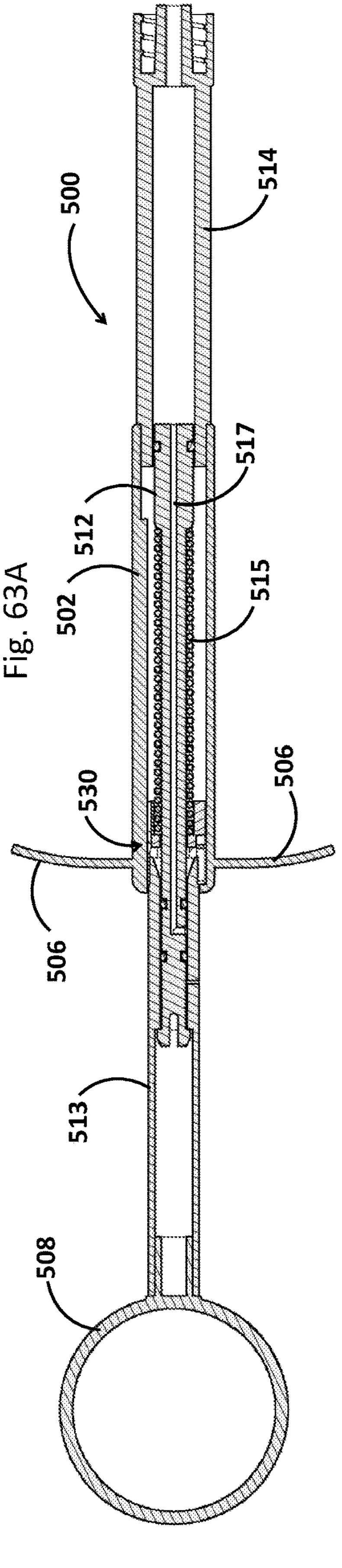
FIGS. 63A and B are sectional views of the second embodiment of the handheld balloon catheter pressurization device in different configurations.

FIGS. 62, 63A-B, and 64A-C show a second embodiment of the handheld pressurization device 500. FIG. 60 shows the second embodiment of the handheld pressurization device 500 in an elevated view with its device body 502 with its two thrusters/finger engagement plates 506 integral therewith, a Luer lock at its distal end for connection to a balloon catheter, and the thruster rod 513 therein with its thruster/finger ring 508 at the proximal end of the thruster rod 513. FIG. 63A shows the second embodiment of the handheld pressurization device 500 in a loaded configuration with the chamber in the syringe barrel 514 prefilled with water. The plunger rod 512 is like in the first embodiment of the handheld pressurization device slidably received into an axial bore in the thruster rod 513, with a helical spring 515 transmitting axial force between the thruster rod 513 and the plunger rod 512. A locking mechanism 530 is shown and will be explained in detail below. An axial relief conduit 517 that is connected fluidically to the chamber in the syringe barrel 514 is arranged in the plunger rod 512 and has a proximal radial section that opens to the radially outer surface of the plunger rod 512. The function of the relief conduit 517 is explained below.

Figure 63B:
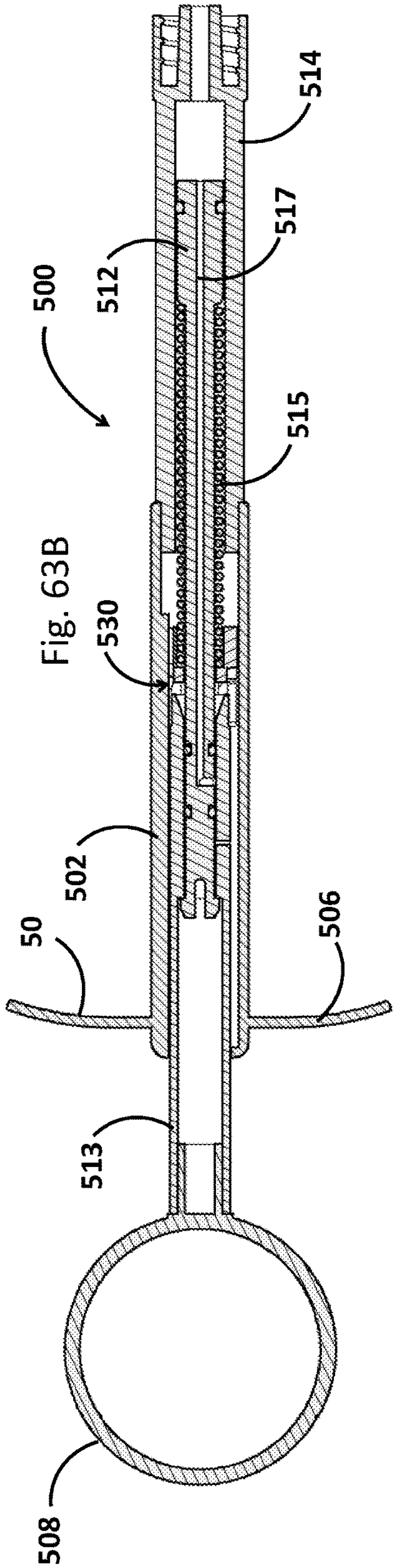

FIG. 63B shows the configuration of the handheld pressurization device 500 during inflation of a balloon catheter (balloon catheter connection not depicted).

Figures 64A, 64B, 64C:
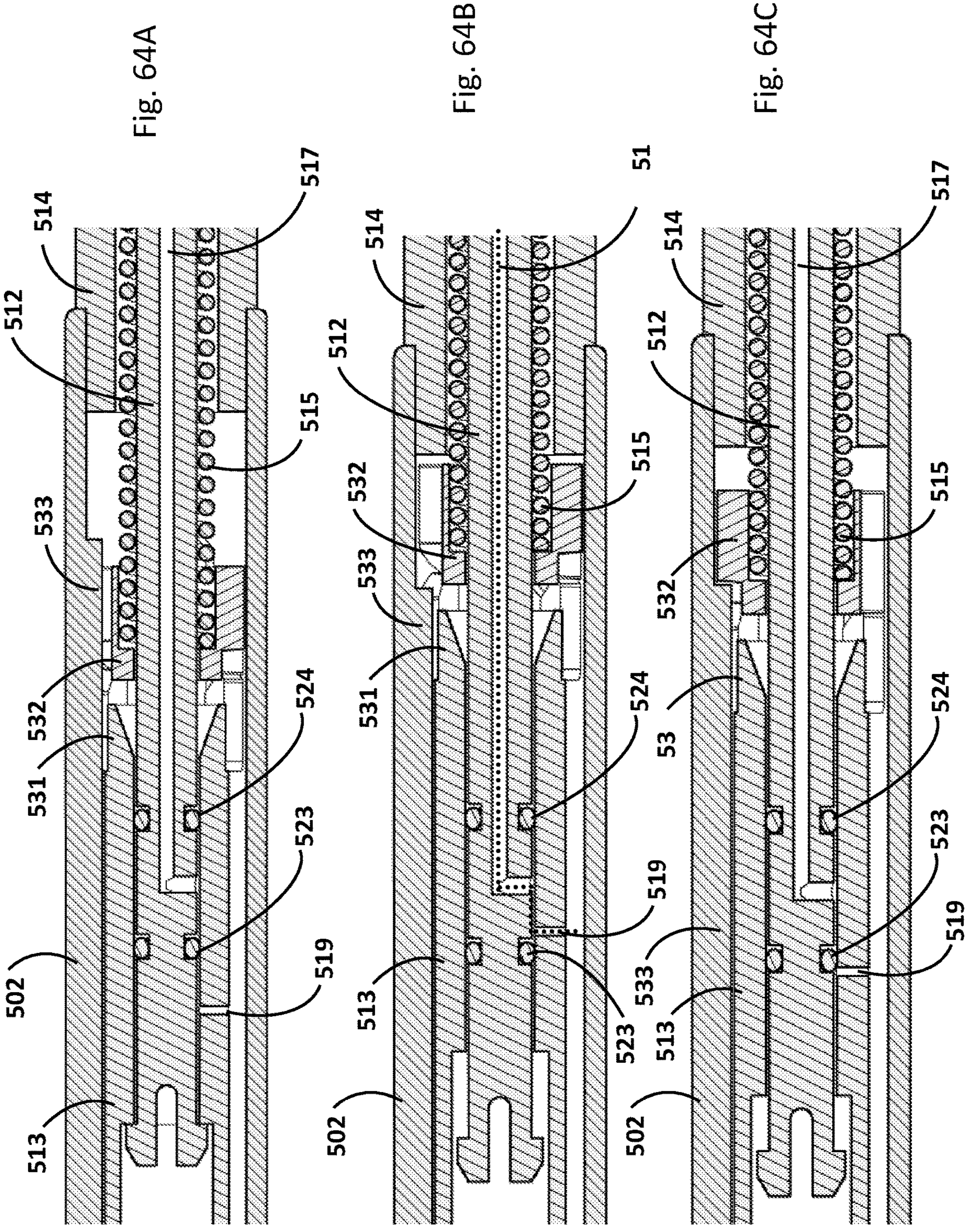
FIGS. 64A-C are detailed cross-sectional views of a pressure relief and locking mechanism used in the second embodiment of the handheld balloon catheter pressurization device.

FIGS. 64A-C show a detailed sectional view of a locking mechanism 530 and relief valve of the handheld pressurization device 500. The locking mechanism 530 is similar in construction and operation to the second locking mechanism 230 of the embodiment of FIGS. 53-57

The locking mechanism 530 comprises a first cylindrical cam body 531 that moves in unison with the thruster rod 513 and is preferably an integral part thereof. The first cylindrical cam body 531 interacts with a second cylindrical cam body 532 that has a common axis with the first cylindrical cam body 531 and is arranged rotatable along the common axis. The second cylindrical cam body 532 engages the helical spring 515. The first cylindrical cam body 531 is provided with a plurality of cam surfaces interacting with a plurality of cam surfaces on the second cylindrical cam 532 to impart unidirectional rotational movement of the second cylindrical cam body 532. Preferably at least two or more inner axially extending ribs 533 project into the bore in the device body 502 that receives the first and second cylindrical cam bodies 531,532 to interact with corresponding axial grooves in the first and second cam bodies 531,532 and prevent rotation of the second cylindrical cam body 532 for most of the axial positions of the second cylindrical cam body 532 (such as in FIG. 64A), except the fully inserted, i.e. most distal position of the second cylindrical cam body 532 (such as in FIG. 64B), where the inner ribs 533 end and allow the second cylindrical cam body 532 to rotate and thereafter abut with the distal end of the ribs 533, thereby preventing the second cylindrical cam body 532 from moving in a proximal direction, thereby maintaining pressure on the helical spring 515 and thus the plunger rod 512, as shown in FIG. 64C.

In the plunger rod 512 of FIG. 64A, the external balloon catheter may already be sufficiently filled and fully partly pressurized. However, the locking mechanism has not yet engaged. In FIG. 64BB the operator has pressed the thruster rod 513 further forward even if the balloon is fully dilated. The helical spring 515 is consequently compressed, increasing the force exerted onto the plunger rod 512, resulting in an increased hydraulic pressure in the chamber in the syringe barrel 514 and the balloon catheter. As the thruster rod 513 moves forward relative to the plunger rod 512, the hydraulic pressure increases. When the hydraulic pressure is below the setpoint of e.g. 10 bar, the radial channel 519 in the thruster rod 513 is positioned proximally to the proximal O-ring 523 on the plunger rod 512. When the pressure is above the setpoint, the radial channel 519 on the thruster rod 513 is placed distally to the proximal O-ring 523 of the plunger rod 512, and the pressure relief system is open. When the pressure relief system opens, the plunger rod 512 may be moved forward relative to the syringe barrel 514, as water is evacuated. Eventually, the second cylindrical cam body 532 will reach the axial position, in which it can rotate and be locked axially against internal axially directed locking ribs 533 in the device body 502 of the lock housing part. In FIG. 64C the second cylindrical cam body 532 is rotated and locked. The present embodiment relies on deliberate overfilling of the syringe chamber compared to the expected water volume needed in balloon catheter and tubing. The pressure relief function is generally always used, and a varying portion of water will be released out and into a cavity of the device.

Figures 65A, 65B, 65C, 65D, 65E:
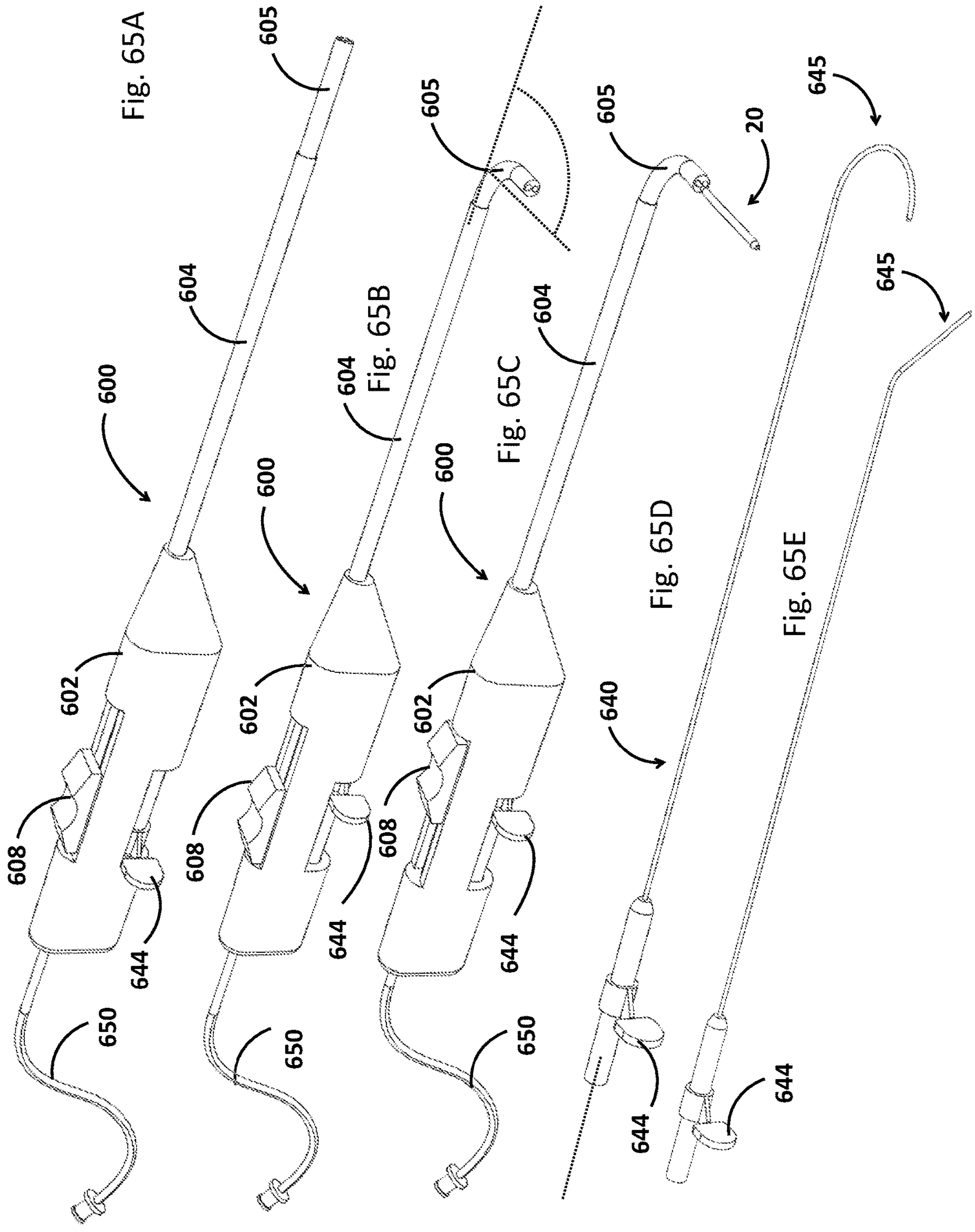
FIGS. 65A-C are elevated views of a thirteenth embodiment of the handheld balloon catheter insertion device.
FIGS. 65D and E are elevated views of a resilient control mandrel used in the thirteenth embodiment of the handheld balloon catheter insertion device.

FIGS. 65-66 show a thirteenth embodiment of the handheld balloon catheter insertion device 600. The handheld insertion device has a device body 602 with a proximal end of a balloon guiding tube 604 connected to the device body 602. A first trigger 608 is operably coupled to the balloon catheter 20 for advancing the balloon catheter 20, the distal inflatable part thereof shown protruding from the tip of the balloon guiding tube 604 in FIG. 65B. In the retracted (proximal) position of the trigger 608 the complete balloon catheter 20 is received in the handheld device. A tube 650 is provided for connection to a separate balloon catheter pressurization device, i.e. this embodiment is not shown with an integral pressurization device, but an internal pressurization device can be used in this embodiment).

The balloon guiding tube 604 has a straight proximal stiff portion and a distal flexible portion 605, that normally straight when it is not forced into a non-straight shape. The flexible portion of the balloon guiding tube 605 has two lumens 641,642 (FIG. 66A) where a first lumen 641 is for the balloon catheter and a second lumen 642 is for a resilient control mandrel 640. The proximal end of the resilient control mandrel 640 is operably coupled to a second trigger 644 placed in conjunction with the device body 602. In one variation of the thirteenth embodiment, shown in FIG. 65D, the distal end 645 of the resilient control mandrel 640 is pre-bend into the shape of a half-circle shape with a certain radius. In a second variation of the thirteenth embodiment, shown in FIG. 65E, the distal end of the resilient control mandrel 640 is prebend into an angle.

When the resilient control mandrel 640 is retracted fully into the proximal stiff straight portion of the guiding tube 604, the distal flexible portion 605 of the guiding tube 604 will be straight, yet flexible and soft. It will be easy and painless to insert the guiding tube 604 with its soft and flexible distal guiding portion 605 into the nose of a patient.

Figures 66A, 66B, 66C, 66D, 66E:
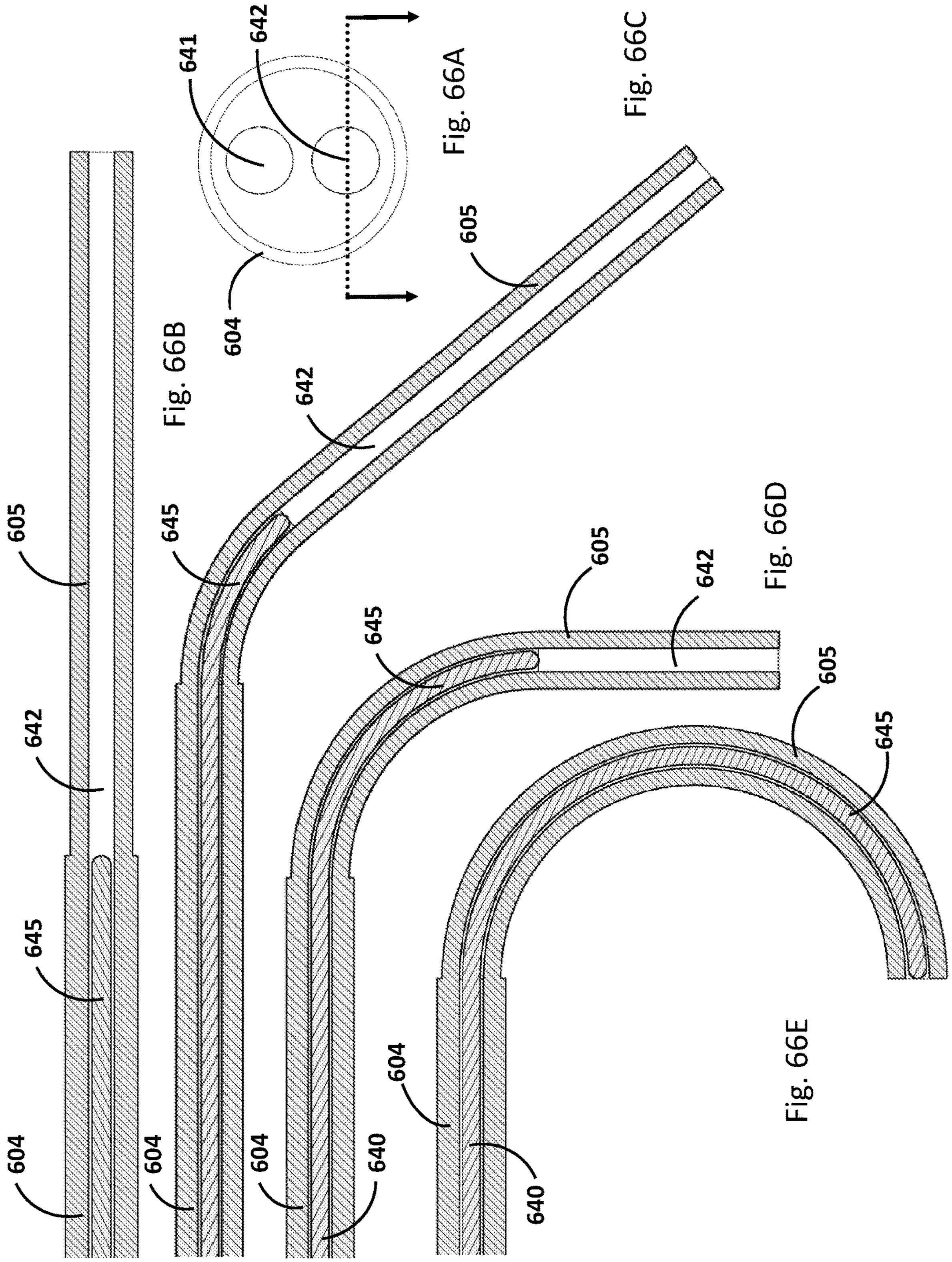
FIGS. 66A-E are detailed cross-sectional and sectional views of the controllably deformable distal end of the balloon catheter guide tube of the handheld balloon catheter insertion device according to the thirteenth embodiment.
Figures 67A, 67B, 67C, 67D, 67E:
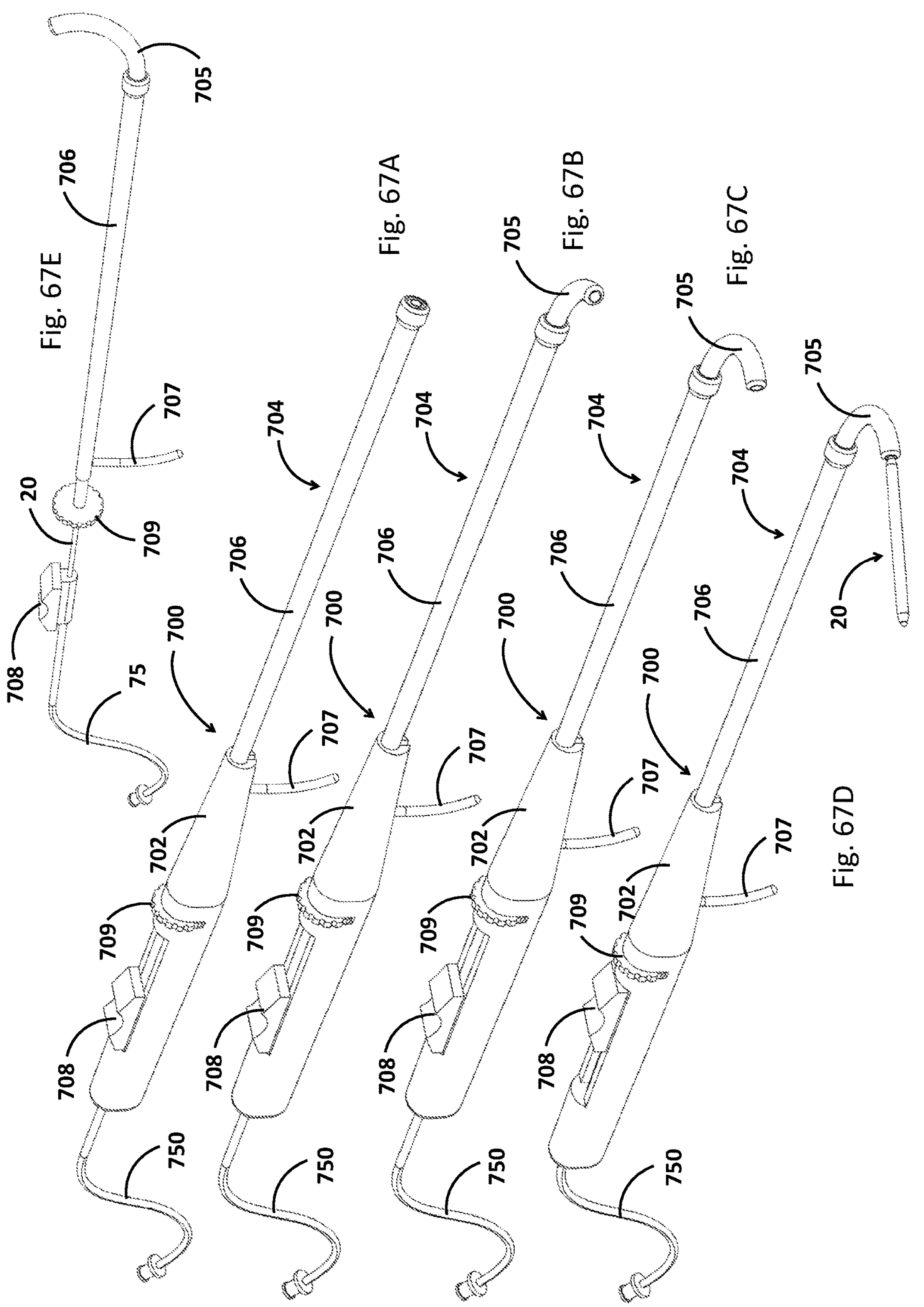
FIGS. 67A-D are elevated views of a fourteenth embodiment of the handheld balloon catheter insertion device.
FIG. 67E is an elevated view of the balloon catheter guiding tube and balloon catheter used in the fourteenth embodiment of the handheld balloon catheter insertion device.

In the first variation of the thirteenth embodiment (FIGS. 65A-D and 66A-E), the resilient control mandrel 640 is pre-bend into a semi-circular shape of up to 180 degrees with a radius of e.g. 10 mm. In this first variation, forward movement of the resilient control mandrel 640 over a length L1 will result in a first angle A1 of the flexible tip 605. Further forward movement of the resilient control mandrel 640 by the operator pushing the second trigger 644 over a length L2 will result in a greater angle A2. When the resilient control mandrel 640 is fully retracted the angle of the flexible tip 605 is 0 degrees. With the resilient control mandrel 640 fully advanced, the flexible tip 605 may be bent 180 degrees as seen in FIG. 66E. Alternatively, a fully advanced resilient control mandrel may provide a fully deflected angle of the flexible tip 605 of only 90 degrees or any other angle between 20-180 degrees. Thus, the operator can control the angle of the distal tip of the balloon guiding tube 604 by axially displacing the resilient control mandrel 640 relative to guiding tube 604 in the second lumen 642 between e.g. 0 and 180 degrees. The resilient control mandrel 640 is preferably made of stainless steel with high elasticity and resilience to ensure that the distal portion 645 thereof is capable of bending the flexible distal portion 605 whilst also being easy enough to be straightened out without excessive force in the straight portion of the second lumen 642 in the straight and rigid portion of the guiding tube 604. The stiffness of the resilient control mandrel 640, especially the curved distal portion 645 is balanced to overcome the stiffness of the flexible distal portion 605 and needs to be slidable effortlessly inside the straight and rigid portion of the longitudinal extent of the second lumen 642. Lubricant may be applied in the clearance between the resilient control mandrel 640 and the second lumen 642. Low friction surfaces/materials can be used for the surfaces of the resilient control mandrel 640 and the second lumen 642.

In a second variation of the thirteenth embodiment (FIG. 65E) the required angle is known and the resilient control mandrel 640 may be pre-bend into an angle either by the manufacturer or the operator. In this second configuration, the resilient control mandrel 640 may be toggled between a first position where the resilient control mandrel 640 is fully retracted inside the stiff portion of the guiding tube 604 and where the distal tip 605 of the guide tube is straight, and a second position where the resilient control mandrel 640 is fully advanced into the second lumen 642 and where the flexible distal tip 605 of the guiding tube follows the angle and shape of the resilient control mandrel 640.

The operator may deform the resilient control mandrel 640 into any shape or angle while the resilient control mandrel 640 is fully advanced by making a plastic deformation of the resilient control mandrel 640 material. For ease of insertion into the patient nose, this custom shape or angle may be retracted into the stiff portion of the guiding tube 604. When the distal part 605 of the guiding tube has passed the narrow area of the nose and is placed in the spacious part of the nose, the operator may advance the pre-formed resilient control mandrel 640 and the custom shape reappears, due to the properties of the resilient control mandrel 640 material.

The resilient control mandrel 640 may be rotated around its axis to thereby change the plane of the angled distal portion 645 of the resilient control mandrel 640 and thereby the direction of the angled tip 605 of the flexible part of the guiding tube 604. With a translatory movement of the second trigger 644 and thereby the resilient control mandrel 640, the operator may adjust the bend angle of the distal tip 605 of the guiding tube 604. With a rotational movement of the second trigger 644 and thereby the resilient control mandrel 640, the operator may adjust the direction of the bend distal tip 605 of the guiding tube 604 to be either upwards, downwards, left, right or any position in between. With only one finger on the trigger, the user may achieve any orientation and any tip angle of the distal tip 605 of the guiding tube 604.

The flexible part 605 of guiding tube 604 is preferably made of thermoplastic polymer material for extrusion and for tip forming by melting. The dual lumen extruded tube may preferably be post-processed in the tip 605 by applying heat and a tip mold to seal the flexible core lumen and to create a rounded narrow tip. The stiff part of guiding tube 604 can be a steel tube placed around the flexible extruded tube, the extruded tube stretching all the way from the distal tip 605 and into the device body 602, receiving the balloon catheter 20 and the resilient control rod mandrel respectively.

In another embodiment, that can apply to all handheld insertion tools described herein, an additional (second or third) lumen in the extruded tube is included to provide a suction port. The additional lumen in the extruded tube may alternatively serve as an irrigation port. In total, the extruded profile may comprise four lumens selected from a balloon catheter guide tube lumen, a lumen for a resilient control mandrel, a suction port lumen and an irrigation port lumen.

FIGS. 67A-E show a fourteenth embodiment of the handheld balloon catheter insertion device 700. The handheld insertion device has a device body 702 and a balloon guiding tube 704 extending from the device body 702. A first trigger 708 is operably coupled to the balloon catheter 20 for advancing the balloon catheter 20, the distal inflatable part thereof shown protruding from the tip of the balloon guiding tube 704 in FIG. 67D. In the retracted (proximal) position of the trigger 708 the complete balloon catheter 20 is received in the handheld device 700. A flexible tube 750 is provided for connection to a separate balloon catheter pressurization device, i.e. this embodiment is not shown with an integral pressurization device, but an internal pressurization device can be used in this embodiment).

The balloon guiding tube 704 has a straight proximal stiff outer tube 706 and a concentrically arranged therein an inner tube 705 that has a distal portion that has been pre-shaped or pre-bend into a shape that substantially corresponds to a half circle with a given radius. The lumen for the balloon catheter 20 extends longitudinally in the inner tube 705, and the inner tube 705 with its proximal end is secured to the device body 702 to allow for rotation about its longitudinal axis relative to the device body 702 but not for translative movement relative to the device body 702. The rotation is imparted by the operator turning disk 709 that is coupled to the internal tube 705 and that at least partially protrudes from the device body 702. The external tube 706 is configured to be moved axially relative to the device body 702 and thus relative to the internal tube 705, the axial movement of the outer tube 706 is imparted by a trigger/handle 707 that can be engaged by a finger or hand of the operator. Thus, the inner tube 705 and the outer tube 706 are configured to rotate and translate relative to one another. When the external tube 706 is fully advanced, the guiding tube 704 is completely straight and easy to insert into the nose of a patient. When external tube 706 is completely or partially retracted, the pre-bend distal part of the internal tube 705 is exposed to obtain a desired angle.

Figures 68A, 68B, 68C:
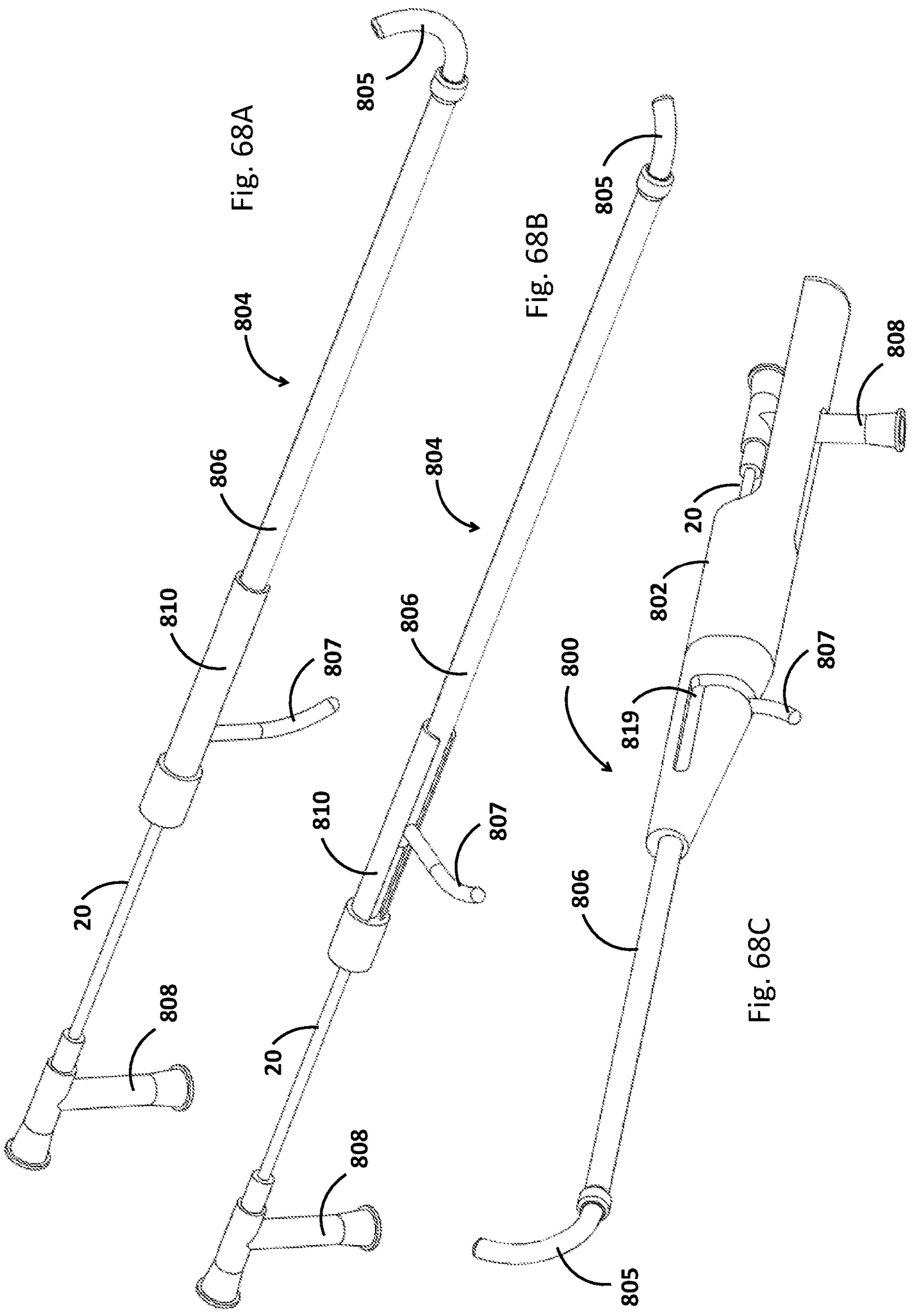
FIGS. 68A-C are elevated views illustrating a variation of the fourteenth embodiment of the handheld balloon catheter insertion device.

FIGS. 68A-C show a variation of the fourteenth embodiment, which is essentially identical to the thirteenth embodiment, except that only one thruster/handle 807 is used by an operator to move outer tube 806 of the balloon catheter guiding tube 804 both back and forward and to rotate internal tube 805. The balloon catheter 20 may have a proximal axial connection port for an illuminated guide wire and a radial connection port for connection with a pressurization device. The device body 802 may be provided with an L-shaped slit with an axial section and a circumferential section, for guiding the one thruster/handle 807 in one or more certain rotational planes. Alternatively, the opening in the device body 802 may allow the thruster/handle 807 to rotate and translate freely. A sleeve in 810 is provided for guiding the axial displacement and rotational movement of the outer tube 806 relative to the inner tube 805 and the device body 802. In this embodiment, the balloon catheter 20 may comprise a handle/thruster-like element 808 for advancing and retracting the balloon catheter.

FIGS. 69A-69J show a first embodiment of a handheld balloon catheter insertion device 900 with a controllable deflectable guiding tube tip 904.

Figure 69A:
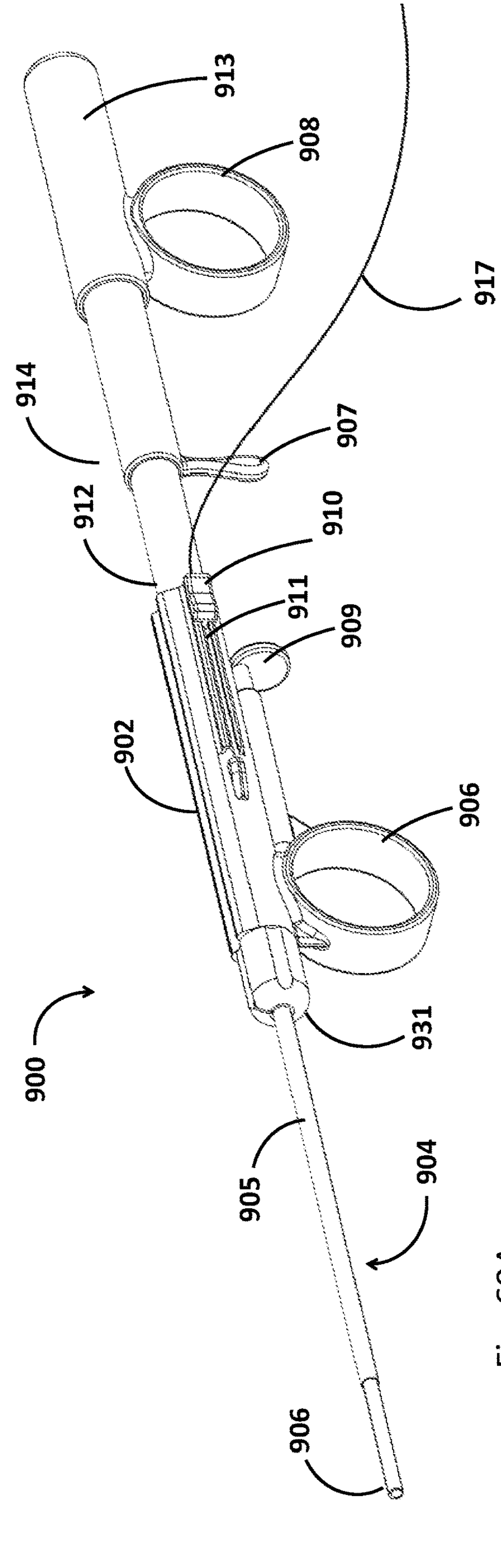
FIGS. 69A-H are elevated, side, and sectional views of a first embodiment of a controllably deformable tip for a handheld balloon catheter insertion device.

FIG. 69A shows the device 900 in a first state before insertion of the device into the nostril of a human. The device 900 comprises a device body 902 and a guiding tube 904 having a distal deflectable portion 906 and a proximal portion 905. The distal deflectable portion is resiliently biased to a straight configuration, and the distal deflectable portion is preferably deflectable in one plane of de-flection only. A rotatable knob 931 is arranged to rotate the guiding tube 904 relative to the device body 902. A device body grasping portion 906 is provided for being engaged by a finger of an operator.

A first actuator 909 is provided for moving the guiding tube 904 forward in a distal direction relative to the device body 902 for deflection of the deflectable distal portion 906. The first actuator 909 is shown in its first position where the deflectable portion of the guiding tube 906 is still in a straight configuration. A second actuator 910 is arranged to slide linearly relative to the device body 902 in a guiding track 911 for advancement of a guide wire 917 out from the tip of the guiding tube 904. The second actuator 910 is shown in its first position with the guide wire 917 retracted. A third actuator 907 is provided for moving a syringe assembly 914 forward relative to the device body 902 for advancement a balloon catheter 920 out from the distal tip of the guiding tube 904. The third actuator 907 is shown in its first position with the balloon catheter 920 fully retracted inside the guiding tube 904. A fourth actuator 908 is provided for moving the proximal end of the syringe assembly 912 forward relative to the distal end of the syringe assembly 913 for moving an internal plunger 915 into an internal syringe barrel 916 with a water volume 918, for inflation and pressurization of the balloon catheter 920. The fourth actuator 908 is shown in its first position with the internal plunger 915 in a fully retracted position relative to the internal syringe barrel 916.

Figure 69B:
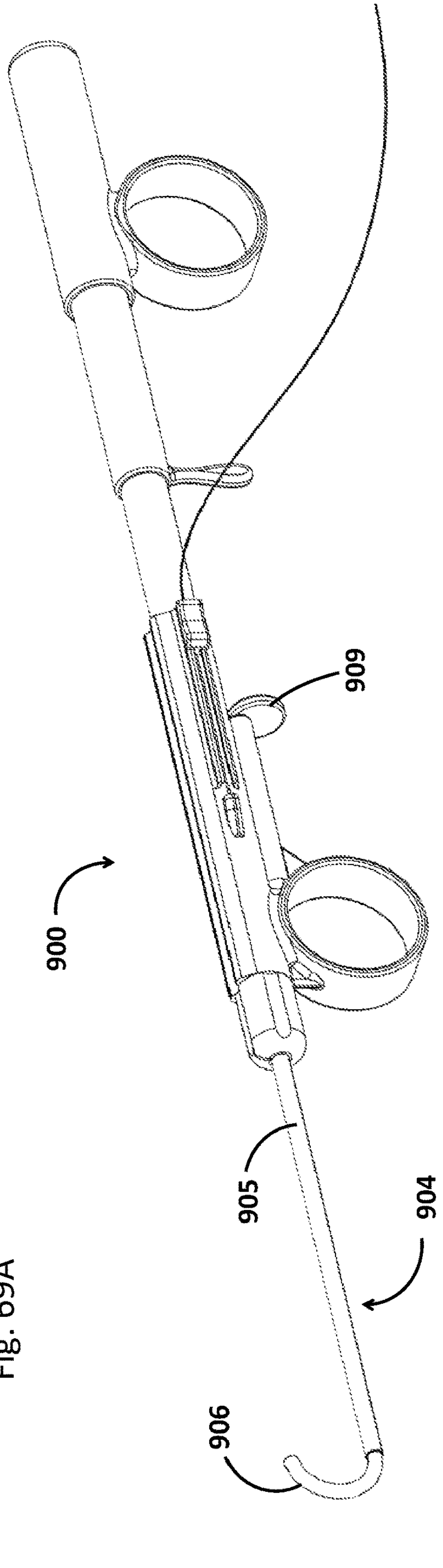

FIG. 69B shows the device 900 in the second state possible after insertion of the guiding tube 904 into to nostril of a human with the first actuator 909 is a second position and with the distal deflectable portion of the guiding tube 906 is in a deflected state.

Figures 69C, 69D, 69E:
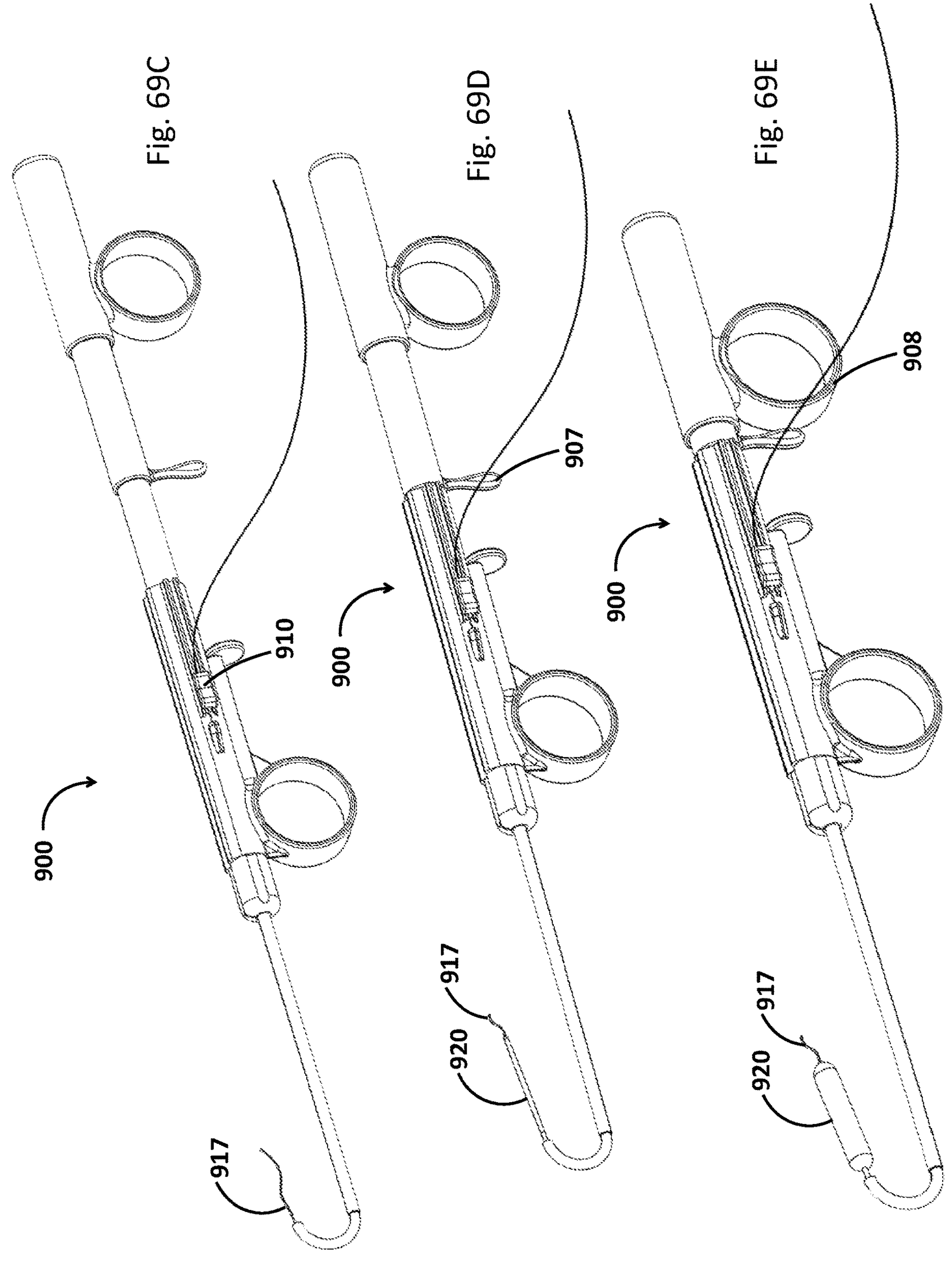

FIG. 69C shows the device 900 in the third state with the second actuator 910 also in a second position and the guide wire 917 advanced out from the tip of the guiding tube 904.

FIG. 69D shows the device 900 in the fourth state with the third actuator 907 also in a second position and the balloon catheter 920 advanced out from the tip of the guiding tube 904 over the guide wire 917.

FIG. 69E shows the device 900 in the fifth state with the fourth actuator 908 also in a second position and the balloon catheter 920 being inflated.

Figure 69F:
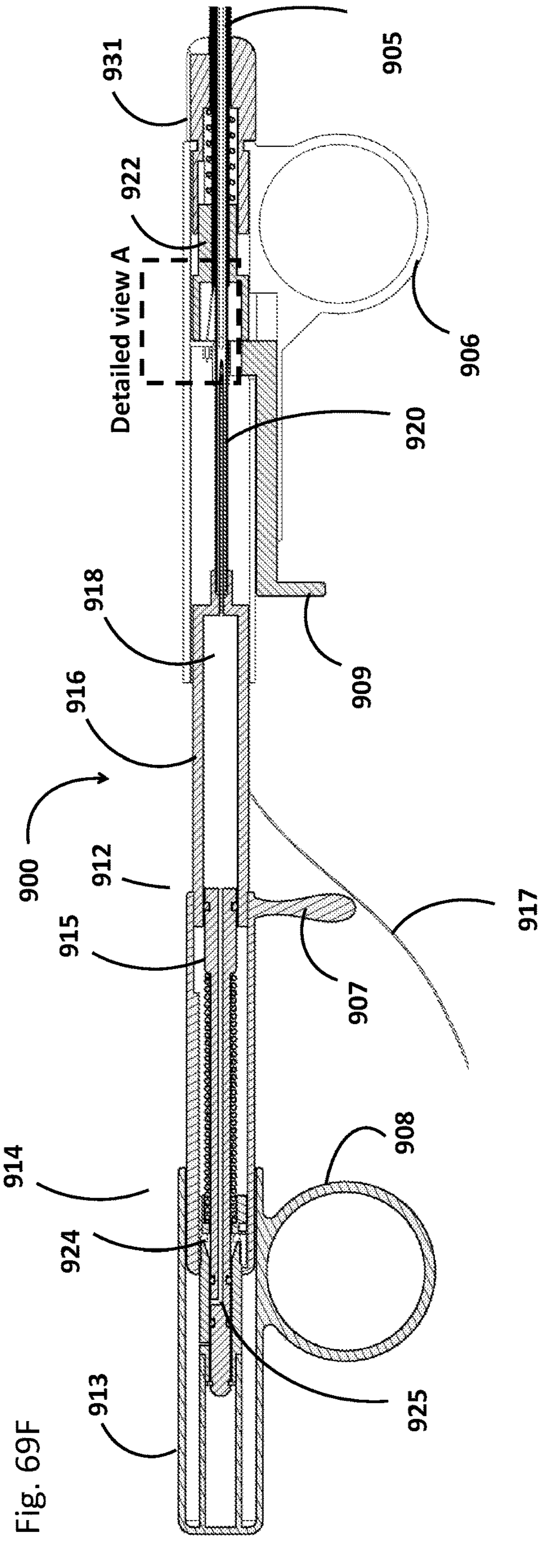

FIG. 69F shows a partial section view of the device 900 in its first state. The syringe assembly 914 has a proximal end 914 connected to the internal plunger 915 and a distal end 912 with a syringe barrel 916 having an internal water volume 918. The syringe barrel is connected directly to the balloon catheter 920 such that the water volume 918 is in fluid connection with the inflatable portion of the balloon catheter 920. An internal locking mechanism 924 is provided for locking the proximal end of the syringe assembly 913 to the distal end of the syringe assembly 912, the locking mechanism being substantially identical to that of FIG. 64. and an internal pressure relief valve 925 in the syringe assembly 913 configured to avoid overinflation of the balloon catheter, the relief valve 925 being substantially identical to that of FIG. 64.

Figure 69G:
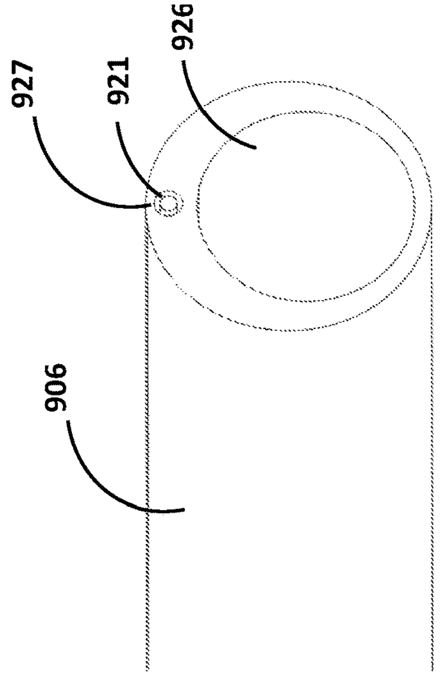

FIG. 69G shows the tip of the deflectable portion of the guiding tube 906 with one lumen 926 for guidance of the balloon catheter 920 and another lumen 927 for a pull wire 921.

Figure 69H:
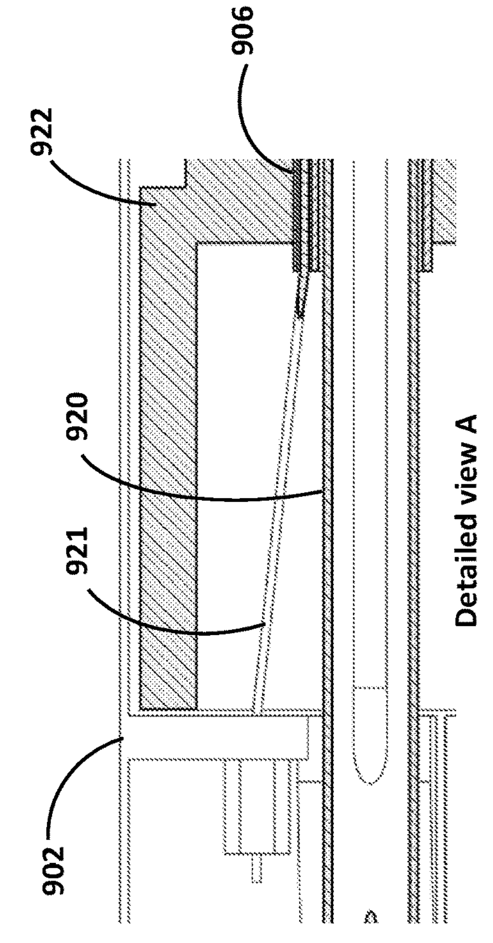

FIG. 69H shows a detailed section view of the device 900. A proximal hub 922 is connected to the guiding tube 906 and is arranged to move linearly inside the device body 902. The pull wire 921 is attached to the device body 902 at one end and attached to the guiding tube 906 at or near the distal end of the guiding tube 906 at the other end for fixating the pull wire 921. The balloon catheter 920 is inserted into the proximal end of the guiding tube 906.

Figure 69I:
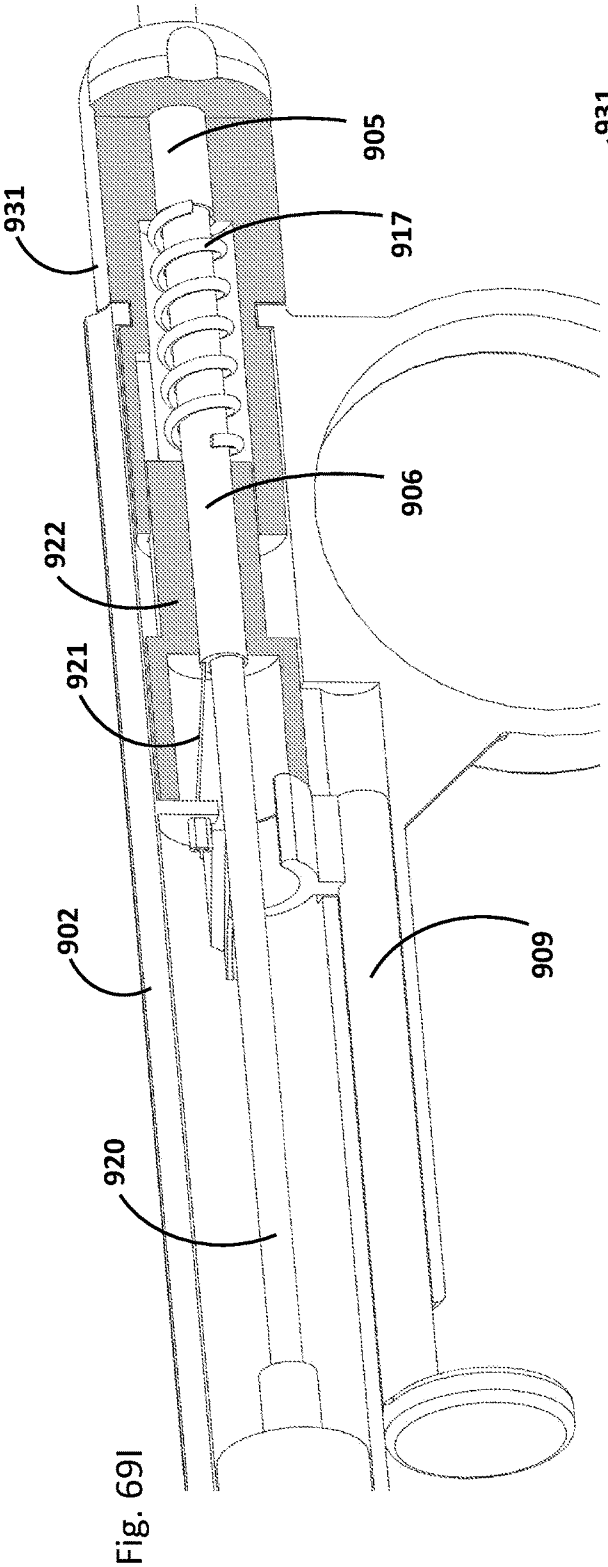
FIGS. 69I and 69J are sectional views of a first embodiment of a controllably deformable tip for a handheld balloon catheter insertion device of FIG. 69A.

FIG. 69I shows a partially elevated sectional view of device 900 in the first state. One half of the device body 902 is not mounted to better show internal components. The proximal hub 922 is shown in a cross-sectional view. Rotatable knob 931 is shown in a partial cross-sectional view. The first actuator 909 is in its first position. The first actuator is shown connected to push the proximal hub 922 forward in a distal direction. The proximal hub 922 is guided inside the device 902 for linear movement and is partly inserted into the rotatable knob 931 with a key and keyway interface that allows linear axial translation and transfers rotation. A spring 917 between the proximal hub 922 and the rotatable knob 931 is shown in a first uncompressed length. The balloon catheter 920 is inserted into the proximal end of the deflectable portion of the balloon catheter 906 which is inserted into the proximal end of the stiff portion of the guiding tube 905. The deflectable portion of the guiding tube 906 may rotate and translate freely inside the stiff portion of the guiding tube 905. Pull wire 921 is rigidly connected to the device body 902 and inserted into the pull wire lumen 927.

Figure 69J:
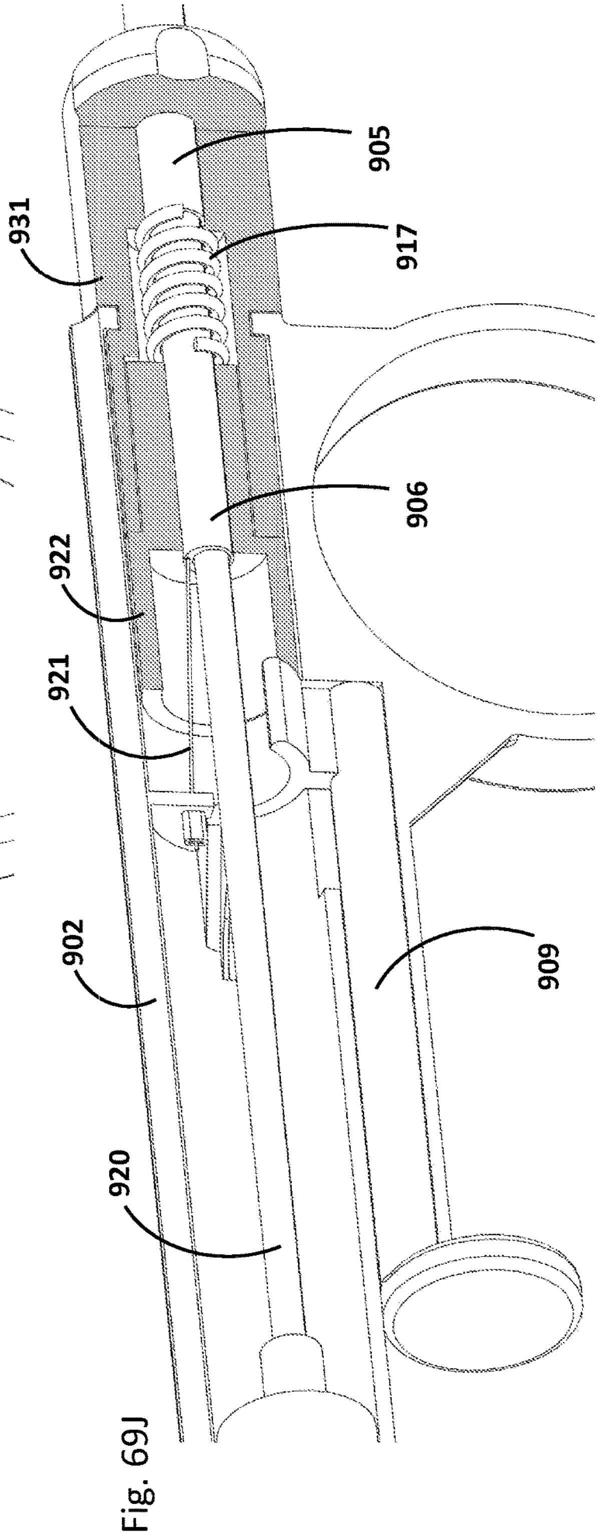

FIG. 69J shows the device 900 same view and in the second state where the first actuator 909 is in its second position. The proximal hub 922 and the deflectable portion of the guiding tube 906 have moved correspondingly in a distal direction relative to the device body 902 and relative to the pull wire 921 and consequently, the deflectable portion of the guiding tube 906 is fully deflected. The spring 917 is in its second compressed length. A serrated surface (not visible) on the rod of the first actuator 909 engages with a serrated cam (not visible) of the device body 902 and serves as a releasable one-way lock for holding and locking any position of the actuator 909 between the first and the second position such that locking of any level of deflection is possible.

Figure 70A:
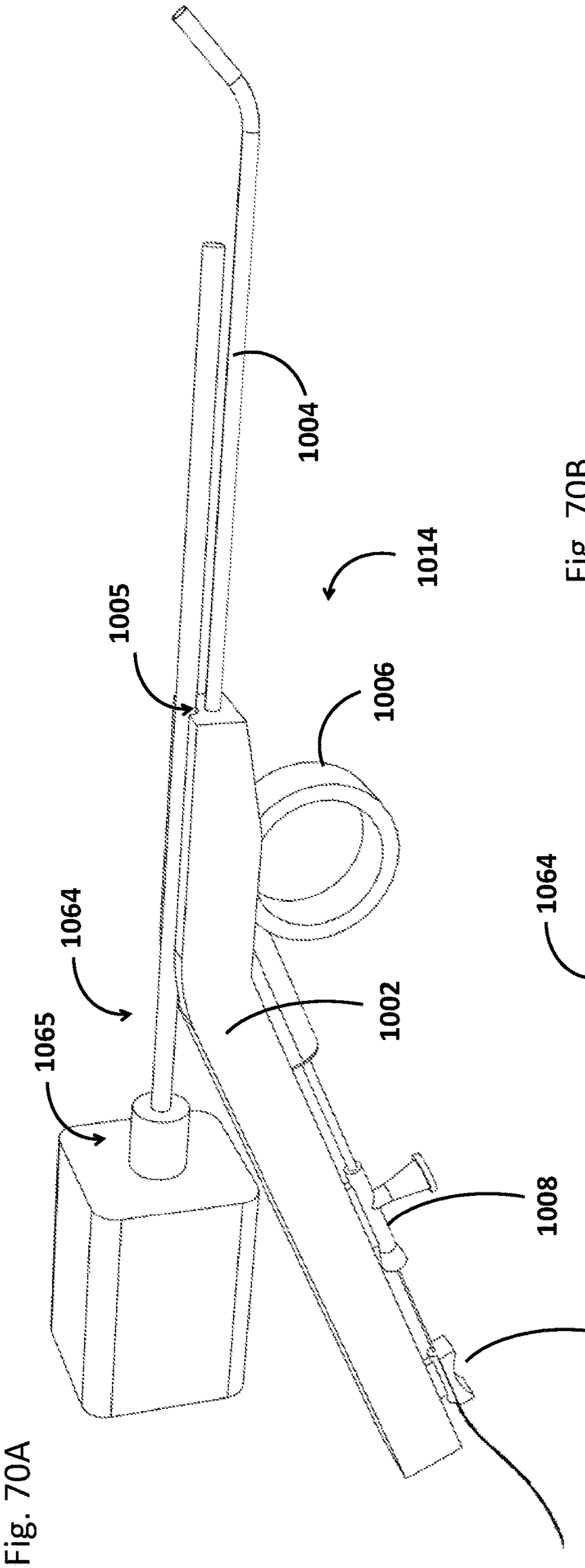
FIGS. 70A and 70B are elevated and side views of an embodiment of a handheld balloon catheter insertion device with a kinked device body.
Figure 70B:
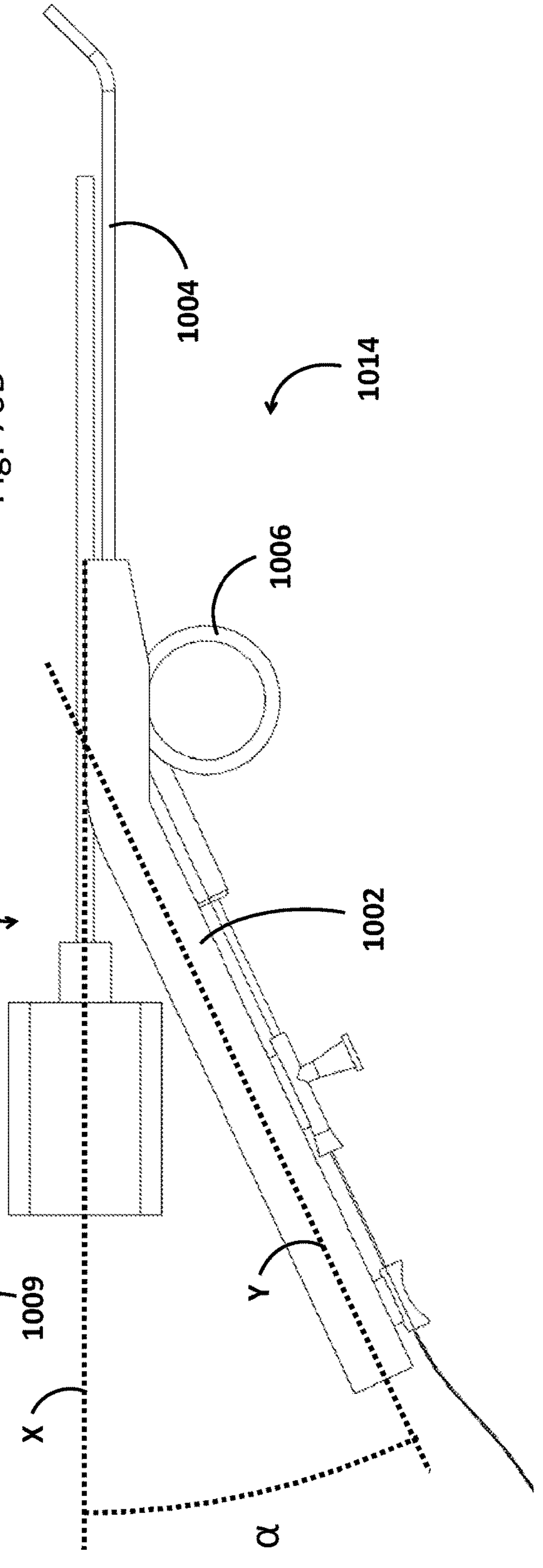

FIGS. 70A-70B show a fifteenth embodiment of a handheld balloon catheter insertion device 1014 with a straight track 1005 in the distal end and on top of the device body 1002 for supporting a part of the shaft of an endoscope 1064. A proximal kinked device body 1002 with a first actuator 1009 for advancement of a guidewire and a second actuator 1008 for advancement of the balloon catheter. The kinked device body 1002 allows space for proximal larger hub 1065 of stiff digital endoscope 1064. Accordingly, there is an angle between the first center axis X defined by the straight track for supporting the endoscope 1064, and the second center axis Y defined by the proximal elongate portion of the device body 1002. Preferably, the proximal elongate portion of the device body is distanced from the center axis of an endoscope shaft when supported by the straight track to allow space for a larger proximal end of the static endoscope. The angle α preferably being between 5 to 90 degrees, the angle α more preferably being 10 to 60 degrees, and the angle α most preferably being 20 to 45 degrees.

Actuators are disposed on the underside of device body 1002 to avoid conflict with any part of the endoscope shaft 1064 or endoscope hub 1065. The second actuator is arranged in a linear guiding track. The first actuator is arranged in the same linear guiding track. A perpendicular connection port on the second actuator is provided for connection with an external pressurization device.

Figure 71:
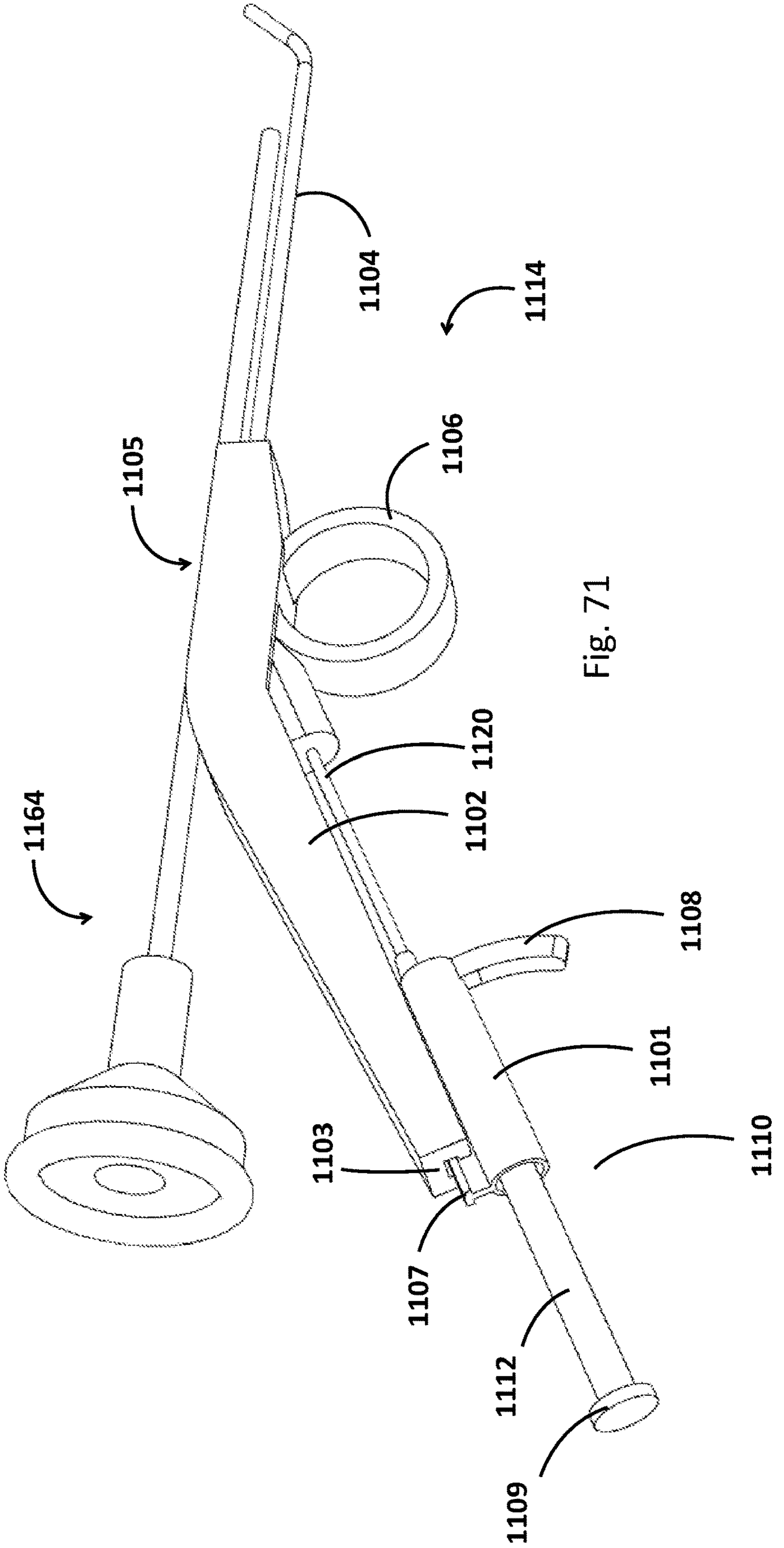
FIG. 71 is an elevated and side views of a fifteenth embodiment of a handheld balloon catheter insertion device with a kinked device body.

FIG. 71 shows a sixteenth embodiment of a handheld balloon catheter insertion device 1114 with a straight track 1105 in the distal end and on top of the device body 1102 for supporting a part of the shaft of an endoscope 1164. A proximal kinked body 1102 with a linear guiding track 1103 for guiding a syringe assembly 1110 towards the guiding tube 1104. The angle between the proximal portion of the device body and the straight track for supporting the shaft of the endoscope 1164 is the same as for the embodiment of FIGS. 70A-B. The syringe barrel 1101 of the syringe assembly has a rail 1107 that fits inside the linear guiding track 1103 for guiding a linear movement relative to the device body 1102. A grasping portion 1006 is provided, preferably for grasping by the middle finger of an operator such that the index finger of the operator may be placed over the endoscope shaft and press it down against the straight track 1105. The syringe barrel 1101 is connected to a balloon catheter 1120 such that a water volume inside the syringe barrel 1101 is in fluid connection with the inflatable part of the balloon catheter 1120. An actuator 1108 is provided on the syringe barrel 1101 for advancement of the balloon catheter 1120 in a distal direction and out of the distal tip of the guiding tube 1104 when moving the syringe assembly 1110 towards the guiding tube 1104. A plunger rod 1112 with a proximal thumb interface 1109 may subsequently be pushed into the syringe barrel 1101 for inflation of the balloon catheter 1120. The kinked device body 1102 allows space for a proximal larger hub of stiff analogue endoscopes. The actuator assembly is disposed on the underside of the device body to avoid conflict with any part of an endoscope.

Figure 72A:
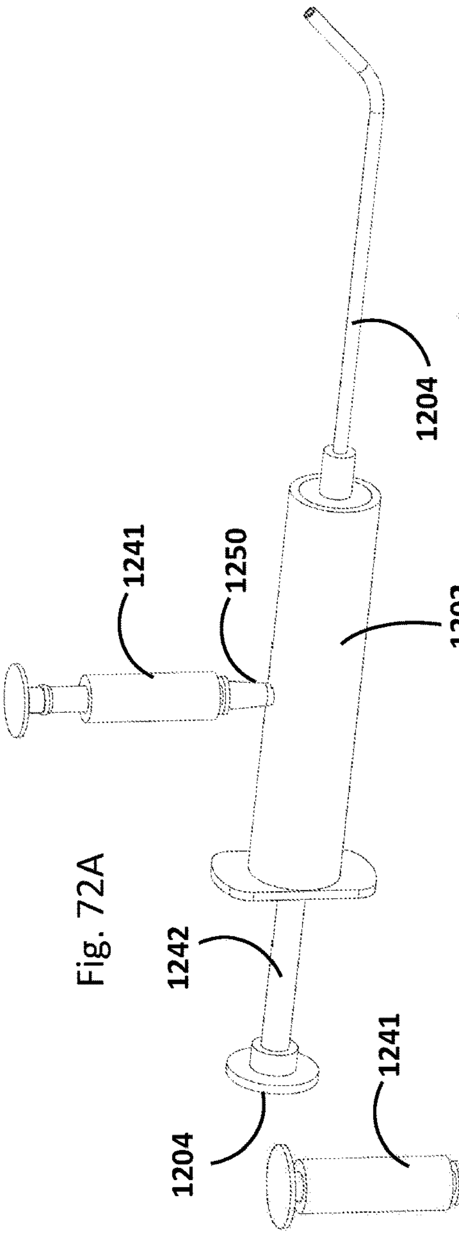
FIGS. 72A-C are elevated views of an embodiment of a handheld balloon catheter insertion device constructed to allow inflation and pressurization of the balloon only when the balloon catheter is fully advanced.
Figure 72B:
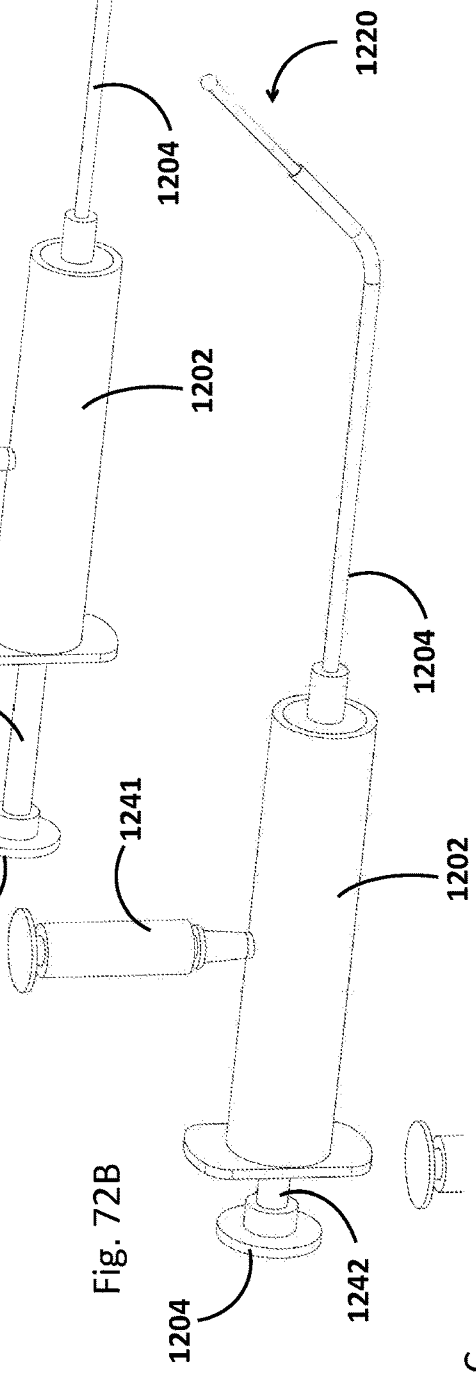
Figure 72C:
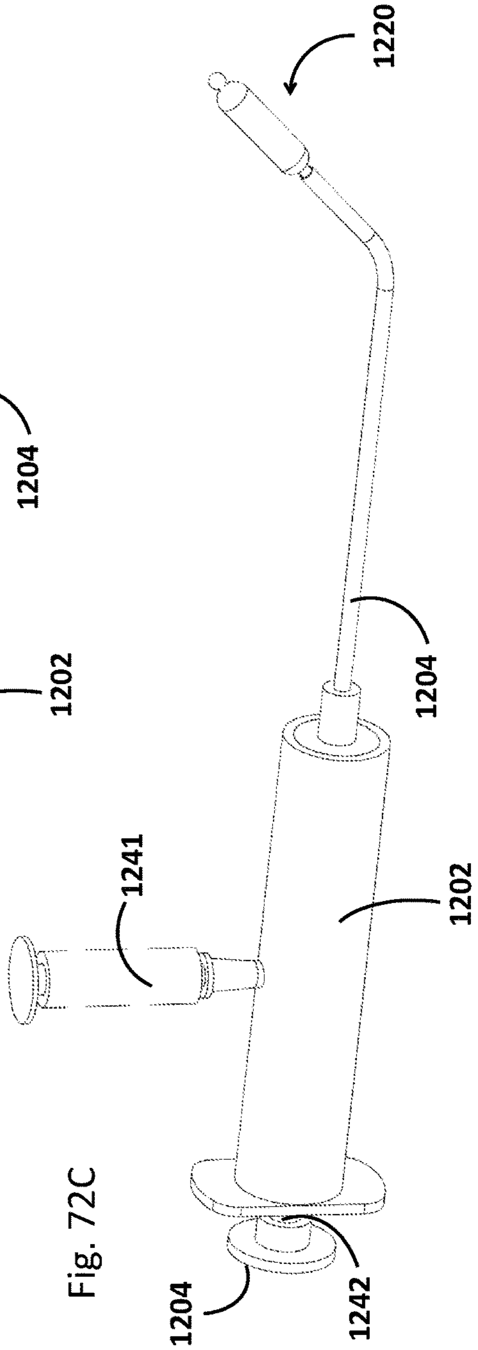
Figures 72D, 72E, 72F:
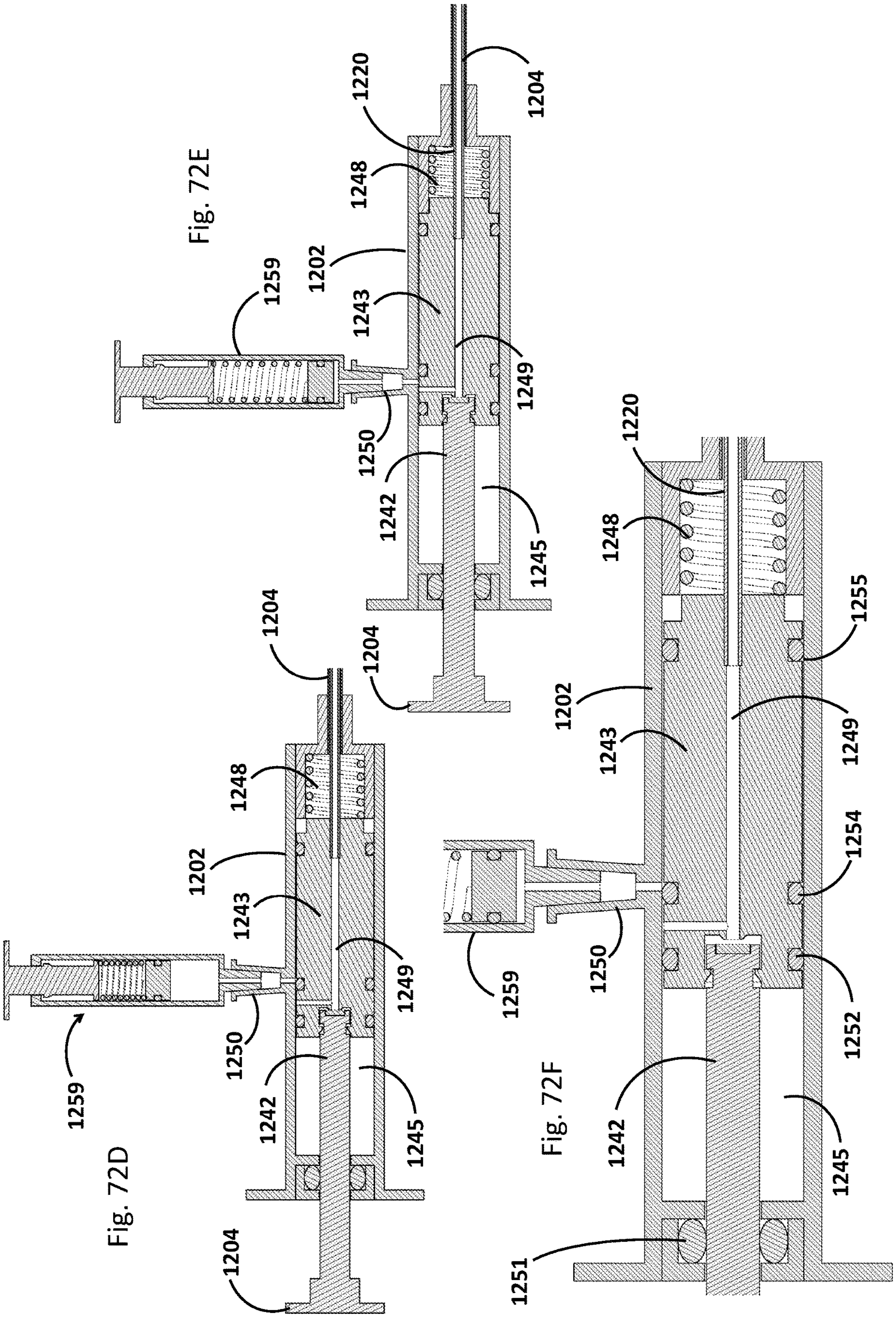
FIGS. 72D-F are sectional views of the handheld balloon catheter insertion device of the embodiment of FIGS. 72A-C.

FIGS. 72A-72F show a seventeenth embodiment of a handheld balloon catheter insertion device with a balloon catheter 1220, a guiding tube 1204, a device body 1202 connected to the proximal end of the guiding tube 1204, the device body 1202 with a cylindrical internal cavity and a side port 1250 for fluid connection with an external pressurization device, a cylindrical valve member 1243 fluidically and operably connected to the proximal end of the balloon catheter 1220 having three axially spaced sealing rings 1252 and 1254 and 1255 for sealing against the inner surface of the cylindrical cavity of the device body 1202. Any external pressurization device may be connected to the side port 1250 directly or via extension tubes. The depicted pressurization device 1259 may be preloaded and locked as part of the preparation. The valve member 1243 is connected to a thruster rod 1242 to move in unison therewith and may be pushed in a distal direction for advancement of the balloon catheter 1220 as seen in FIG. 72B. The thruster rod is sealed against the device body with a thruster rod seal 1251. FIG. 72D shows a position of the valve member 1243 where the balloon catheter 1220 is almost fully advanced and where the side port 1250 is positioned between sealing ring 1254 and sealing ring 1255 and where there is no connection the internal channel 1249 of the valve member. Only in a fully advanced position of the valve member 1243 is a fluid connection established between the side port 1250 and the lumen in the balloon catheter 1220 via a channel 1249 in the valve member 1243, as shown in FIG. 72E, and with the pressurization device having delivered the fluid (typically water) the balloon is inflated, as seen in FIG. 72C. The channel 1249 extends from the distal end of the valve member 1243 axially through the valve member 1243 and comprises a radially extending portion that opens to the circumferential surface of the valve member 1243 between the axially spaced radial sealing rings 1252 and 1254. When the valve member 1243 is in its fully advanced position the side port 1250 is positioned between the axially spaced radial sealing rings 1252 and 1254 to establish a fluidic connection with channel 1249. This arrangement eliminates premature inflation of the balloon inside guiding tube 1204. Sub-atmospheric pressure (partial vacuum) is created in the chamber 1245 on the proximal side of the valve element 1243 when the valve member is in advanced positions and acts as return spring on the valve member 1243. An optional distal spring 1248 can provide a tactile resistance before the valve member 1243 reaches an open position such that the operator knows exactly when the connection between the pressurization device and the balloon catheter is open. The thruster rod 1242 needs to be pressed relatively hard (by the operator's thumb pressing on thumb plate 1204) to move valve member 1243 to its open position of FIG. 72E against the bias of the return spring and optionally a helical spring 1248 disposed between the distal end of the valve member 1243 and an inner distal surface of the device body 1202. The helical spring is optional and only serves to provide tactical feedback to the operator, for the operator to be able to decide when to start inflation. A slight release of the force applied by the operator on the thumb plate 1204 suffices to close the valve and hold pressure in the balloon. Full Release of the thruster rod 1242 will open a channel between chamber 1245 with its partial vacuum and the lumen in the balloon catheter 1202 for deflation of the balloon and the remaining vacuum may pull back the balloon catheter 1220 into guiding tube 1204 once it is deflated. The distal end of the plunger rod 1242 acts as a seat valve to close an axial proximal port in the valve member 1243 in connection with the channel 1249, such that only a small force applied to the plunger rod 1242 in a distal direction will close this proximal port and such that release of force on the plunger rod 1242 will open the port.

Figure 73A:
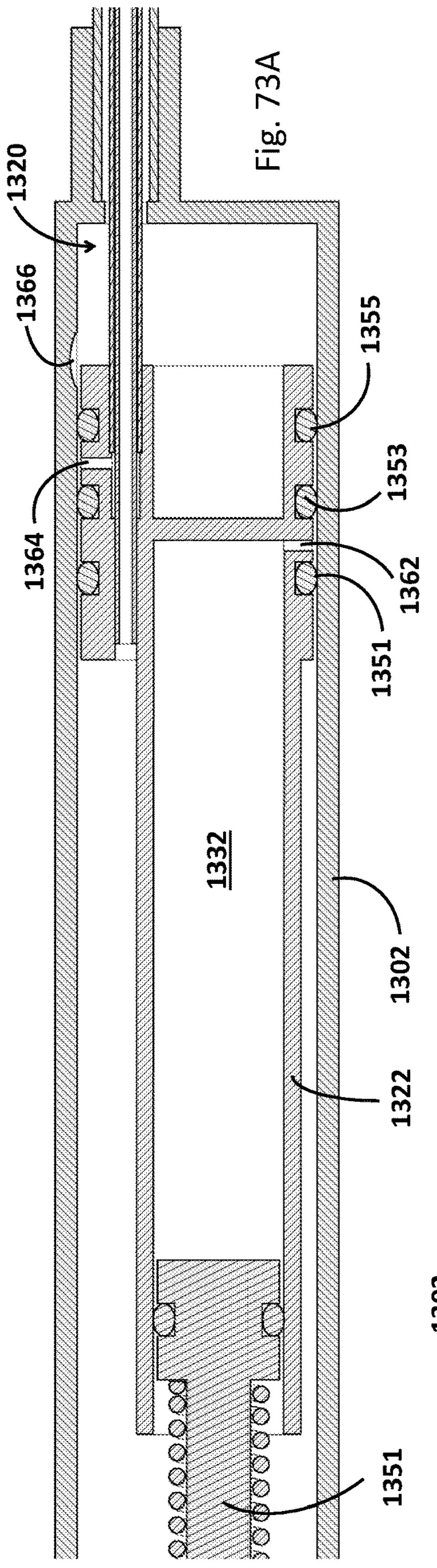
FIGS. 73A and B are cross-sectional detail views of another embodiment of a handheld insertion device with a hydraulic lock.
Figure 73B:
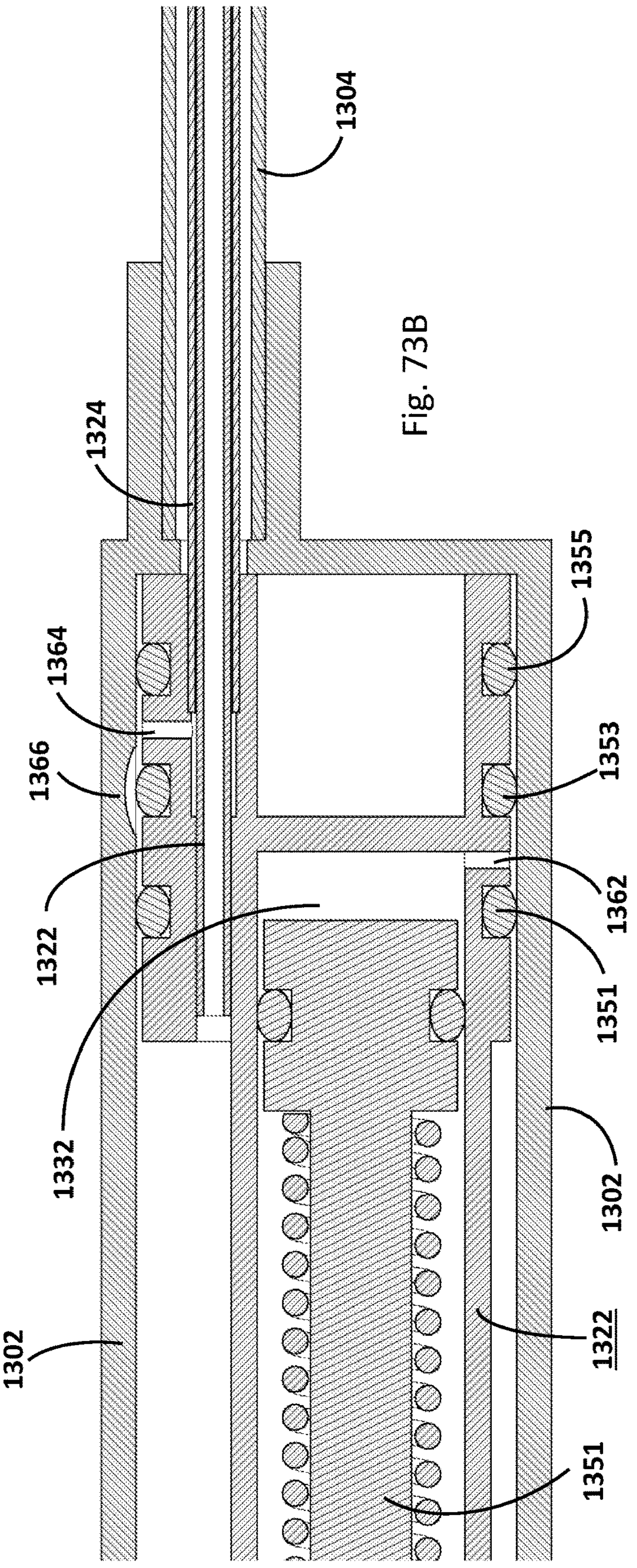

FIGS. 73A-B shows a locking arrangement in a sectional view that can be used with all of the embodiments of the handheld insertion device. This locking arrangement and method prevents premature inflation of the balloon before it is fully advanced out of the guiding tube. A plunger 1351 is slidably and in a syringe barrel 1322 to define a syringe chamber 1332 filled with fluid. The syringe barrel 1322 is slidably and sealingly received in a cylindrical cavity in the device body 1302. Hereto, the distal end of the syringe barrel 1322 is provided with an enlarged diameter section (eccentrically arranged) that is provided with three axially spaced radial seals, first radial seal 1351, second radial seal 1353 and third radial seal 1355 that each seal against a cylindrical inner surface of the device body 1302.

The proximal end of the balloon catheter 1320 is mechanically and fluidly connected to the syringe barrel 1332 to move in unison therewith.

A first radial port 1362 is arranged at or near the distal end of the syringe chamber 1332 and is disposed between the first radial seal 1351 and the second radial seal 1353. The enlarged diameter section of the syringe barrel 1322 is provided with a second radial port 1364 that is arranged between the second radial seal 1353 and the third radial seal 1355. The second radial port 1364 connects to the lumen in the balloon catheter 1320.

The cylindrical inner surface of the device body 1302 provided with a recess 1366 that coincides with the second radial seal 1353 when the syringe barrel 1332 is fully advanced and thereby 1366 creates a bypass that extends to both axial sides of the second radial seal 1353 as shown in FIG. 73B. This bypass creates a hydraulic connection between the syringe chamber 1332 and the lumen in the balloon catheter 1320 via the first radial port 1362 and the second radial port 1364 when the syringe barrel 1332 is fully advanced, thereby allowing the plunger rod 1351 to be pushed into the syringe chamber 1332 and the fluid in the syringe chamber 1332 to be forced into the lumen of the balloon catheter 1322 to inflate and pressurize the balloon of the balloon catheter 1320.

When the syringe body 1332 is not yet fully advanced, evacuation of fluid from the syringe chamber 1332 is prevented by the first and second radial seals 1351 and 1353 sealing against the cylindrical inner wall of the device body 1302. This prevents the plunger rod 1351 being inserted into the syringe chamber 1332 and thus, when the plunger of 1351 is advanced the syringe barrel 1322 moves in unison therewith until the fully advanced position of the syringe barrel 1322 is reached, or after the bypass is established and further forwarding of the plunger rod 1351 evacuates the liquid in the syringe chamber 1332 and inflates and pressurizes the balloon.

The space in the device body 1302 that is not occupied by the plunger rod 1351 and the syringe barrel 1351 is vented to the atmosphere (surroundings) to avoid overpressure or underpressure in the device body cavity on either side of the sealing rings.

FIG. 74 shows a flowchart describing the balloon dilation procedure using the handheld insertion device according to embodiments 1 to 8 and embodiment 11 and embodiment 15 and any combinations thereof. The operator may optionally as the first step bend a portion of the guiding tube and rotate it to accommodate for the passageway to be dilated. When ready, the operator may with one hand only grasp the handheld insertion device and insert the guiding tube into the nostril of a human until located correctly at the passageway to be dilated. For some anatomical passageways, it may be required to insert a guidewire into the passageway to confirm the position. The guide wire may be an optional part of the device and advancement of the guide wire may be an optional step of the procedure. When the position of the guiding tube is confirmed by the use of an endoscope, the operator may, with one finger only, and without changing grip on the device, push a movable member forward from a first position to a second position for advancing the balloon catheter out from the distal end of the guiding tube and into the passageway. The operator may subsequently push the same movable member further from the second position to a third position using the same finger of the same hand and without changing grip on the device, for inflation and pressurization of the device. Bringing the movable member to the third position may automatically lock the movable member such that the hydrostatic pressure in the balloon catheter is held steady without applying any external force. After dilation of the passageway, the operator may unlock the locked movable member to release the hydrostatic pressure in the balloon catheter. The operator may subsequently push the movable member in the opposite direction from the third position to the second position to deflate the balloon and may subsequently push the movable member further from the second position to the first position to retract the balloon. Lastly, the operator will release the movable member and retract the guiding tube from the nostril.

In some occasions, the operator may just hold the movable member in the third position during the dilation of the passageway without locking and unlocking it. In some occasions, the operator may simply pull the guiding tube out of the nostril of the person as soon as the pressure is released from the balloon and deflation and retraction of the balloon will be omitted. In some occasions, the pre-bend tip on the guiding tube and the angle of the guiding tube may fit the procedure and neither bending nor rotation of the guiding tube may be needed.

Figure 75:
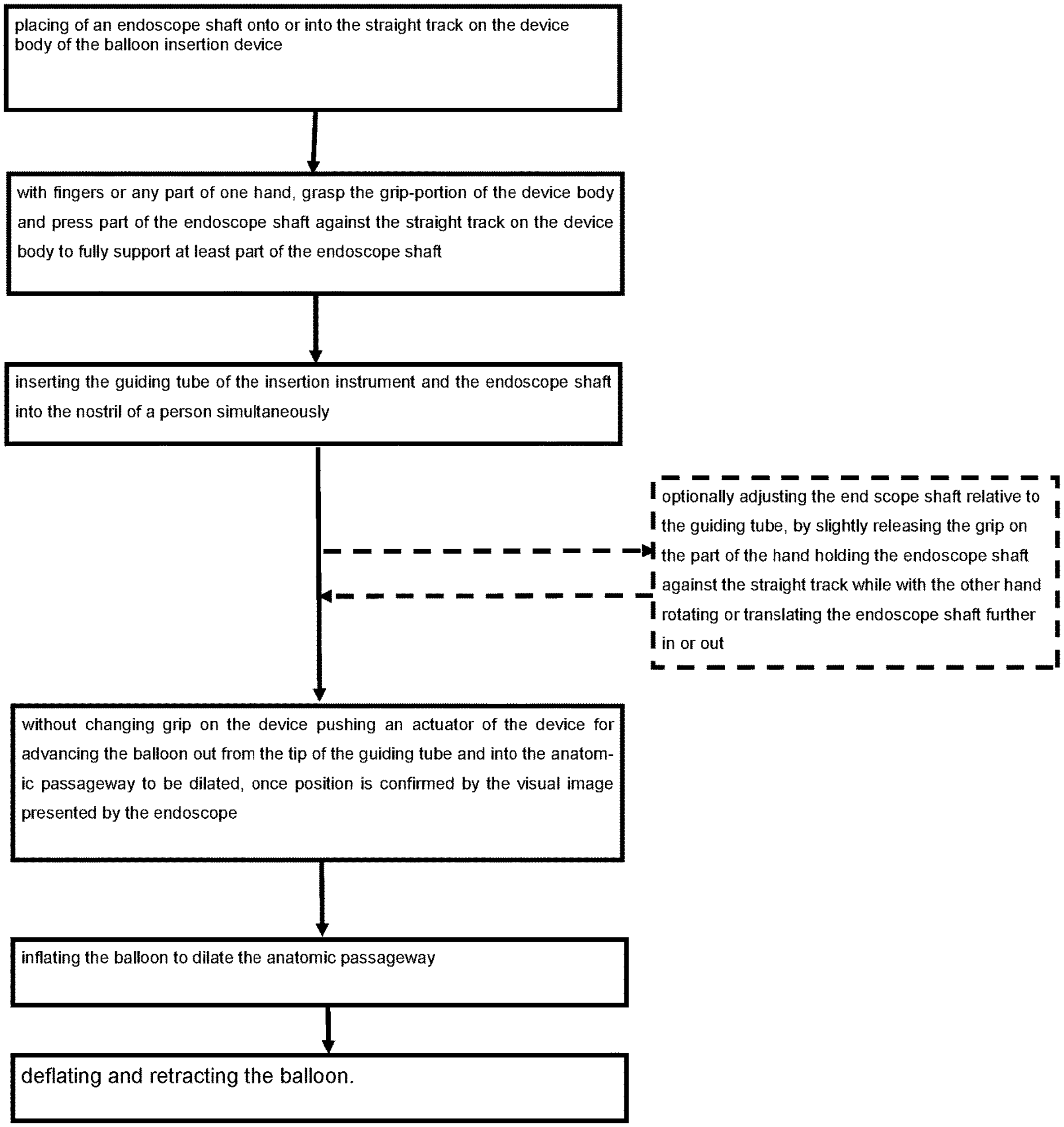
FIG. 75 is a flowchart describing the balloon dilation procedure using the handheld insertion device according to the ninth embodiment.

FIG. 75 shows a flowchart describing the balloon dilation procedure using the handheld insertion device according to the ninth embodiment. The operator will first place the shaft of an endoscope in the straight track of the device body and grasp the grip portion of the device with one hand such that part of a finger or part of the hand is pressing the endoscope shaft down against the straight track to fully support part of the endoscope shaft. The operator may then, with one hand only, insert the guiding tube of the device and the endoscope shaft into the nostril of a person. The operator may desire to adjust the position of the endoscope to change the field of view or to create better access through the nose and may do so by releasing the pressure applied with the finger or part of the hand onto the endoscope, then translating or rotating or slightly adjusting the angle of the endoscope shaft relative to the guiding tube, then re-applying the pressure onto the endoscope to fixate the adjusted position. Once the guiding tube is placed correctly and the field of view is acceptable, the operator may push the actuator of the device to advance the balloon catheter out from the distal tip of the guiding tube and into the passageway and without changing the grip position of the one hand on the device. Once the balloon is fully inserted into the passageway, the balloon may be inflated using a pressurization device such as a syringe assembly. The pressurization device may be integrated into the insertion device or may be externally operated. After the dilation of the passageway, the balloon may be deflated, and the device may be retracted from the nose.

FIG. 76A shows a flowchart describing the procedure of using a pressurization device according to FIGS. 60A to 64C or any possible combinations or variations thereof. The pressurization device may preferably come preassembled with a balloon catheter and with a prefilled water volume inside the syringe barrel of the device. Alternatively, the device may need to be assembled with a balloon catheter and may need to be filled with water as the first step. In case the device needs to be assembled and filled with water, these will be the initial steps; the operator will immerse the distal fluid port of the syringe barrel into a water basin and retract the thruster from a fully inserted position to a fully retracted position to pull water into the syringe barrel. Air bubbles may need to be evacuated from the syringe barrel as usual for filling a syringe.

The operator will connect the balloon catheter to the distal fluid port of the syringe assembly as the final preparation step. When the device is ready after the preparation steps or if it is prepared and preassembled already, the following steps are used. The operator will hold the device with one hand and push the thruster all the way to an end stop to inflate the balloon and achieve the desired predetermined hydrostatic pressure needed for the balloon. The operator may then lock the thruster in the position of the end stop to hold the hydrostatic pressure in the balloon without applying external force. The operator may then release the thruster lock. The operator may lastly retract the thruster to deflate the balloon.

FIG. 76B shows a flowchart describing the procedure of using a pressurization device according to FIGS. 60A to 64C or any possible combinations or variations thereof. The pressurization device may preferably come preassembled with a balloon catheter and with a prefilled water volume inside the syringe barrel of the device. Alternatively, the device may need to be assembled with a balloon catheter and may need to be filled with water as the first step. In case the device needs to be assembled and filled with water, these will be the initial steps; the operator will immerse the distal fluid port of the syringe barrel into a water basin and retract the thruster from a fully inserted position to a fully retracted position to pull water into the syringe barrel. Air bubbles may need to be evacuated from the syringe barrel as usual for filling a syringe.

The operator will connect the balloon catheter to the distal fluid port of the syringe assembly as the final preparation step. When the device is ready after used preparation steps or if it is prepared and preassembled already, the following steps are needed. The operator will hold the device with one hand and push the thruster all the way to an end stop to inflate the balloon and achieve the desired predetermined hydrostatic pressure needed for the balloon. The thruster will automatically be locked at the end stop position and the hydrostatic pressure in the balloon will be held without applying external force. The operator may then push the thruster again in the same direction to release the thruster lock. The operator may lastly retract the thruster to deflate the balloon.

Figure 77:
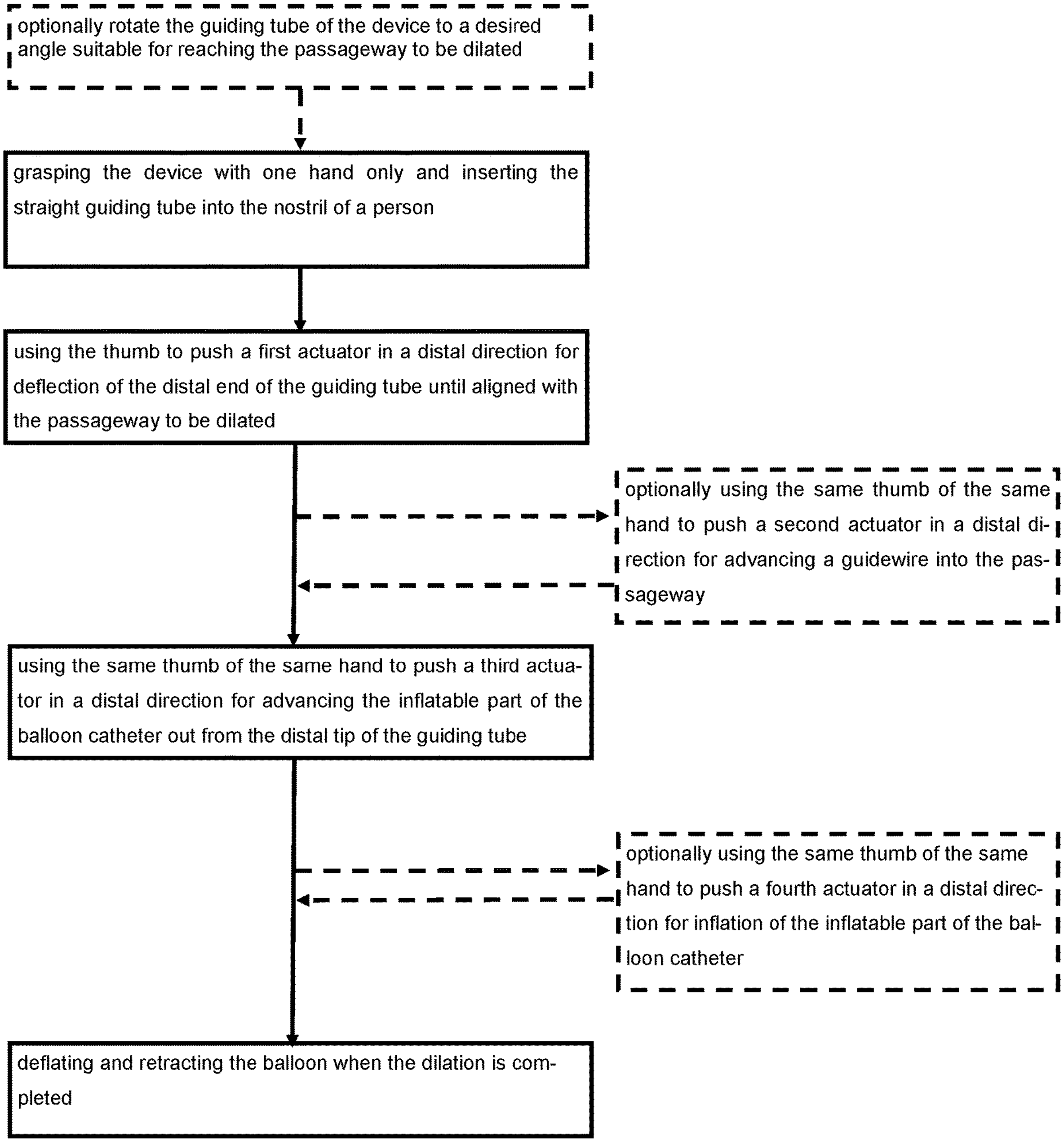
FIG. 77 is a flowchart describing the balloon dilation procedure using handheld balloon insertion device with the deflectable guiding tube according to FIG. 69A to 69J.

FIG. 77 shows a flowchart describing the procedure of using a balloon insertion device with a deflectable guiding tube according to FIGS. 69A to 69J or any obvious variants thereof.

As the first step, the operator may want to rotate the guiding tube of the device to decide the plane and direction of deflection for the deflectable distal portion of the guiding tube. If the default angle of the device is acceptable, then this step may be omitted.

The operator will grasp the device with one hand only and insert the straight guiding tube into the nostril of a person until the distal end of the guiding tube is placed in the proximity of the passageway to be dilated. Without changing grip position of the one hand on the device, the operator may use the thumb to push a first actuator in a distal direction for deflection of the distal end of the guiding tube until aligned with the passageway to be dilated. Without changing grip position of the one hand on the device, the operator may optionally use the same thumb to push a second actuator in a distal direction to advance a guide wire into the passageway. For some anatomic passageways it may not be needed, and the step can be omitted. Without changing grip position of the one hand on the device, the operator may use the thumb to push a third actuator in a distal direction for advancing the inflatable part of the balloon catheter out from the distal end of the guiding tube and into the passageway. Without changing grip position of the one hand on the device, the operator may use the thumb to push a fourth actuator in a distal direction to inflate the balloon. The third and the fourth actuator may be the same actuator being pushed in two steps. The device may in some variants be made without an integrated syringe assembly and without the fourth actuator. In such cases, the step of pushing the fourth actuator may be omitted and the step will be replaced by pressurizing the balloon using an external pressurization device. After the dilation is completed, the balloon will be deflated, and the device will be retracted. The above procedure allows the operator to have a completely free hand to operate an endoscope and the operator may perform the procedure without any assistants and with very little discomfort for the patient.

It should be understood that any of the embodiments described herein may include various other features in addition to or in lieu of those described above. It should be understood that any one or more of the teachings, expressions, examples, embodiments, etc. described herein may be combined with any one or more of the other teachings, expressions, examples, embodiments, etc. that are described herein. The above-described teachings, expressions, examples, embodiment, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples and embodiments, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

In the claims, the word “comprising” does not exclude other elements or steps, and the indefinite article “a” or “an” does not exclude a plurality.

The reference signs used in the claims shall not be construed as limiting the scope. Unless otherwise indicated, the drawings are intended to be read (e.g., cross-hatching, arrangement of parts, proportion, degree, etc.) together with the specification, and are to be considered a portion of the entire written description of this disclosure. As used in the description, the terms “horizontal”, “vertical”, “left”, “right”, “up” and “down”, as well as adjectival and adverbial derivatives thereof (e.g., “horizontally”, “rightwardly”, “upwardly”, etc.), simply refer to the orientation of the illustrated structure as the particular drawing figure faces the reader. Similarly, the terms “inwardly” and “outwardly” generally refer to the orientation of a surface relative to its axis of elongation, or axis of rotation, as appropriate. The term distal for the device will refer to a direction towards the patient and the term proximal will refer to a direction towards the operator of the device.

The invention claimed is:

1. A handheld insertion device for balloon dilation of the Eustachian tube or any other anatomic passageway in the head of a person, the device comprising:

a balloon catheter, a syringe assembly comprising several parts, the several parts comprising a syringe barrel, a sealing element and a plunger rod, a balloon catheter guiding tube for receiving and guiding the balloon catheter, a device body rigidly attached to a proximal end of the balloon catheter guiding tube, the balloon catheter having a distal inflatable part to be advanced out from a distal end of the balloon catheter guiding tube and a proximal part being fluidically connectable to the syringe assembly for inflation and pressurization of the balloon catheter, wherein the device body comprises guiding means for movement of one or more parts of the syringe assembly towards the balloon catheter guiding tube, and wherein, the balloon catheter is operably coupled to one or more parts of the syringe assembly for advancing the balloon catheter out from the distal end of the balloon catheter guiding tube by linear motion of the one or more parts of the syringe assembly, wherein:

the guiding means for movement of one or more parts of the syringe assembly towards the balloon catheter guiding tube comprises guiding means for movement of the syringe barrel towards the balloon catheter guiding tube;

the syringe barrel is fluidically connectable to the proximal part of the balloon catheter to cause inflation and pressurization of the distal inflatable part of the balloon catheter; and the syringe barrel is the part of the syringe assembly which is operably coupled to the balloon catheter for advancing the balloon catheter out from the distal end of the balloon catheter guiding tube by linear motion of the syringe barrel.

2. The handheld insertion device according to claim 1, wherein:

the guiding means for movement of one or more parts of the syringe assembly towards the balloon catheter guiding tube comprises guiding means for movement of the entire syringe assembly towards the balloon catheter guiding tube.

3. The handheld insertion device according to claim 1, wherein:

the one or more parts of the syringe assembly coupled to the balloon catheter includes the plunger rod, coupled to the balloon catheter such that the plunger rod and balloon catheter move in unison.

4. The handheld insertion device according to claim 1, wherein:

the one or more parts of the syringe assembly coupled to the balloon catheter includes the syringe barrel, coupled to the balloon catheter such that the syringe barrel and balloon catheter move in unison.

5. The handheld insertion device according to claim 1, wherein:

the plunger rod is configured for linear motion within the syringe barrel to cause inflation and pressurization of the distal inflatable part;

and the plunger rod is the part of the syringe assembly which is operably coupled to the balloon catheter for advancing the balloon catheter out from the distal end of the balloon catheter guiding tube.

6. The handheld insertion device according to claim 1, wherein:

the handheld insertion device has a primary configuration, in which the syringe assembly and the balloon catheter are in a first position where the distal inflatable part of the balloon catheter is uninflated and fully retracted inside the balloon catheter guiding tube with the plunger rod retracted relative to the syringe barrel, the syringe barrel being filled with water, a secondary configuration in which the syringe assembly and balloon catheter are in a second position where the distal inflatable part of the balloon catheter is advanced out from the distal end of the balloon catheter guiding tube and wherein the plunger rod is retracted relative to the syringe barrel, and a tertiary configuration in which the syringe assembly and balloon catheter are in the second position with the plunger rod inserted into the syringe barrel and the balloon catheter in an inflated configuration.

7. The handheld insertion device according to claim 6, wherein:

the guiding means comprises a first thruster operably coupled to a distal part of the syringe assembly configured to move the syringe assembly and the balloon catheter from the first position to the second position and comprises a second thruster operably coupled to a proximal part of the syringe assembly configured to move the plunger rod relative to the syringe barrel for inflation and pressurization of the balloon catheter.

8. The device according to claim 6, comprising only one single thruster operably coupled to a proximal end of the syringe assembly, the single thruster being configured to first move the syringe assembly and the balloon catheter from the first position to the second position and subsequently to move the plunger rod relative to the syringe barrel for inflation and pressurization of the balloon catheter.

9. A handheld insertion device for balloon dilation of the Eustachian tube or any other anatomic passageway in the head of a person, the device comprising:

a balloon catheter, a syringe assembly comprising several parts, the several parts comprising a syringe barrel, a sealing element and a plunger rod, a balloon catheter guiding tube for receiving and guiding the balloon catheter, a device body rigidly attached to a proximal end of the balloon catheter guiding tube, the balloon catheter having a distal inflatable part to be advanced out from the distal end of the balloon catheter guiding tube and a proximal part being fluidically connectable to the syringe assembly for inflation and pressurization of the balloon catheter, wherein the device body comprises guiding means for movement of one or more parts of the syringe assembly towards the balloon catheter guiding tube, and wherein the balloon catheter is operably coupled to one or more parts of the syringe assembly for advancing the balloon catheter out from the distal end of the balloon catheter guiding tube by linear motion of the one or more parts of the syringe assembly, wherein:

the guiding means for movement of one or more parts of the syringe assembly towards the balloon catheter guiding tube comprises guiding means for movement of the entire syringe assembly towards the balloon catheter guiding tube.

10. The handheld insertion device according to claim 9, wherein:

the handheld insertion device has a primary configuration, in which the syringe assembly and the balloon catheter are in a first position where the distal inflatable part of the balloon catheter is uninflated and fully retracted inside the balloon catheter guiding tube with the plunger rod retracted relative to the syringe barrel, the syringe barrel being filled with water, a secondary configuration in which the syringe assembly and balloon catheter are in a second position where the distal inflatable part of the balloon catheter is advanced out from the distal end of the balloon catheter guiding tube and wherein the plunger rod is retracted relative to the syringe barrel, and a tertiary configuration in which the syringe assembly and balloon catheter are in the second position with the plunger rod inserted into the syringe barrel and the balloon catheter in an inflated configuration.

11. The handheld insertion device according to claim 10, wherein:

the guiding means comprises a first thruster operably coupled to a distal part of the syringe assembly configured to move the syringe assembly and the balloon catheter from the first position to the second position and comprises a second thruster operably coupled to a proximal part of the syringe assembly configured to move the plunger rod relative to the syringe barrel for inflation and pressurization of the balloon catheter.

12. The device according to claim 11, comprising a locking arrangement for preventing movement of the plunger rod relative to the syringe barrel when the syringe assembly and the balloon catheter are in the first position or between the first position and the second position.

13. The handheld insertion device according to claim 9, wherein:

the one or more parts of the syringe assembly coupled to the balloon catheter includes the plunger rod, coupled to the balloon catheter such that the plunger rod and balloon catheter move in unison.

14. The device according to claim 10, comprising only one single thruster operably coupled to a proximal end of the syringe assembly, the single thruster being configured to first move the syringe assembly and the balloon catheter from the first position to the second position and subsequently to move the plunger rod relative to the syringe barrel for inflation and pressurization of the balloon catheter.

15. The device according to claim 10, comprising a locking arrangement for preventing movement of the plunger rod relative to the syringe barrel when the syringe assembly and the balloon catheter are in the first position or between the first position and the second position.

16. The device according to claim 15, wherein the locking arrangement comprises one or more resistance elements creating a resistance between the plunger rod and syringe barrel such that a second force F2 required to move the plunger rod relative to the syringe barrel is substantially higher than a first force F1 required to move the syringe assembly and the balloon catheter from the first position to the second position.

17. A handheld insertion device for balloon dilation of the Eustachian tube or any other anatomic passage way in the head of a person, the device comprising:

a balloon catheter, a syringe assembly comprising several parts, the several parts comprising a syringe barrel, a sealing element and a plunger rod, a balloon catheter guiding tube for receiving and guiding the balloon catheter, a device body rigidly attached to a proximal end of the balloon catheter guiding tube, the balloon catheter having a distal inflatable part to be advanced out from the distal end of the balloon catheter guiding tube and a proximal part being fluidically connectable to the syringe assembly for inflation and pressurization of the balloon catheter, wherein the device body comprises guiding means for movement of one or more parts of the syringe assembly towards the balloon catheter guiding tube, and wherein the balloon catheter is operably coupled to one or more parts of the syringe assembly for advancing the balloon catheter out from the distal end of the balloon catheter guiding tube by linear motion of the one or more parts of the syringe assembly, wherein:

the one or more parts of the syringe assembly coupled to the balloon catheter includes the syringe barrel, coupled to the balloon catheter such that the syringe barrel and balloon catheter move in unison.

18. The handheld insertion device according to claim 17, wherein:

the one or more parts of the syringe assembly coupled to the balloon catheter includes the plunger rod, coupled to the balloon catheter such that the plunger rod and balloon catheter move in unison.

19. The handheld insertion device according to claim 17, wherein:

the handheld insertion device has a primary configuration, in which the syringe assembly and the balloon catheter are in a first position where the distal inflatable part of the balloon catheter is uninflated and fully retracted inside the balloon catheter guiding tube with the plunger rod retracted relative to the syringe barrel, the syringe barrel being filled with water, a secondary configuration in which the syringe assembly and balloon catheter are in a second position where the distal inflatable part of the balloon catheter is advanced out from the distal end of the balloon catheter guiding tube and wherein the plunger rod is retracted relative to the syringe barrel, and a tertiary configuration in which the syringe assembly and balloon catheter are in the second position with the plunger rod inserted into the syringe barrel and the balloon catheter in an inflated configuration.

20. The handheld insertion device according to claim 19, wherein:

the guiding means comprises a first thruster operably coupled to a distal part of the syringe assembly configured to move the syringe assembly and the balloon catheter from the first position to the second position and comprises a second thruster operably coupled to a proximal part of the syringe assembly configured to move the plunger rod relative to the syringe barrel for inflation and pressurization of the balloon catheter.

21. The device according to claim 19, comprising only one single thruster operably coupled to a proximal end of the syringe assembly, the single thruster being configured to first move the syringe assembly and the balloon catheter from the first position to the second position and subsequently to move the plunger rod relative to the syringe barrel for inflation and pressurization of the balloon catheter.

22. The device according to claim 19, comprising a locking arrangement for preventing movement of the plunger rod relative to the syringe barrel when the syringe assembly and the balloon catheter are in the first position or between the first position and the second position.

23. The device according to claim 22, wherein the locking arrangement comprises a first locking mechanism, where in the first locking mechanism comprises a movable locking member, in the form of a spherical locking member, the movable locking member having a locked position in which relative movement between the syringe barrel and the plunger rod is prevented and an unlocked position in which relative movement between the syringe barrel and the plunger rod is enabled.

* * * * *